US010485431B1

(12) United States Patent
Khachaturian et al.

(10) Patent No.: US 10,485,431 B1
(45) Date of Patent: Nov. 26, 2019

(54) GLUCOSE MULTI-VITAL-SIGN SYSTEM IN AN ELECTRONIC MEDICAL RECORDS SYSTEM

(71) Applicant: ARC Devices Limited

(72) Inventors: Mark Khachaturian, Boca Raton, FL (US); Michael Smith, Lakeway, TX (US)

(73) Assignee: ARC Devices Ltd., Dublin (IE)

( * ) Notice: Subject to any disclaimer, the term of this patent is extended or adjusted under 35 U.S.C. 154(b) by 0 days.

(21) Appl. No.: 15/985,672

(22) Filed: May 21, 2018

(51) Int. Cl.

| | | |
|---|---|---|
| *A61B 17/00* | (2006.01) | |
| *A61B 5/0205* | (2006.01) | |
| *A61B 5/145* | (2006.01) | |
| *A61B 5/00* | (2006.01) | |
| *A61B 5/01* | (2006.01) | |
| *A61B 5/1455* | (2006.01) | |
| *G06T 3/40* | (2006.01) | |
| *G16H 10/60* | (2018.01) | |
| *A61B 5/08* | (2006.01) | |
| *A61B 5/024* | (2006.01) | |
| *A61B 5/022* | (2006.01) | |

(52) U.S. Cl.
CPC ........ *A61B 5/02055* (2013.01); *A61B 5/0008* (2013.01); *A61B 5/01* (2013.01); *A61B 5/14532* (2013.01); *A61B 5/14551* (2013.01); *G06T 3/40* (2013.01); *G16H 10/60* (2018.01); *A61B 5/0077* (2013.01); *A61B 5/02241* (2013.01); *A61B 5/02405* (2013.01); *A61B 5/0816* (2013.01); *A61B 2562/0219* (2013.01); *G06T 2210/22* (2013.01)

(58) Field of Classification Search
CPC ..... A61B 5/02055; A61B 5/0008; A61B 5/01; A61B 5/14532; A61B 5/14551; A61B 5/0077; A61B 5/02241; A61B 5/02405; A61B 5/0816; A61B 2562/0219; G16H 10/60; G06T 3/40; G06T 2210/22
USPC ........................................................ 600/301
See application file for complete search history.

(56) References Cited

U.S. PATENT DOCUMENTS

| | | |
|---|---|---|
| 4,315,150 A | 2/1982 | Darringer et al. |
| 4,322,012 A | 3/1982 | Conti |
| (Continued) | | |

FOREIGN PATENT DOCUMENTS

| | | |
|---|---|---|
| CN | 1271562 A | 11/2000 |
| CN | 102198004 A | 9/2011 |
| (Continued) | | |

OTHER PUBLICATIONS

Pitzer et al., Detection of Hypoglycemia With the GlucoWatch Biographer, Diabetes Care, vol. 24, No. 5, May 2001, pp. 881-885, retrieved from the Internet from http://citeseerx.ist.psu.edu/viewdoc/download?doi=10.1.1.915.1360&rep=rep1&type=pdf on Nov. 9, 2018.
(Continued)

*Primary Examiner* — Aaron F Roane
(74) *Attorney, Agent, or Firm* — Michael G. Smith, Esq.

(57) ABSTRACT

A device measures blood glucose levels, temperature, heart rate, heart rate variability, respiration, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and/or EEG of a human.

7 Claims, 54 Drawing Sheets

(56) References Cited

U.S. PATENT DOCUMENTS

| | | | |
|---|---|---|---|
| 4,394,773 | A | 7/1983 | Ruell |
| 4,602,642 | A | 7/1986 | O'Hara et al. |
| 4,634,294 | A | 1/1987 | Christol et al. |
| 4,709,690 | A | 12/1987 | Haber |
| 4,797,840 | A | 1/1989 | Fraden |
| 5,017,018 | A | 5/1991 | Iuchi et al. |
| 5,067,162 | A | 11/1991 | Driscoll, Jr. et al. |
| 5,077,476 | A | 12/1991 | Rosenthal |
| 5,133,605 | A | 7/1992 | Nakamura |
| 5,150,969 | A | 9/1992 | Goldberg et al. |
| 5,272,340 | A | 12/1993 | Anbar |
| 5,325,442 | A | 6/1994 | Knapp |
| 5,351,303 | A | 9/1994 | Willmore |
| 5,368,038 | A | 11/1994 | Fraden |
| 5,398,681 | A | 3/1995 | Kupershmidt |
| 5,689,576 | A | 11/1997 | Schneider et al. |
| 5,737,439 | A | 4/1998 | Lapsley et al. |
| 5,743,644 | A | 4/1998 | Kobayashi |
| 5,909,501 | A | 6/1999 | Thebaud |
| 5,940,526 | A | 8/1999 | Setlak et al. |
| 5,953,441 | A | 9/1999 | Setlak |
| 6,001,066 | A * | 12/1999 | Canfield ............... G01J 5/0022 374/E13.003 |
| 6,095,682 | A | 8/2000 | Hollander et al. |
| 6,118,890 | A | 9/2000 | Senior |
| 6,134,340 | A | 10/2000 | Hsu et al. |
| 6,241,288 | B1 | 6/2001 | Bergenek et al. |
| 6,286,994 | B1 | 9/2001 | Boesel et al. |
| 6,289,114 | B1 | 9/2001 | Mainguet |
| 6,292,685 | B1 | 9/2001 | Pompei |
| 6,327,376 | B1 | 12/2001 | Harkin |
| 6,343,141 | B1 | 1/2002 | Okada et al. |
| 6,358,216 | B1 | 3/2002 | Kraus et al. |
| 6,445,938 | B1 | 9/2002 | Berman et al. |
| 6,466,202 | B1 * | 10/2002 | Suso ............... G06F 1/1616 345/169 |
| 6,483,929 | B1 | 11/2002 | Murakami et al. |
| 6,505,059 | B1 | 1/2003 | Kollias et al. |
| 6,546,122 | B1 | 4/2003 | Russo |
| 6,560,352 | B2 | 5/2003 | Rowe et al. |
| 6,587,701 | B1 | 7/2003 | Stranc et al. |
| 6,728,560 | B2 | 4/2004 | Kollias et al. |
| 6,742,927 | B2 | 6/2004 | Bellifemine |
| 6,751,342 | B2 | 6/2004 | Shepard |
| 6,757,412 | B1 | 6/2004 | Parsons |
| 6,819,950 | B2 | 11/2004 | Mills |
| 6,832,000 | B2 | 12/2004 | Herman et al. |
| 7,092,376 | B2 | 8/2006 | Schuman |
| 7,140,768 | B2 | 11/2006 | Prabhakar |
| 7,214,953 | B2 | 5/2007 | Setlak et al. |
| 7,321,701 | B2 | 1/2008 | Setlak et al. |
| 7,339,685 | B2 | 3/2008 | Carlson et al. |
| 7,346,386 | B2 | 3/2008 | Pompei |
| 7,351,974 | B2 | 4/2008 | Setlak |
| 7,358,514 | B2 | 4/2008 | Setlak et al. |
| 7,358,515 | B2 | 4/2008 | Setlak et al. |
| 7,361,919 | B2 | 4/2008 | Setlak |
| 7,433,729 | B2 | 10/2008 | Setlak et al. |
| 7,520,668 | B2 | 4/2009 | Chen |
| 7,572,056 | B2 | 8/2009 | Lane |
| 7,671,351 | B2 | 3/2010 | Setlak et al. |
| 7,787,938 | B2 | 8/2010 | Pompei |
| 7,915,601 | B2 | 3/2011 | Setlak et al. |
| 8,194,942 | B2 | 6/2012 | Tobe et al. |
| 8,213,689 | B2 | 7/2012 | Yagnik et al. |
| 8,249,547 | B1 | 8/2012 | Fellner |
| 8,401,285 | B1 | 3/2013 | Rezaee et al. |
| 8,452,382 | B1 | 5/2013 | Roth |
| 8,493,482 | B2 | 7/2013 | Cote et al. |
| 8,517,603 | B2 | 8/2013 | Fraden |
| 8,527,038 | B2 | 9/2013 | Moon et al. |
| 8,617,081 | B2 | 12/2013 | Mestha et al. |
| 8,693,739 | B2 | 4/2014 | Weng et al. |
| 8,849,379 | B2 | 9/2014 | Abreu |
| 9,008,458 | B2 | 4/2015 | Pack |
| 9,321,394 | B2 | 4/2016 | Bouffay et al. |
| 9,442,065 | B2 | 9/2016 | Gulati et al. |
| 9,497,534 | B2 | 11/2016 | Prest et al. |
| 2001/0005424 | A1 | 6/2001 | Marksteiner |
| 2002/0067845 | A1 | 6/2002 | Griffis |
| 2002/0076089 | A1 | 6/2002 | Muramatsu et al. |
| 2002/0077850 | A1 | 6/2002 | McMenimen et al. |
| 2002/0138768 | A1 | 9/2002 | Murakami et al. |
| 2002/0143257 | A1 | 10/2002 | Newman et al. |
| 2002/0172410 | A1 | 11/2002 | Shepard |
| 2003/0069486 | A1 | 4/2003 | Sueppel et al. |
| 2003/0069487 | A1 | 4/2003 | Mortara |
| 2003/0078622 | A1 | 4/2003 | Cansell et al. |
| 2003/0123714 | A1 | 7/2003 | O'Gorman et al. |
| 2003/0126448 | A1 | 7/2003 | Russo |
| 2003/0169910 | A1 | 9/2003 | Reisman et al. |
| 2003/0190062 | A1 | 10/2003 | Noro et al. |
| 2004/0013162 | A1 | 1/2004 | Beerwerth |
| 2004/0019293 | A1 | 1/2004 | Schweitzer et al. |
| 2004/0097818 | A1 | 5/2004 | Schmid et al. |
| 2004/0116822 | A1 | 6/2004 | Lindsey |
| 2004/0120383 | A1 | 6/2004 | Kennedy et al. |
| 2004/0153341 | A1 | 8/2004 | Brandt et al. |
| 2004/0186357 | A1 | 9/2004 | Soderberg et al. |
| 2004/0193068 | A1 | 9/2004 | Burton et al. |
| 2005/0023991 | A1 | 2/2005 | Kemper |
| 2005/0054908 | A1 | 3/2005 | Blank et al. |
| 2005/0203350 | A1 | 9/2005 | Beck |
| 2005/0206518 | A1 | 9/2005 | Welch et al. |
| 2005/0209515 | A1 | 9/2005 | Hockersmith et al. |
| 2005/0288571 | A1 | 12/2005 | Perkins et al. |
| 2006/0004271 | A1 | 1/2006 | Peyser et al. |
| 2006/0030759 | A1 | 2/2006 | Weiner et al. |
| 2006/0045316 | A1 | 3/2006 | Hauke et al. |
| 2006/0110015 | A1 | 5/2006 | Rowe |
| 2006/0116555 | A1 * | 6/2006 | Pavlidis ............... A61B 5/01 600/300 |
| 2006/0155589 | A1 | 7/2006 | Lane et al. |
| 2006/0195024 | A1 | 8/2006 | Benni |
| 2006/0209631 | A1 | 9/2006 | Melese et al. |
| 2006/0225737 | A1 | 10/2006 | Lobbi |
| 2006/0238333 | A1 | 10/2006 | Welch et al. |
| 2006/0278293 | A1 | 12/2006 | Weber et al. |
| 2006/0293921 | A1 | 12/2006 | McCarthy et al. |
| 2007/0013511 | A1 | 1/2007 | Weiner et al. |
| 2007/0049834 | A1 | 3/2007 | Tao et al. |
| 2007/0069887 | A1 | 3/2007 | Welch et al. |
| 2007/0080233 | A1 | 4/2007 | Forster et al. |
| 2007/0135866 | A1 | 6/2007 | Baker et al. |
| 2007/0142731 | A1 | 6/2007 | Ye et al. |
| 2007/0183475 | A1 | 8/2007 | Hutcherson |
| 2007/0185390 | A1 | 8/2007 | Perkins et al. |
| 2007/0189358 | A1 | 8/2007 | Lane et al. |
| 2008/0033308 | A1 | 2/2008 | Cen et al. |
| 2008/0064967 | A1 | 3/2008 | Ide |
| 2008/0149701 | A1 | 6/2008 | Lane |
| 2008/0175301 | A1 | 7/2008 | Chen |
| 2008/0281167 | A1 | 11/2008 | Soderberg et al. |
| 2008/0281168 | A1 | 11/2008 | Gibson et al. |
| 2008/0300473 | A1 | 12/2008 | Benni |
| 2009/0062674 | A1 | 3/2009 | Jin et al. |
| 2009/0100333 | A1 | 4/2009 | Xiao |
| 2009/0103469 | A1 | 4/2009 | Smith et al. |
| 2009/0105549 | A1 | 4/2009 | Smith et al. |
| 2009/0105566 | A1 | 4/2009 | Smith et al. |
| 2009/0105567 | A1 | 4/2009 | Smith et al. |
| 2009/0131774 | A1 | 5/2009 | Sweitzer et al. |
| 2009/0141124 | A1 | 6/2009 | Liu et al. |
| 2009/0172591 | A1 | 7/2009 | Pomper |
| 2009/0175317 | A1 | 7/2009 | Chan et al. |
| 2009/0177248 | A1 | 7/2009 | Roberts |
| 2009/0182526 | A1 | 7/2009 | Quinn et al. |
| 2009/0196475 | A1 | 8/2009 | Demirli et al. |
| 2009/0221880 | A1 | 9/2009 | Soderberg et al. |
| 2010/0049077 | A1 | 2/2010 | Sadleir et al. |
| 2010/0056928 | A1 | 3/2010 | Zuzak |
| 2010/0094098 | A1 | 4/2010 | Smith et al. |
| 2010/0094145 | A1 | 4/2010 | Ye et al. |
| 2010/0121164 | A1 | 5/2010 | Donars et al. |

(56) References Cited

U.S. PATENT DOCUMENTS

| | | |
|---|---|---|
| 2010/0191472 A1 | 7/2010 | Doniger et al. |
| 2010/0265986 A1 | 10/2010 | Mullin et al. |
| 2010/0280331 A1 | 11/2010 | Kaufman et al. |
| 2010/0284436 A1 | 11/2010 | Lane et al. |
| 2010/0298650 A1 | 11/2010 | Moon et al. |
| 2010/0322282 A1 | 12/2010 | Lane et al. |
| 2010/0324380 A1 | 12/2010 | Perkins et al. |
| 2011/0047298 A1 | 2/2011 | Eaton et al. |
| 2011/0054267 A1 | 3/2011 | Fidacaro et al. |
| 2011/0112791 A1 | 5/2011 | Pak et al. |
| 2011/0121978 A1 | 5/2011 | Schwörer et al. |
| 2011/0140896 A1 | 6/2011 | Menzel |
| 2011/0148622 A1 | 6/2011 | Judy et al. |
| 2011/0152629 A1 | 6/2011 | Eaton et al. |
| 2011/0158283 A1 | 6/2011 | Meyerson et al. |
| 2011/0178376 A1 | 7/2011 | Judy et al. |
| 2011/0199203 A1 | 8/2011 | Hsu |
| 2011/0228810 A1 | 9/2011 | O'Hara et al. |
| 2011/0228811 A1 | 9/2011 | Fraden |
| 2011/0230731 A1 | 9/2011 | Rantala et al. |
| 2011/0237906 A1 | 9/2011 | Kabakov |
| 2011/0251493 A1 | 10/2011 | Poh et al. |
| 2011/0276698 A1 | 11/2011 | Bigioi et al. |
| 2011/0285248 A1 | 11/2011 | Cewers |
| 2011/0286644 A1 | 11/2011 | Kislal |
| 2011/0291837 A1 | 12/2011 | Rantala |
| 2011/0291838 A1 | 12/2011 | Rantala |
| 2012/0004516 A1 | 1/2012 | Eng et al. |
| 2012/0005248 A1 | 1/2012 | Garudadri et al. |
| 2012/0022348 A1 | 1/2012 | Droitcour et al. |
| 2012/0026119 A1 | 2/2012 | Judy et al. |
| 2012/0053422 A1 | 3/2012 | Rantala |
| 2012/0094600 A1 | 4/2012 | DelloStritto et al. |
| 2012/0096367 A1 | 4/2012 | DelloStritto et al. |
| 2012/0130197 A1 | 5/2012 | Kugler et al. |
| 2012/0130251 A1 | 5/2012 | Huff |
| 2012/0130252 A1 | 5/2012 | Pohjanen et al. |
| 2012/0136559 A1 | 5/2012 | Rothschild |
| 2012/0150482 A1 | 6/2012 | Yildizyan et al. |
| 2012/0154152 A1 | 6/2012 | Rantala et al. |
| 2012/0165617 A1 | 6/2012 | Vesto et al. |
| 2012/0179011 A1 | 7/2012 | Moon et al. |
| 2012/0242844 A1 | 9/2012 | Walker et al. |
| 2012/0271130 A1 | 10/2012 | Benni |
| 2012/0302905 A1 | 11/2012 | Kaski |
| 2012/0319848 A1 | 12/2012 | Coffeng |
| 2013/0002420 A1 | 1/2013 | Perkins et al. |
| 2013/0006093 A1 | 1/2013 | Raleigh et al. |
| 2013/0023772 A1 | 1/2013 | Kinsley et al. |
| 2013/0035599 A1 | 2/2013 | De Bruijn et al. |
| 2013/0085348 A1 | 4/2013 | Devenyi et al. |
| 2013/0085708 A1 | 4/2013 | Sattler |
| 2013/0085758 A1 | 4/2013 | Csoma et al. |
| 2013/0086122 A1 | 4/2013 | Devenyi et al. |
| 2013/0109927 A1 | 5/2013 | Menzel |
| 2013/0109929 A1 | 5/2013 | Menzel |
| 2013/0137939 A1 | 5/2013 | He et al. |
| 2013/0138003 A1 | 5/2013 | Kaski |
| 2013/0172770 A1 | 7/2013 | Muehlsteff |
| 2013/0178719 A1 | 7/2013 | Balji et al. |
| 2013/0211265 A1 | 8/2013 | Bedingham et al. |
| 2013/0215928 A1 | 8/2013 | Bellifemine |
| 2013/0245457 A1 | 9/2013 | Kinsley et al. |
| 2013/0245462 A1 | 9/2013 | Capdevila et al. |
| 2013/0245467 A1 | 9/2013 | St. Pierre et al. |
| 2013/0245488 A1 | 9/2013 | Quinn et al. |
| 2013/0245489 A1 | 9/2013 | Mullin et al. |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1 | 10/2013 | Vassallo et al. |
| 2013/0267873 A1 | 10/2013 | Fuchs |
| 2013/0268283 A1 | 10/2013 | Vann et al. |
| 2013/0271283 A1 | 10/2013 | Judy et al. |
| 2013/0271591 A1 | 10/2013 | Van Leest et al. |
| 2013/0296716 A1 | 11/2013 | Kurzenberger |
| 2013/0307536 A1 | 11/2013 | Feng et al. |
| 2013/0322729 A1 | 12/2013 | Mestha et al. |
| 2013/0334298 A1 | 12/2013 | Sakpal et al. |
| 2013/0342691 A1 | 12/2013 | Lewis et al. |
| 2014/0003461 A1 | 1/2014 | Roth |
| 2014/0003462 A1 | 1/2014 | Roth |
| 2014/0031637 A1 | 1/2014 | Fidacaro et al. |
| 2014/0032241 A1 | 1/2014 | Coffeng |
| 2014/0058213 A1 | 2/2014 | Abu-Tarif et al. |
| 2014/0171805 A1 | 2/2014 | Mullin et al. |
| 2014/0064327 A1 | 3/2014 | Roth |
| 2014/0064328 A1 | 3/2014 | Roth |
| 2014/0064333 A1 | 3/2014 | Roth |
| 2014/0072190 A1 | 3/2014 | Wu et al. |
| 2014/0072228 A1 | 3/2014 | Rubinstein |
| 2014/0072229 A1 | 3/2014 | Wadhwa |
| 2014/0073860 A1 | 3/2014 | Uriti |
| 2014/0088434 A1 | 3/2014 | Roth |
| 2014/0088435 A1 | 3/2014 | Roth |
| 2014/0088436 A1 | 3/2014 | Roth |
| 2014/0088446 A1 | 3/2014 | St. Pierre et al. |
| 2014/0112367 A1 | 4/2014 | Roth |
| 2014/0114600 A1 | 4/2014 | Roth |
| 2014/0121481 A1 | 5/2014 | Abrams et al. |
| 2014/0155759 A1 | 6/2014 | Kaestle et al. |
| 2014/0189576 A1 | 7/2014 | Carmi |
| 2014/0221766 A1 | 8/2014 | Kinast |
| 2014/0221796 A1 | 8/2014 | Lia et al. |
| 2014/0232516 A1 | 8/2014 | Stivoric et al. |
| 2014/0235963 A1 | 8/2014 | Edwards et al. |
| 2014/0247058 A1 | 9/2014 | Mortara |
| 2014/0253709 A1 | 9/2014 | Bresch et al. |
| 2014/0321505 A1 | 10/2014 | Rill et al. |
| 2014/0330098 A1 | 11/2014 | Merritt et al. |
| 2014/0331298 A1 | 11/2014 | Baker et al. |
| 2015/0025344 A1 | 1/2015 | Benni |
| 2015/0036350 A1 | 2/2015 | Palikaras et al. |
| 2015/0045663 A1 | 2/2015 | Palikaras et al. |
| 2015/0073828 A1 | 3/2015 | Mortara et al. |
| 2015/0077268 A1 | 3/2015 | Lane et al. |
| 2015/0088538 A1 | 3/2015 | Dykes et al. |
| 2015/0110153 A1 | 4/2015 | Hoblit et al. |
| 2015/0126847 A1 | 5/2015 | Balji et al. |
| 2015/0157275 A1 | 6/2015 | Swamy et al. |
| 2015/0182114 A1 | 7/2015 | Wang et al. |
| 2015/0201872 A1 | 7/2015 | Benni |
| 2015/0257653 A1 | 9/2015 | Hyde et al. |
| 2015/0265159 A1 | 9/2015 | Lane et al. |
| 2015/0272452 A1 | 10/2015 | Mullin et al. |
| 2015/0308946 A1 | 10/2015 | Duffy et al. |
| 2015/0327811 A1 | 11/2015 | Mortara |
| 2015/0339805 A1 | 11/2015 | Ohba |
| 2016/0000335 A1 | 1/2016 | Khachaturian et al. |
| 2016/0007922 A1 | 1/2016 | Sen et al. |
| 2016/0035084 A1 | 2/2016 | Khachaturian et al. |
| 2016/0051171 A1 | 2/2016 | Pikov et al. |
| 2016/0117813 A1* | 4/2016 | Gross .................. H04W 76/10 600/474 |
| 2016/0136367 A1 | 5/2016 | Vamey |
| 2016/0150978 A1 | 6/2016 | Yuen et al. |
| 2016/0302666 A1 | 10/2016 | Shaya et al. |
| 2016/0361002 A1 | 12/2016 | Palikaras et al. |
| 2018/0125431 A1* | 5/2018 | Newberry .......... A61B 5/02416 |

FOREIGN PATENT DOCUMENTS

| | | |
|---|---|---|
| CN | 202619644 U | 4/2013 |
| CN | 203861234 U | 10/2014 |
| CN | 105662434 A | 4/2016 |
| CN | 105919601 A | 9/2016 |
| CN | 206342477 U | 7/2017 |
| CN | 206443702 U | 8/2017 |
| DE | 19827343 A1 | 12/1999 |
| EP | 0404562 A2 | 11/1991 |
| EP | 0537383 A1 | 4/1993 |
| EP | 0630203 B1 | 12/1994 |
| EP | 2045590 A1 | 4/2009 |
| EP | 2380493 A1 | 10/2011 |

(56) References Cited

FOREIGN PATENT DOCUMENTS

| | | | |
|---|---|---|---|
| EP | 2674735 A1 | 12/2013 |
| EP | 2836107 A1 | 2/2015 |
| GB | 2291498 A | 1/1996 |
| GB | 2500719 A1 | 10/2013 |
| GB | 1322906.7 A | 1/2015 |
| GB | 2521620 A | 1/2015 |
| GB | 2523741 A | 9/2015 |
| JP | 2002527136 A | 8/2002 |
| WO | 1992002792 A1 | 2/1992 |
| WO | 1998001730 A1 | 1/1998 |
| WO | 1999039166 A1 | 8/1999 |
| WO | 1999067611 A1 | 12/1999 |
| WO | 2000021437 A3 | 7/2001 |
| WO | 2005024710 A1 | 3/2005 |
| WO | 2005024712 A1 | 3/2005 |
| WO | 2005078636 A3 | 1/2006 |
| WO | 2008053474 A2 | 5/2008 |
| WO | 2011013132 A1 | 2/2011 |
| WO | 2011063266 A2 | 5/2011 |
| WO | 2012093311 A1 | 7/2012 |
| WO | 2013144559 A1 | 10/2013 |
| WO | 2013144652 A1 | 10/2013 |
| WO | 2014082071 A1 | 5/2014 |
| WO | 2015049268 A1 | 4/2015 |
| WO | 2015128657 A1 | 9/2015 |
| WO | 2015154105 A1 | 10/2015 |
| WO | 2016005050 A1 | 1/2016 |
| WO | 2016040540 A1 | 3/2016 |
| WO | 2016054079 A1 | 4/2016 |
| WO | 2016120870 A1 | 8/2016 |
| WO | 2017120615 A3 | 7/2017 |
| WO | 2017125397 A1 | 7/2017 |

OTHER PUBLICATIONS

Balakrishnan, Guha, Fredo Durand, and John Guttag. "Detecting pulse from head motions in video." Computer Vision and Pattern Recognition (CVPR), 2013 IEEE Conference on. IEEE, 2013.
Islam, S. M. R., et al., "Internet of Things for Health Care: A Comprehensive Survey", Jun. 1, 2015, Digital Object Identifier 10.1109/ACCESS.2015.2437951, IEEE Access vol. 3, 2015, retrieved from the Internet on Oct. 1, 2018.
Hassanalieragh Moon, et al., Health Monitoring and Management Using Internet-of-Things (IoT) Sensing with Cloud-based Processing: Opportunities and Challenges, 2015 IEEE International Conference on Services Computing, pp. 285-292, 978-1-4673-7281-7/15, DOI 10.1109/SCC.2015.47, retrieved from the Internet on Oct. 1, 2018.
Covidien, Filac 3000 EZ-EZA Electronic Thermometer Operating Manual, 2012, http://www.covidien.com/imageServer.aspx?contentID=31819&contenttype=application/pdf, retrieved from the Internet on Jul. 24, 2015.
Gravina et al., Multi-Sensor Fusion in Body Sensor Networks: State-of-the-art and research challenges, DOI: 10.1016/j.inffus.2016.09.005, Information Fusion, Sep. 13, 2016, retrieved from the Internet on Oct. 1, 2018 at https://www.researchgate.net/publication/308129451.
Klonoff, David C., Noninvasive Blood Glucose Monitoring, Diabetes Care, vol. 20, No. 3, Mar. 1997, pp. 433-437, DOI: 10.2337/diacare.20.3.433, Source: PubMed, retrieved from the Internet on Oct. 2, 2018.
Rossetti et el., Estimating Plasma Glucose from Interstitial Glucose: The Issue of Calibration Algorithms in Commercial Continuous Glucose Monitoring Devices, Sensors 2010, 10, 10936-10952; doi:10.3390/s101210936, ISSN 1424-8220, retrieved from www.mdpi.com/journal/sensors on Oct. 2, 2018.
Gautama, T. and Van Hulle, M., "A phase-based approach to the estimation of the optical flow field using spatial filtering", Neural Netlvorks, IEEE Transactions, 13(5): 1127-1136 (Sep. 2002).
Yole, "Non-Invasive Glucose Monitoring Patent Landscape", KnowMade, 2405 route des Dolines, 06902 Sophia Antipolis, France, Tel: +33 489 89 16 20, http://www.knowmade.com, retrieved from the Internet on Oct. 2, 2018, published Sep. 2015.
Berger, Andrew J., Multicomponent blood analysis by near-infrared Raman spectroscopy, Applied Optics, vol. 38, No. 13, May 1, 1999, pp. 2916-2926, retrieved from the Internet on Oct. 2, 2018.
Darwish et al., Wearable and Implantable Wireless Sensor Network Solutions for Healthcare Monitoring, Sensors 2011, 11, 5561-5595; doi:10.3390/s110605561, ISSN 1424-8220, retrieved from www.mdpi.com/journal/sensors on Oct. 2, 2018.
Oliver et al., Glucose sensors: a review of current and emerging technology, Diabetic Medicine, 26, pp. 197-210, 2009 Diabetes UK, retrieved from https://onlinelibrary.wiley.com/doi/epdf/10.1111/j.1464-5491.2008.02642.x on Oct. 2, 2018.
Jurik, Andrew D. et al., Remote Medical Monitoring, University of Virginia, retrieved from http://www.cs.virginia.edu/iurik/docs/jurik-rmm-2008.pdf on Oct. 1, 2018.
Tura, Andrew et al., A Low Frequency Electromagnetic Sensor for Indirect Measurement of Glucose Concentration: In Vitro Experiments in Different Conductive Solutions, Sensors 2010, 10, 5346-5358; doi:10.3390/s100605346, ISSN 1424-8220, retrieved from www.mdpi.com/journal/sensors on Oct. 2, 2018.
Rubinstein, M., et al., "Motion denoising with application to time-lapse photography," IEEE Computer Vision and Pattern Recognition, CVPR, pp. 313-320 (Jun. 2011).
Pfützner, Andreas et al., Evaluation of System Accuracy of the GlucoMen LX Plus Blood Glucose Monitoring System With Reference to ISO 15197:2013, Journal of Diabetes Science and Technology 2016, vol. 10(2) 618-619, Diabetes Technology Society, DOI: 10.1177/1932296815613803, retrieved from https://www.ncbi.nlm.nih.gov/pmc/articles/PMC4773971/pdf/10.1177_1932296815613803.pdf on Nov. 2, 2018.
Poveda, Carlos G. Juan, Fundamentals of Microwave Technology for Non-Invasive Blood Glucose Monitoring And Review of the Most Significant Works Developed, Revista Doctorado UMH vol. 1, n°1, 2015—Articulo p6, PhD Program on Industrian and Telecommunication Technologies (TECNIT) nBio Research Group at Systems Engineering Department, Miguel Hernández University, Elche, Spain, Apr. 2015, retrieved from https://www.researchgate.net/publication/298715332 on Nov. 2, 2018.
Timoner Samson J., and Dennis M. Freeman. "Multi-image gradient-based algorithms for motion estimation." Optical engineering 40.9 (2001): 2003-2016.
Saha et al., A Glucose Sensing System Based on Transmission Measurements at Millimetre Waves using Micro strip Patch Antennas, Scientific Reports, 7: 6855, D0I:10.1038/s41598-017-06926-1, Jul. 31, 2017, retrieved from https://www.ncbi.nlm.nih.gov/pmc/articles/PMC5537249/pdf/41598_2017_Article_6926.pdf on Nov. 2, 2018.
Verkruysse, Wim, Lars O. Svaasand, and J. Stuart Nelson. "Remote plethysmographic imaging using ambient light." Optics express 16.26 (2008): 21434-21445.
Todd, Catherine, et al., Towards Non-Invasive Extraction and Determination of Blood Glucose Levels, Bioengineering 2017, 4, 82, Sep. 27, 2017, retrieved from https://www.ncbi.nlm.nih.gov/pmc/articles/PMC5746749/pdf/bioengineering-04-00082.pdf on Nov. 2, 2018.
Pfützner, Andreas, Journal of Diabetes Science and Technology 2016, vol. 10(1) 101-103, Diabetes Technology Society, DOI: 10.1177/1932296815619183, retrieved from retrieved from www.mdpi.com/journal/sensors on Nov. 2, 2018.
Stankovic, John A., Wireless Sensor Networks, Department of Computer Science, University of Virginia Charlottesville, Virginia 22904, Jun. 19, 2006, retrieved from https://www.cs.virginia.edu/~stankovic/psfiles/wsn.pdf on Oct. 1, 2018.
Wang J., et al., "The cartoon animation filter," ACM Trans. Graph., 25: 1169-1173 (2006).
Lai, Xiaochen et al., A Survey of Body Sensor Networks, Sensors 2013, 13, 5406-5447; doi:10.3390/s130505406, ISSN 1424-8220, retrieved from www.mdpi.com/journal/sensors on Oct. 1, 2018.
Bruen et al., Glucose Sensing for Diabetes Monitoring: Recent Developments, Sensors DOI:10.3390/s17081866,Aug. 12, 2017,retrieved from https://pdfs.semanticscholar.org/9a8b/

(56) References Cited

OTHER PUBLICATIONS

8f1abdd11eae279204c81dbb5525fe473106.pdf?_ga=2.60896047. 2075682402.1541162314-1823527149.1541162314 on Nov. 2, 2018.
Facchinetti, Andrea, Continuous Glucose Monitoring Sensors: Past, Present and Future Algorithmic Challenges, Sensors 2016, 16(12), 2093; https://doi.org/10.3390/s16122093, Dec. 9, 2016, retrieved from https://pdfs.semanticscholar.org/6dc7/75fb79fc7ca85d795d8f520d79a03ea45311.pdf?_ga=2.91420569. 2075682402.1541162314-1823527149.1541162314 on Nov. 2, 2018.
Larin, Kirill V., et al., Noninvasive Blood Glucose Monitoring With Optical Coherence Tomography, Diabetes Care, vol. 25, No. 12, Dec. 2002, retrieved from the Internet on Oct. 2, 2018.
Chung et al., Simultaneous Measurements of Glucose, Glutamine, Ammonia, Lactate, and Glutamate in Aqueous Solutions by Near-Infrared Spectroscopy, DOI: 10.1366/0003702963906447, Applied Spectroscopy, Feb. 1996, retrieved from www.researchgate.com on Oct. 2, 2018.
R Fisher, S. Perkins, A. Waiker and E. Wolfart, Frequency Filter, Image Processing Learning Resources, 2003, retrieved from the Internet on Jun. 24, 2014 at http://homepages.inf.ed.ac.uk/rbf/HIPR2/freqfilt.htm.
Bandodkar et al., Tattoo-Based Noninvasive Glucose Monitoring: A Proof-of-Concept Study, dx.doi.org/10.1021/ac504300n, Anal. Chem. 2015, 87, 394-398, American Chemical Society, retrieved from the Internet on Oct. 2, 2018 at https://pubs.acs.org/doi/pdf/10.1021/ac504300n.
Grose, Julianne H. et al., The Role of PAS Kinase in PASsing the Glucose Signal, Sensors 2010, 10, 5668-5682; doi:10.3390/s100605668, ISSN 1424-8220, www.mdpi.com/journal/sensors, Jun. 4, 2010, retrieved from the Internet on Oct. 2, 2018.
Fernandez, Clara Rodriguez, Needle-Free Diabetes Monitoring: An Interview with the Founder of GlucoWise, Nov. 28, 2016, Labiotech IG, retrieved from the Internet on Oct. 1, 2018.
Routh, Fourier Transform, Glucose Sensing Neurons in the Ventromedial Hypothalamus, Sensors 2010, 10, 9002-9025; doi:10.3390/s101009002, ISSN 1424-8220, www.mdpi.com/journal/sensors, Aug. 10, 2010, retrieved from the Internet on Oct. 2, 2018 at https://www.researchgate.net/publication/47369031_Glucose_Sensing_Neurons_in_the_Ventromedial_Hypothalamus/download, p. 9009.
Choi, Heungjae et al., Design and In Vitro Interference Test of Microwave Noninvasive Blood Glucose Monitoring Sensor, IEEE Trans Microw Theory Tech. Oct. 1, 2015; 63(10 Pt 1): 3016-3025, doi: 10.1109/TMTT.2015.2472019, PMCID: PMC4641327, EMSID: EMS65843, PMID: 26568639, retrieved from the Internet on Oct. 2, 2018.
Yilmaz, Tuba et al., Detecting Vital Signs with Wearable Wireless Sensors, Sensors 2010, 10, 10837-10862; doi:10.3390/s101210837, ISSN 1424-8220, Dec. 2, 2010, retrieved from www.mdpi.com/journal/sensors on Oct. 2, 2018.
Vashist, Sandeep Kumar, Non-Invasive Glucose Monitoring Technology in Diabetes Management: A Review, Analytica Chimica Acta 750 (2012) 16-27, NUS Nanosience and Nanotechnology Initiative (NUSNNI) NanoCore, National University of Singapore, T-Lab Level 11, 5A Engineering Drive 1, Singapore 117580, Singapore, Elsevier B. V., Apr. 2, 2012, retrieved from the Internet on Oct. 2, 2016.
Hao-Yu Wu, Eulerian Video Magnification for Revealing Subtle Changes in the World, ACM Transactions on Graphics (TOG)—SIGGRAPH 2012 Conference Proceedings, vol. 31 Issue 4, Jul. 2012, Article No. 65, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://people.csail.mit.edu/billf/publications/Eulearian_Video_Magnification.pdf.
Eduardo S.L. Gastal, Adaptive Manifolds for Real-Time High-Dimensional Filtering, ACM Transactions on Graphics (TOG)—SIGGRAPH 2012 Conference Proceedings, vol. 31 Issue 4, Jul. 2012, Article No. 33, ACM New York, NY, USA, ISSN: 0730-0301 EISSN: 1557-7368, doi10.1145/2185520.2185529, retrieved from the Internet on on Jul. 9, 2013 from http://inf.ufrgs.br/~eslgastal/AdaptiveManifolds/Gastal_Oliveira_SIGGRAPH2012_Adaptive_Manifolds.pdf.
Sunghyun Cho, Video deblurring for hand-held cameras using patch-based synthesis, ACM Transactions on Graphics (TOG)—SIGGRAPH 2012 Conference Proceedings, vol. 31 Issue 4, Jul. 2012, Article No. 64, ACM New York, NY, USA, ISSN: 0730-0301 EISSN: 1557-7368 doi 10.1145/2185520.2185561, published on Jul. 1, 2012, retrieved from the Internet on Jul. 9, 2014 from http://juew.org/publication/video_deblur.pdf.
C. Liu, Motion magnification, ACM SIGGRAPH 2005, pp. 519-526, 2005, retrieved from http://people.csail.mit.edu/celiu/pdfs/motionmag.pdf on Jul. 9, 2014.
O. Arikan, Interactive Motion Generation from Examples, ACM Transactions on Graphics (TOG), Proceedings of ACM SIGGRAPH 2002, vol. 21 Issue 3, Jul. 2002, pp. 483-490, ACM New York, NY, USA, ISBN:1-58113-521-1, doi 10.1145/566654.566606, retrieved from the Internet on Jul. 9, 2014 from http://www.okanarikan.com/Papers/SynthesisFromExamples/paper.pdf.
John L. Smith, The Pursuit of Noninvasive Glucose: "Hunting the Deceitful Turkey", Fourth Edition, 2015, retrieved from the Internet on Oct. 1, 2018 from http://www.mendosa.com/The%20Pursuit%20of%20Noninvsive%20Glucose,%20Fourth%20Edition.pdf.
Yali Zheng, Unobtrusive Sensing and Wearable Devices for Health Informatics, IEEE Transactions on Biomedical Engineering, Mar. 2014, DOI: 10.1109/TBME.2014.2309951, retrieved from the Internet on Oct. 1, 2018 from https://www.researchgate.net/publication/260419901.
Yitzhak Mendelson, Pulse Oximetry: Theory and Applications for Noninvasive Monitoring, CLIN.CHEM. 38/9, 1601-1607, (1992), retrieved from the Internet on Oct. 2, 2018.
Stephen F. Mallin, Noninvasive Prediction of Glucose by Near-Infrared Diffuse Reflectance Spectroscopy, Clinical Chemistry 45:9, 1651-1658 (1999), Oak Ridge Conference, retrieved from the Internet on Oct. 2, 2018 from http://clinchem.aaccjnls.org/content/clinchem/45/9/1651.full.pdf.
Thennadil et al., Comparison of Glucose Concentration in Interstitial Fluid, and Capillary and Venous Blood During Rapid Changes in Blood Glucose Levels, Diabetes Technology & Therapeutics, vol. 3, No. 3, 2001, Mary Ann Liebert, Inc., retrieved from the Internet on Oct. 2, 2018 from http://thenemiirblog.ubiquilight.com/pdf/GlucoseInterstitialvCapillaryvVenous.pdf.
Khalil et al., Non-Invasive Glucose Measurement Technologies: An Update from 1999 to the Dawn of the New Millennium, Diabetes Technology & Therapeutics, vol. 6, No. 5, 2004, Mary Ann Liebert, Inc., retrieved from the Internet on Oct. 2, 2018 from http://bme240.eng.uci.edu/students/06s/eclin/articles/long.pdf.
Caduff et al., First human experiments with a novel non-invasive, non-optical continuous glucose monitoring system, Biosensors and Bioelectronics xxx (2003) 1-9, retrieved from the Internet on Oct. 2, 2018.

\* cited by examiner

MULTI-VITAL-SIGN FINGER CUFF ACCESSORY 1200

VALVE 1406

AIR LINE 1404

PUMP 1402 PRESSURE SENSOR

BATTERY 1408

MULTI-VITAL-SIGN FINGER CUFF ACCESSORY 1200

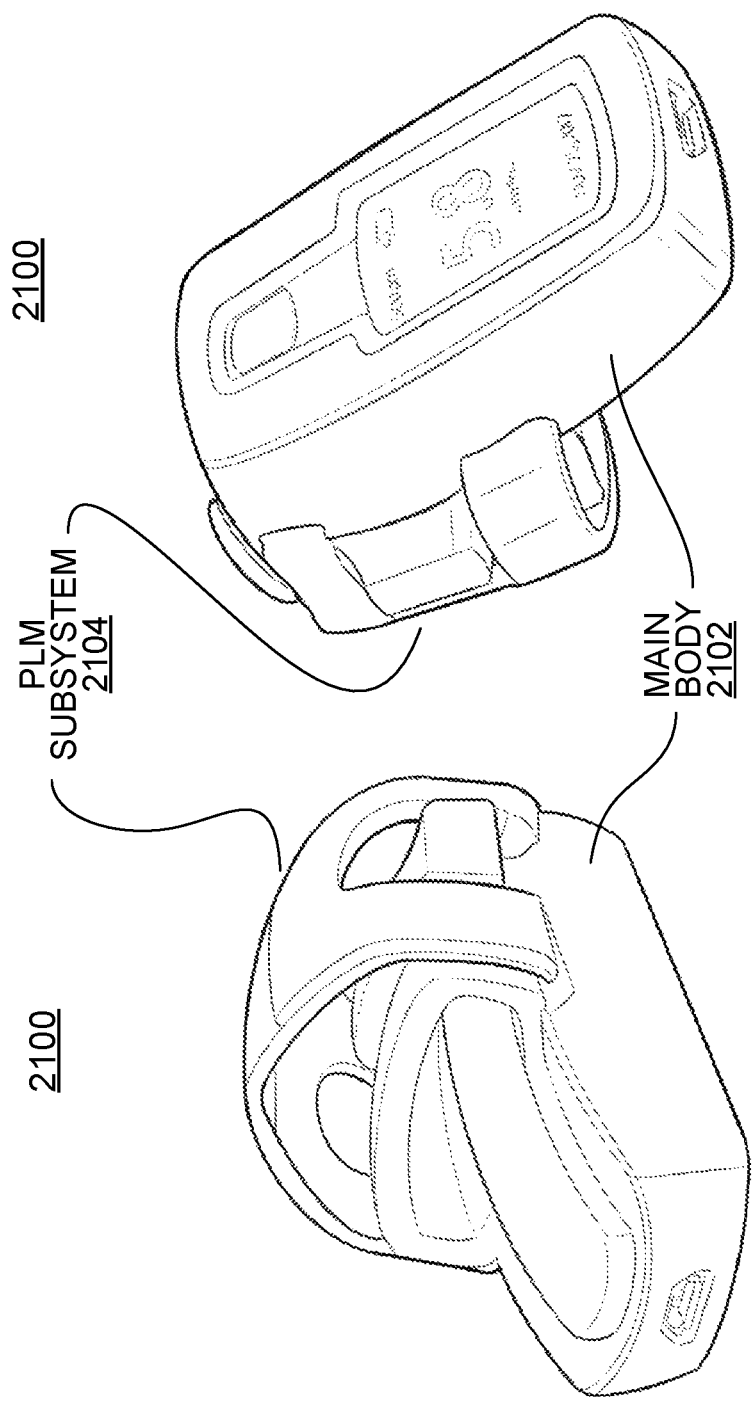

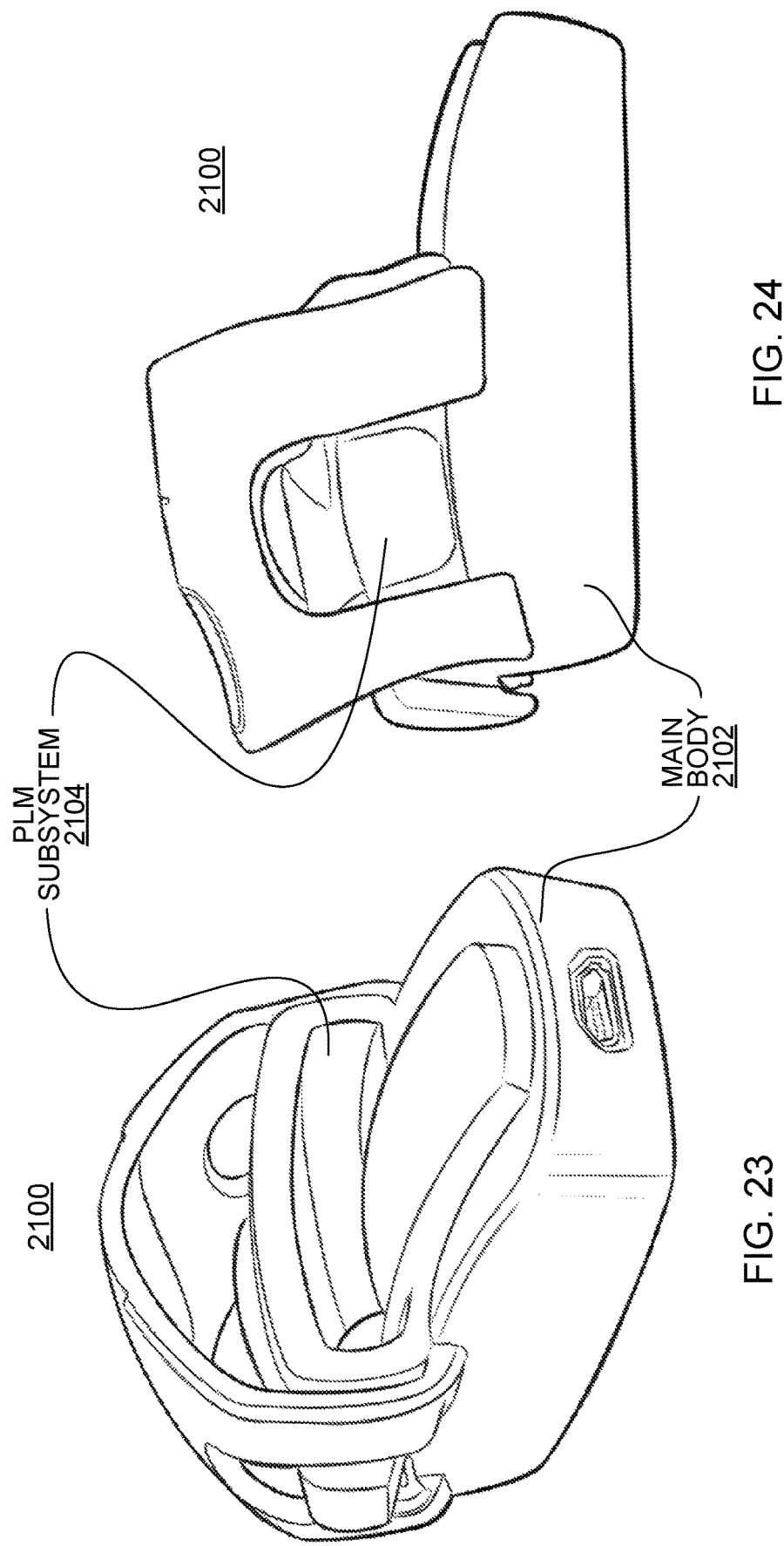

FIG. 39 — PRIOR ART

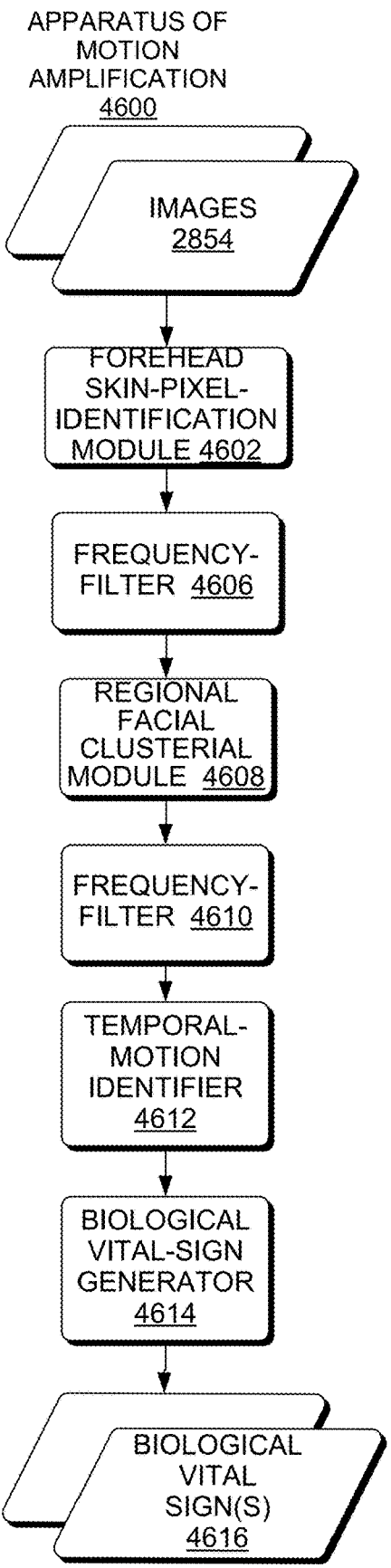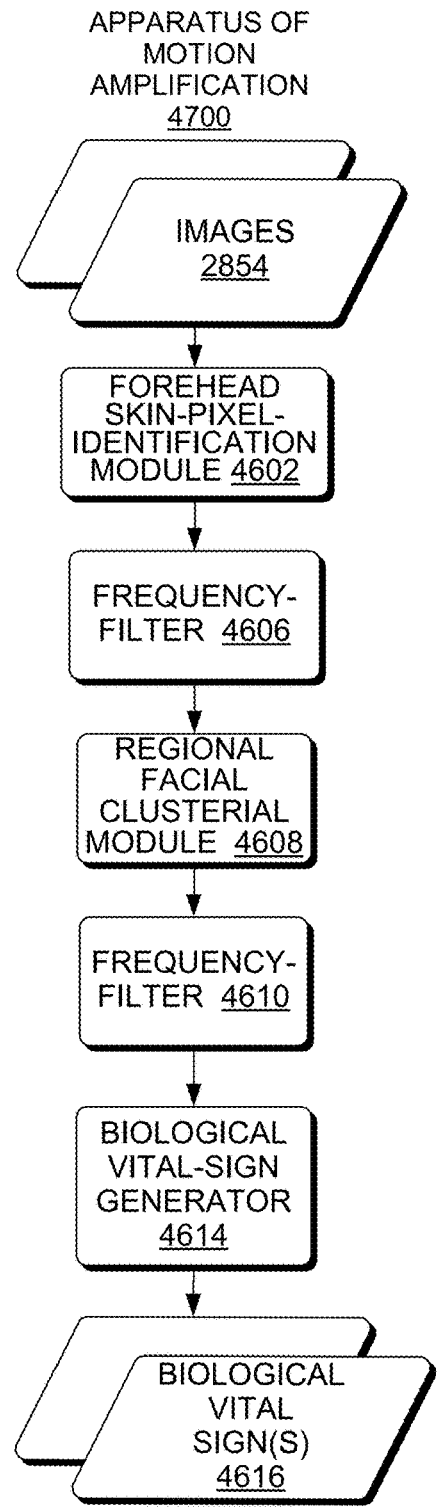
FIG. 46    PRIOR ART
FIG. 47

METHOD TO ESTIMATE A BODY CORE TEMPERATURE FROM AN EXTERNAL SOURCE POINT IN REFERENCE TO A BODY CORE TEMPERATURE CORRELATION TABLE 6200

PRIOR ART

METHOD TO ESTIMATE A BODY CORE TEMPERATURE FROM AN EXTERNAL SOURCE POINT AND OTHER MEASUREMENTS IN REFERENCE TO A BODY CORE TEMPERATURE CORRELATION TABLE 6300

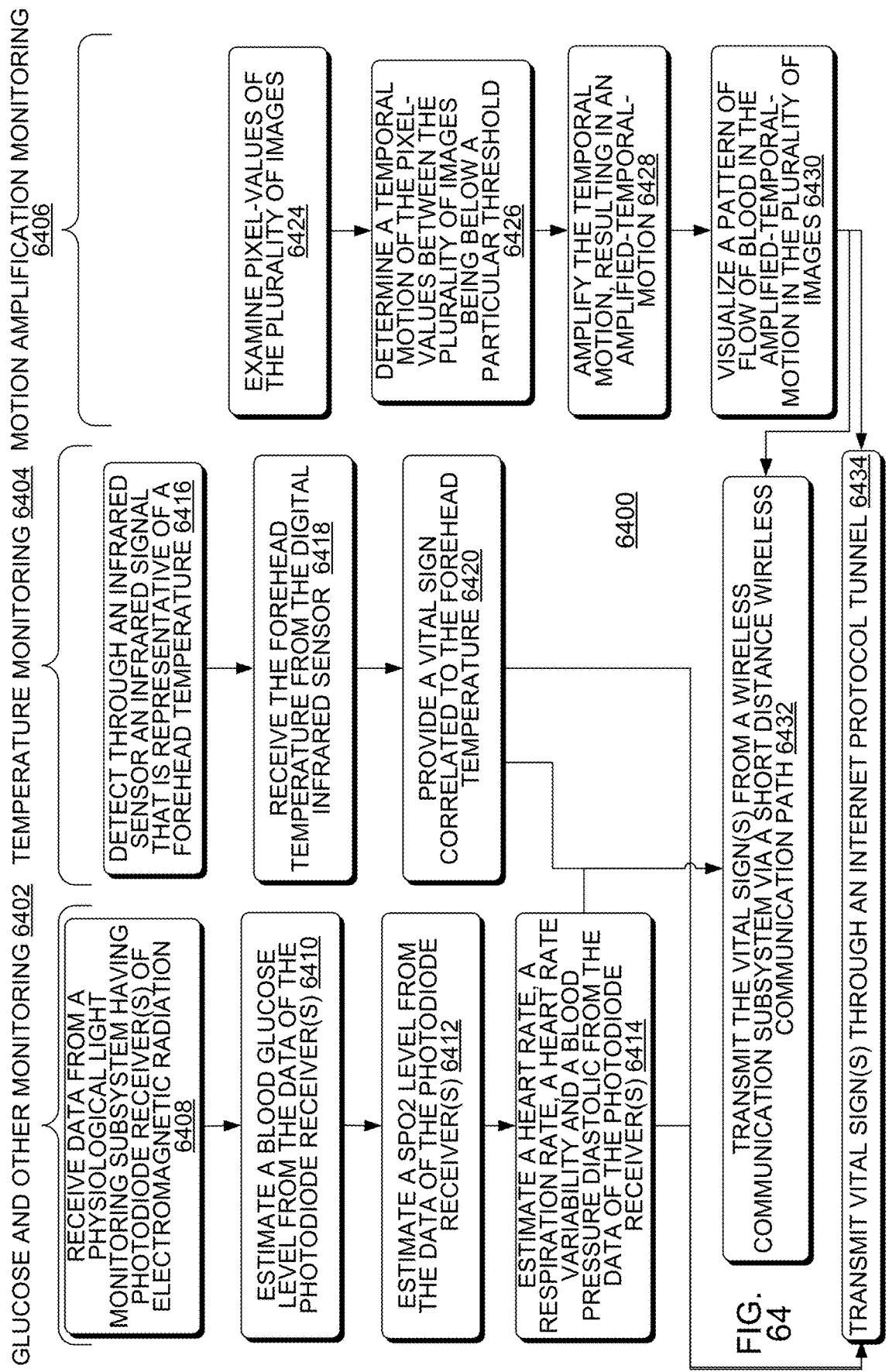

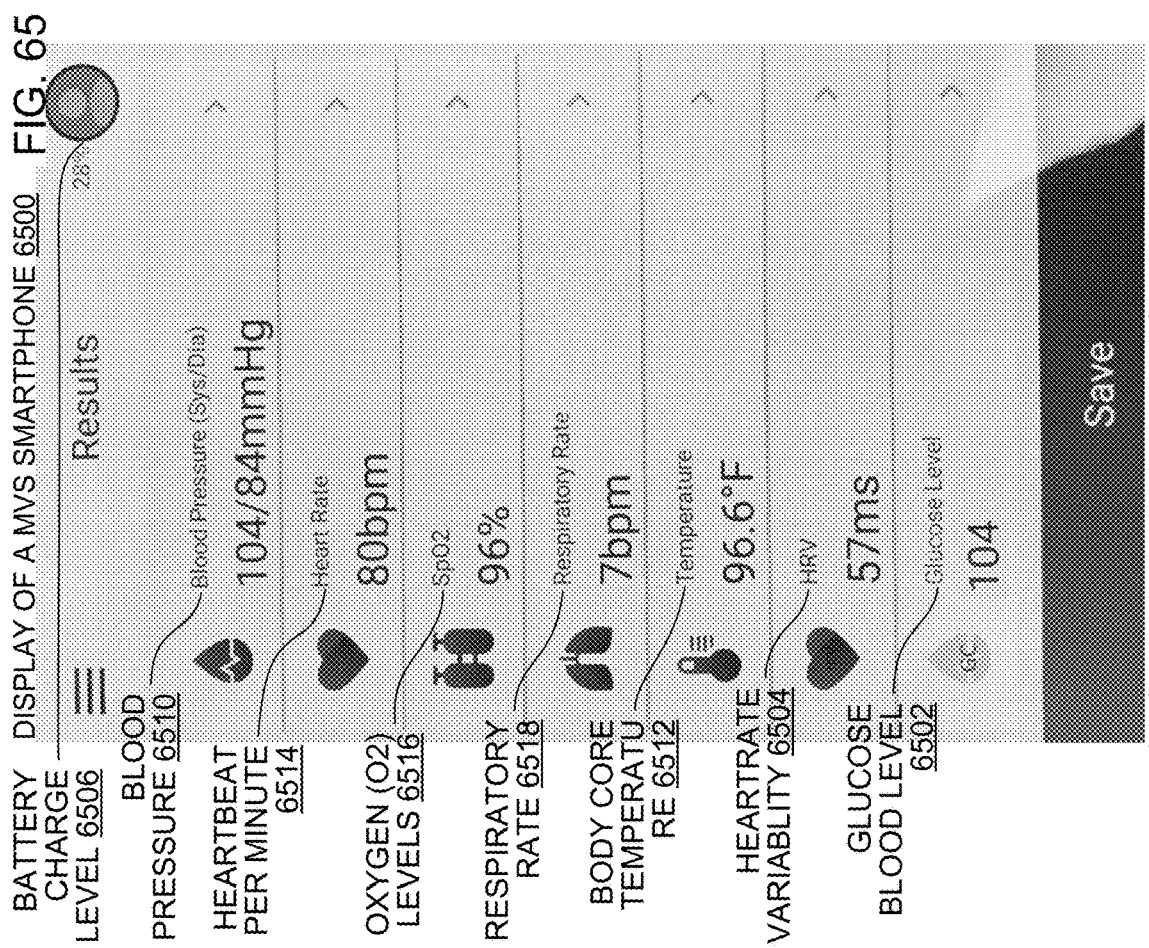

GLUCOSE MULTI-VITAL-SIGN SYSTEM IN AN ELECTRONIC MEDICAL RECORDS SYSTEM

FIELD

This disclosure relates generally to detecting multiple vital signs such as blood glucose levels and communicating the detected multiple vital signs to a medical records system.

BACKGROUND

Prior techniques of capturing multiple vital signs including blood glucose levels from human subjects have implemented problematic sensors and have been very cumbersome in terms of affixing the sensors to the patient, recording, analyzing, storing and forwarding the vital signs to appropriate parties.

BRIEF DESCRIPTION

In one aspect, a device measures blood glucose levels, temperature, heart rate, heart rate variability, respiration, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and/or EEG of a human.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 21-27 are views of a MVS finger clip that reads physiological light signals and other vital signs, but not blood pressure, according to implementations;

FIG. 46 is a block diagram of an apparatus of motion amplification, according to an implementation;

FIG. 47 is a block diagram of an apparatus of motion amplification, according to an implementation;

FIG. 64 is a block diagram of a method of MVS detection and communication method, according to an implementation;

FIG. 65 is a display screen of the MVS smartphone showing results of successful MVS measurements, according to an implementation; and FIG. 66 is a display screen of the MVS smartphone showing history of successful MVS measurements, according to an implementation.

DETAILED DESCRIPTION

Figure 1:
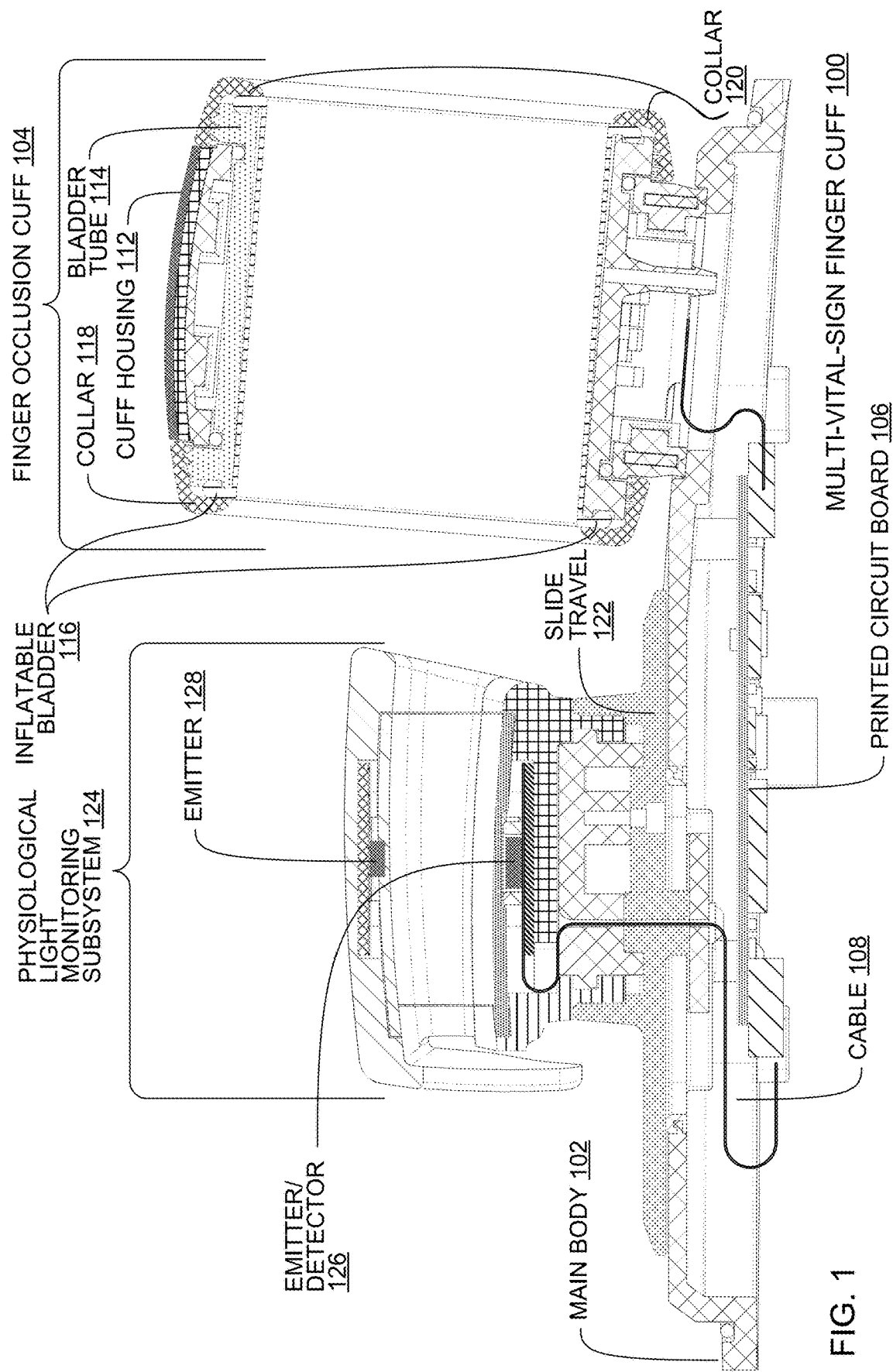
FIG. 1 is a cross-section diagram of a multi-vital-sign (MVS) finger cuff that determines transmissive SpO2, reflective SpO2, reflective glucose and other vital signs such as blood pressure, according to an implementation.

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into twelve sections. In the first section, an overview is described. In the second section, apparatus of multi-vital-sign (MVS) finger cuffs are described in FIG. 1-11. In the third section, implementations of apparatus of MVS finger cuff accessories are described in FIG. 12-20. In the fourth section, implementations of apparatus of MVS finger clips are described in FIG. 21-27. In the fifth section, implementations of MVS smartphones are described in FIG. 28-29. In the sixth section, implementations of MVS smartphone systems are described in FIG. 30-34. In the seventh section, implementations of MVS devices are described in FIG. 35-37. In the eighth section, implementations of vital-sign components are described in FIG. 38-54. In the ninth section, implementations of interoperability device manager components of an EMR System are described in FIG. 55-57. In the tenth section, methods of MVS detection and communication are described in FIG. 58-64. In the eleventh section, implementations of displays of MVS smartphones are described in FIG. 65-66. Finally, in the twelfth section a conclusion of the detailed description is provided.

1. Overview

Table 1 below shows seven implementations of physiological light monitoring of glucose and/or SpO2 with blood pressure and other vital-signs. In Table 1, transmissive electromagnetic radiation (ER) is read by emitting an amount of ER at a specific wavelength and then detecting an amount of the ER at the specific wavelength (or within a range such as the specific wavelength±20 nm) that passes through the subject. 'nm' is nanometers. Reflective ER is read by emitting an amount of ER at a specific wavelength and then detecting an amount of the ER at that specific wavelength (or within a range of wavelengths) that is reflected by the subject. Measurements of ER at 395 nm are performed to determine the amount of nitric oxide (NO) in the subject as a proxy for the amount of glucose in the subject. Measurements of ER at 395 nm are performed to determine the amount of oxygen in the subject. Measurements of ER at 940 nm are performed as a baseline reference that is not affected by oxygen or nitric oxide.

In Table 1 below, in implementation #1, transmissive SpO2 is determined by reading transmissive ER (electromagnetic radiation) at 660 nm and transmissive ER at 940 nm and then dividing the amount of transmissive ER at 660 nm by the amount of transmissive ER at 940 nm, reflective SpO2 is determined by reading reflective ER at 660 nm and reflective ER at 940 nm and then dividing the amount of reflective ER at 660 nm and by the amount of reflective ER at 940 nm and the reflective glucose is determined by reading reflective ER at 395 nm and reflective ER at 940 nm, and then dividing the amount of reflective ER at 395 nm by the amount of reflective ER at 940 nm.

In implementation #2, transmissive SpO2 is determined by reading transmissive ER at 660 nm and transmissive ER at 940 nm and then dividing the amount of transmissive ER at 660 nm by the amount of transmissive ER at 940 nm.

In implementation #3, reflective SpO2 is determined by reading reflective ER at 660 nm and reflective ER at 940 nm and then dividing the amount of reflective ER at 660 nm and by the amount of reflective ER at 940 nm. In implementation #4, reflective glucose is determined by reading reflective ER at 395 nm and reflective ER at 940 nm, and then dividing the amount of reflective ER at 395 nm by the amount of reflective ER at 940 nm.

In implementation #5, reflective SpO2 is determined by reading reflective ER at 660 nm and reflective ER at 940 nm and then dividing the amount of reflective ER at 660 nm and by the amount of reflective ER at 940 nm and reflective glucose is determined by reading reflective ER at 395 nm and reflective ER at 940 nm, and then dividing the amount of reflective ER at 395 nm by the amount of reflective ER at 940 nm. In implementation #6, transmissive SpO2 is determined by reading transmissive ER at 660 nm and transmissive ER at 940 nm and then dividing the amount of transmissive ER at 660 nm by the amount of transmissive ER at 940 nm and reflective glucose is determined by reading reflective ER at 395 nm and reflective ER at 940 nm, and then dividing the amount of reflective ER at 395 nm by the amount of reflective ER at 940 nm.

In implementation #7, reflective SpO2 is determined by reading reflective ER at 660 nm and reflective ER at 940 nm and then dividing the amount of reflective ER at 660 nm and by the amount of reflective ER at 940 nm and transmissive SpO2 is determined by reading transmissive ER at 660 nm and transmissive ER at 940 nm and then dividing the amount of transmissive ER at 660 nm by the amount of transmissive ER at 940 nm.

In implementations that use transmissive configurations for at least some of the measurements rather than reflective transmissions (such as transmissive SPO2 in implementations 1, 2, 6 and 7), transmissive configurations are used because transmissive is more accurate than reflective. Transmissive techniques have higher accuracy because more of the signal is transmitted through the finger than reflected, so transmissive techniques have a stronger detected signal, and assuming the same emitted signal strength from a signal that is reflected and a signal that is transmitted and assuming that background ER noise is the same for both transmissive configurations and reflective configurations, the result is a higher signal-to-noise ratio for transmissive techniques.

TABLE 1

| IMPLEMENTATON | DETERMINATION(S) | READING(S) | DETECT(S) |
|---|---|---|---|
| 1 | transmissive SpO2 | a) reflective 395 nm | transmissive 660 nm/ transmissive 940 nm |
|  | reflective SpO2 | b) transmissive 660 nm | reflective 660 nm/reflective 940 nm |
|  | reflective glucose | c) reflective 660 nm | reflective 395 nm/reflective 940 nm |
|  |  | d) transmissive 940 nm |  |
|  |  | e) reflective 940 nm |  |
| 2 | transmissive SpO2 | a) transmissive 660 nm | transmissive 660 nm/ transmissive 940 nm |
|  |  | b) transmissive 940 nm |  |
| 3 | reflective SpO2 | a) reflective 660 nm | reflective 660 nm/reflective 940 nm |
|  |  | b) reflective 940 nm |  |
| 4 | reflective glucose | a) reflective 395 nm | reflective 395 nm/reflective 940 nm |
|  |  | b) reflective 940 nm |  |
| 5 | reflective SpO2 | a) reflective 395 nm | reflective 660 nm/reflective 940 nm |
|  | reflective glucose | b) reflective 660 nm | reflective 395 nm/reflective 940 nm |
|  |  | c) reflective 940 nm |  |
| 6 | transmissive SpO2 | a) reflective 395 nm | transmissive 660 nm/ transmissive 940 nm |
|  | reflective glucose | b) transmissive 660 nm | reflective 395 nm/reflective 940 nm |
|  |  | c) transmissive 940 nm |  |
|  |  | d) reflective 940 nm |  |
| 7 | transmissive SpO2 | a) transmissive 660 nm | transmissive 660/ transmissive 940 nm |
|  | reflective SpO2 | b) reflective 660 nm | reflective 660/reflective 940 nm |
|  |  | c) transmissive 940 nm |  |
|  |  | d) reflective 940 nm |  |

Furthermore, the devices in FIGS. 1-37 can determine within reasonable clinical accuracy the following vital signs: blood glucose levels, heart rate, heart rate variability, respiration rate, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and EEG. More specifically, heart rate, heart rate variability, respiration rate, SpO2, blood flow, blood pressure, total hemoglobin (SpHb), PVi, methemoglobin (SpMet), acoustic respiration rate (RRa), carboxyhemoglobin (SpCO), oxygen reserve index (ORi), oxygen content (SpOC) and EEG can be determined by reading ER at 660 nm and ER at 940 nm by the PLM subsystem and then dividing the amount of ER at 660 nm by the amount of ER at 940 nm and then applying a transformation function that is specific to the vital sign to the quotient of the division.

$$R_Y = \frac{\log\left(\frac{I_{AC}+I_{DC}}{I_{DC}}\right)_{Y[nm]}}{\log\left(\frac{I_{AC}+I_{DC}}{I_{DC}}\right)_{940[nm]}}$$

where Y={660 [nm], 395 [nm]}

The relationship between $R_Y$ and the parameters, P, below is a general transfer function $T(R_Y)$, where $$Z_N = \begin{Bmatrix} SpO2 \\ \text{total hemoglobin } (SpHb) \\ PVi \\ \text{methemoglobin } (SpMet) \\ \text{acoustic respiration rate } (RRa) \\ \text{carboxyhemoglobin } (SpCO) \\ \text{oxygen reserve index } (ORi) \\ \text{oxygen content } (SpOC) \end{Bmatrix}$$

$Z_N = T_N(R_{660}, R_{395})$

The respiration rate and heart rate variability and the blood pressure diastolic is estimated from data from the mDLS sensor and the PLM subsystem. The respiration and the blood pressure systolic is estimated from data from the mDLS sensor. The blood flow is estimated from data from the PLM subsystem.

2. Apparatus of Multi-Vital-SignFinger Cuffs

FIGS. 1-11 are diagrams of multi-vital-sign (MVS) finger cuffs that read physiological light signals to determine vital signs such as blood glucose level, according to implementations. The MVS finger cuffs in FIGS. 1-11 include a main body that is mechanically and electrically coupled to a Physiological Light Monitoring (PLM) subsystem. The PLM subsystem is mechanically and electrically coupled to a finger occlusion cuff 104. In some implementations, the PLM subsystem includes one or more emitters of electromagnetic radiation (ER) and one or more detectors of ER which are discussed in greater detail below.

The main body 102 includes a printed circuit board that is mechanically and electrically coupled to a cable 108 that is mechanically and electrically coupled to a detector of ER in a range of 350 to 1100 nanometers (nm). ER in a range of 350 to 1100 nm includes both visible and near-infrared light. The printed circuit board includes a microprocessor.

The finger occlusion cuff 104 includes a cuff housing 112 that surrounds a bladder tube 114 that mounts an inflatable bladder 116. Two identical collars 118 and 120 at open ends of the cuff housing 112 position the bladder tube 114 and the inflatable bladder 116. The MVS finger cuff 100 also includes a slide travel 122 that slideably mounts the PLM subsystem to the main body.

In FIGS. 1-37, only transmissive/transmissive or reflective/reflective measurements are performed. In FIGS. 1-27, reflective/transmissive measurements or transmissive/reflective measurements are never performed because there is no usefulness to these measurements. In implementations 1 and 4-6 in table 1 above and in FIGS. 1 and 4-6, nitric oxide measurements that are performed as a proxy for glucose are always reflective measurements and never transmissive measurements because the 395 nm ER emission that is performed to measure nitric oxide as a proxy for glucose is visible light which will not be transmitted all the way through a human finger.

FIG. 1 is a cross-section diagram of a multi-vital-sign (MVS) finger cuff 100 that determines transmissive SpO2, reflective SpO2, reflective glucose and other vital signs such as blood pressure, according to an implementation. MVS finger cuff 100 operates in accordance with Table 1 above, in implementation #1. MVS finger cuff 100 is particularly useful for clinical applications.

In MVS finger cuff 100, the PLM subsystem is PLM subsystem 124 that includes an emitter in an emitter/detector 126 that emits ER at 395 nm, 660 nm and 940 nm and that includes a detector in the emitter/detector 126 that detects the ER in the ranges of 375-415 nm, 640-680 nm and 920-960 nm to measure ER that is reflected by the subject finger that is positioned in the PLM subsystem 124 at 395 nm, 660 nm and 940 nm. The PLM subsystem 124 also includes an emitter 128 that emits ER in the ranges of 640-680 nm and 920-960 nm to transmit the ER through the subject finger that is positioned in the PLM subsystem 124 at 660 nm and 940 nm and the detector in the emitter/detector 126 detects the ER that is emitted by the emitter 128 at 660 nm and 940 nm and that is transmitted through the subject finger that is positioned in the PLM subsystem 124.

A microprocessor of a printed circuit board 106 or a microprocessor that is mounted on a printed circuit board in FIG. 18-37 determines transmissive SpO2 at 660 nm by dividing the amount of transmissive ER at 660 nm by the amount of transmissive ER at 940 nm, reflective SpO2 is determined by dividing the amount of reflective ER at 660 nm and by the amount of reflective ER at 940 nm and the reflective glucose is determined by dividing the amount of reflective ER at 395 nm by the amount of reflective ER at 940 nm. MVS finger cuff 100 includes non-volatile memory such as flash memory on the printed circuit board 106 or non-volatile memory in the microprocessor of the printed circuit board 106.

In MVS finger cuff 100, the emitter/detector 126 includes both an emitter and a detector so that an amount of the electromagnetic energy that is reflected by the subject is detected, such as the finger of the patient. The amount or level of glucose in the blood of a subject is determined by a ratio of the amount of ER in the 375-415 nm range that detected by the detector in the emitter/detector 126 is divided by the amount of ER in the 920-960 nm range that detected by the emitter/detector 126, which is then converted to units of mg/dL or mmol/L in reference to a non-linear serpentine function. Only the amount of radiation detected by the emitter/detector 126 in the 375-415 nm range during the resting period of the heartbeat (in between heartbeats) is included in the determination of the amount or level of glucose in the blood of the subject. The resting period of the heartbeat is determined by a ratio of the amount of ER detected in the 640-680 nm range by the emitter/detector 126 divided by the amount of radiation detected in the 920-960 nm range by the emitter/detector 126.

Figure 2:
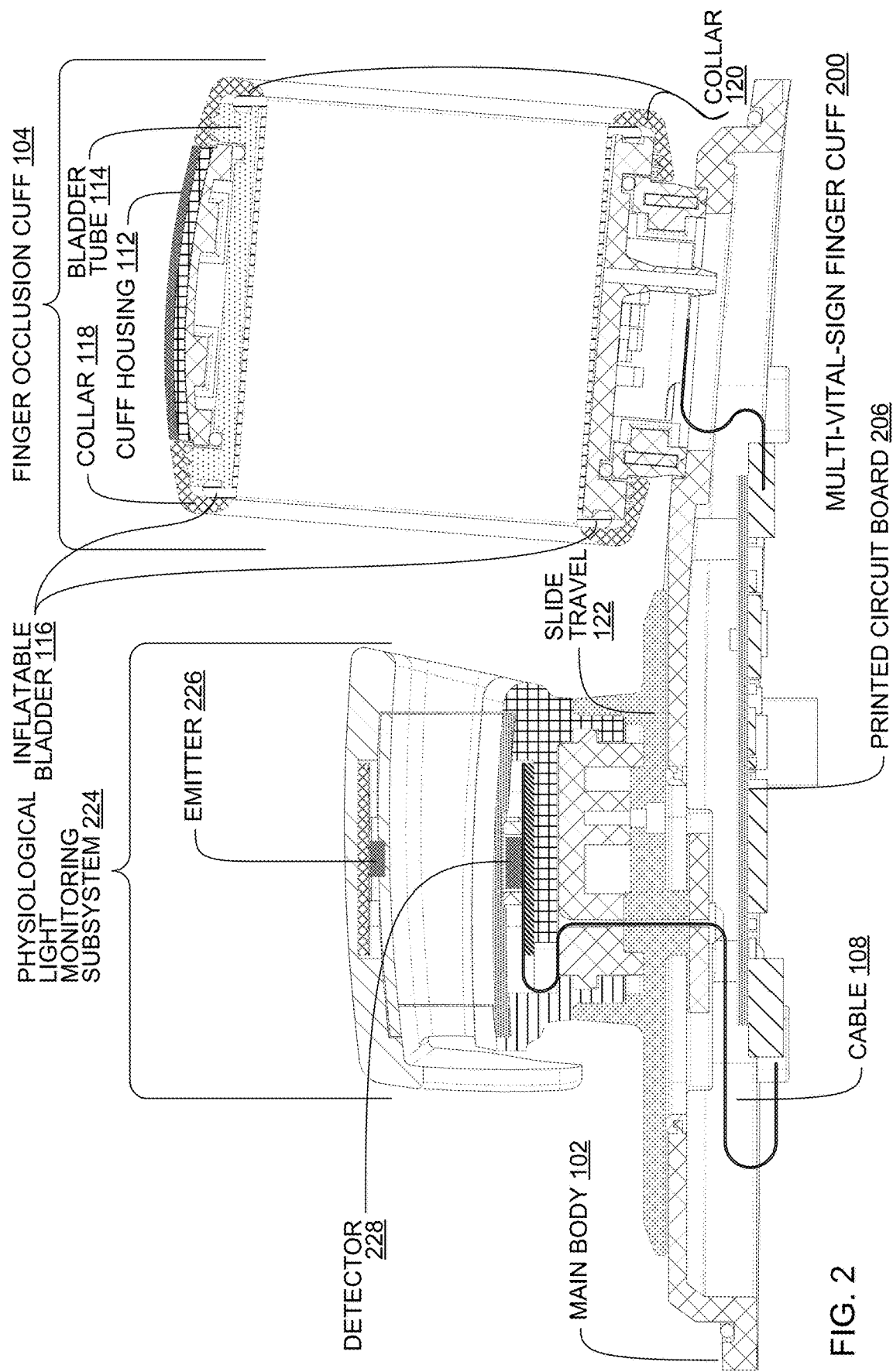
FIG. 2 is a cross-section diagram of a MVS finger cuff that determines transmissive SpO2 and other vital signs such as blood pressure, according to an implementation.

FIG. 2 is a cross-section diagram of a multi-vital-sign (MVS) finger cuff 200 that determines transmissive SpO2 and other vital signs such as blood pressure, according to an implementation. MVS finger cuff 200 operates in accordance with Table 1 above, in implementation #2.

In MVS finger cuff 200, the PLM subsystem is PLM subsystem 224 that includes an emitter 226 of 660 nm ER and 940 nm ER. The PLM subsystem 224 also includes an detector 228 that detects ER in the ranges of 640-680 nm and 920-960 nm that is transmitted from the emitter 226 through the subject finger that is positioned in the PLM subsystem 224 at 660 nm and 940 nm.

The microprocessor of the printed circuit board 206 or a microprocessor that is mounted on a printed circuit board in FIGS. 2 and 8-37 determines transmissive SpO2 at 660 nm by dividing the amount of transmissive ER at 660 nm by the amount of transmissive ER at 940 nm.

Figure 3:
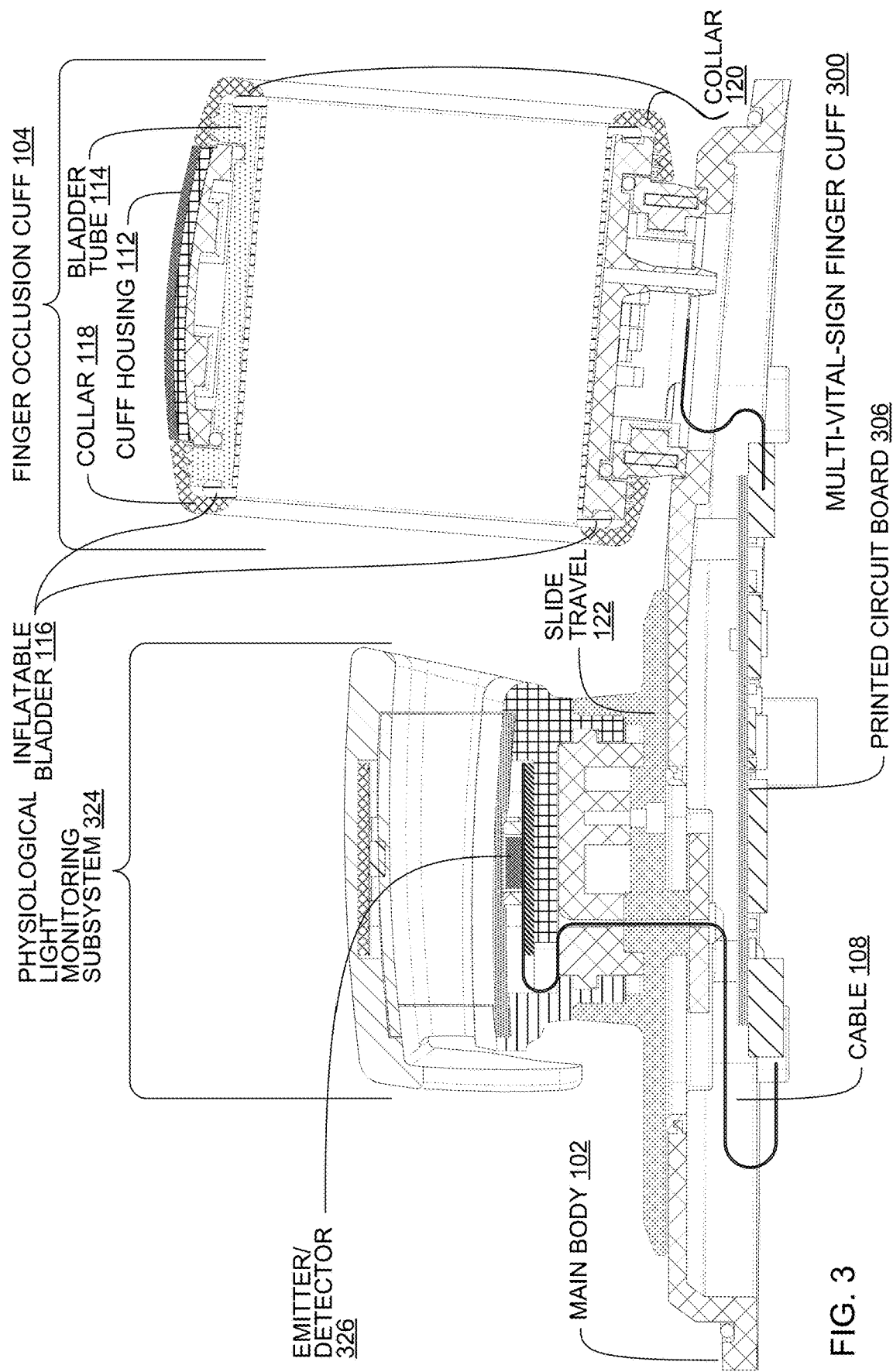
FIG. 3 is a cross-section diagram of a MVS finger cuff that determines reflective SpO2 and other vital signs such as blood pressure, according to an implementation.

FIG. 3 is a cross-section diagram of a multi-vital-sign (MVS) finger cuff 300 that determines reflective SpO2 and other vital signs such as blood pressure, according to an implementation. MVS finger cuff 300 operates in accordance with Table 1 above, in implementation #3.

In MVS finger cuff 300, the PLM subsystem is PLM subsystem 324 that includes an emitter in an emitter/detector 326 that emits ER at 660 nm and 940 nm. The emitter/detector 326 also includes a detector that detects ER in the ranges of 640-680 nm and 920-960 nm to measure ER that is reflected by the subject finger that is positioned in the PLM subsystem 324 at 660 nm and 940 nm. The PLM subsystem 324 does not include a detector on the opposite side of the PLM subsystem from the emitter/detector 326 to detect ER that is transmitted through the subject finger that is positioned in the PLM subsystem.

The microprocessor of the printed circuit board 306 or a microprocessor that is mounted on a printed circuit board in FIGS. 3 and 8-37 determines reflective SpO2 by dividing the amount of reflective ER at 660 nm and by the amount of reflective ER at 940 nm.

Figure 4:
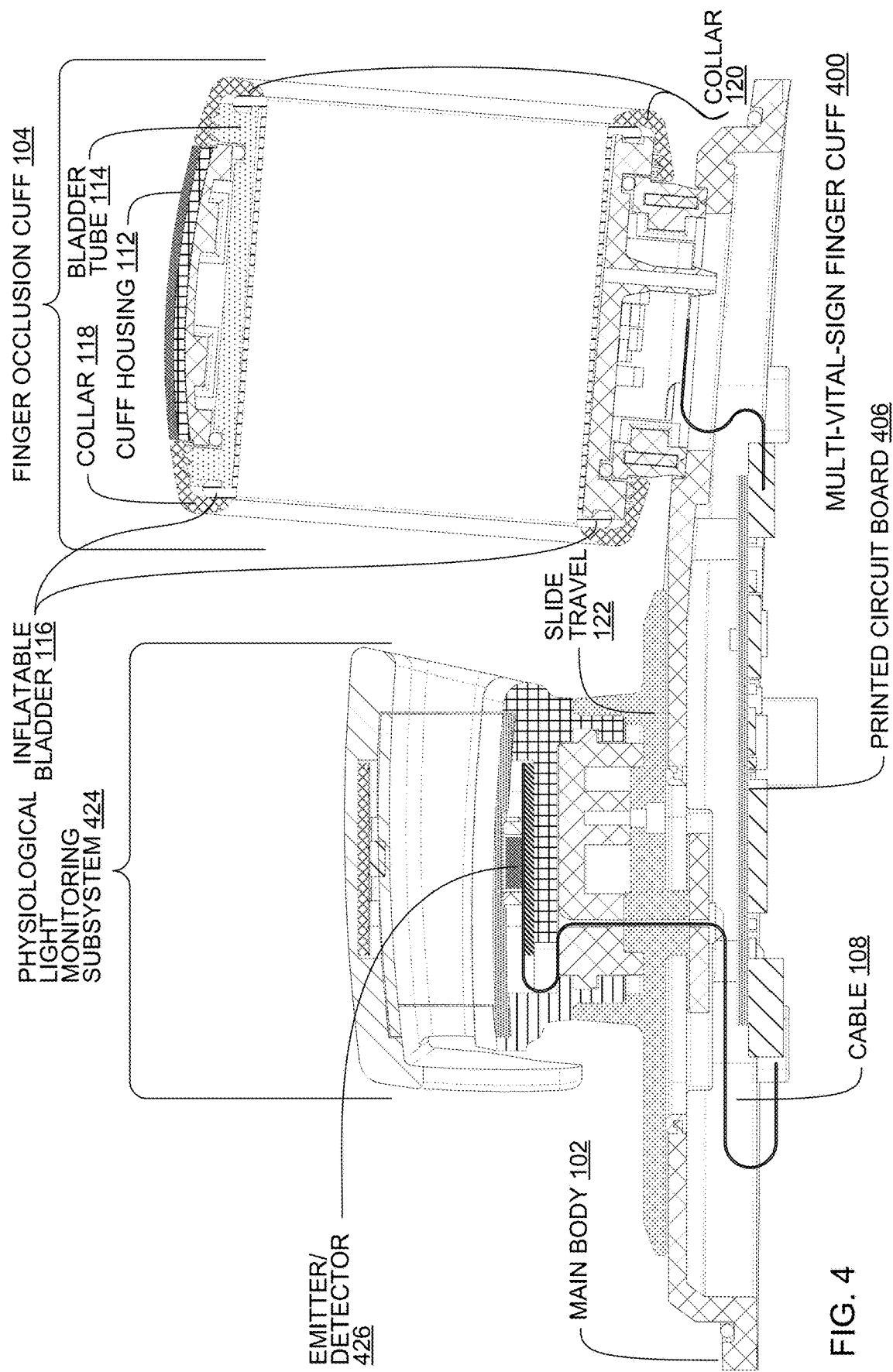
FIG. 4 is a cross-section diagram of a MVS finger cuff that determines reflective glucose and other vital signs such as blood pressure, according to an implementation.

FIG. 4 is a cross-section diagram of a multi-vital-sign (MVS) finger cuff 400 that determines reflective glucose and other vital signs such as blood pressure, according to an implementation. MVS finger cuff 400 operates in accordance with Table 1 above, in implementation #4.

In MVS finger cuff 400, the PLM subsystem is PLM subsystem 424 that includes an emitter in an emitter/detector 426 that emits ER at 395 nm and 940 nm and the emitter/detector 426 also includes a detector that detects ER in the ranges of 375-415 nm and 920-960 nm to measure ER that is reflected by the subject finger that is positioned in the PLM subsystem 424 at 395 nm and 940 nm. The PLM subsystem 424 does not include a detector on the opposite side of the PLM subsystem from the emitter/detector 426 to detect ER that is transmitted through the subject finger that is positioned in the PLM subsystem.

The microprocessor of the printed circuit board 406 or a microprocessor that is mounted on a printed circuit board in FIGS. 4 and 8-37 determines reflective glucose by dividing the amount of reflective ER at 395 nm by the amount of reflective ER at 940 nm.

Figure 5:
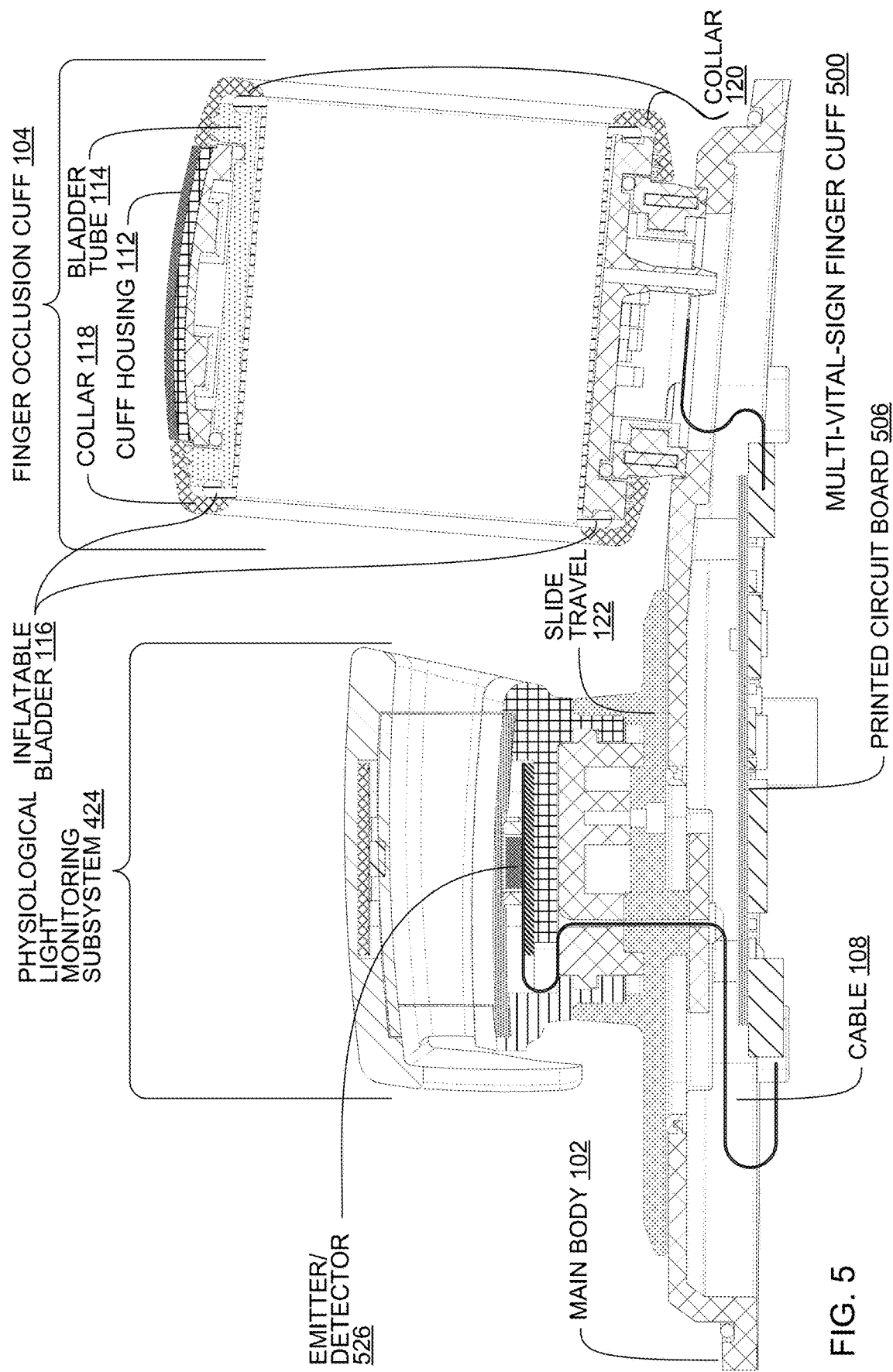
FIG. 5 is a cross-section diagram of a MVS finger cuff that determines transmissive SpO2, reflective SpO2, reflective glucose and other vital signs such as blood pressure, according to an implementation.

FIG. 5 is a cross-section diagrams of a multi-vital-sign (MVS) finger cuff 500 that determines transmissive SpO2, reflective SpO2, reflective glucose and other vital signs such as blood pressure, according to an implementation. MVS finger cuff 500 operates in accordance with Table 1 above, in implementation #5. MVS finger cuff 100 is particularly useful for non-clinical wellness applications.

In MVS finger cuff 500, the PLM subsystem is PLM subsystem 524 that includes an emitter in an emitter/detector 526 that emits ER at 395 nm, 660 nm and 940 nm and the emitter/detector 526 includes a detector that detects ER in the ranges of 375-415 nm, 640-680 nm and 920-960 nm to measure ER that is reflected by the subject finger that is positioned in the PLM subsystem 524 at 395 nm, 660 nm and 940 nm. The detector in the emitter/detector 526 is mounted on the same side of the PLM subsystem 524 as the emitter in the emitter/detector 526 so that the detector in the emitter/detector 526 detects an amount of the electromagnetic energy that is reflected by the subject, such as the finger of the patient.

The microprocessor of the printed circuit board or a microprocessor that is mounted on a printed circuit board in FIGS. 5 and 8-37 determines reflective SpO2 by dividing the amount of reflective ER at 660 nm and by the amount of reflective ER at 940 nm and the reflective glucose is determined by dividing the amount of reflective ER at 395 nm by the amount of reflective ER at 940 nm.

The amount or level of glucose in the blood of a subject is determined by a ratio of the amount of radiation detected by the emitter/detector 526 in the 375-415 nm range divided by the amount of radiation detected by the emitter/detector 526 in the 920-960 nm range, which is then converted to units of mg/dL or mmol/L in reference to a non-linear serpentine function, regardless of the amount of radiation detected by the emitter/detector 526 in the 375-415 nm range during the resting period of the heartbeat (in between heartbeats). All of radiation detected by the emitter/detector 526 in the 375-415 nm range during the resting period of the heartbeat is used in the determination of the amount or level of glucose in the blood of the subject.

Figure 6:
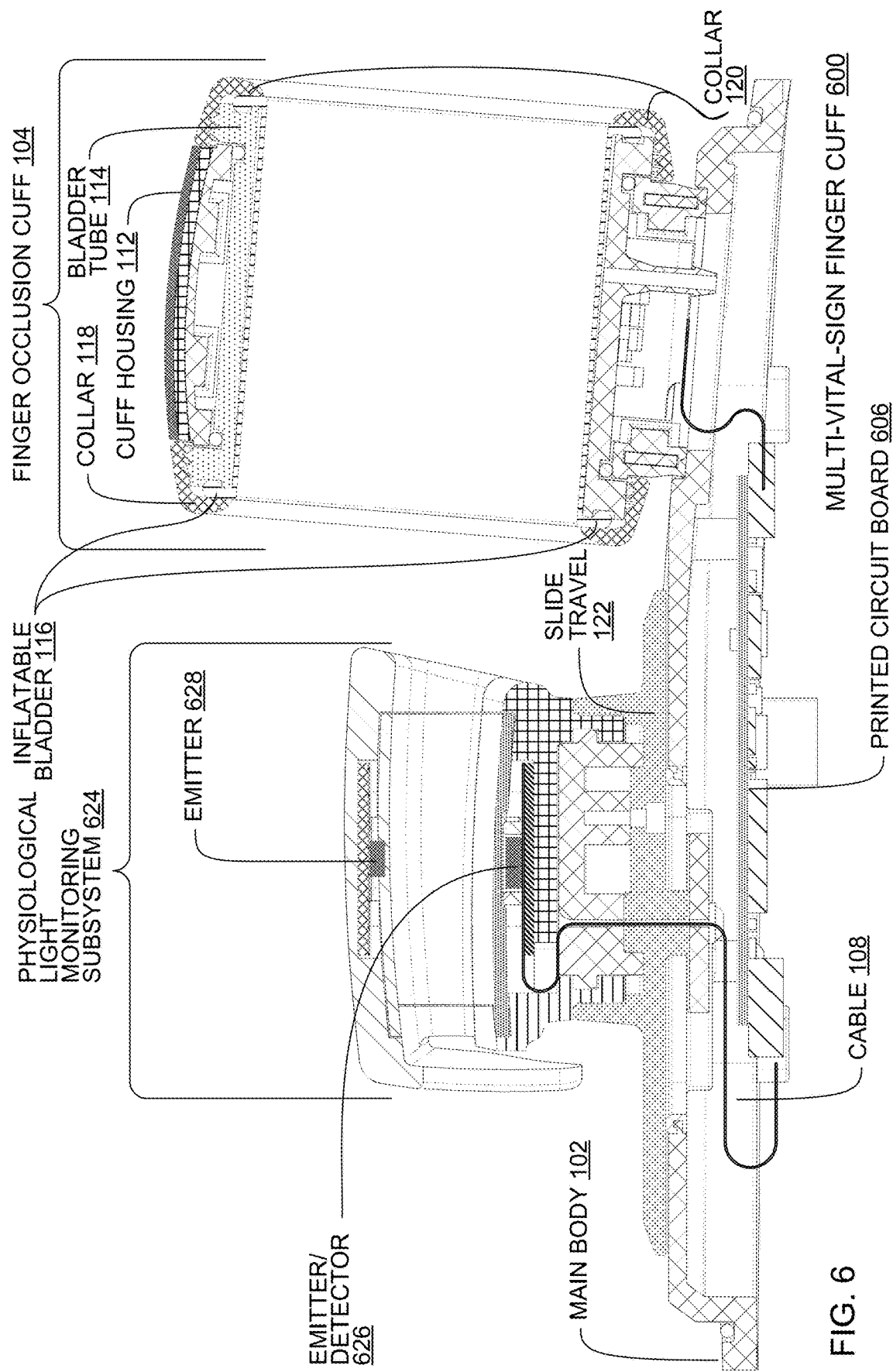
FIG. 6 is a cross-section diagram of a MVS finger cuff that determines transmissive SpO2, reflective glucose and other vital signs such as blood pressure, according to an implementation.

FIG. 6 is a cross-section diagram of a multi-vital-sign (MVS) finger cuff 600 that determines transmissive SpO2, reflective glucose and other vital signs such as blood pressure, according to an implementation. MVS finger cuff 600 operates in accordance with Table 1 above, in implementation #6.

In MVS finger cuff 600, the PLM subsystem is PLM subsystem 624 that includes an emitter in an emitter/detector 626 that emits ER at 395 nm, 660 nm and 940 nm and the emitter/detector 626 includes a detector that detects ER in the ranges of 375-415 nm and 920-960 nm to measure ER that is reflected by the subject finger that is positioned in the PLM subsystem 624 at 395 nm and 940 nm. The PLM subsystem 624 also includes an emitter 628 that emits ER in the ranges of 640-680 nm and 920-960 nm to transmit ER through the subject finger that is positioned in the PLM subsystem 624 at 660 nm and 940 nm. The detector in the emitter/detector 626 detects the ER in the ranges of 640-680 nm and 920-960 nm that is emitted by the emitter 628.

The microprocessor of the printed circuit board 606 or a microprocessor that is mounted on a printed circuit board in FIGS. 6 and 8-37 determines transmissive SpO2 at 660 nm by dividing the amount of transmissive ER at 660 nm by the amount of transmissive ER at 940 nm and the reflective glucose is determined by dividing the amount of reflective ER at 395 nm by the amount of reflective ER at 940 nm.

Figure 7:
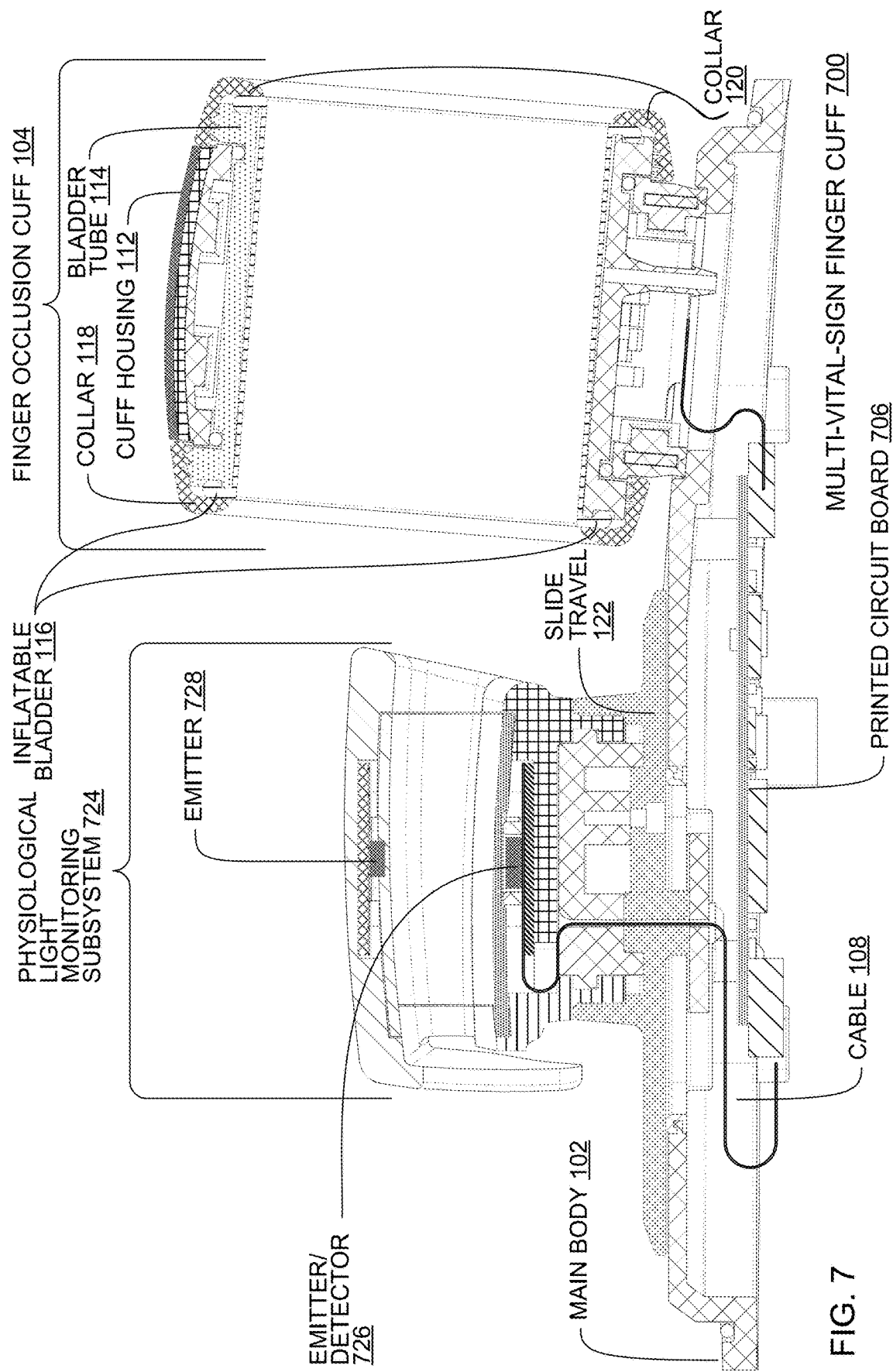
FIG. 7 is a cross-section diagram of a MVS finger cuff that determines transmissive SpO2 and reflective SpO2 and other vital signs such as blood pressure, according to an implementation.

FIG. 7 is a cross-section diagram of a multi-vital-sign (MVS) finger cuff 700 that determines transmissive SpO2 and reflective SpO2 and other vital signs such as blood pressure, according to an implementation. MVS finger cuff 700 operates in accordance with Table 1 above, in implementation #1.

In MVS finger cuff 700, the PLM subsystem is PLM subsystem 724 that includes an emitter in an emitter/detector 726 that emits ER at 660 nm and 940 nm and the emitter/detector 726 includes a detector that detects ER in the ranges of 375-415 nm, 640-680 nm and 920-960 nm to measure ER that is reflected by the subject finger that is positioned in the PLM subsystem 724 at 660 nm and 940 nm. The PLM subsystem 724 also includes an emitter 728 that emits ER in the ranges of 640-680 nm and 920-960 nm to transmit ER through the subject finger that is positioned in the PLM subsystem 724 at 660 nm and 940 nm. The detector in the emitter/detector 726 detects the ER in the ranges of 640-680 nm and 920-960 nm that is emitted by the emitter 628.

The microprocessor of the printed circuit board 706 or a microprocessor that is mounted on a printed circuit board in FIGS. 7 and 8-37 determines transmissive SpO2 at 660 nm by dividing the amount of transmissive ER at 660 nm by the amount of transmissive ER at 940 nm and reflective SpO2 is determined by dividing the amount of reflective ER at 660 nm and by the amount of reflective ER at 940 nm.

Figure 8:
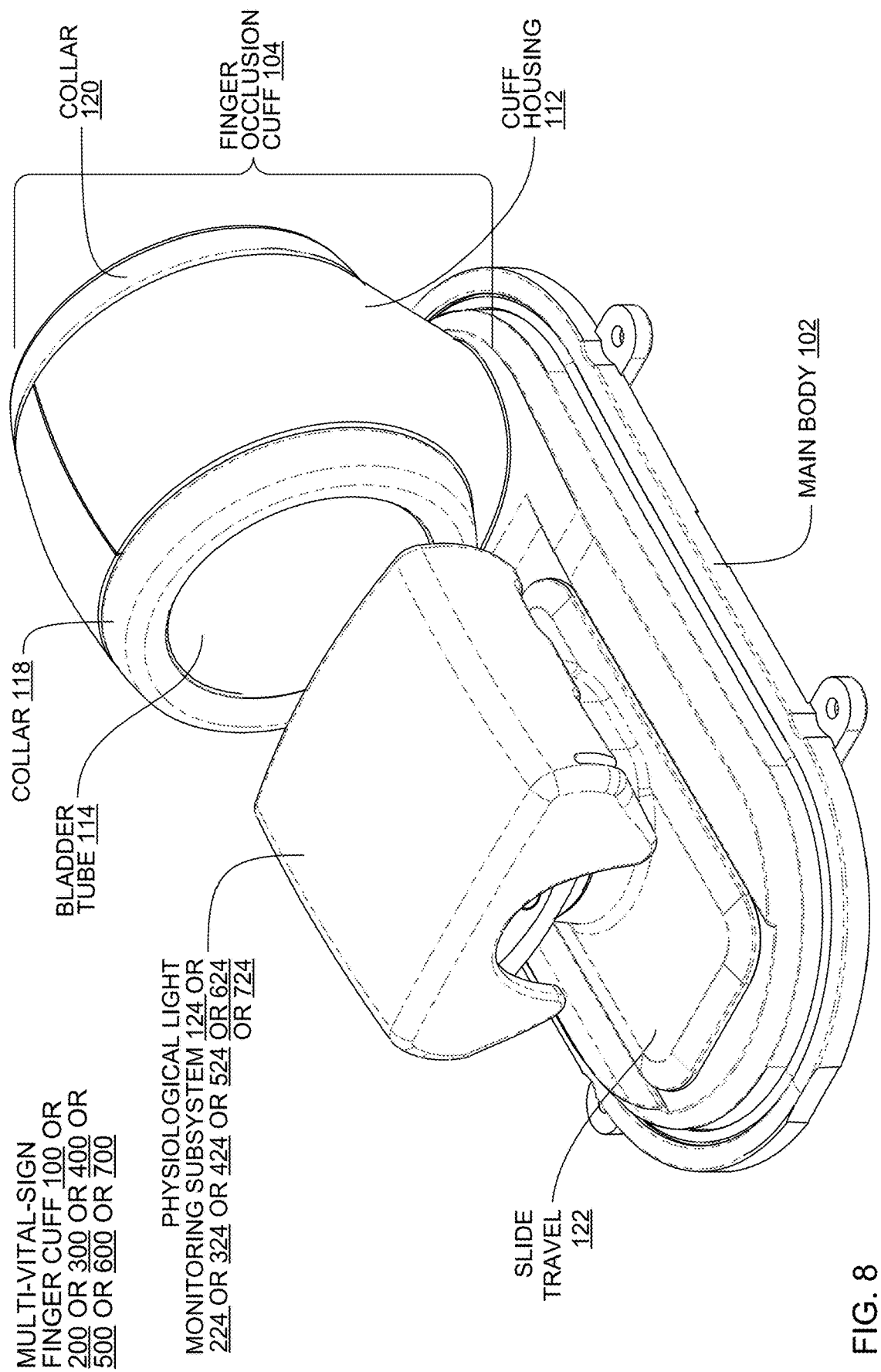
FIG. 8 is an isometric diagram of a MVS finger cuff in FIGS. 1-7, according to an implementation.

FIG. 8 is an isometric diagram of a MVS finger cuff 800, according to an implementation.

Figure 9:
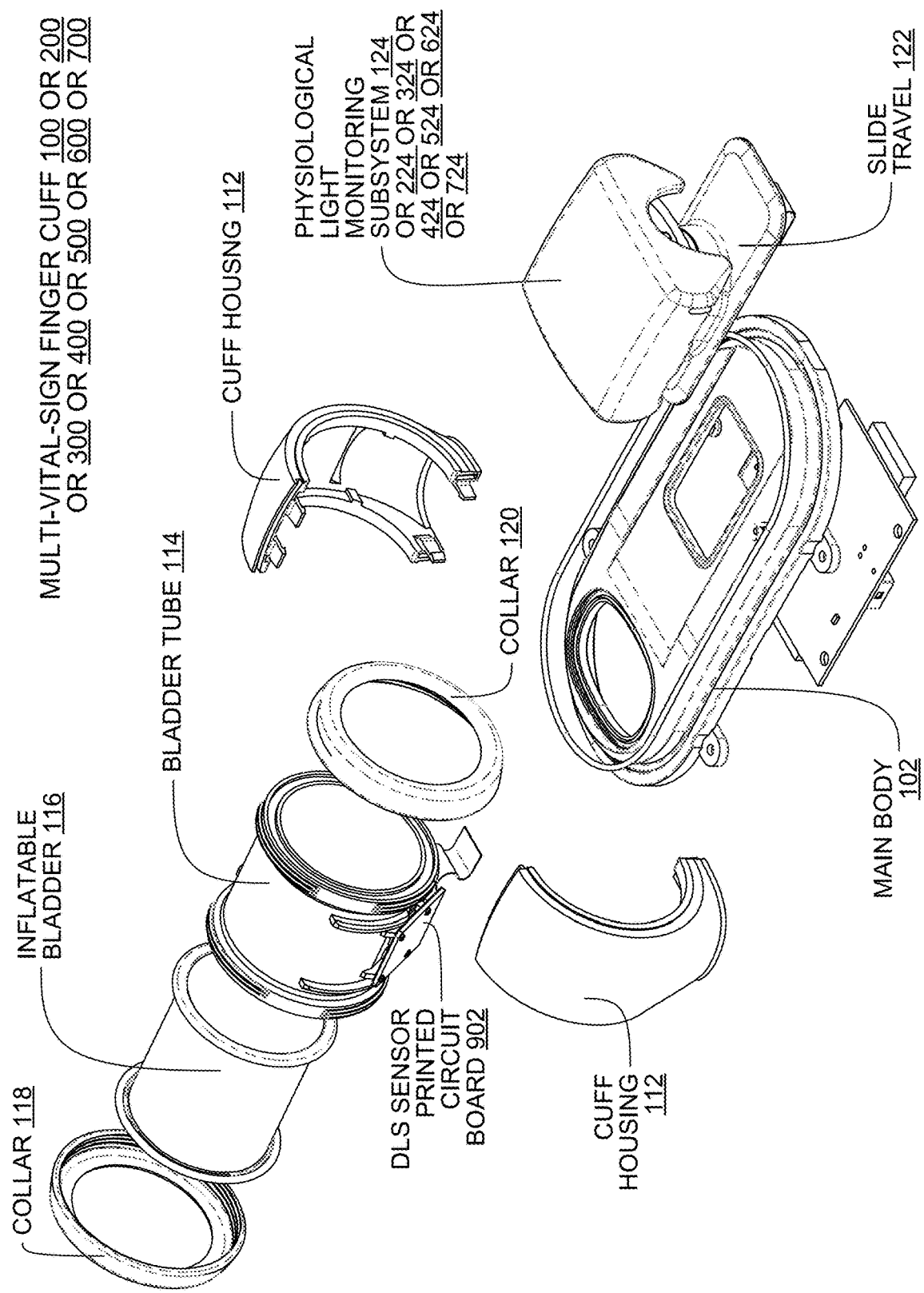
FIG. 9 is an exploded isometric diagram of the MVS finger cuff in FIGS. 1-8, according to an implementation.

FIG. 9 is an exploded isometric diagram of the MVS finger cuff 800, according to an implementation.

Figure 10:
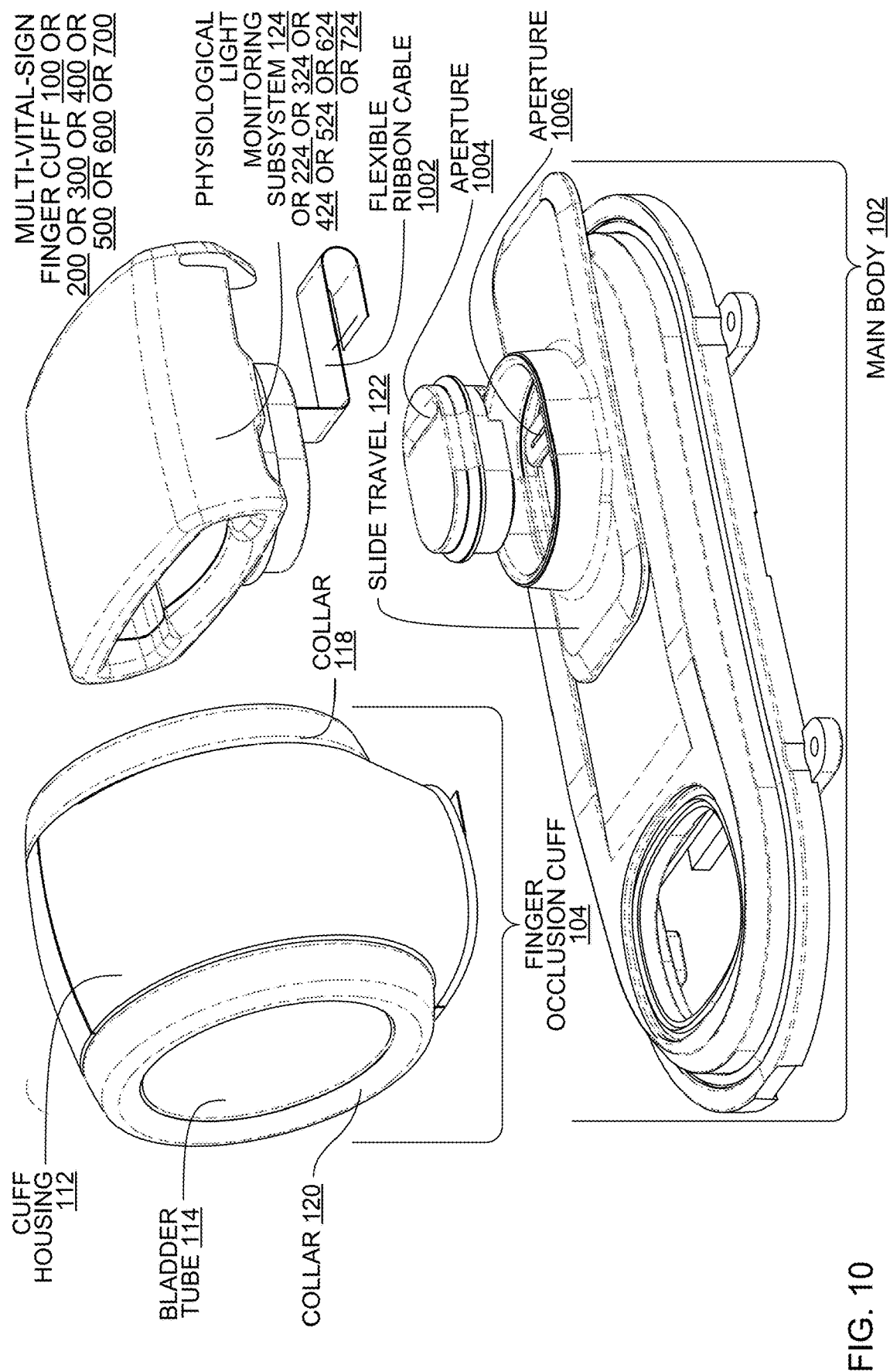
FIG. 10 is an exploded isometric diagram of a MVS finger cuff in FIGS. 1-9, according to an implementation.

FIG. 10 is an exploded isometric diagram of the (MVS finger cuff 700, according to an implementation. FIG. 10 shows a flexible ribbon cable 1002 that electrically couples the PLM subsystem to the PCB board in the main body 102 through apertures 1004 and 1006 in the slide travel 122.

In FIG. 8-10, MVS finger cuff 800 includes a slide travel 122 that slidably mounts the MVS finger cuff in FIG. 1-7 to the main body 102, the finger occlusion cuff 104 includes the cuff housing 112 that surrounds the bladder tube 114 that mounts the inflatable bladder 116 and the identical collars 118 and 120 at open ends of the cuff housing 112 position the bladder tube 114 and the inflatable bladder 116.

Figure 11:
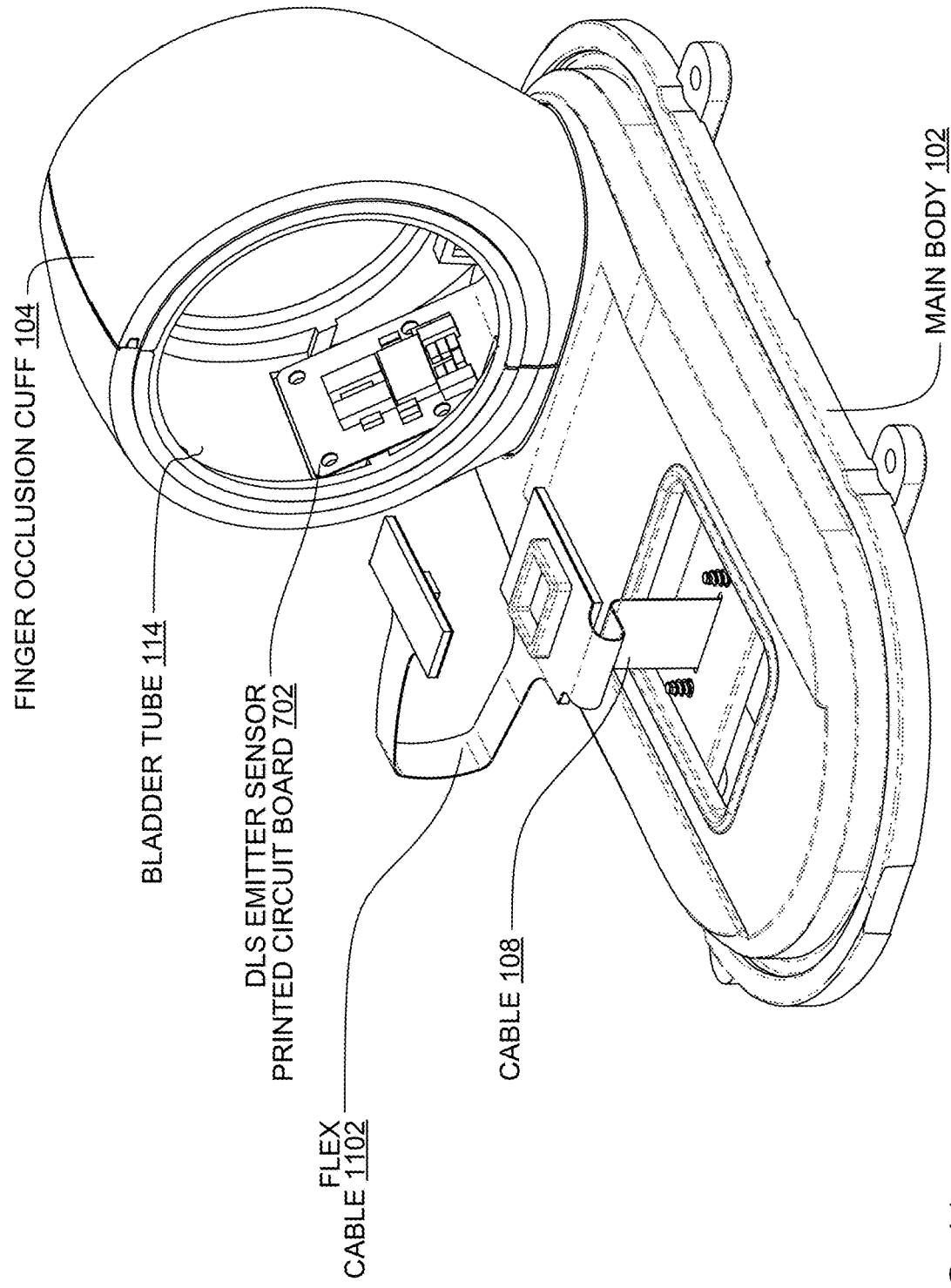
FIG. 11 is an exploded isometric diagram of the MVS finger cuff in FIGS. 1-2 and 6-7.

FIG. 11 is an exploded isometric diagram of the MVS finger cuff 1100 in FIGS. 1-2 and 6-7. The MVS finger cuff 1100 includes a finger occlusion cuff 104 that includes a DLS emitter printed circuit board 702 mounted on the interior of the bladder tube 114. The finger occlusion cuff 104 is mounted on a main body 102, and the main body 102 includes a cable that connects the printed circuit board 106 to the emitter/detector 126 of FIG. 1, the detector 228 of FIG. 2, the emitter/detector 626 of FIG. 6 and the emitter/detector 726 of FIG. 7. A flexible ribbon cable 1102 electrically connects the emitter/detector 126 to the emitter 128 of FIG. 1, the detector 228 to the emitter 226 of FIG. 2, the emitter/detector 626 to the emitter 628 of FIG. 6 and the emitter/detector 726 to the emitter 728 of FIG. 7; and to the cable 108.

3. Apparatus of Multi-Vital-Sign Smartphone Accessory

Figure 12:
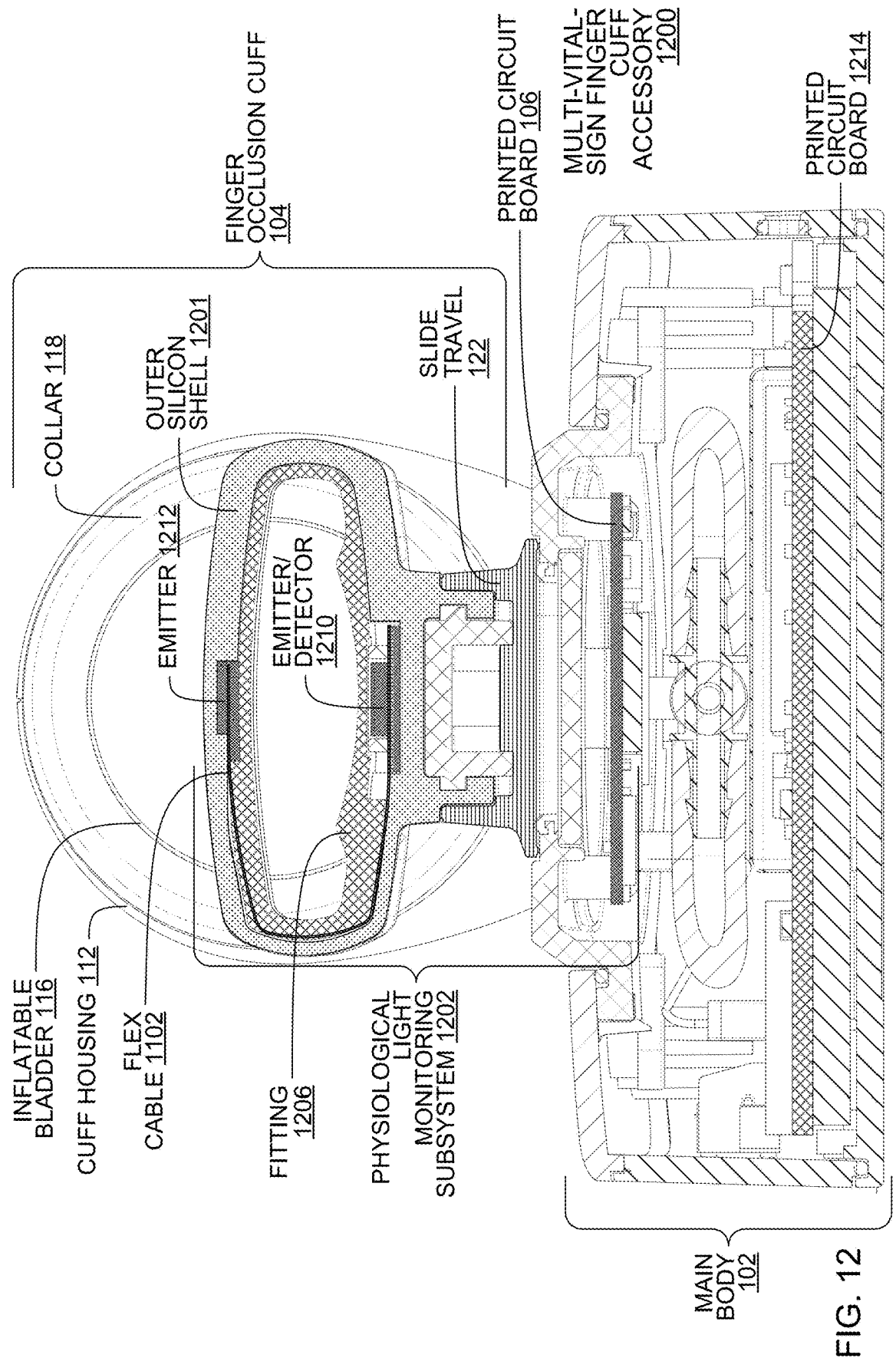
FIG. 12 is a cross section diagram of a MVS finger cuff accessory, according to an implementation.

FIG. 12 is a cross-section diagrams of a multi-vital-sign finger cuff accessory (MVSFCA) that can determine transmissive SpO2, reflective SpO2, reflective glucose and other vital signs such as blood pressure, according to an implementation. An outer silicon shell 1201 is a solid piece with tongues for securing into a base of a PLM subsystem 1202, and an internal recess for a flexible ribbon cable 1102 to fit into and the rigid parts with components to sit in the slide travel 122. Examples of the PLM subsystem 1202 include the PLM subsystems 124 in FIG. 1, 224 in FIG. 2, 324 in FIG. 3, 424 in FIG. 4, 524 in FIG. 5, 624 in FIGS. 6 and 724 in FIG. 7. A translucent silicone fitting 1206, which is a little wider than the flexible ribbon cable 1102, is positioned over the cable/components and glued in place. The translucent silicone fitting 1206 has shape effects 1208 in the interior to aid in location and positioning of a finger in the PLM subsystem 1202. The flexible ribbon cable 1102 electrically connects the emitter/detector 1210 and an emitter 1212 to the cable 108. The cable 108 is electrically coupled to a printed circuit board 1214. The printed circuit board 1214 includes a microprocessor that performs the determinations described in FIGS. 1-7 and the methods in FIGS. 38-40, 45-54 and/or 58-64 a non-volatile memory such as flash memory. The printed circuit board 106 of the MVS finger cuff (such as 100, 200, 300, 400, 500, 600 or 700) is electrically coupled to the printed circuit board 1214 of the MVSFCA 1200.

Figure 19:
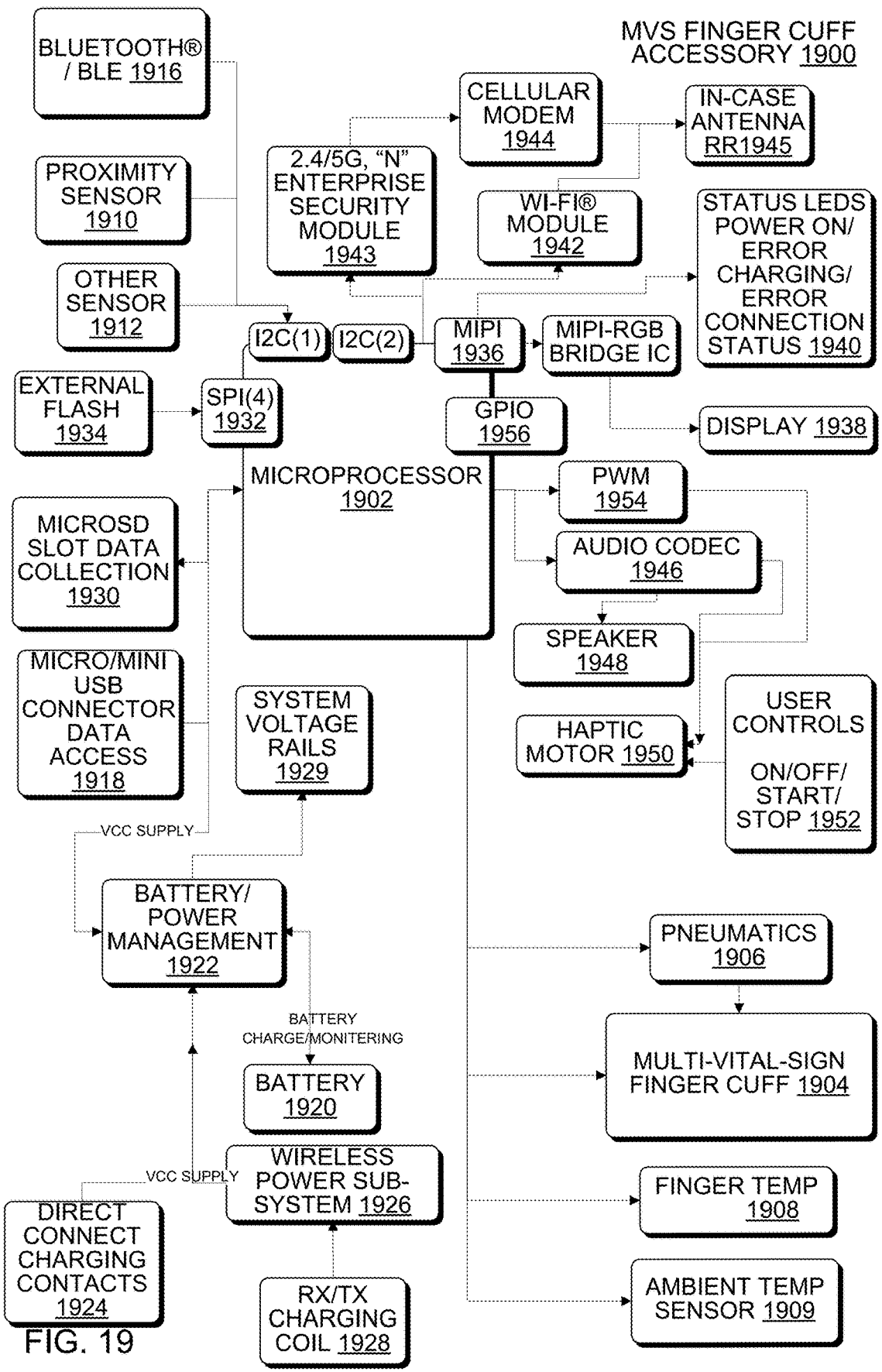
FIG. 19 is a block diagram of a MVS finger cuff smartphone system, according to an implementation.

In some implementations, the MVSFCA 1200 operably couples to a MVS smartphone via direct connect charging contacts 1924 of the MVS finger cuff smartphone system in FIG. 19 and/or a charging port on the end of the MVS smartphone in which the MVSFCA 1200 receives power and control signals from the MVS smartphone and through which data from the MVSFCA 1200 is transmitted to the MVS smartphone. In some implementations, the MVSFCA 1200 operably couples to the MVS smartphone via the contact charging of the MVS smartphone 3103 in FIG. 31 or the direct connect charging contacts 1924 of the MVS finger cuff accessory in FIG. 19 and a charging port on the back of the MVS smartphone in which the MVSFCA 1200 receives power and control signals from the MVS smartphone and through which data from the MVSFCA 1200 is transmitted to the MVS smartphone. In some implementations, the MVSFCA 1200 operably couples to the MVS smartphone via the Bluetooth® or other wireless communication modules of the MVSFCA 1200, such as Zigbee® or Z-Wave®. The MVS smartphone in which the MVSFCA 1200 includes a battery and receives control signals from the MVS smartphone and through which data from the MVSFCA 1200 is transmitted to the MVS smartphone. The MVS smartphone is a smartphone whose memory stores software that causes the microprocessor of the smartphone to analyze vital sign data from the MVSFCA 1200 and to display the vital sign data from the MVSFCA 1200, to display the result of the analysis of vital sign data from the MVSFCA 1200 and to transmit the vital sign data from the MVSFCA 1200, to transmit the result of the analysis of vital sign data from the MVSFCA 1200.

Figure 13:
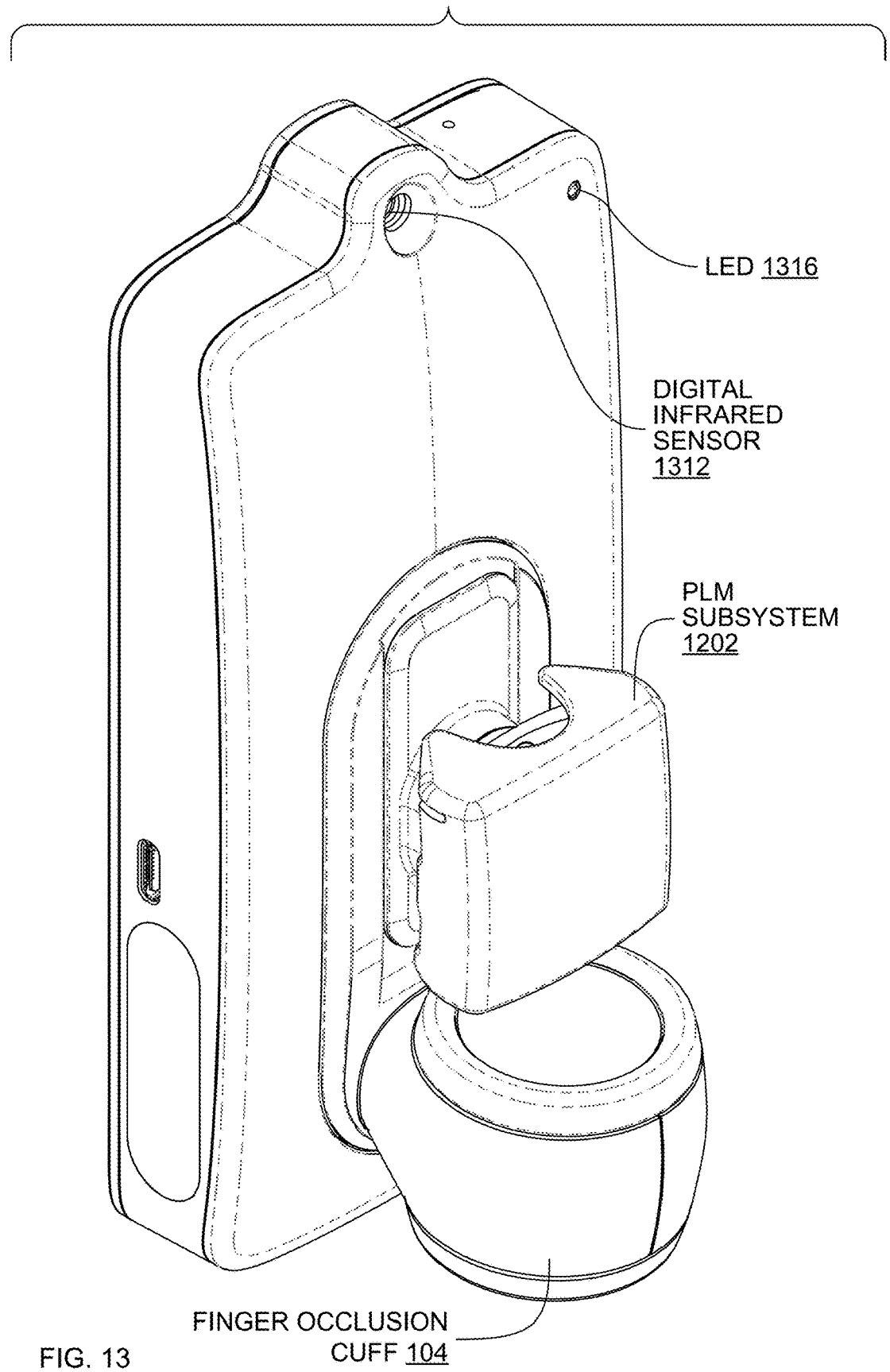
FIG. 13 is an isometric diagram of a mechanical design of a MVS finger cuff accessory, according to an implementation.

FIG. 13 is an isometric diagram of a mechanical design of a MVS finger cuff accessory (MVSFCA) 1200, according to an implementation. The MVSFCA 1200 can be coupled to a MVS smartphone, such as MVS smartphone 2800 in FIG. 28, MVS smartphone 2900 in FIG. 29, MVS smartphone 3200 in FIG. 32, MVS smartphone 3004 in FIG. 30, MVS smartphone 3103 in FIG. 31, and MVS smartphone 3402 in FIG. 34. The MVSFCA 1200 includes a MVS finger cuff (such as 100, 200, 300, 400, 500, 600 or 700) that includes the PLM subsystem 1202 and a finger occlusion cuff 104. Some implementations of the MVS finger cuff accessory 1200 also include a camera and/or a digital infrared sensor 1312. LED 1316 in the MVSFCA 1200 displays in indication of temperature of a subject detected through the digital infrared sensor.

Figures 14, 15:
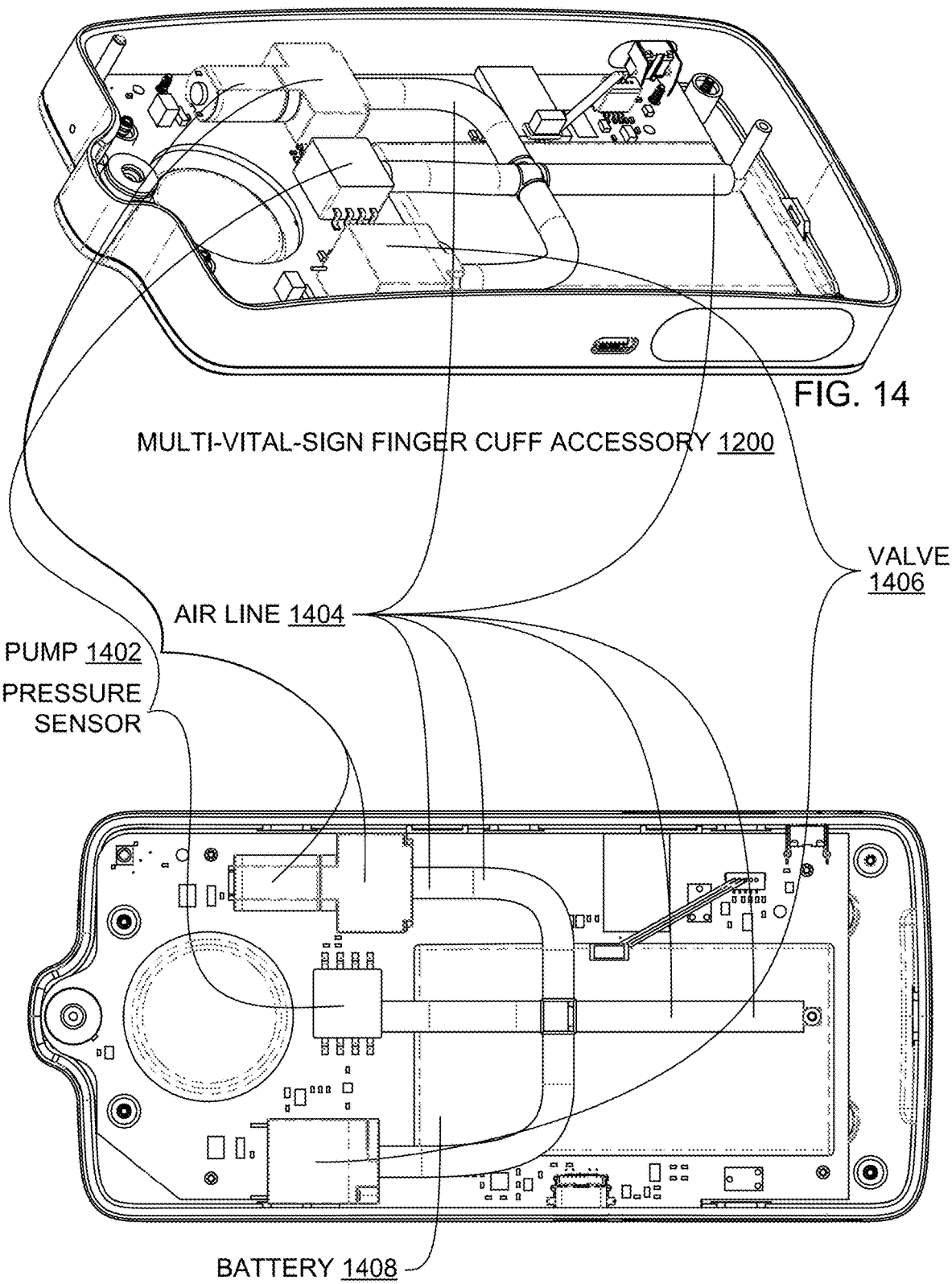
FIG. 14 is an isometric diagram of a MVS finger cuff accessory with the topskin removed to view the interior components, according to an implementation.
FIG. 15 is block diagram of a MVS finger cuff accessory with the topskin removed to view the interior components, according to an implementation.

FIG. 14 is an isometric diagram of a mechanical design of a multi-vital-sign finger (MVS) cuff accessory (MVSFCA) 1200 with the topskin removed to view the interior components, according to an implementation. FIG. 15 is a block diagram of a MVSFCA with the topskin removed to view the interior components, according to an implementation. The MVSFCA 1200 includes an air pump 1402 that is operably coupled to an air line 1404 and a pressure sensor 1406. The MVSFCA 1200 also includes a battery 1408.

Figure 16:
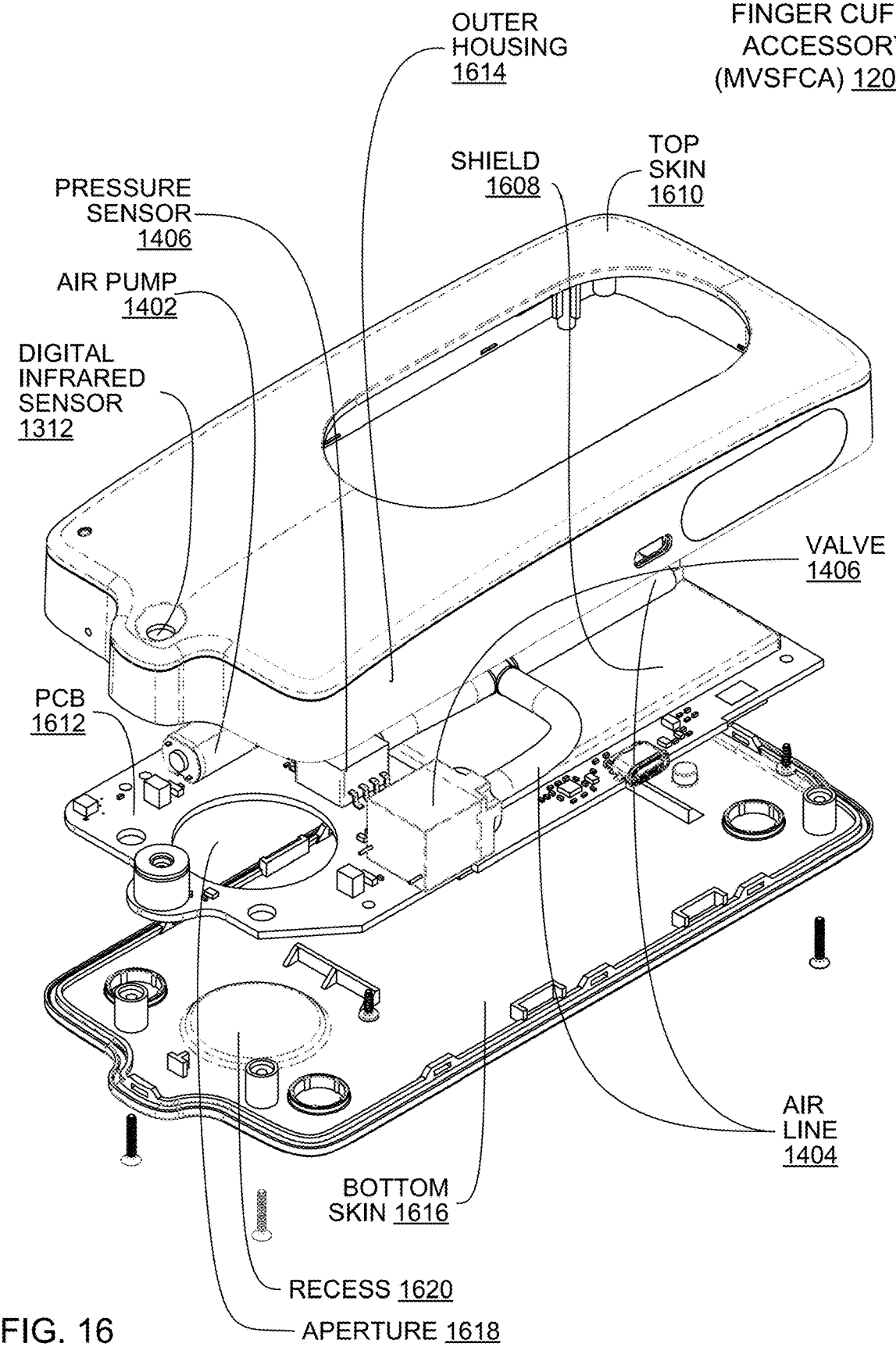
FIG. 16 is an exploded isometric diagram of a MVS finger cuff accessory, according to an implementation.

FIG. 16 is an exploded isometric diagram of a multi-vital-sign (MVS) finger cuff accessory (MVSFCA) 1200, according to an implementation. The MVSFCA 1200 includes a MVS finger cuff (such as MVS finger cuff 100 in FIG. 1 or MVS finger cuff 300 in FIG. 3) that includes a finger occlusion cuff 104. In some implementations, the MVSFCA 1200 operably couples to the MVS smartphone (such as MVS smartphone 3004 in FIG. 30, MVS smartphone 3103 in FIG. 31, MVS smartphone 2800 in FIG. 28 and MVS smartphone 3402 in FIG. 34) via the direct connect charging contacts 1924 of the MVS finger cuff smartphone system in FIG. 3400 and a charging port on the end of the MVS smartphone in which the MVSFCA 1200 receives power and control signals from the MVS smartphone and through which data from the MVSFCA 1200 is transmitted to the MVS smartphone. In some implementations, the MVSFCA 1200 operably couples to the MVS smartphone via the direct connect charging contacts 1924 of the MVS finger cuff smartphone system in FIG. 34 and a charging port on the back of the MVS smartphone in which the MVSFCA 1200 receives power and control signals from the MVS smartphone and through which data from the MVSFCA 1200 is transmitted to the MVS smartphone. In some implementations, the MVSFCA 1200 operably couples to the MVS smartphone via the Bluetooth® or other wireless communication modules of the MVSFCA 1200, such as Zigbee® or Z-Wave®. The MVS smartphone in which the MVSFCA 1200 includes a battery and receives control signals from the MVS smartphone and through which data from the MVSFCA 1200 is transmitted to the MVS smartphone. LED 1316 in the MVSFCA 1200 displays temperature of a subject detected through the digital infrared sensor. The MVS smartphone is a smartphone whose memory stores software that causes the microprocessor of the smartphone to analyze vital sign data from the MVSFCA 1200 and to display the vital sign data from the MVSFCA 1200, to display the result of the analysis of vital sign data from the MVSFCA 1200 and to transmit the vital sign data from the MVSFCA 1200, to transmit the result of the analysis of vital sign data from the MVSFCA 1200.

The MVSFCA 1200 includes an air pump 1402 that is operably coupled to an air line 1404, a pressure sensor 1406 and a valve 1406, that is ultimately coupled to the finger occlusion cuff 104. The MVSFCA 1200 also includes a shield 1608 over electronic components. The MVSFCA 1200 includes a top skin 1610, a printed circuit board (PCB) 1612, an outer housing 1614 and a bottom skin 1616. PCB 1612 also includes an aperture 1618 and the bottom skin 1616 includes a recess 1620.

Figure 17:
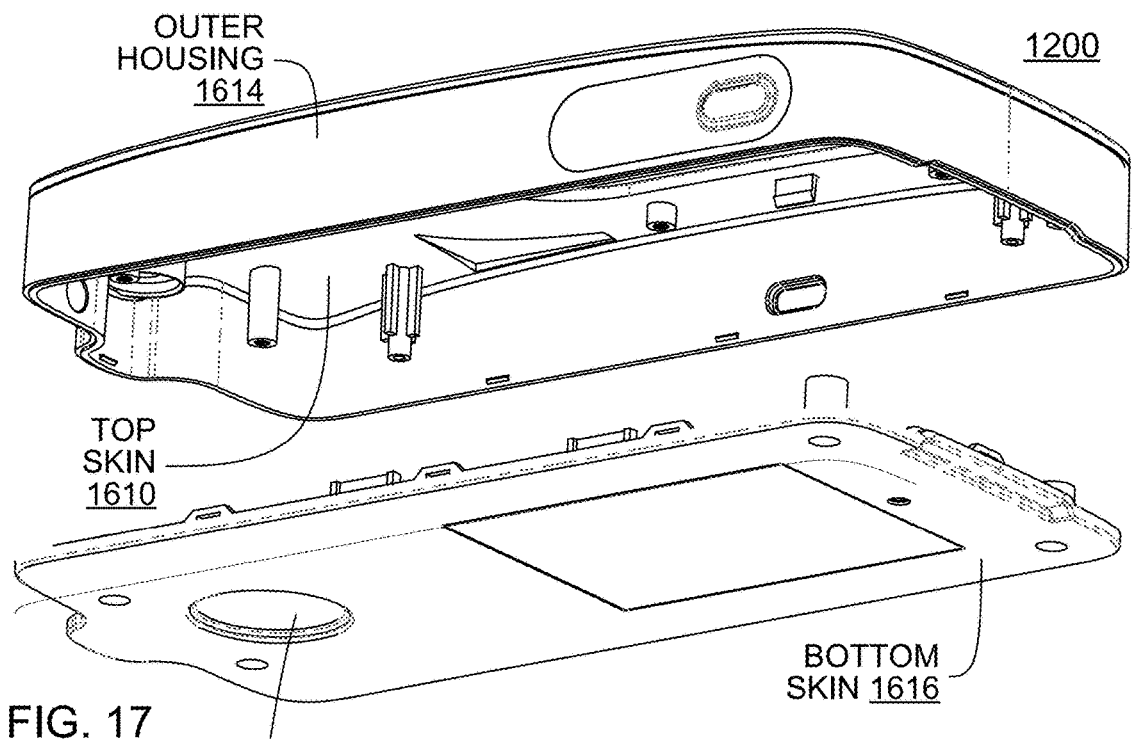
FIG. 17-18 are exploded isometric diagrams of the mechanical housing of the MVS finger cuff accessory, according to an implementation.
Figure 18:
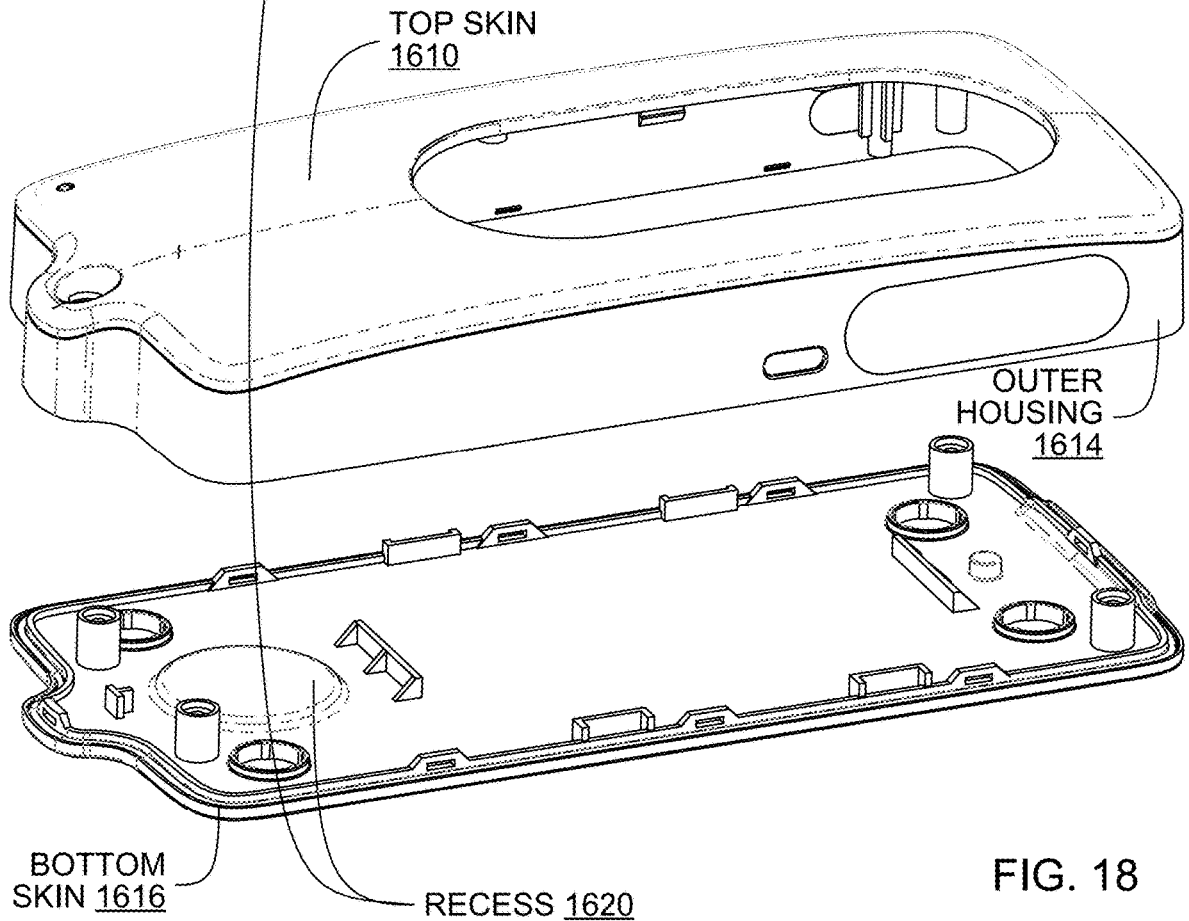

FIG. 17-18 are exploded isometric diagrams of the mechanical housing of the multi-vital-sign (MVS) finger cuff accessory (MVSFCA) 1200, according to an implementation.

FIG. 19 is a block diagram of a multi-vital-sign finger cuff accessory (MVSFCA) 1900, according to an implementation. MVSFCA 1900 is one implementation of MVSFCA 3002 in FIG. 30, MVSFCA 1900 is one implementation of MVSFCA 3102 in FIG. 31, MVSFCA 1900 is one implementation of MVSFCSS 3300 in FIG. 33 and MVSFCA 1900 is one implementation of MVSFCSS 3404 in FIG. 34. The MVSFCA 1900 captures, stores and exports raw data from all supported sensors in the system. MVSFCA 1900 supports a variety measurement methods and techniques. The MVSFCA 1900 can be used in a clinical setting for the collection of human vital signs.

A microprocessor 1902 controls and receives data from a multi-vital-sign finger cuff 1904 (such as 100, 200, 300, 400, 500, 600 or 700), a pneumatic engine 1906, an infrared finger temperature sensor 1908, ambient temperature sensor 1909, a proximity sensor 1910 and another sensor 1912. In some implementations the microprocessor 1902 is an advanced reduced instruction set processor.

Figure 30:
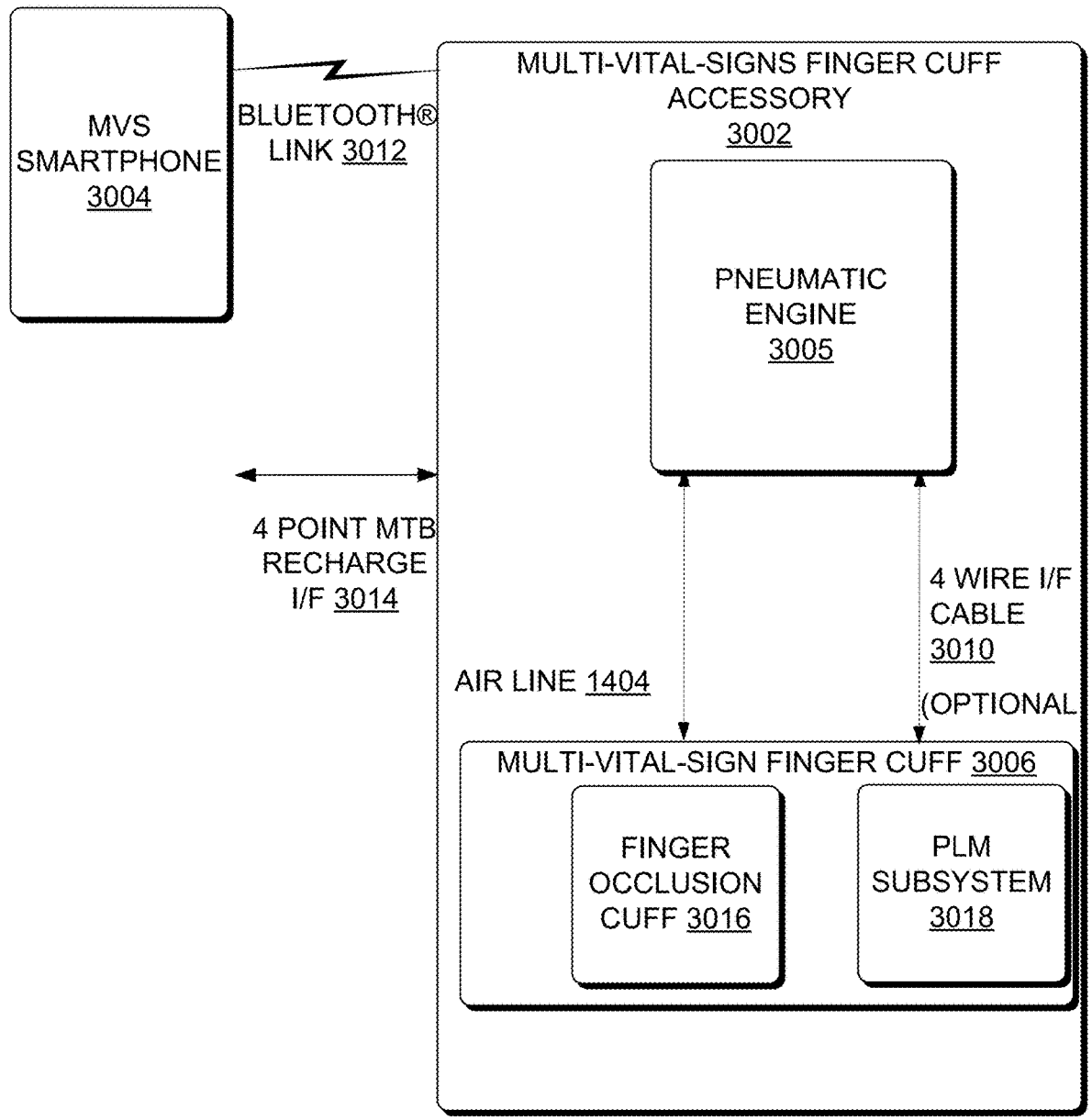
FIG. 30 is a block diagram of a MVS smartphone system, according to an implementation.

The MVS finger cuff 1904 is affixed into the MVSFCA 1900, rather than the replaceable, detachable and removable MVS finger cuff 3006 in FIG. 30. The MVS finger cuff 1904 includes a PLM subsystem (such as 124, 224, 324, 424, 524, 624 or 724) and at least one mDLS sensor. The MVS finger cuff 1904 is powered via an air line (e.g. 3006 in FIG. 30) by the pneumatic engine 1906 that provides air pressure to inflate the cuff bladder of the MVS finger cuff 1904 and the that provides control signal to deflate the cuff bladder of the MVS finger cuff 1904.

In some implementations, a body surface temperature of a human is also sensed by the infrared finger temperature sensor 1908 that is integrated into the MVSFCA 1900 in which the body surface temperature is collected and managed by the MVSFCA 1900.

In some implementations, a single stage measurement process is required to measure all vital signs in one operation by the MVSFCA 1900 by the replaceable, detachable and removable MVS finger cuff 3006 or the MVS finger cuff 1904 or the infrared finger temperature sensor 1908. However, in some implementations, a two stage measurement process is performed in which the MVSFCA 1900 measures some vital signs through the replaceable, detachable and removable MVS finger cuff 3006 or the MVS finger cuff 1904; and in the second stage, the body surface temperature is measured through an infrared finger temperature sensor 1908 in the MVS Smartphone device 3103.

The MVS smartphone 3103, when connected to a wireless Bluetooth® communication component 1916 of the MVSFCA 1900 via a wireless Bluetooth® communication component 3114, is a slave to the MVSFCA 1900. In other implementations, Zigbee® or Z-Wave® can be used instead of Bluetooth®. The MVS Smartphone 3103 reports status, measurement process, and measurements to the user via the MVSFCA 1900.

In some implementations, the measurement process performed by the MVSFCA 1900 is controlled and guided from the MVS Smartphone 3103 via the GUI on the MVS Smartphone 3103. The measurements are sequenced and configured to minimize time required to complete all measurements. In some implementations, the MVSFCA 1900 calculates the secondary measurements of heart rate variability and blood flow. The MVSFCA 1900 commands and controls the MVS Smartphone 3103 via a wireless Bluetooth® protocol communication path. In other implementations, Zigbee® or Z-Wave® can be used instead of Bluetooth®. In some further implementations, the MVS Smartphone 3103 communicates with the MVSFCA 1900, which could also be concurrent.

MVSFCA 1900 includes a USB port 1918 that is operably coupled to the microprocessor 1902 for interface with slave devices only, such as the MVS Smartphone 3103, to perform the following functions: recharge internal rechargeable batteries 1920, export sensor data sets to a windows based computer system, firmware update of the MVSFCA 1900 via an application to control and manage the firmware update of the MVSFCA 1900 and configuration update of the MVSFCA 1900.

In some implementation recharging the internal rechargeable batteries 1920 via the USB port 1918 is controlled by a battery power management module 1922. The battery power management module 1922 receives power from a direct connect charging contact(s) 1924 and/or a wireless power subsystem 1926 that receives power from a RX/TX charging coil 1928. The internal rechargeable batteries 1920 of the MVSFCA 1900 can be recharged when the MVSFCA 1900 is powered-off but while connected to USB port 1918 or DC input via the direct connect charging contacts 1924. In some implementations, the MVSFCA 1900 can recharge the MVS Smartphone 3103 from its internal power source over a wireless charging connection. In some implementations, the internal rechargeable batteries 1920 provide sufficient operational life of the MVSFCA 1900 on a single charge to perform at least 2 full days of measurements before recharging of the internal rechargeable batteries 1920 of the MVSFCA 1900 is required. In some implementations, system voltage rails 1929 are operably coupled to the battery power management module 1922.

In some implementations, the MVSFCA 1900 includes an internal non-volatile, non-user removable, data storage device 1930 for up to 2 full days of human raw measurement data sets. In some implementations, the MVSFCA 1900 includes a Serial Peripheral Interface (SPI) 1932 that is configured to connect to an eternal flash storage system 1934.

In some implementations, the MVSFCA 1900 includes a Mobile Industry Processor Interface (MIPI) 1936 that is operably connected to the microprocessor 1902 and a display screen 1938. The microprocessor 1902 is also operably coupled to the visual indicators 1940.

The MVSFCA 1900 also includes a Wi-Fi® communication module 1942 for communications via Wi-Fi® communication frequencies and the MVSFCA 1900 also includes an enterprise security module 1943 a cellular communication module 1944 for communications via cell phone communication frequencies. The Wi-Fi® communication module 1942 and the cellular communication module 1944 are operably coupled to an antenna 1945 that is located with a case/housing of the MVSFCA 1900.

The MVSFCA 1900 also includes an audio sub-system 1946 that controls at one or more speakers 1948 to enunciate information to an operator or patient. In some implementations, the microprocessor 1902 also controls a haptic motor 1950 through the audio sub-system 1946. User controls 1952 also control the haptic motor 1950. A pulse-width modulator 1954 that is operably coupled to a general-purpose input/output (GPIO) 1956 (that is operably coupled to the microprocessor 1902) provides control to the haptic motor 1950.

The MVSFCA 1900 is hand held and portable. The MVSFCA 1900 includes non-slip/slide exterior surface material.

Figure 33:
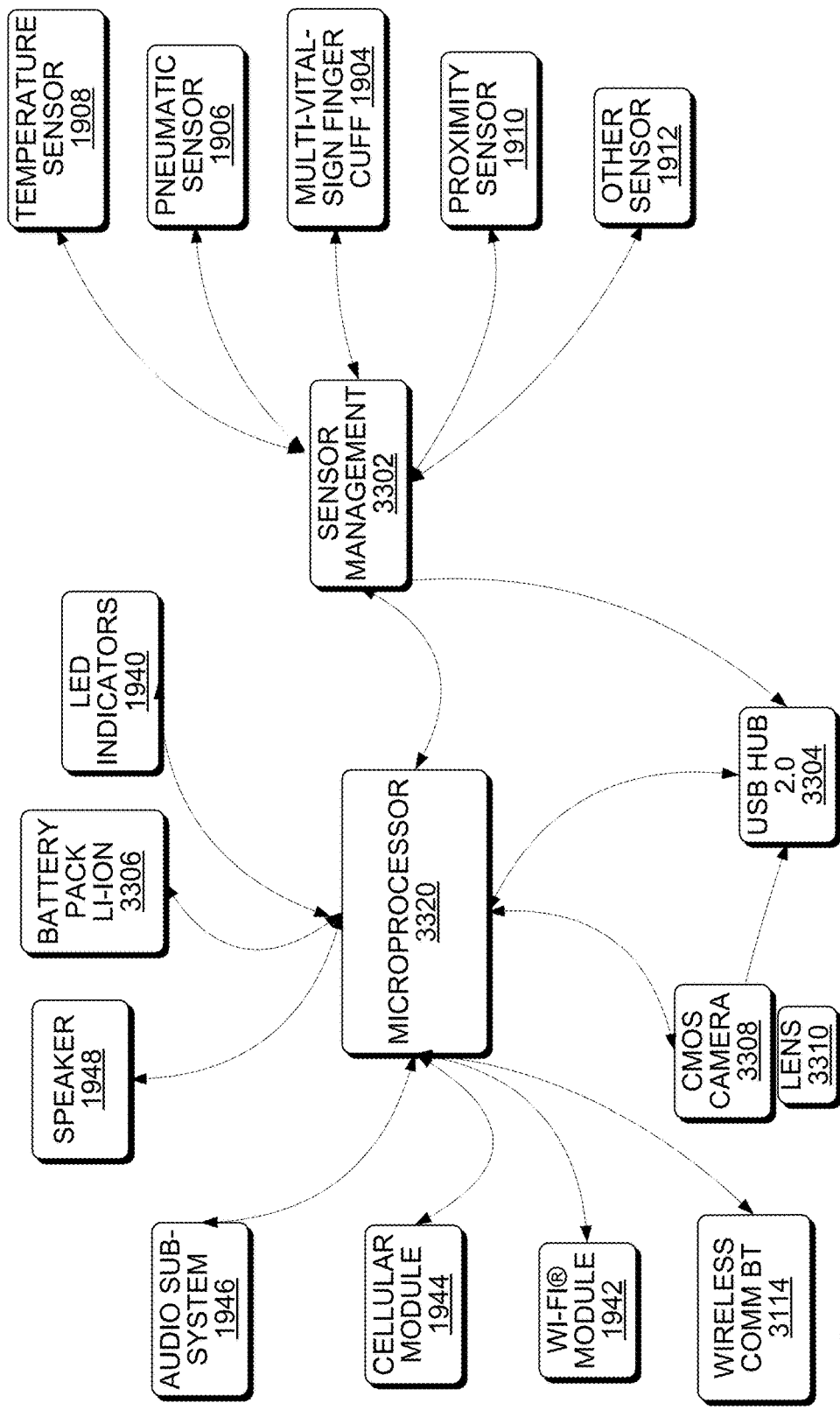
FIG. 33 is a block diagram of a MVS smartphone system, according to an implementation.

In some further implementations the MVSFCSS 3300 in FIG. 33 and MVSFCA 1900 in FIG. 19 perform continuous spot monitoring on a predetermined interval with automatic transfer to remote systems via Wi-Fi®, cellular or Bluetooth® communication protocols, with and without the use of a MVS Smartphone device, and alarm monitoring and integration into clinical or other real time monitoring systems, integration with the sensor box, with the MVSFCSS acting as a hub, for third party sensors, such as ECG, or from direct connect USB or wireless devices, e.g. Bluetooth® patches.

In other implementations, Zigbee® or Z-Wave® can be used instead of Bluetooth®. Wireless/network systems (Wi-Fi®, cellular 3G, 4G, 5G or Bluetooth®) are quite often unreliable. Therefore in some implementations, the MVS Smartphone devices and the MVSFCSS devices store vital sign measurements for later transmission.

Figure 20:
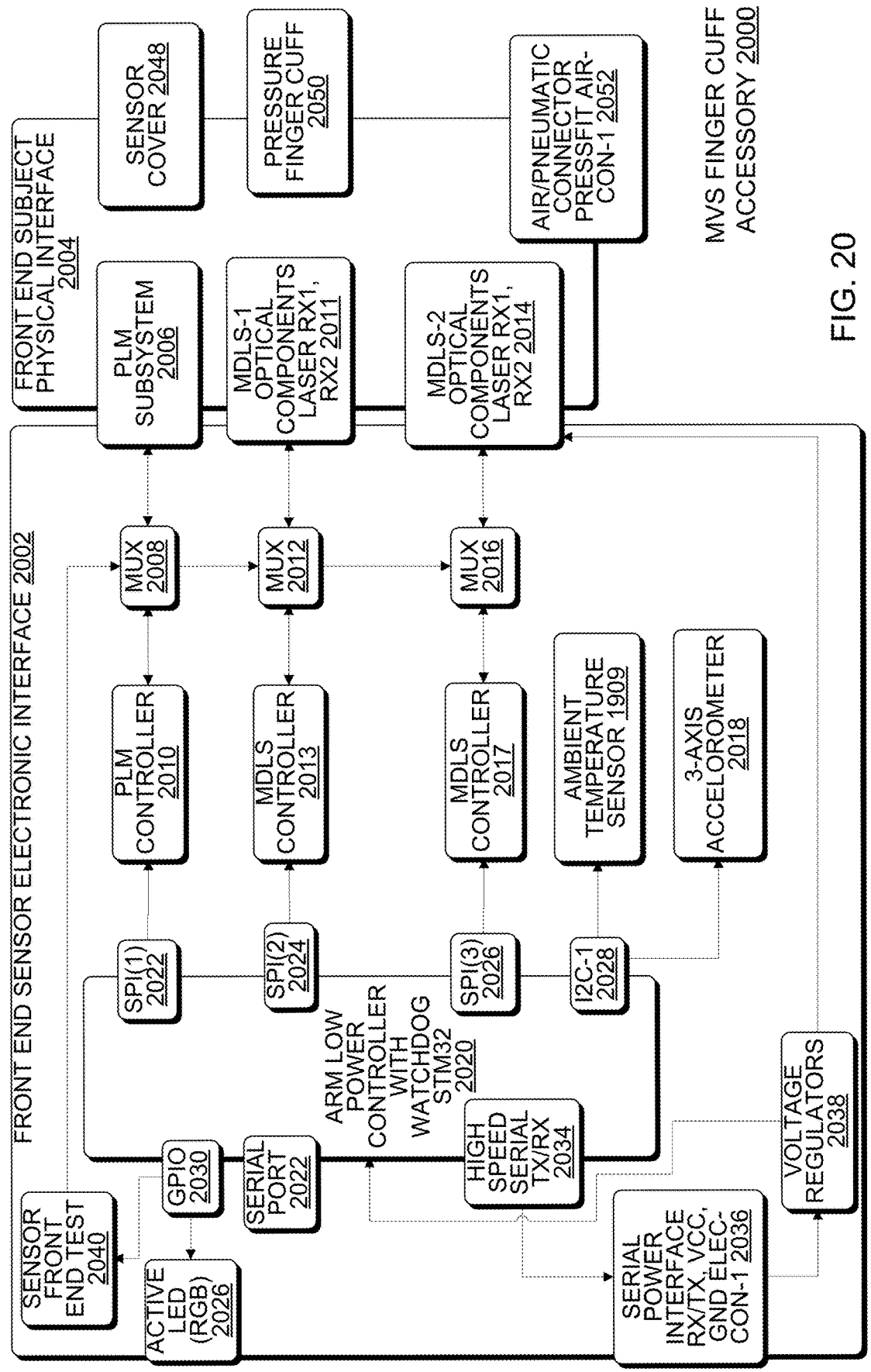
FIG. 20 is a block diagram of a front end of a MVS finger cuff accessory, according to an implementation.
Figure 25:
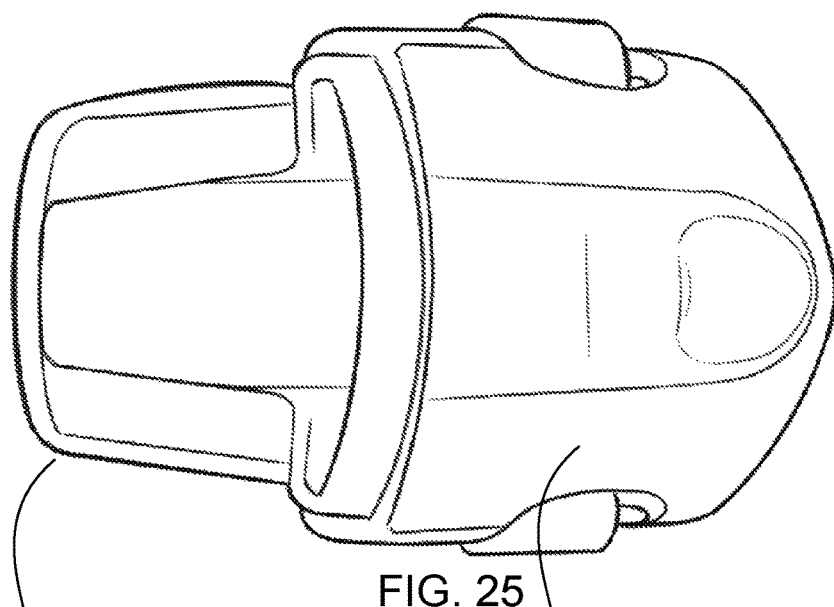
Figures 26, 27:
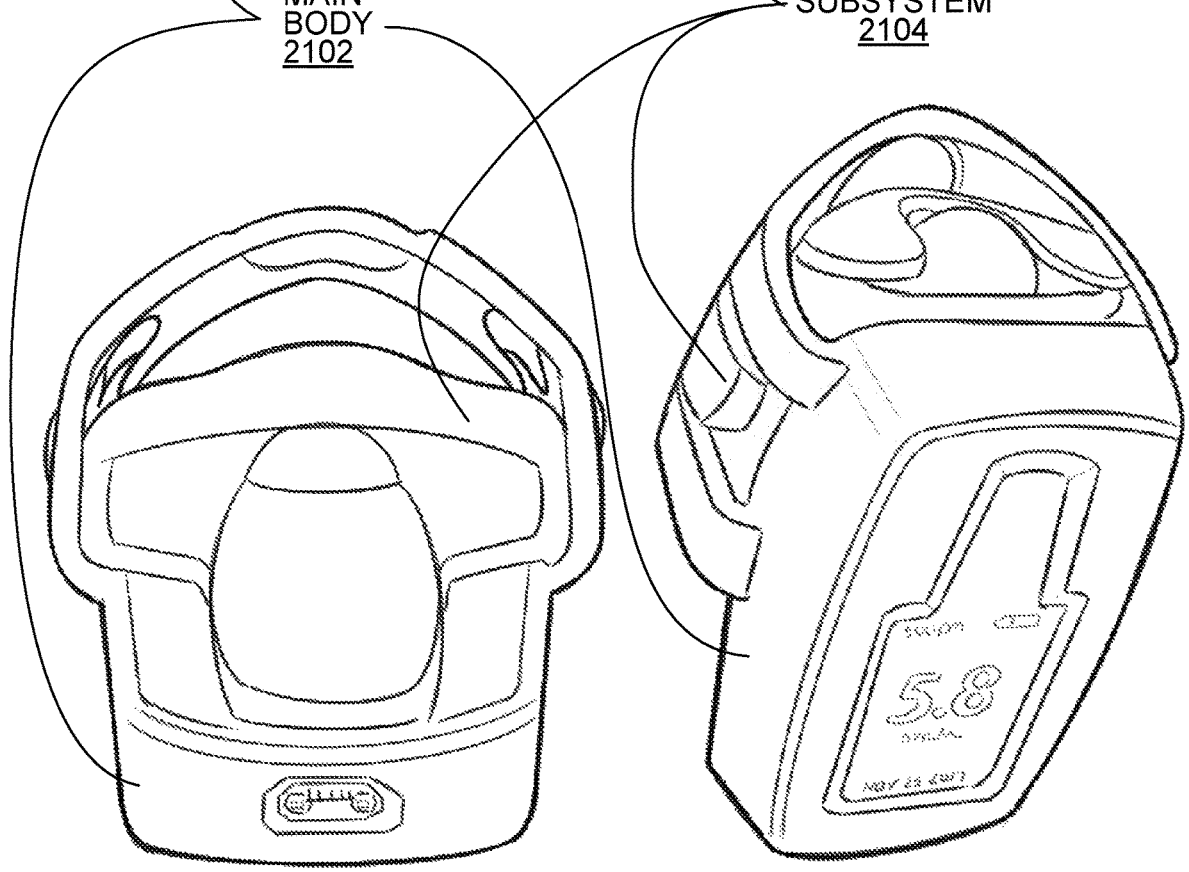

FIG. 20 is a block diagram of a front end of a multi-vital-sign (MVS) finger cuff accessory 2000, according to an implementation. The front end of a MVS finger cuff 2000 is one implementation of a portion of a MVS finger cuff 3006 in FIG. 30. The front end of a MVS finger cuff 2000 captures, stores and exports raw data from all supported sensors in the system. The front end of a MVS finger cuff 2000 supports a variety measurement methods and techniques. The front end of a MVS finger cuff 2000 can be used in a clinical setting for the collection of human vital signs.

The front end of a MVS finger cuff 2000 includes a front-end sensor electronic interface 2002 that is mechanically coupled to a front-end subject physical interface 2004. The front-end sensor electronic interface 2002 includes a PLM subsystem 2006 that is electrically coupled to a multiplexer 2008 and to a PLM controller 2010. The front-end sensor electronic interface 2002 includes a mDLS sensor 2011 that is electrically coupled to a multiplexer 2012 which is coupled to a mDLS controller 2013. The front-end sensor electronic interface 2002 includes a mDLS sensor 2014 that is electrically coupled to a multiplexer 2016 and mDLS controller 2017. The front-end sensor electronic interface 2002 includes an ambient air temperature sensor 1909. The front-end sensor electronic interface 2002 includes a 3-axis accelerator 2018.

The PLM controller 2010 is electrically coupled to a controller 2020 through a Serial Peripheral Interface (SPI) 2022. The mDLS controller 2013 is electrically coupled to the controller 2020 through a SPI 2024. The mDLS sensor 2014 is electrically coupled to the controller 2020 through SPI 2026. The ambient air temperature sensor 1909 is electrically coupled to the controller 2020 through a I2C interface 2028. The 3-axis accelerator 2018 is electrically coupled to the controller 2020 through the I2C interface 2028.

Visual indicator(s) 1940 are electrically coupled to the controller 2020 through a general-purpose input/output (GPIO) interface 2030. A serial port 2032 and a high speed serial port 2034 are electrically coupled to the controller 2020 and a serial power interface 2036 is electrically coupled to the high speed serial port 2034. A voltage regulator 2038 is electrically coupled to the controller 2020. A sensor front-end test component is electrically coupled to the controller 2020 through the GPIO interface 2030.

A sensor cover 2048 is mechanically coupled to the PLM subsystem 2006, a pressure finger cuff 2050 is mechanically coupled to the front-end subject physical interface 2004 and a pneumatic connector 2052 is mechanically coupled to the pressure finger cuff 2050.

4. Apparatus of Multi-Vital-Sign Finger Clip

FIG. 21-27 are views of a multi-vital-sign (MVS) finger clip 2100 that reads physiological light signals and other vital signs, but not blood pressure, according to implementations.

The MVS finger clip in FIGS. 21-27 include a main body 2102 that is mechanically and electrically coupled to a Physiological Light Monitoring (PLM) subsystem 2104. The MVS finger clip in FIGS. 21-27 does not include a finger occlusion cuff, such as finger occlusion cuff 104 in FIG. 1-7. In some implementations, the PLM subsystem 2104 includes one or more emitters of electromagnetic radiation (ER) and one or more detectors of ER which are discussed in greater detail below.

The main body 2102 includes a printed circuit board that is mechanically and electrically coupled to a cable that is mechanically and electrically coupled to a detector of ER in a range of 350 to 1100 nanometers. ER in a range of 350 to 1100 nm includes both visible and near-infrared light. The printed circuit board includes a microprocessor. A flexible ribbon cable electrically connects the detector and an emitter printed circuit board to the cable.

Similar to FIG. 1-7, in FIG. 21-27, only transmissive/transmissive or reflective/reflective measurements are performed. In FIG. 21-27, reflective/transmissive measurements or transmissive/reflective measurements are never performed because there is no usefulness to these measurements. In implementations 1 and 4-6 in table 1 above and in FIG. 21-27, the nitric oxide measurements that are performed as a proxy for glucose are always reflective measurements and never transmissive measurements because the 395 nm ER emission that is performed to measure nitric oxide as a proxy for glucose is visible light which will not be transmitted all the way through a human finger.

Some implementations of the MVS finger clip 2100 includes a digital infrared sensor, such as digital IR sensor 1312 in FIG. 13 and FIG. 16 to measure skin surface temperature. Some implementations of the MVS finger clip 2100 includes a thermistor or a thermocouple to measure skin surface temperature.

In accordance with implementation #1 in Table 1 that is particularly useful for clinical applications, the multi-vital-sign (MVS) finger clip 2100 that determines transmissive SpO2, reflective SpO2, reflective glucose and other vital signs but not blood pressure, according to an implementation. In MVS finger clip 2100, the PLM subsystem 2104 includes an emitter in an emitter/detector that emits ER at 395 nm, 660 nm and 940 nm and that detects ER in the ranges of 375-415 nm, 640-680 nm and 920-960 nm to measure ER that is reflected by the subject finger that is positioned in the PLM subsystem 2104 at 395 nm, 660 nm and 940 nm. The PLM subsystem 2104 also includes a detector that detects ER in the ranges of 640-680 nm and 920-960 nm to transmit ER through the subject finger that is positioned in the PLM subsystem 2104 at 660 nm and 940 nm. The microprocessor of the printed circuit board or a microprocessor that is mounted on a printed circuit board determines transmissive SpO2 at 660 nm by dividing the amount of transmissive ER at 660 nm by the amount of transmissive ER at 940 nm, reflective SpO2 is determined by dividing the amount of reflective ER at 660 nm and by the amount of reflective ER at 940 nm and the reflective glucose is determined by dividing the amount of reflective ER at 395 nm by the amount of reflective ER at 940 nm. In MVS finger clip 2100, the emitter/detector includes both an emitter and a detector so that an amount of the electromagnetic energy that is reflected by the subject is detected, such as the finger of the patient. The amount or level of glucose in the blood of a subject is determined by a ratio of the amount of ER in the 375-415 nm range that detected by the detector in the emitter/detector is divided by the amount of ER in the 920-960 nm range that detected by the emitter/detector, which is then converted to units of mg/dL or mmol/L in reference to a non-linear serpentine function. Only the amount of radiation detected by the emitter/detector in the 375-415 nm range during the resting period of the heartbeat (in between heartbeats) is included in the determination of the amount or level of glucose in the blood of the subject. The resting period of the heartbeat is determined by a ratio of the amount of ER detected in the 640-680 nm range by the emitter/detector divided by the amount of radiation detected in the 920-960 nm range by the emitter/detector.

In accordance with implementation #2 in Table 1, the multi-vital-sign (MVS) finger clip 2100 that determines transmissive SpO2 and other vital signs but not blood pressure, according to an implementation. In MVS finger clip 2100, the PLM subsystem 2104 includes an emitter in an emitter 226 of 660 nm ER and 940 nm ER. The PLM subsystem 2104 also includes a detector that detects ER in the ranges of 640-680 nm and 920-960 nm to transmit ER through the subject finger that is positioned in the PLM subsystem 2104 at 660 nm and 940 nm. The microprocessor of the printed circuit board 2606 or a microprocessor that is mounted on a printed circuit board determines transmissive SpO2 at 660 nm by dividing the amount of transmissive ER at 660 nm by the amount of transmissive ER at 940 nm.

In accordance with implementation #3 in Table 1, the multi-vital-sign (MVS) finger clip 2100 that determines reflective SpO2 and other vital signs but not blood pressure, according to an implementation. In MVS finger clip 2100, the PLM subsystem 2104 includes an emitter in an emitter/detector that emits ER at 660 nm and 940 nm and that detects ER in the ranges of 640-680 nm and 920-960 nm to measure ER that is reflected by the subject finger that is positioned in the PLM subsystem 2104 at 660 nm and 940 nm. The PLM subsystem 2104 does not include a detector on the opposite side of the PLM subsystem 2104 from the emitter that detects ER that is transmitted through the subject finger that is positioned in the PLM subsystem 2104. The microprocessor of the printed circuit board or a microprocessor that is mounted on a printed circuit board determines reflective SpO2 by dividing the amount of reflective ER at 660 nm and by the amount of reflective ER at 940 nm.

In accordance with implementation #4 in Table 1, the multi-vital-sign (MVS) finger clip 2100 that determines reflective glucose and other vital signs but not blood pressure, according to an implementation. In MVS finger clip 2100, the PLM subsystem 2104 includes an emitter in an emitter/detector that emits ER at 395 nm and 940 nm and that detects ER in the ranges of 375-415 nm and 920-960 nm to measure ER that is reflected by the subject finger that is positioned in the PLM subsystem 2104 at 395 nm and 940 nm. The microprocessor of the printed circuit board 406 or a microprocessor that is mounted on a printed circuit board determines reflective glucose by dividing the amount of reflective ER at 395 nm by the amount of reflective ER at 940 nm.

In accordance with implementation #5 in Table 1 that is particularly useful for non-clinical wellness applications, the multi-vital-sign (MVS) finger clip 2100 that determines transmissive SpO2, reflective SpO2, reflective glucose and other vital signs but not blood pressure, according to an implementation. In MVS finger clip 2100, the PLM subsystem 2104 that includes an emitter in an emitter/detector that emits ER at 395 nm, 660 nm and 940 nm and that detects ER in the ranges of 375-415 nm, 640-680 nm and 920-960 nm to measure ER that is reflected by the subject finger that is positioned in the PLM subsystem 2104 at 395 nm, 660 nm and 940 nm. The detector in the emitter/detector is mounted on the same side of the PLM subsystem 2104 as the emitter in the emitter/detector so that the detector in the emitter/detector detects an amount of the electromagnetic energy that is reflected by the subject, such as the finger of the patient. The microprocessor of the printed circuit board or a microprocessor that is mounted on a printed circuit board determines reflective SpO2 by dividing the amount of reflective ER at 660 nm and by the amount of reflective ER at 940 nm and the reflective glucose is determined by dividing the amount of reflective ER at 395 nm by the amount of reflective ER at 940 nm. The amount or level of glucose in the blood of a subject is determined by a ratio of the amount of radiation detected by the emitter/detector in the 375-415 nm range divided by the amount of radiation detected by the emitter/detector in the 920-960 nm range, which is then converted to units of mg/dL or mmol/L in reference to a non-linear serpentine function, regardless of the amount of radiation detected by the emitter/detector in the 375-415 nm range during the resting period of the heartbeat (in between heartbeats). All of radiation detected by the emitter/detector in the 375-415 nm range during the resting period of the heartbeat is used in the determination of the amount or level of glucose in the blood of the subject.

In accordance with implementation #6 in Table 1, the multi-vital-sign (MVS) finger clip 2100 that determines transmissive SpO2, reflective glucose and other vital signs but not blood pressure, according to an implementation. In MVS finger clip 2100, the PLM subsystem 2104 includes an emitter in an emitter/detector that emits ER at 395 nm, 660 nm and 940 nm and that detects ER in the ranges of 375-415 nm and 920-960 nm to measure ER that is reflected by the subject finger that is positioned in the PLM subsystem 2104 at 395 nm and 940 nm. The PLM subsystem 2104 also includes a detector that detects ER in the ranges of 640-680 nm and 920-960 nm to transmit ER through the subject finger that is positioned in the PLM subsystem 2104 at 660 nm and 940 nm. The microprocessor of the printed circuit board or a microprocessor that is mounted on a printed circuit board determines transmissive SpO2 at 660 nm by dividing the amount of transmissive ER at 660 nm by the amount of transmissive ER at 940 nm and the reflective glucose is determined by dividing the amount of reflective ER at 395 nm by the amount of reflective ER at 940 nm.

In accordance with implementation #7 in Table 1, the multi-vital-sign (MVS) finger clip 2100 that determines transmissive SpO2 and reflective SpO2 and other vital signs but not blood pressure, according to an implementation. In MVS finger clip 2100, the PLM subsystem 2104 that includes an emitter in an emitter/detector that emits ER at 660 nm and 940 nm and that detects ER in the ranges of 375-415 nm, 640-680 nm and 920-960 nm to measure ER that is reflected by the subject finger that is positioned in the PLM subsystem 2104 at 660 nm and 940 nm. The PLM subsystem 2104 also includes a detector that detects ER in the ranges of 640-680 nm and 920-960 nm to transmit ER through the subject finger that is positioned in the PLM subsystem 2104 at 660 nm and 940 nm. The microprocessor of the printed circuit board or a microprocessor that is mounted on a printed circuit board determines transmissive SpO2 at 660 nm by dividing the amount of transmissive ER at 660 nm by the amount of transmissive ER at 940 nm and reflective SpO2 is determined by dividing the amount of reflective ER at 660 nm and by the amount of reflective ER at 940 nm.

In some implementations of FIG. 1-37, the PLM subsystem includes a single light-emitting diode structure capable of emitting the three wavelengths required for oximetry and dye dilution measurements. A ring counter causes three semiconductor chips in the device to be energized in sequence. Light is directed toward the blood sample and the reflected light is extended to three synchronous detectors. Each detector operates only when a corresponding semiconductor chip in the light-emitting diode is energized; each detector thus responds only to the intensity of light at a respective wavelength. The outputs of two of the detectors are extended to a ratio circuit for deriving a final measurement. The ratio circuit itself has a high accuracy over the relatively low dynamic range of the ratio values.

In some implementations of FIG. 1-37, the PLM subsystem is an infra-red light emitting and detecting system which has a frequency selected for maximum light absorption by the blood. In some implementations, the PLM subsystem uses a wavelength of approximately 940 nm which measures the light absorption spectrum of oxygenated blood by silicon phototransistors which have peak response at about 940 nm, such as gallium arsenide light emitting diodes. The wavelength (940 nm) is within the absorption spectrum of the hydroxyl constituents of arterial blood. Some devices use measurements of light reflection to indicate blood pulse rates. In some implementations, the PLM subsystem measures light absorption by the blood, using a decrease in back scatter to indicate increased absorption, which in turn indicates increased volume of flow. So the occurrence of each pulse is readily detected. The energy needed in a light absorption device of the type discussed herein is only about $1/1000$ of the energy needed in the light reflecting devices, which causes a reduction in power requirements. In some implementations, the light-detecting photocells and the light-emitting diodes are soldered to one side of a printed circuit board. In some implementations, the PLM subsystem there is no direct electrical connection between the light sources and the detectors. In some implementations of the PLM subsystem, the light which enters detectors does not measure the reflection of light by the artery, but instead the back scatter which remains after the absorption of light by the oxygenated blood in the artery and arterioles. Each light source is an infra-red light emitting diode. Each light emitting diode is essentially monochromatic and does not involve the waste of white light, which has a broad frequency spectrum. The light detectors are photocells which have high sensitivity to the wavelength emitted by the light sources. In some implementations, the PLM subsystem includes a single light detecting device that is very position sensitive, i.e., their placement is vet important because light detection efficiency is dependent on exact location. On the other hand a plurality of detectors eliminates positioning problems, and ensures effective functioning of the sensor in spite of reasonable variations in its location. In some implementations of the PLM subsystem each light detector is physically paired with a light emitter which is the most effective means for obtaining a reliable and consistent sensor signal.

In some implementations of the PLM subsystem of FIG. 1-37, light at two or more frequencies is transmitted through the finger of a subject, and the intensity of the transmitted light is measured on the other side of the finger, which is affected by such variables as depth of blood in the finger and differences in the total hemoglobin concentration in the blood. Inaccuracies caused by these variables can be eliminated or greatly reduced by taking the derivative of the intensity of the transmitted light, and processing the values of these derivatives in association with a set of predetermined pseudo coefficients by applying these to newly developed relationships disclosed in the specification. The result of such processing yields the value of oxygen saturation of the blood of the subject.

In some implementations of FIG. 1-37, the apparatus includes a circuit for the determination of the concentration of any component of a liquid containing three different components having different optical properties, for the determination of the concentration sum of all components and of one other component, for the determination of the product and of the quotient which is formed by the third component, and for the calculation of the blood volume per minute of the heart. One or more light sources, a light sensing element, an optical filter and a lens are disposed in the circuit, and also power supply circuits and control circuits. To these are added a signal converting unit or a sensing system operating on three wavelengths other than the isobestic points or on a range containing these points, containing optical measurement channels, and measuring on the transmission or reflection principle. The signals delivered by the three-channel sensor or by the signal converter, as the case may be, are processed by circuits. The circuits are connected to channel amplifiers, and to the latter are connected subtraction circuits and multiplication circuits. By means of the electronics of suitable construction it is possible to determine in vivo and in vitro both the change with time of the concentration of the dye placed in the blood at any point in the circulatory system, and the volume of the blood.

In some implementations of FIG. 1-37, the PLM subsystem includes a wavelength range within the 700-1300 nm wavelength range. Oxygenated hemoglobin (HbO$_2$) which has extremely low absorption characteristics, whereas disoxygenated hemoglobin (Hb) displays some weak absorption which slowly rises with decreasing wavelengths below 815 nm to a small peak in absorption around 760 nm. Because of these optical properties, the Hb-HbO$_2$ steady state (i.e., the venous-arterial average) can be monitored. In some implementations, the PLM subsystem includes light shielding associated with a light source-detector assembly which is effective both as to extraneous near-infrared as well as extraneous ambient light such that the light entering the body as well as the light detected will be only those wavelengths and only from those light sources intended to be associated with the measurements. Extraneous photon energy at the measuring location which might otherwise enter the body and affect the measurements is therefore desirably absorbed by means associated with the light source-detector assembly of the invention. Another important feature is that the relative space between the light source and the detector elements remain fixed during the measuring period and not be subject to alterations by physical changes in body geometry brought about by breathing, flexing of the body, trauma, and the like. Another spacing important to the invention operation is the relative spacing between the point of light entry, optical face of light source terminal and the point of collecting the measured reflected and scattered light (i.e. optical face) of measuring light detector terminal. In order for the PLM subsystem to accommodate a relatively wide range of body contours, spacing between the points of light entry and exit can be changed. In this regard, an optical module is formed with the light source terminal and the light detector terminal preformed and positioned in optical module.

5. Multi-Vital-Sign Smartphones

Figure 28:
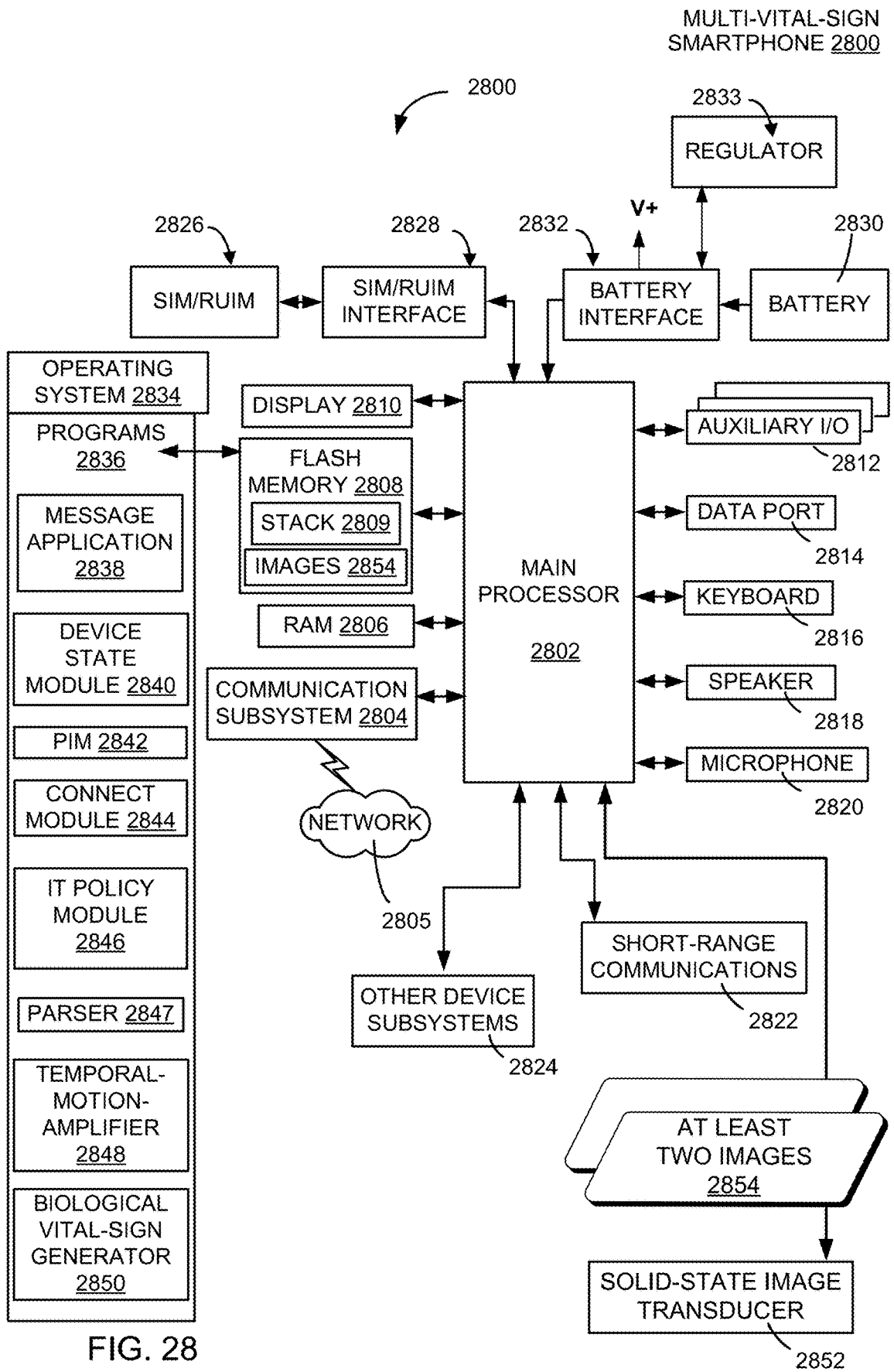
FIG. 28 is a block diagram of a MVS smartphone, according to an implementation.

FIG. 28 is a block diagram of a multi-vital-sign (MVS) smartphone 2800, according to an implementation. The MVS smartphone 2800 includes a number of modules such as a main processor 2802 that controls the overall operation of the MVS smartphone 2800. Communication functions, including data and voice communications, can be performed through a communication subsystem 2804. The communication subsystem 2804 receives messages from and sends messages to wireless networks 2805. In other implementations of the MVS smartphone 2800, the communication subsystem 2804 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 2804 with the wireless network 2805 represents one or more different Radio Frequency (RF) channels. With newer network protocols, these channels are capable of supporting both circuit switched voice communications and packet switched data communications.

The main processor 2802 also interacts with additional subsystems such as a Random Access Memory (RAM) 2806, a flash memory 2808, a display 2810, an auxiliary input/output (I/O) subsystem 2812, a data port 2814, a keyboard 2816, a speaker 2818, a microphone 2820, short-range communications subsystem 2822 and other device subsystems 2824. The other device subsystems 2824 can include any one of the finger occlusion cuff 104 such as and/or the physiological light monitoring (PLM) subsystem 124, 224, 324, 424, 524, 624 or 724 that provide signals to the biological vital sign generator 2850. In some implementations, the flash memory 2808 includes a hybrid femtocell/Wi-Fi® protocol stack 2809. The hybrid femtocell/Wi-Fi® protocol stack 2809 supports authentication and authorization between the MVS smartphone 2800 into a shared Wi-Fi® network and both a 3G, 4G or 5G mobile networks.

The MVS smartphone 2800 can transmit and receive communication signals over the wireless network 2805 after required network registration or activation procedures have been completed. Network access is associated with a subscriber or user of the MVS smartphone 2800. User identification information can also be programmed into the flash memory 2808.

The MVS smartphone 2800 is a battery-powered device and includes a battery interface 2832 for receiving one or more batteries 2830. In one or more implementations, the battery 2830 can be a smart battery with an embedded microprocessor. The battery interface 2832 is coupled to a regulator 2833, which assists the battery 2830 in providing power V+ to the MVS smartphone 2800. Future technologies such as micro fuel cells may provide the power to the MVS smartphone 2800.

The MVS smartphone 2800 also includes an operating system 2834 and modules 2836 to 2850 which are described in more detail below. The operating system 2834 and the modules 2836 to 2850 that are executed by the main processor 2802 are typically stored in a persistent nonvolatile medium such as the flash memory 2808, which may alternatively be a read-only memory (ROM) or similar storage element (not shown). Those skilled in the art will appreciate that portions of the operating system 2834 and the modules 2836 to 2850, such as specific device applications, or parts thereof, may be temporarily loaded into a volatile store such as the RAM 2806. Other modules can also be included.

The subset of modules 2836 that control basic device operations, including data and voice communication applications, will normally be installed on the MVS smartphone 2800 during its manufacture. Other modules include a message application 2838 that can be any suitable module that allows a user of the MVS smartphone 2800 to transmit and receive electronic messages. Various alternatives exist for the message application 2838 as is well known to those skilled in the art. Messages that have been sent or received by the user are typically stored in the flash memory 2808 of the MVS smartphone 2800 or some other suitable storage element in the MVS smartphone 2800. In one or more implementations, some of the sent and received messages may be stored remotely from the MVS smartphone 2800 such as in a data store of an associated host system with which the MVS smartphone 2800 communicates.

The modules can further include a device state module 2840, a Personal Information Manager (PIM) 2842, and other suitable modules (not shown). The device state module 2840 provides persistence, i.e. the device state module 2840 ensures that important device data is stored in persistent memory, such as the flash memory 2808, so that the data is not lost when the MVS smartphone 2800 is turned off or loses power.

The PIM 2842 includes functionality for organizing and managing data items of interest to the user, such as, but not limited to, e-mail, contacts, calendar events, voice mails, appointments, and task items. A PIM application has the ability to transmit and receive data items via the wireless network 2805. PIM data items may be seamlessly integrated, synchronized, and updated via the wireless network 2805 with the MVS smartphone 2800 subscriber's corresponding data items stored and/or associated with a host computer system. This functionality creates a mirrored host computer on the MVS smartphone 2800 with respect to such items.

The MVS smartphone 2800 also includes a connect module 2844, and an IT policy module 2846. The connect module 2844 implements the communication protocols that are required for the MVS smartphone 2800 to communicate with the wireless infrastructure and any host system, such as an enterprise system, with which the MVS smartphone 2800 is authorized to interface. Examples of a wireless infrastructure and an enterprise system are given in FIGS. 28 and 63, which are described in more detail below.

The connect module 2844 includes a set of APIs that can be integrated with the MVS smartphone 2800 to allow the MVS smartphone 2800 to use any number of services associated with the enterprise system. The connect module 2844 allows the MVS smartphone 2800 to establish an end-to-end secure, authenticated communication pipe with the host system. A subset of applications for which access is provided by the connect module 2844 can be used to pass IT policy commands from the host system to the MVS smartphone 2800. This can be done in a wireless or wired manner. These instructions can then be passed to the IT policy module 2846 to modify the configuration of the MVS smartphone 2800. Alternatively, in some cases, the IT policy update can also be done over a wired connection.

The IT policy module 2846 receives IT policy data that encodes the IT policy. The IT policy module 2846 then ensures that the IT policy data is authenticated by the MVS smartphone 2800. The IT policy data can then be stored in the RAM 2806 in its native form. After the IT policy data is stored, a global notification can be sent by the IT policy module 2846 to all of the applications residing on the MVS smartphone 2800. Applications for which the IT policy may be applicable then respond by reading the IT policy data to look for IT policy rules that are applicable.

The programs 2837 can also include a temporal-motion-amplifier 2848 and a biological vital sign generator 2850. In some implementations, the temporal-motion-amplifier 2848 includes a forehead skin-pixel-identification module 4602, a frequency filter (such as frequency filter 4606 in FIG. 46), a regional facial clusterial module (such as regional facial clusterial module 4608 in FIG. 46) and a frequency filter (such as frequency filter 4610 in FIGS. 46 and 47). In some implementations, the temporal-motion-amplifier 2848 includes a forehead skin-pixel-identification module (such as forehead skin-pixel-identification module 4602 in FIG. 46), a spatial bandpass filter (such as spatial bandpass filter 4802 in FIG. 48), a regional facial clusterial module (such as regional facial clusterial module 4608 in FIG. 46) and a temporal bandpass filter (such as temporal bandpass filter 4804 in FIG. 48). In some implementations, the temporal-motion-amplifier 2848 includes a pixel-examiner (such as a pixel-examiner 4902 in FIG. 49), a temporal motion determiner (such as temporal motion determiner 4906 in FIG. 49) and a signal processor (such as signal processor 4908 as in FIG. 49). In some implementations, the temporal-motion-amplifier 2848 includes a forehead-skin pixel identification module (such as forehead-skin pixel identification module 5002 in FIG. 50), a frequency-filter module (such as frequency-filter module 5008 in FIG. 50), a spatial-cluster module (such as spatial-cluster module 5012 in FIG. 50) and a frequency filter module (such as frequency filter module 5016 in FIGS. 50 and 52). In some implementations, the temporal-motion-amplifier 2848 includes the forehead-skin pixel identification module (such as the forehead-skin pixel identification module 5002 in FIG. 50), a spatial bandpass filter module (such as the spatial bandpass filter module 5202 in FIG. 50), a spatial-cluster module (such as the spatial-cluster module 5012 in FIG. 50) and a temporal bandpass filter module (such as the temporal bandpass filter module 5208 in FIG. 52). In some implementations, the temporal-motion-amplifier 2848 includes a pixel-examination-module (such as the pixel-examination-module 5302 in FIG. 50), a temporal motion determiner module (such as the temporal motion determiner module 5306 in FIG. 53) and a signal processing module (such as the signal processing module 5310 in FIG. 53). Furthermore, the solid-state image transducer 2852 captures images 2854 and the biological vital sign generator 28502 generates the biological vital sign(s).

Figure 34:
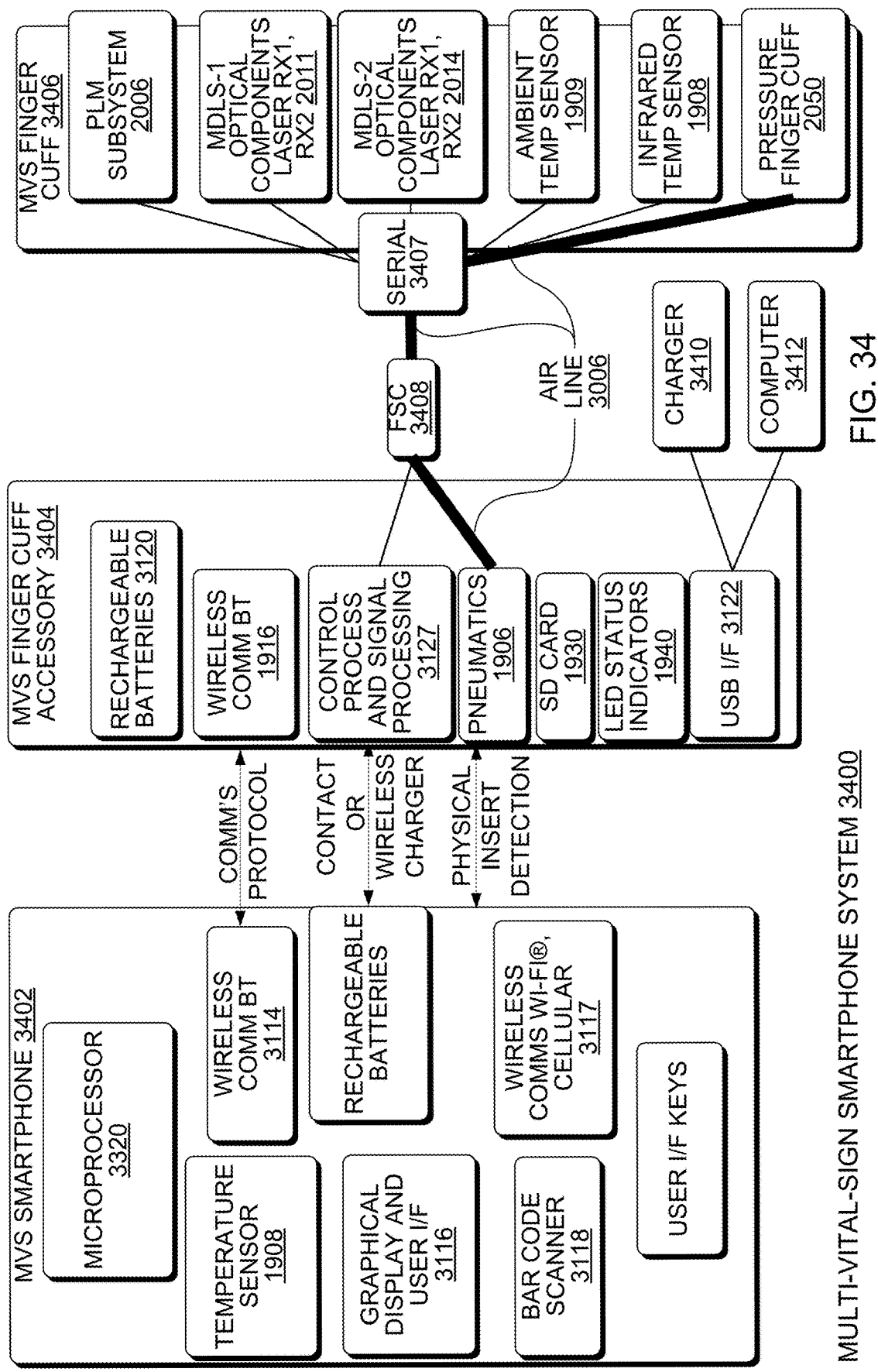
FIG. 34 is a block diagram of a MVS smartphone system, according to an implementation.
Figure 35:
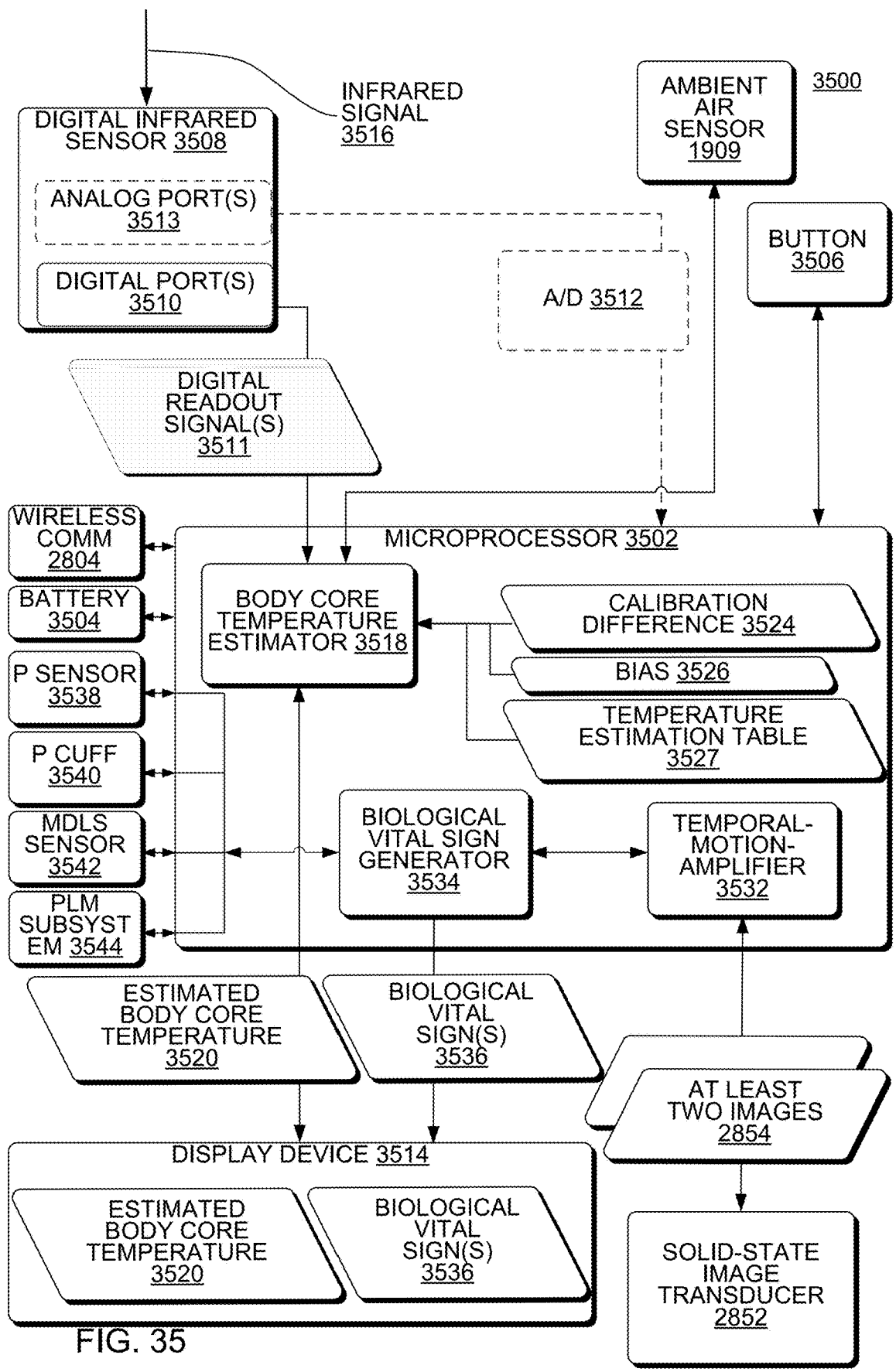
FIG. 35 is a block diagram of a MVS smartphone device that includes a digital infrared sensor, a biological vital sign generator and a temporal motion amplifier, according to an implementation.

In some implementations, the biological vital sign generator 2850 performs the same functions as biological vital sign generator 3534 in FIG. 35 from data received from a MVSFCA in FIGS. 12-20 and 30-34 or a finger clip in FIG. 21-27. In some implementations, the MVS smartphone 2800 includes no biological vital sign generator 2850 and the determined biological vital signs are received through the data port 2814, the communication subsystem 2804 or the short-range communications subsystem 2822 from a MVS-FCA such as the MVSFCAs in FIGS. 12-20 and 30-34 or the MVS finger clip in FIG. 21-27.

The biological vital sign that is generated or received is then is displayed by display 2810 or transmitted by the communication subsystem 2804 or the short-range communications subsystem 2822, enunciated by the speaker 2818 or stored by the flash memory 2808. Examples of the biological vital signs that are displayed on the display 2810 are FIG. 65-66.

Other types of modules can also be installed on the MVS smartphone 2800. These modules can be third party modules, which are added after the manufacture of the MVS smartphone 2800. Examples of third party applications include games, calculators, utilities, etc.

The additional applications can be loaded onto the MVS smartphone 2800 through of the wireless network 2805, the auxiliary I/O subsystem 2812, the data port 2814, the short-range communications subsystem 2822, or any other suitable device subsystem 2824. This flexibility in application installation increases the functionality of the MVS smartphone 2800 and may provide enhanced on-device functions, communication-related functions, or both. For example, secure communication applications enables electronic commerce functions and other such financial transactions to be performed using the MVS smartphone 2800.

The data port 2814 enables a subscriber to set preferences through an external device or module and extends the capabilities of the MVS smartphone 2800 by providing for information or module downloads to the MVS smartphone 2800 other than through a wireless communication network. The alternate download path may, for example, be used to load an encryption key onto the MVS smartphone 2800 through a direct and thus reliable and trusted connection to provide secure device communication.

The data port 2814 can be any suitable port that enables data communication between the MVS smartphone 2800 and another computing device. The data port 2814 can be a serial or a parallel port. In some instances, the data port 2814 can be a USB port that includes data lines for data transfer and a supply line that can provide a charging current to charge the battery 2830 of the MVS smartphone 2800.

The short-range communications subsystem 2822 provides for communication between the MVS smartphone 2800 and different systems or devices, without the use of the wireless network 2805. For example, the short-range communications subsystem 2822 may include an infrared device and associated circuits and modules for short-range communication. Examples of short-range communication standards include standards developed by the Infrared Data Association (IrDA), Bluetooth®, and the 802.11 family of standards developed by IEEE. In other implementations, Zigbee® or Z-Wave® can be used instead of Bluetooth®.

Bluetooth® is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth® was originally conceived as a wireless alternative to RS-232 data cables. Bluetooth® can connect several devices, overcoming problems of synchronization. Bluetooth® operates in the range of 2400-2483.5 MHz (including guard bands), which is in the globally unlicensed Industrial, Scientific and Medical (ISM) 2.4 GHz short-range radio frequency band. Bluetooth® uses a radio technology called frequency-hopping spread spectrum. The transmitted data is divided into packets and each packet is transmitted on one of the 79 designated Bluetooth® channels. Each channel has a bandwidth of 1 MHz. The first channel starts at 2402 MHz and continues up to 2480 MHz in 1 MHz steps. The first channel usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth® 2.0+EDR, π/4-DQPSK and 8DPSK modulation may also be used between compatible devices. Devices functioning with GFSK are said to be operating in basic rate (BR) mode where an instantaneous data rate of 1 Mbit/s is possible. The term Enhanced Data Rate (EDR) is used to describe π/4-DPSK and 8DPSK schemes, each giving 2 and 3 Mbit/s respectively. The combination of these (BR and EDR) modes in Bluetooth® radio technology is classified as a "BR/EDR radio". Bluetooth® is a packet based protocol with a master-slave structure. One master may communicate with up to 7 slaves in a piconet; all devices share the master's clock. Packet exchange is based on the basic clock, defined by the master, which ticks at 312.5 µs intervals. Two clock ticks make up a slot of 625 µs; two slots make up a slot pair of 1250 µs. In the simple case of single-slot packets the master transmits in even slots and receives in odd slots; the slave, conversely, receives in even slots and transmits in odd slots. Packets may be 1, 3 or 5 slots long but in all cases the master transmit will begin in even slots and the slave transmit in odd slots. The devices can switch roles, by agreement, and the slave can become the master (for example, a headset initiating a connection to a phone will necessarily begin as master, as initiator of the connection; but may later become a slave). The Bluetooth® Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion. Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth® can expose private data or allow the connecting party to control the Bluetooth® device. For security reasons it is necessary to be able to recognize specific devices and thus enable control over which devices are allowed to connect to a given Bluetooth® device. At the same time, it is useful for Bluetooth® devices to be able to establish a connection without user intervention (for example, as soon as the Bluetooth® devices of each other are in range). To resolve this conflict, Bluetooth® uses a process called bonding, and a bond is created through a process called pairing. The pairing process is triggered either by a specific request from a user to create a bond (for example, the user explicitly requests to "Add a Bluetooth® device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices.

In use, a received signal such as a text message, an e-mail message, or web page download will be processed by the communication subsystem 2804 and input to the main processor 2802. The main processor 2802 will then process the received signal for output to the display 2810 or alternatively to the auxiliary I/O subsystem 2812. A subscriber may also compose data items, such as e-mail messages, for example, using the keyboard 2816 in conjunction with the display 2810 and possibly the auxiliary I/O subsystem 2812. The auxiliary I/O subsystem 2812 may include devices such as: a touch screen, mouse, track ball, infrared fingerprint detector, or a roller wheel with dynamic button pressing capability. The keyboard 2816 is preferably an alphanumeric keyboard and/or telephone-type keypad. However, other types of keyboards may also be used. A composed item may be transmitted over the wireless network 2805 through the communication subsystem 2804.

For voice communications, the overall operation of the MVS smartphone 2800 is substantially similar, except that the received signals are output to the speaker 2818, and signals for transmission are generated by the microphone 2820. Alternative voice or audio I/O subsystems, such as a voice message recording subsystem, can also be implemented on the MVS smartphone 2800. Although voice or audio signal output is accomplished primarily through the speaker 2818, the display 2810 can also be used to provide additional information such as the identity of a calling party, duration of a voice call, or other voice call related information.

Figure 29:
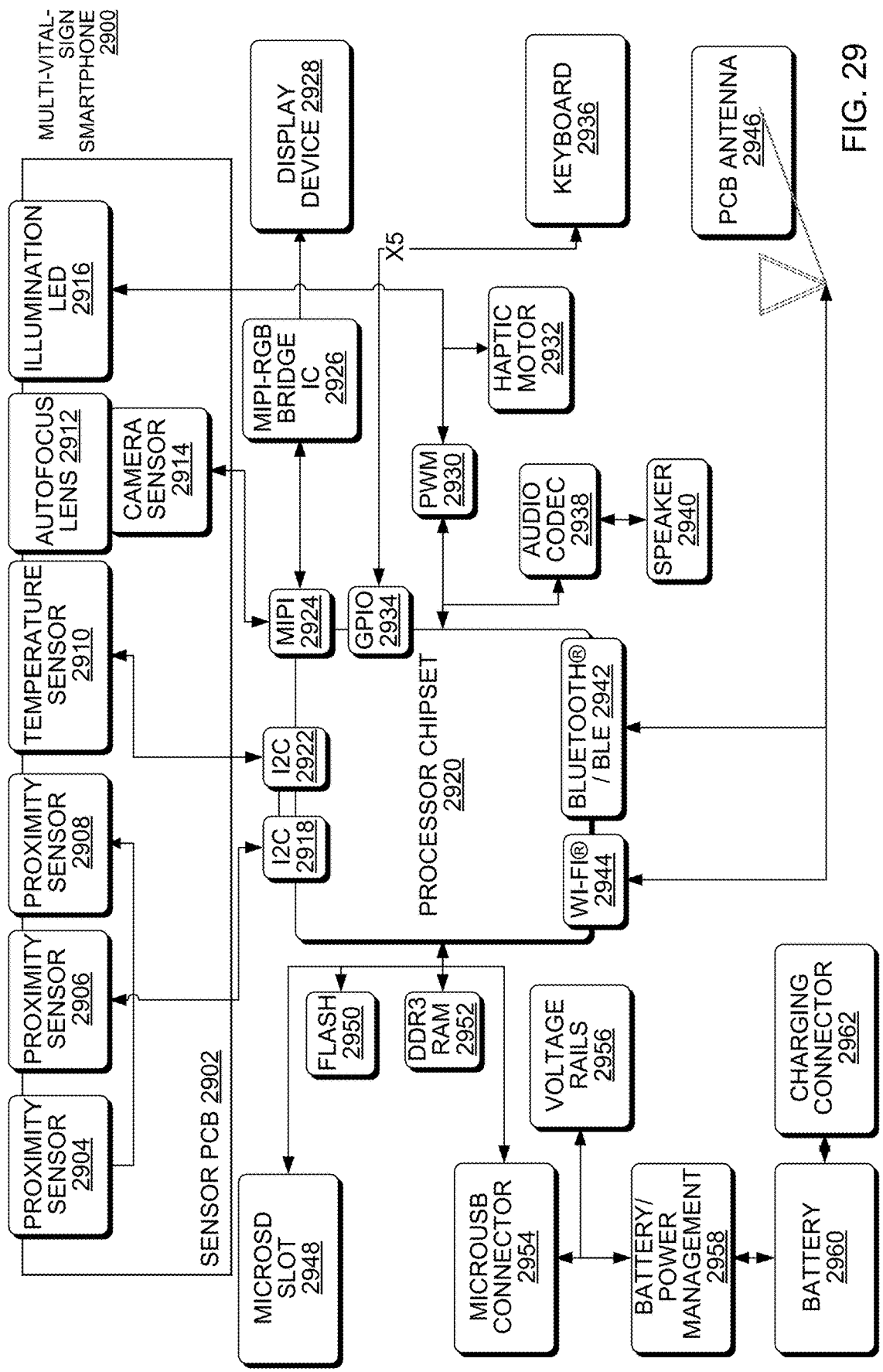
FIG. 29 is a block diagram of a MVS smartphone, according to an implementation.

FIG. 29 is a block diagram of a MVS smartphone 2900, according to an implementation. MVS Smartphone 2900 is one implementation of MVS Smartphone 3004 in FIG. 30. The MVS Smartphone 2900 includes a sensor printed circuit board (PCB) 2902. The sensor PCB 2902 includes proximity sensors 2904, 2906 and 2908, and temperature sensor 2910, autofocus lens 2912 in front of camera sensor 2914 and an illumination light emitting diode (LED) 2916. The includes proximity sensors 2904, 2906 and 2908 are operably coupled to a first I₂C port 2918 of a microprocessor 2920. One example of the microprocessor 2920 is a Qualcomm Snapdragon microprocessor chipset. The temperature sensor 2910 is operably coupled to a second I²C port 2922 of the microprocessor 2920. The I²C standard is a multi-master, multi-slave, single-ended, serial computer bus developed by Philips Semiconductor (now NXP Semiconductors) for attaching lower-speed peripheral ICs to processors and microcontrollers in short-distance, intra-board communication. The camera sensor 2914 is operably coupled to a MIPI port 2924 of the microprocessor 2920. The MIPI standard is defined by the MIPI standard is defined by the MIPI Alliance, Inc. of Piscataway, N.J. The MIPI port 2924 is also operably coupled to a MIPI RGB bridge 2926, and the MIPI RGB bridge 2926 is operably coupled to a display device 2928 such as a TFT Color Display (2.8"). The illumination LED 2916 is operably coupled to a pulse-width modulator (PWM) 2930 of the microprocessor 2920. The PWM 2930 is also operably coupled to a haptic motor 2932. The microprocessor 2920 also includes a GPIO port 2934, the GPIO port 2934 being a general-purpose input/output that is a generic pin on an integrated circuit or computer board whose behavior—including whether GPIO port 2934 is an input or output pin—is controllable by the microprocessor 2920 at run time. The GPIO port 2934 is operably coupled to a keyboard 2936, such as a membrane keypad (3× buttons). The microprocessor 2920 is also operably coupled to an audio codec 2938 with is operably coupled to a speaker 2940. The microprocessor 2920 also includes a Bluetooth® communication port 2942 and a Wi-Fi® communication port 2944, that are both capable of communicating with a PCB antenna 2946. In other implementations, Zigbee® or Z-Wave® can be used instead of Bluetooth®. The microprocessor 2920 is also operably coupled to a micro SD slot (for debugging purposes), a flash memory unit 2950, a DDR3 random access memory unit 2952 and a micro USB port 2954 (for debugging purposes). The micro USB port 2954 is operably coupled to voltage rails and a battery power/management component 2958. The battery power/management component 2958 is operably coupled to a battery 2960, which is operably coupled to a charger connector 2962.

Biological vital signs are received through the micro USB connector 2954, the Wi-Fi® 2944 or the Bluetooth® 2942 from a MVSFCA such as the MVSFCAs in FIGS. 12-20 and 30-34 or the MVS finger clip in FIG. 21-27. The biological vital signs that are received are then displayed by display 2928 and/or transmitted by the Wi-Fi® 2944 or the Bluetooth® 2942, enunciated by the speaker 2940 or stored by the flash memory 2950. Examples of the biological vital signs that are displayed on the display 2928 are FIG. 65-66.

6. Apparatus of Multi-Vital-Sign System

FIG. 30 is a block diagram of a multi-vital-sign (MVS) smartphone system 3000, according to an implementation. The MVS system 3000 includes two communicatively coupled devices; a multi-vital-sign finger cuff accessory MVSFCA 3002 and a multi-vital-sign smartphone (MVS Smartphone) 3004. The MVSFCA 3002 includes a MVS finger cuff 3006. The MVS system 3000 is one example of the MVS apparatus 5504. In some implementations, the MVS system 3000 captures, stores and exports raw data from all supported sensors in the MVS finger cuff 3006.

MVS system 3000 provides a flexible human vital sign measurement methodology that supports different measurement methods and techniques. The MVS system 3000 can be used in a clinical setting or a home setting for the collection of human vital signs. The MVSFCA 3002 can be configured to detect blood pressure only, SpO2 only, heart rate only, respiration only, or any combination of vital signs that the MVSFCA is capable of detecting. The MVS Smartphone 3004 includes non-slip/slide exterior surface material. Heart-rate can be determined in all devices, apparatus and methods disclosed herein from the pulsatile component of the SpO2 measurement. The SpO2 measurement used in the determination of the heart-rate can either transmissive SpO2 (transmissive 660 nm/transmissive 940 nm) or reflective SpO2 (reflective 660 nm/reflective 940 nm). The number of pulses is counted in the pulsatile component to determine the heart-rate. Heart-rate variability can be determined in all devices, apparatus and methods disclosed herein as the maximum deviation time from the average heartbeat duration, in a particular period. The deviation time is the time between any two successive heartbeats in the particular period. The maximum deviation time is the largest or greatest deviation of the deviation times in the particular period. In more specific analysis of heart-rate variability, methods such as time-domain methods, geometric methods, frequency-domain or non-linear methods are implemented. Respiration rate can be determined in all devices, apparatus and methods disclosed herein from cardiac output based on pulse analysis (from SpO2) and stroke volume (from DLS blood pressure sensors). Cardiac output has a linear relationship with respiration rate, as published by Wallin et al.

The MVSFCA 3002 includes a pneumatic engine 3005 and a MVS finger cuff 3006 that are operably coupled to each other through an air line 1404 and a communication path 3010, such as high speed serial link A high speed serial link is especially important because the cable of a serial link is quite a bit a bit thinner and more flexible than a parallel cable, which provides a lighter cable that can be more easily wrapped around the MVSFCA 3002. A cuff bladder of the MVS finger cuff 3006 expands and contracts in response to air pressure from the air line 1404.

Some implementations of the MVS finger cuff 3006 include a finger occlusion cuff 3016 and a PLM subsystem 3018. The MVS finger cuff in FIG. 1-7 are examples of the MVS finger cuff 3006. The finger occlusion cuff 3016 and a PLM subsystem 3018 are shown in greater detail in FIG. 1-12. In some implementations, the MVS finger cuff 3006 includes at least one miniaturized dynamic light scattering (mDLS) sensor and the PLM subsystem 3018. The PLM subsystem in FIG. 1-12 is one example of the PLM subsystem 3018. PLM subsystem 3018 and the finger occlusion cuff 3016 are operably coupled to a common board in the MVS finger cuff 3006 and the common board is operably coupled through the communication path 3010 to a printed circuit board that is in the base of MVSFCA 3002.

In some implementations, the MVS finger cuff 3006 integrates the PLM subsystem and at least one miniaturized dynamic light scattering (mDLS) sensor into a single sensor. Both of the which are attached to the MVS finger cuff 3006. The PLM and mDLS implementation of the MVS finger cuff 3006 measures the following primary and secondary human vital sign measurements through a PLM subsystem from either an index finger or a middle finger; on both the left or right hands at heart height to ensure an accurate measurement: Primary human vital sign measurements such as blood pressure (diastolic and systolic), SpO2, heart rate and respiration rate. Secondary human vital sign measurements include heart rate variability and blood flow. The PLM subsystem optically measures light that passes through tissue from at least one IR light emitters. The PLM subsystem includes one infrared detector that detects infrared energy at two different transmitted wavelengths; red and near infrared. Signal fluctuations of the light are generally attributed to the fluctuations of the local blood volume due to the arterial blood pressure wave, which means that the amount of blood in the illuminated perfused tissue fluctuates at the rate of heartbeats. So does the light transmission or light refraction. Therefore, PLM data is an indirect method of the estimation of the blood volume changes. The blood pressure is estimated from data from the mDLS sensor in conjunction with a blood pressure finger cuff which mimics pressure cycle to create an occlusion like the arm cuff. The biological target is illuminated by a laser, the signal is collected by a detector and the time dependency of the laser speckle characteristics are analyzed. The mDLS geometry is designed to create direct signal scattering reflection of the signal into the detector. Each mDLS sensor includes two photo diode receivers and one laser transmitter.

In some implementations, the MVS finger cuff 3006 is replaceable, detachable and removable from the MVSFCA 3002. In some implementations, the MVS finger cuff 3006 is integrated into the MVSFCA 3002. The MVS finger cuff 300 that is replaceable, detachable and removable from the MVSFCA 3002 is beneficial in two ways: 1) the MVS finger cuff 3006 is replaceable in the event of damage 2) the MVS finger cuff 3006 can be detached from the MVSFCA 3002 and then attached to a custom connector cable (pneumatic and electrical) that allows a patient to wear the MVS finger cuff 3006 for continuous monitoring, and (3) servicing the device. The replaceable MVS finger cuff 3006 can have photo optic component(s) (e.g. 2×mDLS) that are cleanable between patients and replaceable in the event of failure of the inflatable cuff or the photo optic component(s). In some implementations, the cuff bladder of the removable MVS finger cuff 3006 is translucent or transparent to transparent to the mDLS laser wavelengths and which in some implementations allows the position of the MVS finger cuff 3006 to be adjusted in relation to specific parts of human anatomy for optimal function of the sensors and comfort to the patient.

The MVSFCA 3002 and the MVS Smartphone 3004 can be operably coupled to each other through a communication path 3012 to exchange data and control signals and a 4 point electrical recharge interface (I/F) line 3014 recharge from a conventional wall outlet. In some implementations, the 4 point electrical recharge interface (I/F) line 3014 is a 3 point electrical recharge interface (I/F) line. The MVSFCA 3002 and the MVS Smartphone 3004 do not need to be physically attached to each other for measurement operation by either the MVSFCA 3002 or the MVS Smartphone 3004. In some implementations, the MVSFCA 3002 has at least one universal serial bus (USB) port(s) for bi-directional communication, command, control, status and data transfer with another devices with both standard and propriety protocols using USB infrastructure. USB protocol is defined by the USB Implementers Forum at 5440 SW Westgate Dr. Portland Oreg. 94221. In some implementations, the MVS Smartphone 3004 has at least one USB port(s) for communication with other devices via USB, such as connected to a MVSFCA 3002 for the purposes of transferring the raw sensor data from the device to a computer for analysis. Biological vital signs are received by MVS Smartphone 3004 through the Bluetooth® link 3012 from a MVSFCA such as in FIG. 12-20 or a MVS finger cuff in FIG. 21-27 in FIG. 12-20 or the MVS finger clip in FIG. 21-27. The biological vital signs that are received are then displayed by display 2928 an/or transmitted by the Wi-Fi@ 2944 or the Bluetooth® 2942, enunciated by the speaker 2940 or stored by the flash memory 2950. Examples of the biological vital signs that are displayed on the display 2928 are FIG. 65-66. In other implementations, Zigbee® or Z-Wave® can be used instead of Bluetooth®.

Figure 31:
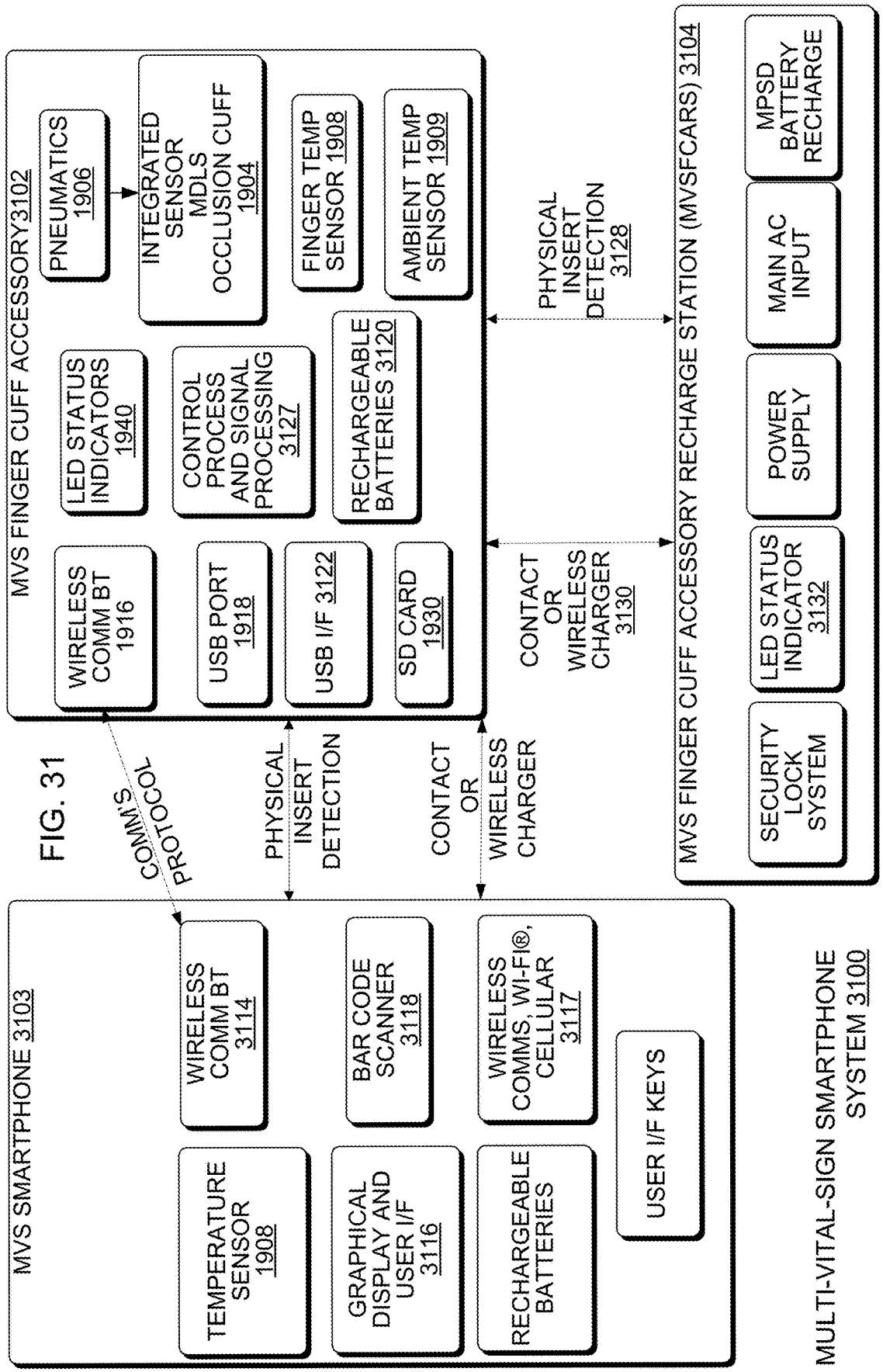
FIG. 31 is a block diagram of a MVS smartphone system, according to an implementation.

FIG. 31 is a block diagram of a MVS smartphone system 3100, according to an implementation. The MVS smartphone system 3100 includes three communicatively coupled devices; a MVS finger cuff accessory (MVSFCA) 3102, a multi-vital-sign smartphone (MVS Smartphone) 3103 and a multi-vital-sign finger cuff accessory Recharge Station (MVSFCARS) 3104. MVSFCA 3102 is one implementation of MVSFCA 3002 in FIG. 30. MVS Smartphone 3103 is one implementation of MVS Smartphone 3004 in FIG. 30. The MVS smartphone system 3100, the MVSFCA 3102 and the MVS Smartphone 3103 are all examples of the MVS apparatus 5504. The MVS Smartphone 3103 captures, stores and exports raw data from all supported sensors in the system. More specifically, the MVS Smartphone 3103 extracts and displays vital signs and transfers the vital-signs to either a remote third party, hub, bridge etc., or a device manager, or directly to remote EMR/HER/Hospital systems or other third party local or cloud based systems. MVS smartphone system 3100 provides a flexible human vital sign measurement methodology that supports different measurement methods and techniques. The MVS smartphone system 3100 can be used in a clinical setting for the collection of human vital signs.

Some implementations of the MVSFCA 3102 include a MVS finger cuff 1904 that is fixed into the MVSFCA 3102, rather than the replaceable, detachable and removable MVS finger cuff 3006 in FIG. 30. The MVS finger cuff 1904 includes a PLM subsystem and at least one mDLS sensor. The MVS finger cuff 1904 is powered via an air line (e.g. 1404 in FIG. 30) by a pneumatic engine 1906 that provides air pressure to inflate the cuff bladder of the MVS finger cuff 1904 and the controlled release of that pressure. In some implementations, the air line 1404 is ⅙" (4.2 mm) in diameter. The MVS finger cuff 1904 in FIGS. 31 and 33 is the same as the MVS finger cuffs in FIGS. 1-11 and 34.

In some implementations, a body surface temperature of a human is also sensed by an infrared finger temperature sensor 1908 that is integrated into the MVSFCA 3102 in which the body surface temperature is collected and managed by the MVSFCA 3102. One example of the pneumatic engine 1906 is the pneumatic engine 3005 and the pneumatic system components 4200 in FIG. 42.

In some implementations, a single stage measurement process is required to measure all vital signs in one operation by the MVS Smartphone 3103 by the replaceable, detachable and removable MVS finger cuff 3006 or the MVS finger cuff 1904 or the infrared finger temperature sensor 1908. However, in some implementations, a two stage measurement process is performed in which the MVSFCA 3102 measures some vital signs through the replaceable, detachable and removable MVS finger cuff 3006 or the MVS finger cuff 1904; and in the second stage, the body surface temperature is measured through an infrared finger temperature sensor 1908 in the MVS Smartphone device 3103. One implementation of the infrared finger temperature sensor 1908 is digital infrared sensor 1312 in FIG. 41.

The MVSFCA 3102 operates in two primary modes, the modes of operation based on who takes the measurements, a patient or an operator. The two modes are: 1) Operator Mode in which an operator operates the MVSFCA 3102 to take a set of vital sign measurements of another human. The operator is typically clinical staff or a home care giver. 2) Patient Mode in which a patient uses the MVSFCA 3102 to take a set of vital sign measurements of themselves. In some implementations, the MVSFCA 3102 provides both the main measurement modes for patient and operator. The primary measurement areas on the human to be measured are 1) Left hand, index and middle finger, 2) right hand, index and middle finger, and 3) human forehead temperature (requires the other device to perform temperature measurement). The MVSFCA 3102 is portable, light weight, hand held and easy to use in primary and secondary modes of operation in all operational environments.

Given the complex nature of integration into hospital networks, in some implementations, in some implementations the MVSFCA 3102 does not include site communication infrastructure, rather the collected data (vital sign) is extracted from the MVSFCA 3102 via a USB port or by a USB mass storage stick that is inserted into the MVSFCA 3102 or by connecting the MVSFCA 3102 directly to a PC system as a mass storage device itself.

The MVS smartphone 3103, when connected to a wireless Bluetooth® communication component 1916 of the MVSFCA 3102 via a wireless Bluetooth® communication component 3114, can be a slave to the MVSFCA 3102. The MVS Smartphone 3103 reports status, measurement process, and measurement measurements to the user via the MVSFCA 3102. The MVS Smartphone 3103 provides a user input method to the MVSFCA 3102 via a graphical user interface on a LCD display 3116 which displays data representative of the measurement process and status. In one implementation, the wireless Bluetooth® communication component 1916 of the MVSFCA 3102 includes communication capability with cellular communication paths (3G, 4G and/or 5G) and/or Wi-Fi® communication paths and the MVSFCA 3102 is not a slave to the captures vital sign data and transmits the vital sign data via the wireless Bluetooth® communication component 1916 in the MVSFCA 3102 to the middle layer 5506 in FIG. 55 or the MVS Smartphone 3103 transmits the vital sign data via the communication component 3117 of the MVS Smartphone 3103 to the bridge 5520, a Wi-Fi® access point, a cellular communications tower, a bridge 5520 in FIG. 55. In other implementations, Zigbee® or Z-Wave® can be used instead of Bluetooth®.

In some implementations, the MVS Smartphone 3103 provides communications with other devices via a communication component 3117 of the MVS Smartphone 3103. The communication component 3117 has communication capability with cellular communication paths (3G, 4G and/or 5G) and/or Wi-Fi® communication paths. For example, the MVSFCA 3102 captures vital sign data and transmits the vital sign data via the wireless Bluetooth® communication component 1916 in the MVSFCA 3102 to the wireless Bluetooth® communication component 3114 in the MVS Smartphone 3103, and the MVS Smartphone 3103 transmits the vital sign data via the communication component 3117 of the MVS Smartphone 3103 to the middle layer 5506 in FIG. 55 or the MVS Smartphone 3103 transmits the vital sign data via the communication component 3117 of the MVS Smartphone 3103 to the bridge 5520, a Wi-Fi® access point, a cellular communications tower, a bridge 5520 in FIG. 55.

In some implementations, when the MVS Smartphone 3103 is connected to the MVSFCA 3102, the MVS Smartphone 3103 performs human bar code scan by a bar code scanner 3118 or identification entry as requested by MVSFCA 3102, the MVS Smartphone 3103 performs an operator bar code scan or identification entry as requested by MVSFCA 3102, the MVS Smartphone 3103 performs human temperature measurement as requested by MVSFCA 3102, the MVS Smartphone 3103 displays information that is related to the MVSFCA 3102 direct action, the MVS Smartphone 3103 starts when the MVSFCA 3102 is started, and the MVS Smartphone 3103 is shutdown under the direction and control of the MVSFCA 3102, and the MVS Smartphone 3103 has a self-test mode that determines the operational state of the MVSFCA 3102 and sub systems, to ensure that the MVSFCA 3102 is functional for the measurement. In other implementations, when the MVS Smartphone 3103 is connected to the MVSFCA 3102, the MVS Smartphone 3103 performs human bar code scan or identification entry as requested by MVS Smartphone 3103, the MVS Smartphone 3103 performs an operator bar code scan or identification entry as requested by MVS Smartphone 3103, the MVS Smartphone 3103 performs human temperature measurement as requested by MVS Smartphone 3103 and the MVS Smartphone 3103 displays information that is related to the MVSFCA 3102 direct action. In some implementations, the information displayed by the MVS Smartphone 3103 includes date/time, human identification number, human name, vitals measurement such as blood pressure (diastolic and systolic), SpO2, heart rate, temperature, respiratory rate, MVSFCA 3102 free memory slots, battery status of the MVS Smartphone 3103, battery status of the MVSFCA 3102, device status of the MVSFCA 3102, errors of the MVS Smartphone 3103, device measurement sequence, measurement quality assessment measurement, mode of operation, subject and operator identification, temperature, measurement, display mode and device revision numbers of the MVS Smartphone 3103 and the MVSFCA 3102. In some implementations, when a body surface temperature of a human is also sensed by an infrared sensor in the MVS smartphone 3103, the body surface temperature is collected and managed by the MVSFCA 3102. In other implementations, when a body surface temperature of a human is sensed by an infrared sensor in the MVS smartphone 3103, the body surface temperature is not collected and managed by the MVSFCA 3102.

In some implementations, the multi-vital-sign finger cuff accessory (MVSFCA) 3102 includes the following sensors and sensor signal capture and processing components that are required to extract the required primary and secondary human vital signs measurements: the MVS finger cuff 1904 that includes a PLM subsystem and two mDLS sensors, the infrared finger temperature sensor 1908 and an ambient air temperature sensor 1909, and in some further implementation, non-disposable sensors for other human measurements. In some implementations, data sample rates for PLM subsystem is 2×200 Hz×24 bit=9600 bits/sec, for each of the mDLS sensors is 32 kHz×24 bit=1,572,864 bit/sec and for the ambient air temperature sensor is less than 1000 bps. Two mDLS sensors are included in the MVSFCA 3102 to ensure that one or both sensors delivers a good quality signal, thus increasing the probability of obtaining a good signal from a mDLS sensor.

The MVS Smartphone 3103 performs concurrent two stage measurement processes for all measurements. The measurement process performed by the MVS Smartphone 3103 is controlled and guided from the MVS Smartphone 3103 via the GUI on the MVSFCA 3102. The measurements are sequenced and configured to minimize time required to complete all measurements. In some implementations, the MVS Smartphone 3103 calculates the secondary measurements of heart rate variability and blood flow. The MVS Smartphone 3103 commands and controls the MVSFCA 3102 via a wireless Bluetooth® protocol communication path 3012 and in some further implementations, the MVSFCA 3102 communicates to other devices through Bluetooth® protocol communication line (not shown), in addition to the communications with the MVS Smartphone 3103 which could also be concurrent. In some further implementations, the MVS Smartphone 3103 communicates to other devices through Bluetooth® protocol communication line (not shown), in addition to the communications with the MVSFCA 3102 device, which could also be concurrent.

MVSFCA 3102 includes a USB port 1918 for interface with the MVS Smartphone 3103 only, such as the MVS Smartphone 3103, to perform the following functions: recharge the internal rechargeable batteries 1920 of the MVSFCA 3102, export sensor data sets to a windows based computer system, firmware update of the MVSFCA 3102 via an application to control and manage the firmware update of the MVSFCA 3102 and configuration update of the MVSFCA 3102. The MVSFCA 3102 does not update the MVS Smartphone 3103 firmware. The MVSFCA 3102 also includes internal rechargeable batteries 1920 that can be recharged via a USB port 3122, which transmits charge, and the MVSFCA 3102 also includes an external direct DC input providing a fast recharge. The internal batteries of the MVSFCA 3102 can be recharged when the MVSFCA 3102 is powered-off but while connected to USB or DC input. In some implementations, the MVSFCA 3102 can recharge the MVS Smartphone 3103 from its internal power source over a wireless charging connection. In some implementations, the internal rechargeable batteries 1920 provide sufficient operational life of the MVSFCA 3102 on a single charge to perform at least 2 days of full measurements before recharging of the internal rechargeable batteries 1920 of the MVSFCA 3102 is required.

In some implementations, the MVSFCA 3102 includes an internal non-volatile, non-user removable, data storage device 1930 for up to 20 human raw measurement data sets. The data storage device 1930 can be removed by a technician when the data storage device 1930 is determined to be faulty. A human measurement set contains all measurement data and measurements acquired by the MVSFCA 3102, including the temperature measurement from the MVS Smartphone 3103. The internal memory is protected against data corruption in the event of an abrupt power loss event. The MVSFCA 3102 and the MVS Smartphone 3103 have a human-form fit function sensor and device industrial/mechanical design. The MVSFCA 3102 also includes antimicrobial exterior material to and an easy clean surface for all sensor and device surfaces. The MVSFCA 3102 stores in the data storage device 1930 an "atomic" human record structure that contains the entire data set recording for a single human measurement containing all human raw sensor signals and readings, extracted human vitals, and system status information. The MVSFCA 3102 includes self-test components that determine the operational state of the MVSFCA 3102 and sub systems, to ensure that the MVSFCA 3102 is functional for measurement. The MVSFCA 3102 includes a clock function for date and time. In some implementations. The date and time of the MVSFCA 3102 is be updated from the MVS Smartphone 3103. In some implementations, the MVSFCA 3102 includes user input controls, such as a power on/off switch (start/stop), an emergency stop control to bring the MVS finger cuff to a deflated condition. In some implementations, all other input is supported via the MVS Smartphone 3103 via on screen information of the MVS Smartphone 3103. In some implementations, the MVSFCA 3102 includes visual indicators 1940 such as a fatal fault indicator that indicates device has failed and will not power up, a device fault indicator (that indicates the MVSFCA 3102 has a fault that would affect the measurement function), battery charging status indicator, battery charged status indicator, a battery fault status indicator.

The components (e.g. 1904, 1906, 1908, 1909, 1916, 1918, 1920, 3122, 1930 and 1940) in the MVSFCA 3102 are controlled by a control process and signal processing component 3127. The control process and signal processing component can implemented by a microprocessor or by a FPGA.

The multi-vital-sign finger cuff accessory Recharge Station (MVSFCARS) 3104, provides electrical power to recharge the MVSFCA 3102. The MVSFCARS 3104 can provide electrical power to recharge the batteries of the MVSFCA 3102 either via a physical wired connection or via a wireless charger 3130. In some implementations, the MVSFCARS 3104 does not provide electrical power to the MVSFCA 3102 because the MVSFCA 3102 includes internal rechargeable batteries 1920 that can be recharged via either USB port 3122 or a DC input.

MVS Smartphone 3103 includes a connection status indicator (connected/not connected, fault detected, charging/not charging), a connected power source status indicator, (either USB or DC input) and a power On/Off status indicator. The visual indicators are visible in low light conditions in the home and clinical environment.

The MVSFCA 3102 is hand held and portable. The MVSFCA 3102 includes non-slip/slide exterior surface material.

Vital signs are received through the wireless Bluetooth® communication component 3114 from a MVSFCA such as the MVSFCAs in FIGS. 12-20 and 30-34 or the MVS finger clip in FIG. 21-27. The vital signs that are received are then displayed by LCD display 3116 and/or transmitted by the communication component 3117, enunciated by a speaker or stored by a flash memory. Examples of the biological vital signs that are displayed on the display 3116 are FIG. 65-66.

Figure 32:
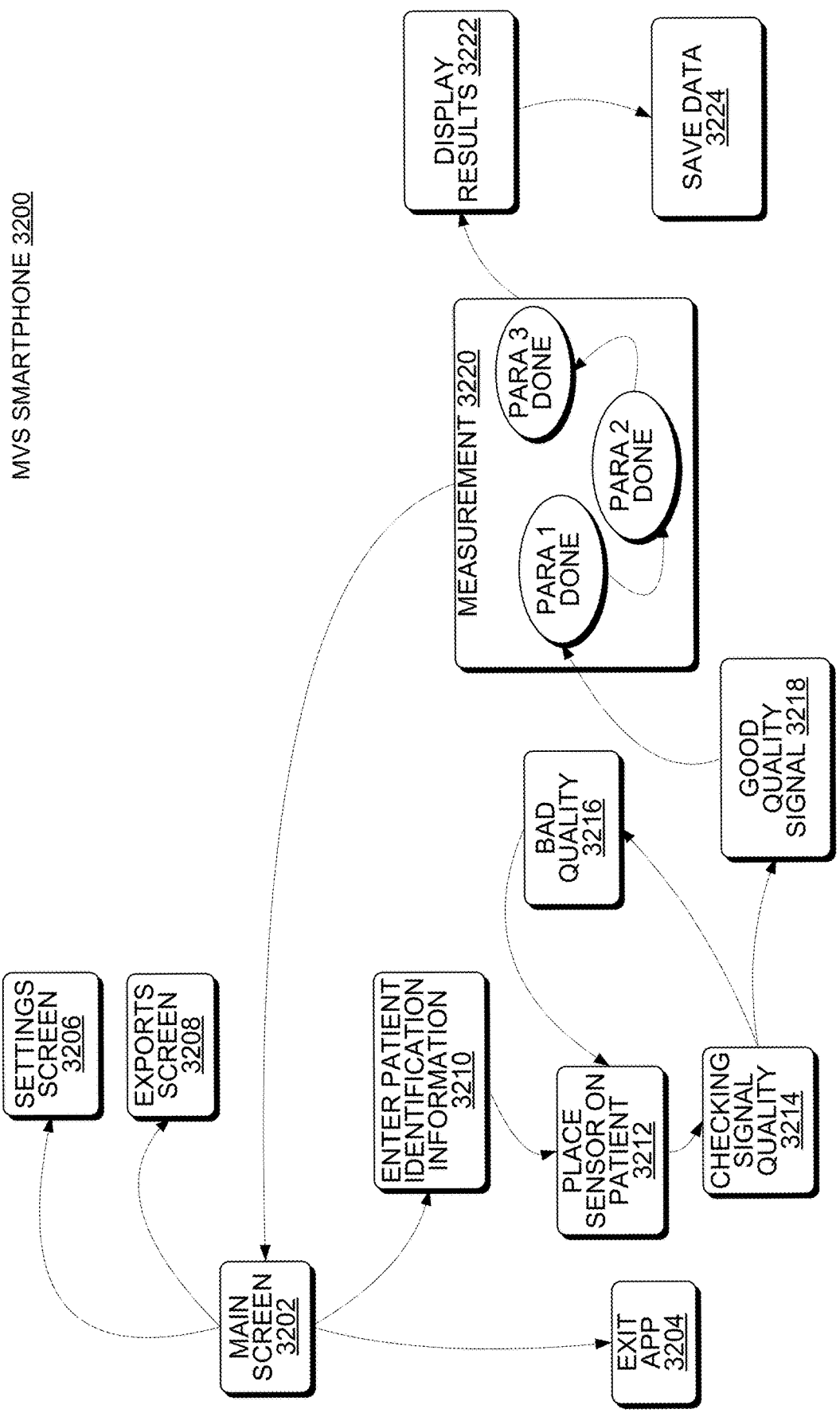
FIG. 32 is a data flow diagram of the MVS smartphone, according to an implementation.

FIG. 32 is a data flow diagram 3200 of the MVS smartphone 3103, according to an implementation. Data flow diagram 3200 is a process of the MVSFCA 3102 via a graphical user interface on a LCD display 3116 on the MVS smartphone device 3103.

Figure 38:
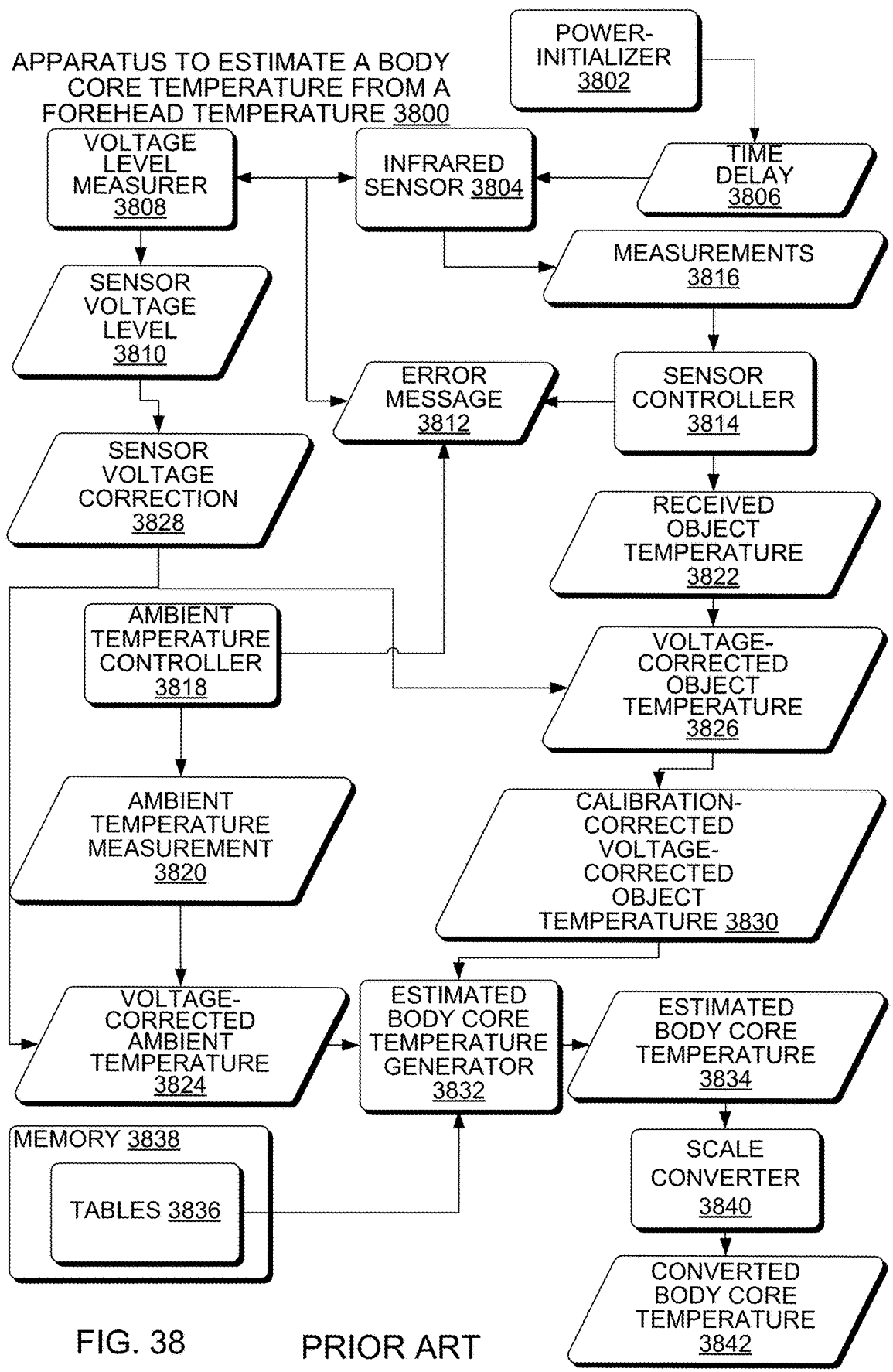
FIG. 38 is a block diagram of an apparatus to estimate a body core temperature from a forehead temperature sensed by an infrared sensor, according to an implementation.

In data flow diagram 3200, a main screen 3202 is displayed by the MVS Smartphone device 3103 that provides options to exit the application 3204, display configuration settings 3206, display data export settings 3208 or display patient identification entry screen 3210. The configuration settings display 3206 provides options for the configuration/management of the MVS Smartphone device 3103. In some implementations, the data flow diagram 3200 includes low power operation and sleep, along startup, initialization, self check and measurement capability of the MVS Smartphone device 3103. The display of data export settings 3208 provides options to take individual measurement of a given vital sign. After the patient identification entry screen 3210 or and alternatively, bar code scanning of both operator and subject, has been completed, one or more sensors are placed on the patient 3212, the MVS Smartphone device 3103 verifies 3214 that signal quality from the sensors is at or above a predetermined minimum threshold. If the verification 3214 fails 3216 as shown in FIG. 65, then the process resumes where one or more sensors are placed on the patient 3212. If the verification 3214 succeeds 3218 as shown in FIG. 66, then measurement 3220 using the one or more sensors is performed and thereafter the results of the measurements are displayed 3222 as shown in FIG. 38 and thereafter the results of the measurements are saved to EMR or clinical cloud 3224, and then the process continues at the main screen 3202. The "para n done" actions the measurement 3220 are indications that the sensing of the required vital-signs is complete. Examples of the measurements 3220 that are displayed 3222 are FIG. 65-66.

FIG. 33 is a block diagram of a multi-vital-sign finger cuff smartphone system (MVSFCSS) 3300, according to an implementation. MVSFCSS 3300 is one implementation of MVSFCA 3002 in FIG. 30 and MVSFCSS 3300 is one implementation of MVSFCA 3102 in FIG. 31. The MVSFCSS 3300 captures, stores and exports raw data from all supported sensors in the system. MVSFCSS 3300 supports a variety measurement methods and techniques. The MVSFCSS 3300 can be used in a clinical setting for the collection of human vital signs.

A sensor management component 3302 controls and receives data from a MVS finger cuff 1904, a pump, valve, and pressure sensor (shown in FIG. 42) an infrared finger temperature sensor 1908, a proximity sensor 1910 and another sensor 1912. The sensor management component 3302 can be implemented in the control process and signal processing component 3127 in FIG. 31, which can be implemented by a microprocessor or by a FPGA.

MVSFCSS 3300 also includes a CMOS camera 3308 that is operably coupled to a USB port 3304. The CMOS camera captures images that are processed for reading a barcode to identify the patient and by motion amplification components for determining heart rate, respiratory rate, and blood pressure, a lens 3310 is coupled to the CMOS camera 3308.

The MVS finger cuff 1904 is integrated into the MVSFCSS 3300, rather than the replaceable, detachable and removable MVS finger cuff 3006 in FIG. 30. The MVS finger cuff 1904 includes a PLM subsystem and at least one mDLS sensor. The MVS finger cuff 1904 is powered via an air line (e.g. 1404 in FIG. 30) by the pneumatic engine 1906 that provides air pressure to inflate and deflate the cuff bladder of the MVS finger cuff 1904 and real time measurement.

In some implementations, a body surface temperature of a human is also sensed by the infrared finger temperature sensor 1908 that is integrated into the MVSFCSS 3300 in which the body surface temperature is collected and managed by the MVSFCSS 3300.

In some implementations, a single stage measurement process is required to measure all vital signs in one operation by the MVSFCSS 3300 by the replaceable, detachable and removable MVS finger cuff 3006 or the MVS finger cuff 1904 or the infrared finger temperature sensor 1908. However, in some implementations, a two stage measurement process is performed in which the MVSFCSS 3300 measures some vital signs through the replaceable, detachable and removable MVS finger cuff 3006 or the MVS finger cuff 1904; and in the second stage, the body surface temperature is measured through an infrared finger temperature sensor 1908 in the MVS Smartphone device 3103.

The MVSFCSS 3300 operates in two primary modes, the modes of operation based on who takes the measurements, a patient or an operator. The two modes are: 1) Operator Mode in which an operator operates the MVSFCSS 3300 to take a set of vital sign measurements of another human. The operator is typically clinical staff or a home care giver. 2) Patient Mode in which a patient uses the MVSFCSS 3300 to take a set of vital sign measurements of themselves. In some implementations, the MVSFCSS 3300 provides both the main measurement modes for patient and operator. The primary measurement areas on the human to be measured are 1) face 2) forehead 3) Left hand, index and middle finger and 4) right hand, index and middle finger. The MVSFCSS 3300 is portable, light weight, hand held and easy to use in primary and secondary modes of operation in all operational environments.

Given the complex nature of integration into hospital networks, in some implementations, the MVSFCSS 3300 does not include site communication infrastructure, rather the collected data (vital sign) is extracted from the MVSFCSS 3300 via a USB port or by a USB mass storage stick that is inserted into the MVSFCSS 3300 or by connecting the MVSFCSS 3300 directly to a PC system as a mass storage device itself.

The MVS smartphone 3103, when connected to a wireless Bluetooth® communication component 1916 of the MVSFCSS 3300 via a wireless Bluetooth® communication component 3114, is a slave to the MVSFCSS 3300. The MVS Smartphone 3103 reports status, measurement process, and measurement measurements to the user via the MVSFCSS 3300.

When the MVS Smartphone 3103 is connected to the MVSFCSS 3300, the MVS Smartphone 3103 performs patient bar code scan or identification entry as requested by MVSFCSS 3300, the MVS Smartphone 3103 performs an operator bar code scan or identification entry as requested by MVSFCSS 3300, the MVS Smartphone 3103 performs human temperature measurement as requested by MVSFCSS 3300, the MVS Smartphone 3103 displays information that is related to the MVSFCSS 3300 direct action, the MVSFCSS 3300 starts when the MVS Smartphone 3103 is started, and the MVSFCSS 3300 is shutdown under the direction and control of the MVS Smartphone 3103. In some implementations, the information displayed by the MVS Smartphone 3103 includes battery status of the MVSFCSS 3300, device status of the MVSFCSS 3300, MVSFCSS 3300 display mode and device revision numbers of the MVS Smartphone 3103 and the MVSFCSS 3300. In some implementations, when a body surface temperature of a human is also sensed by an infrared finger temperature sensor 1908 in the MVS smartphone 3103, the body surface temperature is collected and managed by the MVSFCSS 3300.

In some implementations, the multi-vital-sign finger cuff smartphone system (MVSFCSS) 3300 includes the following sensors and sensor signal capture and processing components that are required to extract the required primary and secondary human vital signs measurements: the MVS finger cuff 1904 that includes a PLM subsystem and two mDLS sensors, the infrared finger temperature sensor 1908, a proximity sensor 1910 and another non-disposable sensor(s) for other human measurements sensor 1912 or ambient air temperature sensor 1909.

The MVSFCSS 3300 performs concurrent two stage measurement processes for all measurements. The measurement process performed by the MVSFCSS 3300 is controlled and guided from the MVSFCSS 3300 via the GUI on the MVS Smartphone 3103. The measurements are sequenced and configured to minimize time required to complete all measurements. In some implementations, the MVSFCSS 3300 calculates the secondary measurements of heart rate variability and blood flow. The MVSFCSS 3300 commands and controls the MVS Smartphone 3103 via a wireless Bluetooth® protocol communication path 3012 and in some further implementations, the MVS Smartphone 3103 communicates with the MVSFCSS 3300, which could also be concurrent.

In some implementations, the MVSFCSS 3300 includes the USB On-the-Go port 3304 for interface with slave devices only, such as the MVS Smartphone 3103, to perform the following functions: recharge the internal rechargeable batteries 1920, export sensor data sets to a windows based computer system, firmware update of the MVSFCSS 3300 via an application to control and manage the firmware update of the MVSFCSS 3300 and configuration update of the MVSFCSS 3300. The MVSFCSS 3300 does update the MVS Smartphone 3103 firmware. The internal batteries of the MVSFCSS 3300 can be recharged when the MVSFCSS 3300 is powered-off but while connected to USB or DC input. In some implementations, the MVSFCSS 3300 can recharge the MVS Smartphone 3103 from its internal power source over a wireless charging connection. In some implementations, the internal rechargeable batteries 1920 provide sufficient operational life of the MVSFCSS 3300 on a single charge to perform at least 2 days of full measurements before recharging of the internal rechargeable batteries 1920 of the MVSFCSS 3300 is required.

In some implementations, the MVSFCSS 3300 includes visual indicators 1940 such as a fatal fault indicator that indicates the MVSFCSS 3300 has failed and will not power up, a device fault indicator (that indicates the MVSFCSS 3300 has a fault that would affect the measurement function), a battery charging status indicator, a battery charged status indicator, and/or a battery fault status indicator.

The MVSFCSS 3300 also includes a cellular communication module 1944 (this could be integrated into the processor) for communications via cell communication frequencies and a Wi-Fi® communication module 1942 (this could be integrated into the processor) for communications via Wi-Fi® communication frequencies. In some implementations, the MVSFCSS 3300 also includes an audio subsystem 1946 that controls at one or more speakers 1948 to enunciate information to an operator or patient via tones, polymorphic and general music/speech capability.

MVSFCSS 3300 includes a microprocessor 3320 that controls and communicates with the sensor management component 3302, the CMOS camera 3308, the lens 3310, the cellular communication module 1944, the wireless communication module 1942, the audio sub-system 1946, speakers 1948, the USB port 3304, the batteries 3306 and the visual indicators 1940. In some implementations, the sensor management component 3302 is a component of the microprocessor 3320. The MVSFCSS 3300 is hand held and portable. The MVSFCSS 3300 includes non-slip/slide exterior surface material.

Vital signs are received from sensor management component 3302. The vital signs that are received are then displayed by a LCD display 3116 and/or transmitted by the cellular communication module 1944, the wireless communication module 1942 and/or the wireless Bluetooth® communication component 3114, enunciated by a speaker 1948 or stored by a flash memory. Examples of the vital signs that are displayed on the display are FIG. 65-66.

FIG. 34 is a block diagram of a MVS smartphone system 3400, according to an implementation. The MVS smartphone system 3400 includes two communicatively coupled devices; a MVS smartphone 3402 and a MVS finger cuff accessory (MVSFCA) 3404. MVS smartphone 3402 is one implementation of MVS smartphone 3004 in FIG. 30 and one implementation of MVS smartphone 3103 in FIG. 31. MVSFCA 3404 is one implementation of MVSFCA 3002 in FIG. 30 and one implementation of MVSFCA 3102 in FIG. 31. The MVS smartphone system 3400, the MVSFCA 3404 and the MVS smartphone 3402 are all examples of the MVS apparatus 5504. The MVS smartphone 3402 captures, stores and exports raw data from all supported sensors in the MVS smartphone system 3400. More specifically, the MVS smartphone 3402 extracts the vital signs through the MVSFCA 3404, displays the vital signs and transfers the vital signs to either a remote third party, hub, bridge etc., or a device manager, or directly to remote EMR/HER/Hospital systems or other third party local or cloud based systems. MVS smartphone system 3400 provides a flexible human vital sign measurement methodology that supports different measurement methods and techniques. The MVS smartphone system 3400 can be used in a clinical setting for the collection of human vital signs.

The MVSFCA 3404 include a MVS finger cuff 3406 (such as MVS finger cuff 1904 in FIG. 19) that is fixed into the MVSFCA 3404, rather than the replaceable, detachable and removable MVS finger cuff 3006 in FIG. 30. MVS finger cuff 3406 is electrically coupled to the MVSFCA 3404 via a serial line 3407. The MVS finger cuff 3406 includes a PLM subsystem 2006 and at least one mDLS sensor 2011 and/or 2014. The MVS finger cuff 3406 is powered by and connected to a finger sensor cable (FSC) 3408 that includes an air line (e.g. 3006 in FIG. 30), the air line being powered by a pneumatic engine 1906 in the MVSFCA 3404 that provides air pressure to inflate a cuff bladder of the pressure finger cuff 2050 and the controlled release of that air pressure.

In some implementations, a body surface temperature of a human is also sensed by an infrared finger temperature sensor 1908 that is integrated into the MVS finger cuff 3406 in which the body surface temperature is collected and managed by the MVS finger cuff 3406.

In some implementations, a single stage measurement process is required to measure all vital signs in one operation by the MVS smartphone 3402, the MVSFCA 3404 and the MVS finger cuff 3406 working cooperatively. However, in some implementations, a two stage measurement process is performed in which the MVSFCA 3404 measures some vital signs through the MVS finger cuff 3406; and in the second stage, the body surface temperature is measured through an infrared finger temperature sensor 1908 in the MVS smartphone 3402. One implementation of the infrared finger temperature sensor 1908 is digital infrared sensor 1312 in FIG. 41.

The MVSFCA 3404 operates in two primary modes, the modes of operation based on who takes the measurements, a patient or an operator. The two modes are: 1) Operator Mode in which an operator operates the MVSFCA 3404 through the MVS smartphone 3402 to take a set of vital sign measurements of another human. The operator is typically clinical staff or a home care giver. 2) Patient Mode in which a patient uses the MVSFCA 3404 through the MVS smartphone 3402 to take a set of vital sign measurements of themselves. In some implementations, the MVSFCA 3404 provides both the main measurement modes for patient and operator. The primary measurement areas on the human to be measured are 1) Left hand, index and middle finger, 2) right hand, index and middle finger, and 3) human forehead temperature (requires the MVS smartphone 3402 to perform temperature measurement). The MVSFCA 3404 is portable, light weight, hand held and easy to use in primary and secondary modes of operation in all operational environments.

Given the complex nature of integration into hospital networks, in some implementations, in some implementations the MVSFCA 3404 does not include site communication infrastructure, rather the collected data (vital sign) is extracted from the MVSFCA 3404 via a USB port 3122 or by a USB mass storage stick that is inserted into the MVSFCA 3404 or by connecting the MVSFCA 3404 directly to a PC system as a mass storage device itself.

The MVSFCA 3404, when connected to a wireless Bluetooth® communication component 3114 of the MVS smartphone 3402 via a wireless Bluetooth® communication component 1916, can be a slave to the MVS smartphone 3402. The MVSFCA 3404 reports status, measurement process, and measurement measurements to the user via the MVS smartphone 3402. The MVS smartphone 3402 provides a user input method to the MVSFCA 3404 via a graphical user interface on a LCD display 3116 which displays data representative of the measurement process and status. In one implementation, the wireless Bluetooth® communication component 3114 of the MVS smartphone 3402 includes communication capability with cellular communication paths (3G, 4G and/or 5G) and/or Wi-Fi® communication paths, the MVS smartphone 3402 is not a slave to the MVSFCA 3404 and the MVSFCA 3404 captures vital sign data and transmits the vital sign data via the wireless Bluetooth® communication component 3114 in the MVS smartphone 3402 and the MVS smartphone 3402 transmits the vital sign data to the middle layer 5506 in FIG. 55 or the MVSFCA 3404 transmits the vital sign data via the wireless Bluetooth® communication component 1916 of the MVSFCA 3404 to the bridge 5520, a Wi-Fi® access point, a cellular communications tower or a bridge 5520 in FIG. 55. In other implementations, Zigbee® or Z-Wave® can be used instead of Bluetooth®.

In some implementations, the MVS smartphone 3402 provides communications with other devices via a communication component 3117 of the MVS smartphone 3402. The communication component 3117 has communication capability with cellular communication paths (3G, 4G and/or 5G) and/or Wi-Fi® communication paths. For example, the MVSFCA 3404 captures vital sign data and transmits the vital sign data via the wireless Bluetooth® communication component 1916 in the MVSFCA 3404 to the wireless Bluetooth® communication component 3114 in the MVS smartphone 3402, and the MVS smartphone 3402 transmits the vital sign data via the communication component 3117 of the MVS smartphone 3402 to the middle layer 5506 in FIG. 55 or the MVS smartphone 3402 transmits the vital sign data via the communication component 3117 of the MVS smartphone 3402 to the bridge 5520, a Wi-Fi® access point, a cellular communications tower or a bridge 5520 in FIG. 55.

In some implementations, when the MVS smartphone 3402 is connected to the MVSFCA 3404, the MVS smartphone 3402 performs human bar code scan by a bar code scanner 3118 or identification entry as requested by MVSFCA 3404, the MVS smartphone 3402 performs an operator bar code scan or identification entry as requested by MVSFCA 3404, the MVS smartphone 3402 displays information that is related to the MVSFCA 3404, the MVS smartphone 3402 starts when the MVSFCA 3404 is started, and the MVS smartphone 3402 is shutdown under the direction and control of the MVSFCA 3404, and the MVS smartphone 3402 has a self-test mode that determines the operational state of the MVSFCA 3404 and sub systems, to ensure that the MVSFCA 3404 is functional for the measurement. In other implementations, In some implementations, when the MVS smartphone 3402 is connected to the MVSFCA 3404, the MVS smartphone 3402 performs human bar code scan by a bar code scanner 3118 or identification entry as requested by the MVSFCA 3404, the MVS smartphone 3402 performs an operator bar code scan or identification entry as requested by the MVSFCA 3404, and the MVS smartphone 3402 displays information that is related to the MVSFCA 3404. In some implementations, the information displayed by the MVS smartphone 3402 includes date/time, human identification number, human name, vitals measurement such as blood pressure (diastolic and systolic), SpO2, heart rate, temperature, respiratory rate, MVSFCA 3404 free memory slots, battery status of the MVS smartphone 3402, battery status of the MVSFCA 3404, device status of the MVSFCA 3404, errors of the MVS smartphone 3402, device measurement sequence, measurement quality assessment measurement, mode of operation, subject and operator identification, temperature, measurement, display mode and device revision numbers of the MVS smartphone 3402 and the MVSFCA 3404. In some implementations, when a body surface temperature of a human is also sensed by an infrared sensor in the MVS smartphone 3402, the body surface temperature is collected and managed by the MVSFCA 3404. In other implementations, when a body surface temperature of a human is sensed by an infrared sensor in the MVS smartphone 3402, the body surface temperature is not collected and managed by the MVSFCA 3404.

In some implementations, the MVS finger cuff accessory (MVSFCA) 3404 includes the following sensors and sensor signal capture and processing components that are required to extract the required primary and secondary human vital signs measurements: the pressure finger cuff 2050, the PLM subsystem 2006 and two mDLS sensors 2011 and 2014, the infrared finger temperature sensor 1908 and an ambient air temperature sensor 1909, and in some further implementations, non-disposable sensors for other human vital sign measurements. In some implementations, data sample rates for the PLM subsystem 2006 is 2×200 Hz×24 bit=9600 bits/sec, for each of the mDLS sensors 2011 and 2014 is 31 kHz×24 bit=1,572,864 bit/sec and for the ambient air temperature sensor is less than 1000 bps. Two mDLS sensors 2011 and 2014 are included in the MVS finger cuff 3406 to ensure that one or both sensors 2011 and 2014 delivers a good quality signal, thus increasing the probability of obtaining a good signal from at least one of the mDLS sensors 2011 and 2014.

The MVS smartphone 3402 performs concurrent two stage measurement processes for all measurements. The measurement process performed by the MVSFCA 3404 is controlled and guided from the MVS smartphone 3402 via the GUI on the MVSFCA 3404. The measurements are sequenced and configured to minimize time required to complete all measurements. In some implementations, the MVS smartphone 3402 calculates the secondary measurements of heart rate variability and blood flow from signals from the PLM subsystem 2006. The MVS smartphone 3402 commands and controls the MVSFCA 3404 via a wireless Bluetooth® protocol communication line and in some further implementations, the MVSFCA 3404 communicates to other devices through Bluetooth® protocol communication line (not shown), in addition to the communications with the MVS smartphone 3402, which could also be concurrent. In some further implementations, the MVS smartphone 3402 communicates to other devices through Bluetooth® protocol communication line (not shown), in addition to the communications with the MVSFCA 3404 device, which could also be concurrent.

MVSFCA 3404 includes USB port 3122 to perform the following functions: recharge the internal rechargeable batteries 1920 of the MVSFCA 3404, export sensor data sets to a windows based computer system 3412, firmware update of the MVSFCA 3404 via an application to control and manage the firmware update of the MVSFCA 3404 and configuration update of the MVSFCA 3404. The MVSFCA 3404 does not update the MVS smartphone 3402 firmware. The internal rechargeable batteries 1920 can be recharged via a USB port 3122, which provides charge, and the MVSFCA 3404 can also include an external direct DC input providing a fast recharge. The internal batteries 1920 of the MVSFCA 3404 can be recharged when the MVSFCA 3404 is powered-off but while connected to USB or DC input. In some implementations, the MVSFCA 3404 can recharge the MVS smartphone 3402 from its internal power source over a wireless charging connection. In some implementations, the internal rechargeable batteries 1920 provide sufficient operational life of the MVSFCA 3404 on a single charge to perform at least 2 days of full measurements before recharging of the internal rechargeable batteries 1920 of the MVSFCA 3404 is required.

In some implementations, the MVSFCA 3404 includes an internal non-volatile, non-user removable, data storage device 1930 for up to 20 human raw measurement data sets. The data storage device 1930 can be removed by a technician when the data storage device 1930 is determined to be faulty. A human measurement set contains all measurement data and measurements acquired by the MVSFCA 3404, including the temperature measurement from the MVS smartphone 3402. The internal memory is protected against data corruption in the event of an abrupt power loss event. The MVSFCA 3404 and the MVS finger cuff 3406 have a human-form fit function. The MVSFCA 3404 also includes anti-microbial exterior material to and an easy clean surface for all sensor and device surfaces. The MVSFCA 3404 stores in the data storage device 1930 an "atomic" human record structure that contains the entire data set recording for a single human measurement containing all human raw sensor signals and readings, extracted human vitals, and system status information. The MVSFCA 3404 includes self-test components that determine the operational state of the MVSFCA 3404 and sub systems, to ensure that the MVSFCA 3404 is functional for measurement. The MVSFCA 3404 includes a clock function for date and time. In some implementations. The date and time of the MVSFCA 3404 is be updated from the MVS smartphone 3402. In some implementations, the MVSFCA 3404 includes user input controls, such as a power on/off switch (start/stop), an emergency stop control to bring the pressure finger cuff 2050 to a deflated condition. In some implementations, all other input is supported via the MVS smartphone 3402 via on screen information of the MVS smartphone 3402. In some implementations, the MVSFCA 3404 includes visual indicators 1940 such as a fatal fault indicator that indicates device has failed and will not power up, a device fault indicator (that indicates the MVSFCA 3404 has a fault that would affect the measurement function), battery charging status indicator, battery charged status indicator or a battery fault status indicator.

The components (e.g. 1906, 1916, 1920, 3122, 1930 and 1940) in the MVSFCA 3404 are controlled by a control process and signal processing component 3127. The control process and signal processing component 3127 be can implemented in a microprocessor or by a FPGA.

The external USB charger 3410 provides electrical power to recharge the MVSFCA 3404. The external USB charger 3410 can provide electrical power to recharge the batteries of the MVSFCA 3404 either via a physical wired connection or via a wireless charger. In some implementations, the external USB charger 3410 does not provide electrical power to the MVSFCA 3404 because the MVSFCA 3404 includes internal rechargeable batteries 1920 that can be recharged via either USB port 3122 or a DC input. The MVSFCA 3404 is hand held and portable. The MVSFCA 3404 includes non-slip/slide exterior surface material.

Vital signs are received through the wireless Bluetooth® communication component 3114 from a MVSFCA such as the MVSFCAs in FIGS. 12-20 and 30-34 or the MVS finger clip in FIG. 21-27. The vital signs that are received are then displayed by display 2928 an/or transmitted by the communication component 3117, enunciated by a speaker or stored by flash memory. Examples of the vital signs that are displayed on the display 2928 are FIG. 65-66.

MVS Smartphones 2800 in FIG. 28, MVS smartphone 2900 in FIG. 29, MVS smartphone 3200 in FIG. 32, MVS smartphone 3004 in FIG. 30, MVS smartphone 3103 in FIG. 31, and MVS smartphone 3402 in FIG. 34 are production smartphones that have been modified by either downloading software to volatile memory or including non-volatile memory to receive, determine/calculate, display and/or transmit the multi-vital signs. In some implementations, of the apparatus, systems and methods described herein, a heart rate is estimated from data from a PLM subsystem, a respiration rate and a heart rate variability and/or a blood pressure diastolic is estimated from data from a micro dynamic light scattering sensor and the PLM subsystem. In some implementations, SpO2 blood oxygenation is estimated from data from the PLM subsystem, respiration rate is estimated from data from the micro dynamic light scattering sensor and blood pressure is estimated from data from the micro dynamic light scattering sensor in conjunction with data from the finger cuff.

7. Apparatus of Multi-Vital-Sign Devices

FIG. 35 is a block diagram of a MVS device 3500 that includes a digital infrared sensor, a biological vital sign generator and a temporal motion amplifier, according to an implementation. MVS device 3500 is an apparatus to measure body core temperature and other biological vital signs. The MVS device 3500 is one example of the MVS apparatus 5504.

The MVS device 3500 includes a microprocessor 3502. The MVS device 3500 includes a battery 3504, in some implementations a single button 3506, and a digital infrared sensor 3508 that is operably coupled to the microprocessor 3502. The digital infrared sensor 3508 includes digital ports 3510 that provide only digital readout signal 3511. One example of the digital infrared sensor 3508 is digital infrared sensor 1312 in FIG. 41. In some implementations the MVS device 3500 includes a display device 3514 that is operably coupled to the microprocessor 3502. In some implementations, the display device 3514 is a LCD color display device or a LED color display device, which are easy to read in a dark room, and some pixels in the display device 3514 are activated (remain lit) for about 5 seconds after the single button 3506 is released. After the display has shut off, another body core temperature reading can be taken by the apparatus. The color change of the display device 3514 is to alert the operator of the apparatus of a potential change of body core temperature of the human or animal subject. The body core temperature reported on the display device 3514 can be used for treatment decisions.

The microprocessor 3502 is configured to receive from the digital ports 3510 that provide only digital readout signal 3511. In some implementations, the digital readout signal 3511 is representative of an infrared signal 3516 of a forehead surface temperature that is detected by the digital infrared sensor 3508. In other implementations, the digital readout signal 3511 is representative of an infrared signal 3516 of a surface temperature of a human other than the forehead surface that is detected by the digital infrared sensor 3508. A body core temperature estimator 3518 in the microprocessor 3502 is configured to estimate the body core temperature 3520 from the digital readout signal 3511 that is representative of the infrared signal 3516 of the forehead (or other surface), a representation of an ambient air temperature reading from an ambient air sensor 1909, a representation of a calibration difference from a memory location that stores a calibration difference 3524 and a memory location that stores a representation of a bias 3526 in consideration of a temperature sensing mode. In some implementations, the MVS device 3500 does not include an analog-to-digital converter 3512 operably coupled between the digital infrared sensor 3508 and the microprocessor 3502. Furthermore, the digital infrared sensor 3508 also does not include analog readout ports 3513. The dashed lines of the A/D converter 3512 and the analog readout ports 3513 indicates absence of the A/D converter 3512 and the analog readout ports 3513 in the MVS device 3500.

A temperature estimation table 3527 is a lookup table that correlates a sensed forehead temperature to an estimated body core temperature 3520. The sensed forehead temperature is derived from the digital readout signal 3511.

Figure 39:
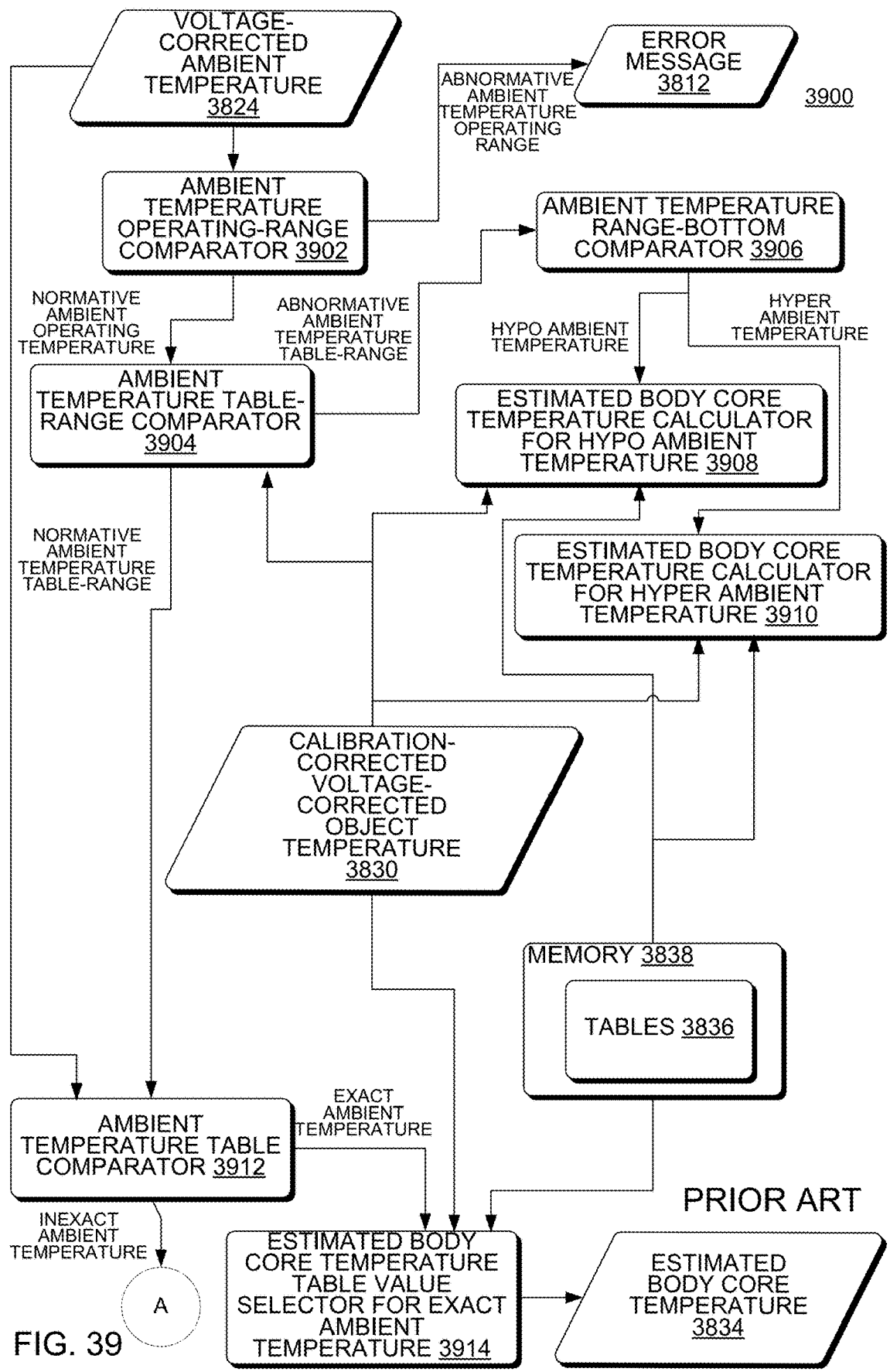
FIG. 39-40 are block diagrams of an apparatus to derive an estimated body core temperature from one or more tables that are stored in a memory that correlate a calibration-corrected voltage-corrected object temperature to the body core temperature in reference to the corrected ambient air temperature, according to an implementation.
Figure 40:
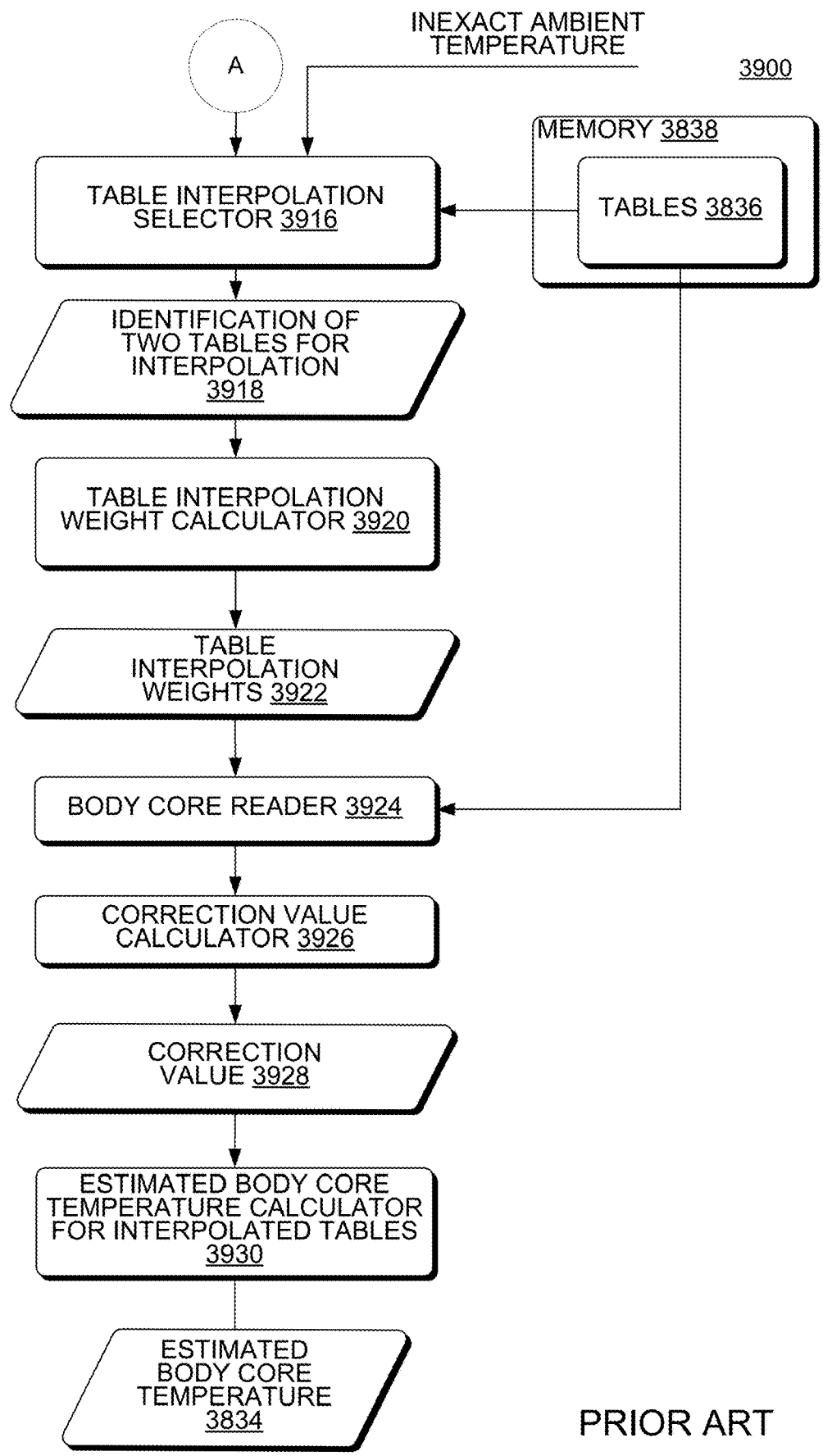

The temperature estimation table 3527 is stored in a memory. In FIG. 38-40, the temperature estimation table 3527 is shown as a component of the microprocessor 3502. The memory that stores the temperature estimation table 3527 can be separate from the microprocessor 3502 or the memory can be a part of the microprocessor 3502, such as cache on the microprocessor 3502. Examples of the memory include Random Access Memory (RAM) 2806 and flash memory 2808 in FIG. 28. In implementations of the MVS smartphone systems in FIG. 30-34, the apparatus that estimates a body core temperature in FIG. 38-40, the apparatus of motion amplification in FIG. 46-54, the MVS smartphone 2800 in which speed of the MVS smartphone systems in FIG. 35-39 and the apparatus that estimate a body core temperature of an external source point in FIG. 38-40 is very important, storing the temperature estimation table 3527 in memory that is a part of the microprocessor 3502, such as cache on the microprocessor 3502, is very important.

The correlation between the sensed forehead temperature to an estimated body core temperature varies based on age, sex, and a febrile (pyretic) or hypothermic condition of the patient and intraday time of the reading. Accordingly, in some implementations, the MVS apparatus 5504 includes temperature estimation tables 3527 that are specific to the combinations and permutations of the various situations of the age, sex, and a febrile (pyretic) or hypothermic condition of the patient and the intraday time of the reading. For example, in one implementation, the MVS apparatus 5504 include a temperature estimation table 3527 for male humans of 3-10 years old, that are neither febrile nor hypothermic, for temperature readings taken between 10 am-2 pm. In another example, in another implementation, the MVS apparatus 5504 include a temperature estimation table 3527 for female humans of greater than 51 years of age, that are febrile and for temperature readings taken between 2 am-8 am.

Some implementations of the MVS device 3500 include a solid-state image transducer 2852 that is operably coupled to the microprocessor 3502 and is configured to provide two or more images 2854 to a temporal-motion-amplifier 3532 and a biological vital sign generator 3534 in the microprocessor 3502 to estimate one or more biological vital signs 3536 that are displayed on the display device 3514.

The MVS device 3500 includes any one of a pressure sensor 3538, a pressure cuff 3540, a micro dynamic light scattering (mDLS) sensor 3542 and/or a physiological light monitoring (PLM) subsystem 3544 that provide signals to the biological vital sign generator 3534. The mDLS sensor uses a laser beam (singular wavelength) of light and a light detector on the opposite side of the finger to detect the extent of the laser beam that is scattered in the flesh of the finger, which indicates the amount of oxygen in blood in the fingertip. The PLM subsystem uses projected light and a light detector on the opposite side of the finger to detect the extent of the laser beam that is absorbed in the flesh of the finger, which indicates the amount of oxygen in blood in the fingertip, which is also known as pulse oximetry. The pressure sensor 3538 is directly linked to the pressure cuff 3540. In some implementations, the MVS device 3500 includes two mDLS sensors to ensure that at least one of the mDLS sensors provides a good quality signal. In some implementations, the biological vital sign generator 3534 generates blood pressure measurement (systolic and diastolic) from signals from the pressure sensor 3538, the finger pressure cuff 3540 and the mDLS sensor 3542. In some implementations, the biological vital sign generator 3534 generates blood glucose levels from signals from the PLM subsystem 3544. In some implementations, the biological vital sign generator 3534 generates SpO2 measurement and heart rate measurement from signals from the PLM subsystem 3544. In some implementations, the biological vital sign generator 3534 generates respiration (breathing rate) measurement from signals from the mDLS sensor 3542. In some implementations, the biological vital sign generator 3534 generates blood flow measurement from signals from the mDLS sensor 3542. In some implementations, the biological vital sign generator 3534 generates heartrate variability from signals from the PLM subsystem 3544. In some implementations, the body core temperature estimator 3518 is implemented in the biological vital sign generator 3534.

The MVS device 3500 also includes a wireless communication subsystem 2804 or other external communication subsystem, such as an Ethernet port, that provides communication to the EMR data capture systems 5500 and 5700 or other devices. In some implementations, the wireless communication subsystem 2804 is communication subsystem 2804 in FIG. 44. The wireless communication subsystem 2804 is operable to receive and transmit the estimated body core temperature 3520 and/or the biological vital sign(s) 3536.

In some implementations, the digital infrared sensor 3508 is a low noise amplifier, 17-bit ADC and powerful DSP unit through which high accuracy and resolution of the estimated body core temperature 3520 by the MVS smartphone systems in FIG. 30-34, the apparatus that estimates a body core temperature in FIGS. 35-40 and 41, the apparatus of motion amplification in FIG. 46-54 and the MVS smartphone 2800.

In some implementations, the digital infrared sensor 3508, 10-bit pulse width modulation (PWM) is configured to continuously transmit the measured temperature in range of −20 . . . 120° C., with an output resolution of 0.14° C. The factory default power on reset (POR) setting is SMBus.

In some implementations, the digital infrared sensor 3508 is packaged in an industry standard TO-39 package.

In some implementations, the generated object and ambient air temperatures are available in RAM of the digital infrared sensor 3508 with resolution of 0.01° C. The temperatures are accessible by 2 wire serial SMBus compatible protocol (0.02° C. resolution) or via 10-bit PWM (Pulse Width Modulated) output of the digital infrared sensor 3508.

In some implementations, the digital infrared sensor 3508 is factory calibrated in wide temperature ranges: −40 . . . 85° C. for the ambient air temperature and −70 . . . 380° C. for the object temperature.

In some implementations of the digital infrared sensor 3508, the measured value is the average temperature of all objects in the Field Of View (FOV) of the sensor. In some implementations, the digital infrared sensor 3508 has a standard accuracy of ±0.5° C. around room temperatures, and in some implementations, the digital infrared sensor 3508 has an accuracy of ±0.2° C. in a limited temperature range around the human body core temperature.

These accuracies are only guaranteed and achievable when the sensor is in thermal equilibrium and under isothermal conditions (there are no temperature differences across the sensor package). The accuracy of the detector can be influenced by temperature differences in the package induced by causes like (among others): Hot electronics behind the sensor, heaters/coolers behind or beside the sensor or by a hot/cold object very close to the sensor that not only heats the sensing element in the detector but also the detector package. In some implementations of the digital infrared sensor 3508, the thermal gradients are measured internally and the measured temperature is compensated in consideration of the thermal gradients, but the effect is not totally eliminated. It is therefore important to avoid the causes of thermal gradients as much as possible or to shield the sensor from the thermal gradients.

In some implementations, the digital infrared sensor 3508 is configured for an object emissivity of 1, but in some implementations, the digital infrared sensor 3508 is configured for any emissivity in the range 0.1 . . . 1.0 without the need of recalibration with a black body.

In some implementations of the digital infrared sensor 3508, the PWM can be easily customized for virtually any range desired by the customer by changing the content of 2 EEPROM cells. Changing the content of 2 EEPROM cells has no effect on the factory calibration of the device. The PWM pin can also be configured to act as a thermal relay (input is To), thus allowing for an easy and cost effective implementation in thermostats or temperature (freezing/boiling) alert applications. The temperature threshold is programmable by the microprocessor 3502 of the MVS smartphone system. In a MVS smartphone system having a SMBus system the programming can act as a processor interrupt that can trigger reading all slaves on the bus and to determine the precise condition.

In some implementations, the digital infrared sensor 3508 has an optical filter (long-wave pass) that cuts off the visible and near infra-red radiant flux is integrated in the package to provide ambient and sunlight immunity. The wavelength pass band of the optical filter is from 5.5 to 14 μm.

In some implementations, the digital infrared sensor 3508 is controlled by an internal state machine, which controls the measurements and generations of the object and ambient air temperatures and does the post-processing of the temperatures to output the body core temperatures through the PWM output or the SMBus compatible interface.

Some implementations of the MVS smartphone system includes 2 IR sensors, the output of the IR sensors being amplified by a low noise low offset chopper amplifier with programmable gain, converted by a Sigma Delta modulator to a single bit stream and fed to a DSP for further processing. The signal is treated by programmable (by means of EEPROM contend) FIR and IIR low pass filters for further reduction of the bandwidth of the input signal to achieve the desired noise performance and refresh rate. The output of the IIR filter is the measurement result and is available in the internal RAM. 3 different cells are available: One for the on-board temperature sensor and 2 for the IR sensors. Based on results of the above measurements, the corresponding ambient air temperature Ta and object temperatures To are generated. Both generated body core temperatures have a resolution of 0.01° C. The data for Ta and To is read in two ways: Reading RAM cells dedicated for this purpose via the 2-wire interface (0.02° C. resolution, fixed ranges), or through the PWM digital output (10 bit resolution, configurable range). In the last step of the measurement cycle, the measured Ta and To are rescaled to the desired output resolution of the PWM) and the regenerated data is loaded in the registers of the PWM state machine, which creates a constant frequency with a duty cycle representing the measured data.

In some implementations, the digital infrared sensor 3508 includes a SCL pin for Serial clock input for 2 wire communications protocol, which supports digital input only, used as the clock for SMBus compatible communication. The SCL pin has the auxiliary function for building an external voltage regulator. When the external voltage regulator is used, the 2-wire protocol for a power supply regulator is overdriven.

In some implementations, the digital infrared sensor 3508 includes a slave deviceA/PWM pin for digital input/output. In normal mode the measured object temperature is accessed at this pin Pulse Width Modulated. In SMBus compatible mode the pin is automatically configured as open drain NMOS. Digital input/output, used for both the PWM output of the measured object temperature(s) or the digital input/output for the SMBus. In PWM mode the pin can be programmed in EEPROM to operate as Push/Pull or open drain NMOS (open drain NMOS is factory default). In SMBus mode slave deviceA is forced to open drain NMOS I/O, push-pull selection bit defines PWM/Thermal relay operation. The PWM/slave deviceA pin the digital infrared sensor 3508 operates as PWM output, depending on the EEPROM settings. When WPWM is enabled, after POR the PWM/slave deviceA pin is directly configured as PWM output. When the digital infrared sensor 3508 is in PWM mode, SMBus communication is restored by a special command In some implementations, the digital infrared sensor 3508 is read via PWM or SMBus compatible interface. Selection of PWM output is done in EEPROM configuration (factory default is SMBus). PWM output has two programmable formats, single and dual data transmission, providing single wire reading of two temperatures (dual zone object or object and ambient). The PWM period is derived from the on-chip oscillator and is programmable.

The microprocessor 3502 has read access to the RAM and EEPROM and write access to 9 EEPROM cells (at addresses 0x00, 0x01, 0x02, 0x03, 0x04, 0x05, 0x0E, 0x0F, 0x09). When the access to the digital infrared sensor 3508 is a read operation, the digital infrared sensor 3508 responds with 16 data bits and 8 bit PEC only if its own slave address, programmed in internal EEPROM, is equal to the SA, sent by the master. A slave feature allows connecting up to 127 devices (SA=0x00 . . . 0x07F) with only 2 wires. In order to provide access to any device or to assign an address to a slave device before slave device is connected to the bus system, the communication starts with zero slave address followed by low R/W bit. When the zero slave address followed by low R/W bit sent from the microprocessor 3502, the digital infrared sensor 3508 responds and ignores the internal chip code information. In some implementations, two digital infrared sensors 3508 are not configured with the same slave address on the same bus.

In regards to bus protocol, after every received 8 bits, the slave device should issue ACK or NACK. When a microprocessor 3502 initiates communication, the microprocessor 3502 first sends the address of the slave and only the slave device which recognizes the address will ACK, the rest will remain silent. In case the slave device NACKs one of the bytes, the microprocessor 3502 stops the communication and repeat the message. A NACK could be received after the packet error code (PEC). A NACK after the PEC means that there is an error in the received message and the microprocessor 3502 attempts resending the message. PEC generation includes all bits except the START, REPEATED START, STOP, ACK, and NACK bits. The PEC is a CRC-8 with polynomial X8+X2+X1+1. The Most Significant Bit of every byte is transferred first.

In single PWM output mode the settings for PWM1 data only are used. The temperature reading can be generated from the signal timing as:

$$T_{OUT} = \left(\frac{2t_2}{T} \times (T_{O\_MAX} - T_{O\_MIN})\right) + T_{O\_MIN}$$

where Tmin and Tmax are the corresponding rescale coefficients in EEPROM for the selected temperature output (Ta, object temperature range is valid for both Tobj1 and Tobj2 as specified in the previous table) and T is the PWM period. Tout is TO1, TO2 or Ta according to Config Register [5:4] settings.

The different time intervals t1 . . . t4 have following meaning:

t1: Start buffer. During t1 the signal is always high. t1=0.125 s×T (where T is the PWM period)

t2: Valid Data Output Band, 0 . . . ½T. PWM output data resolution is 10 bit.

t3: Error band—information for fatal error in EEPROM (double error detected, not correctable).

t3=0.25 s×T. Therefore a PWM pulse train with a duty cycle of 0.875 indicates a fatal error in EEPROM (for single PWM format). FE means Fatal Error.

In regards to a format for extended PWM, the temperature can be generated using the following equation:

$$T_{OUT} = \left(\frac{4t_2}{T} \times (T_{MAX1} - T_{MIN1})\right) + T_{MIN1}$$

For Data 2 field the equation is:

$$T_{OUT} = \left(\frac{4t_5}{T} \times (T_{MAX2} - T_{MIN2})\right) + T_{MIN2}$$

In some implementations of FIG. 38-40, the microprocessor 3502, the image transducer 2852, the pressure sensor 3538, the pressure cuff 3540, the micro dynamic light scattering (mDLS) sensor 3542 and/or the physiological light monitoring (PLM) subsystem 3544 are located in the MVS finger cuff smartphone system and the display devices 3514 and 3614 are located in the MVS smartphone.

In some implementations of FIG. 38-40, the image transducer 2852, the pressure sensor 3538, the pressure cuff 3540, the micro dynamic light scattering (mDLS) sensor 3542 and/or the physiological light monitoring (PLM) subsystem 3544 are located in the MVS finger cuff smartphone system and the microprocessor 3502 and the display devices 3514 and 3614 are located in the MVS smartphone.

Figure 36:
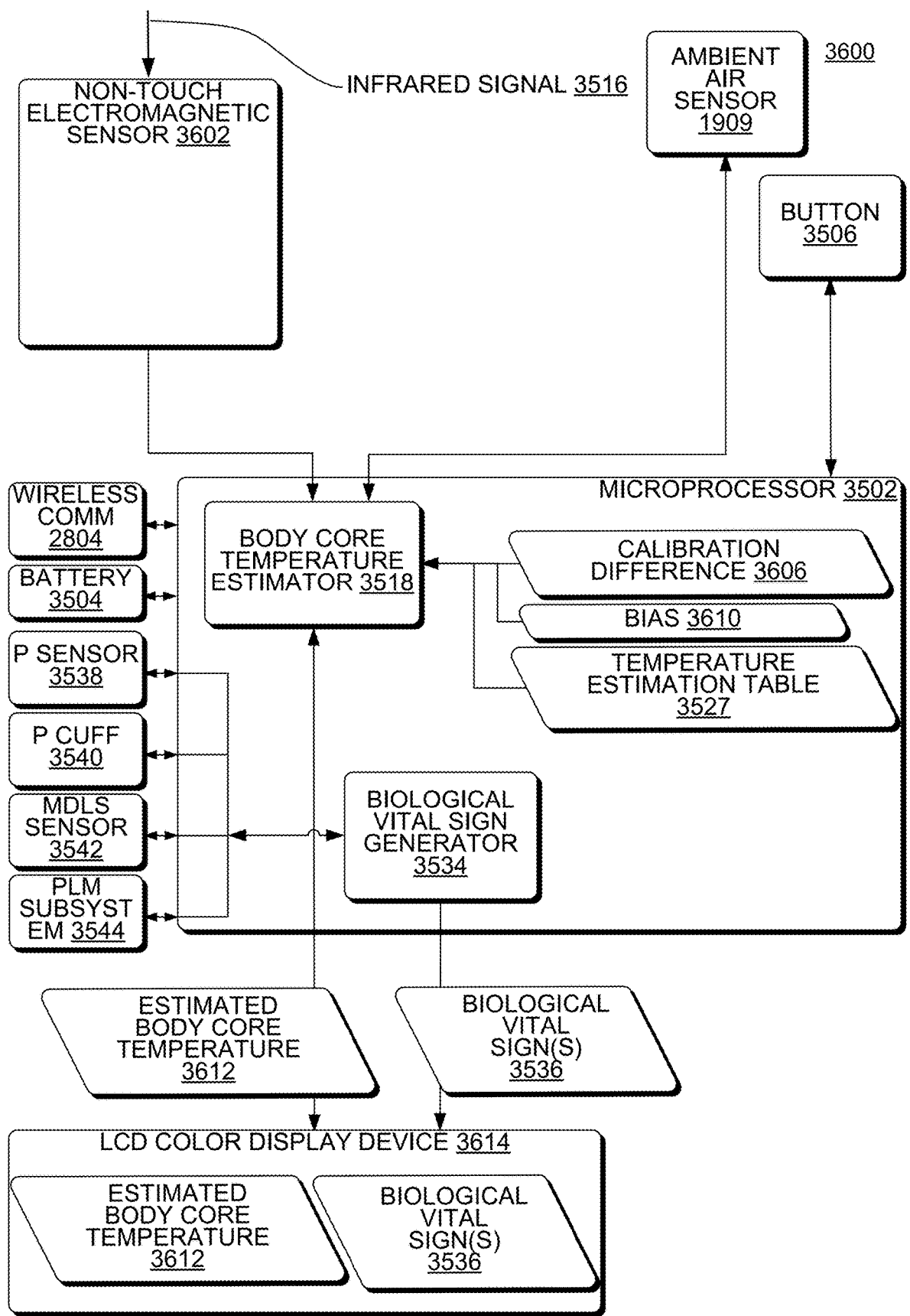
FIG. 36 is a block diagram of a MVS smartphone device that includes a no-touch electromagnetic sensor with no temporal motion amplifier, according to an implementation.

FIG. 36 is a block diagram of a MVS device 3600 that includes a non-touch electromagnetic sensor with no temporal motion amplifier, according to an implementation. The MVS device 3600 is one example of the MVS smartphone system 5504 and one example of the MVS finger cuff accessory (MVSFCA) 3102. The MVS device 3600 includes a battery 3504, in some implementations a single button 3506, in some implementations a display device 3514, a non-touch electromagnetic sensor 3602 and an ambient air sensor 1909 that are operably coupled to the microprocessor 3502. The microprocessor 3502 is configured to receive a representation of an infrared signal 3516 of the forehead or other external source point from the non-touch electromagnetic sensor 3602. The microprocessor 3502 includes a body core temperature estimator 3518 that is configured to estimate the body core temperature 3612 of the subject from the representation of the electromagnetic energy of the external source point.

The MVS device 3600 includes a pressure sensor 3538, a pressure cuff 3540, a mDLS sensor 3542 and a PLM subsystem 3544 that provide signals to the biological vital sign generator 3534. The pressure sensor 3538 is directly linked to the pressure cuff 3540. In some implementations, the MVS device 3600 includes two mDLS sensors to ensure that at least one of the mDLS sensors provides a good quality signal. In some implementations, the biological vital sign generator 3534 generates blood pressure measurement (systolic and diastolic) from signals from the pressure sensor 3538, the finger pressure cuff 3540 and the mDLS sensor 3542. In some implementations, the biological vital sign generator 3534 generates SpO2 measurement and heart rate measurement from signals from the PLM subsystem 3544. In some implementations, the biological vital sign generator 3534 generates respiration (breathing rate) measurement from signals from the mDLS sensor 3542. In some implementations, the biological vital sign generator 3534 generates blood flow measurement from signals from the mDLS sensor 3542. In some implementations, the biological vital sign generator 3534 generates heartrate variability from signals from the PLM subsystem 3544.

The body core temperature correlation table for all ranges of ambient air temperatures provides best results because a linear or a quadratic relationship provide inaccurate estimates of body core temperature, yet a quantic relationship, a quintic relationship, sextic relationship, a septic relationship or an octic relationship provide estimates along a highly irregular curve that is far too wavy or twisting with relatively sharp deviations.

The non-touch electromagnetic sensor 3602 detects temperature in response to remote sensing of a surface a human or animal. In some implementations, the MVS smartphone system having an infrared sensor is an infrared temperature sensor. All humans or animals radiate infrared energy. The intensity of this infrared energy depends on the temperature of the human or animal, thus the amount of infrared energy emitted by a human or animal can be interpreted as a proxy or indication of the body core temperature of the human or animal. The non-touch electromagnetic sensor 3602 measures the temperature of a human or animal based on the electromagnetic energy radiated by the human or animal. The measurement of electromagnetic energy is taken by the non-touch electromagnetic sensor 3602 which constantly analyzes and registers the ambient air temperature. When the operator of apparatus in FIG. 36 holds the non-touch electromagnetic sensor 3602 about 5-8 cm (2-3 inches) from the forehead and activates the radiation sensor, the measurement is instantaneously measured. To measure a temperature using the non-touch electromagnetic sensor 3602, pushing the button 3506 causes a reading of temperature measurement from the non-touch electromagnetic sensor 3602 and in some implementations the measured body core temperature is thereafter displayed on the display device 3514. Various implementations of the non-touch electromagnetic sensor 3602 can be a digital infrared sensor, such as digital infrared sensor 3508 or an analog infrared sensor.

The body core temperature estimator 3518 correlates the temperatures sensed by the non-touch electromagnetic sensor 3602 to another temperature, such as a body core temperature of the subject, an axillary temperature of the subject, a rectal temperature of the subject and/or an oral temperature of the subject. The body core temperature estimator 3518 can be implemented as a component on a microprocessor, such as main processor 2802 in FIG. 28 or on a memory such as flash memory 2808 in FIG. 28.

The MVS device 3600 also detects the body core temperature of a human or animal regardless of the room temperature because the measured temperature of the non-touch electromagnetic sensor 3602 is adjusted in reference to the ambient air temperature in the air in the vicinity of the apparatus. The human or animal must not have undertaken vigorous physical activity prior to temperature measurement in order to avoid a misleading high temperature. Also, the room temperature should be moderate, 50° F. to 80° F.

The MVS device 3600 provides a non-invasive and non-irritating means of measuring human or animal body core temperature to help ensure good health. When evaluating results, the potential for daily variations in body core temperature can be considered. In children less than 6 months of age daily variation is small In children 6 months to 4 years old the variation is about 1 degree. By age 6 variations gradually increase to 4 degrees per day. In adults there is less body core temperature variation.

The MVS device 3600 also includes a wireless communication subsystem 2804 or other external communication subsystem, such as an Ethernet port, that provides communication to the EMR data capture systems 5500 and 5700. In some implementations, the wireless communication subsystem 2804 is communication subsystem 2804 in FIG. 44.

Figure 37:
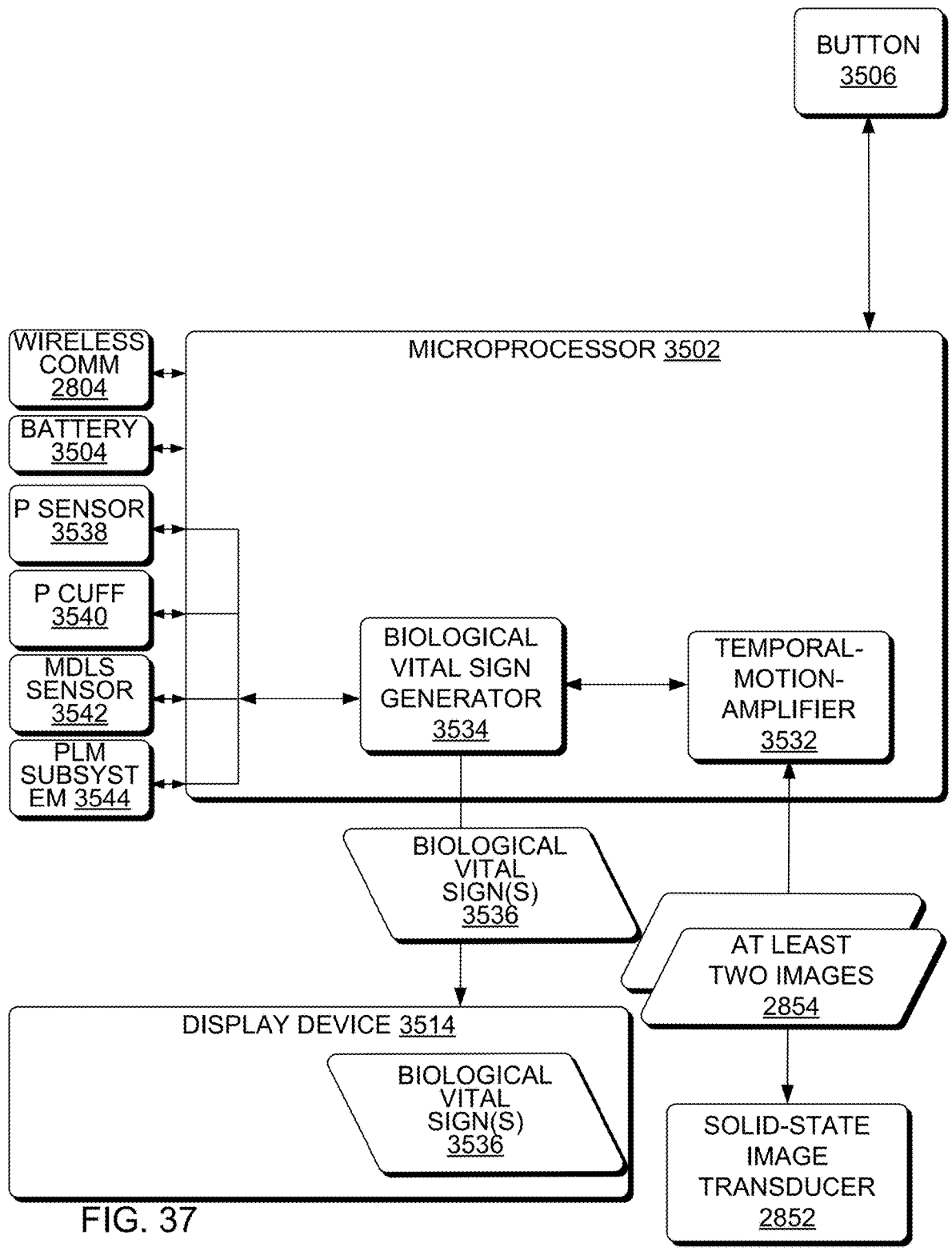
FIG. 37 is a block diagram of a MVS smartphone device that includes a non-touch electromagnetic sensor and that detects biological vital-signs from images captured by a solid-state image transducer, according to an implementation.

FIG. 37 is a block diagram of a MVS device 3700 that includes a non-touch electromagnetic sensor and that detects biological vital-signs from images captured by a solid-state image transducer, according to an implementation. The MVS device 3700 is one example of the MVS smartphone system 5504 and one example of the MVS finger cuff smartphone system (MVSFCSS) 502 in FIG. 5. The MVS device 3700 includes a battery 3504, in some implementations a single button 3506, in some implementations a display device 3514, a non-touch electromagnetic sensor 3602 and an ambient air sensor 1909 that are operably coupled to the microprocessor 3502. The microprocessor 3502 is configured to receive a representation of an infrared signal 3516 of the forehead or other external source point from the non-touch electromagnetic sensor 3602. The microprocessor 3502 includes a body core temperature estimator 3518 that is configured to estimate the body core temperature 3612 of the subject from the representation of the electromagnetic energy of the external source point. The MVS device 3700 includes a solid-state image transducer 2852 that is operably coupled to the microprocessor 3502 and is configured to provide two or more images 2854 to the microprocessor 3502.

The MVS device 3700 include a pressure sensor 3538, a pressure cuff 3540, a mDLS sensor 3542 and a PLM subsystem 3544 that provide signals to the biological vital sign generator 3534. The pressure sensor 3538 is directly linked to the pressure cuff 3540. In some implementations, the MVS device 3700 includes two mDLS sensors to ensure that at least one of the mDLS sensors provides a good quality signal. In some implementations, the biological vital sign generator 3534 generates blood pressure measurement (systolic and diastolic) from signals from the pressure sensor 3538, the finger pressure cuff 3540 and the mDLS sensor 3542. In some implementations, the biological vital sign generator 3534 generates SpO2 measurement and heart rate measurement from signals from the PLM subsystem 3544. In some implementations, the biological vital sign generator 3534 generates respiration (breathing rate) measurement from signals from the mDLS sensor 3542. In some implementations, the biological vital sign generator 3534 generates blood flow measurement from signals from the mDLS sensor 3542. In some implementations, the biological vital sign generator 3534 generates heartrate variability from signals from the PLM subsystem 3544.

8. Apparatus of Multi-Vital-Sign Components

FIG. 38 is a block diagram of an apparatus 3800 to estimate a body core temperature from a forehead temperature sensed by an infrared sensor, according to an implementation. Apparatus 3800 includes a power-initializer 3802 for the infrared sensor 3804 and a time delay 3806 that delays subsequent processing for a period of time specified by the time delay 3806 after power initialization of the infrared sensor 3804 by the power-initializer 3802, such as a delay of a minimum of 340 ms (+20 ms) to a maximum of 360 ms.

Apparatus 3800 includes a voltage level measurer 3808 of the infrared sensor 3804 that outputs a representation of the sensor voltage level 3810 of the infrared sensor 3804. When the sensor voltage level 3810 is below 2.7V or is above 3.5V, a reading error message 3812 is generated and displayed.

Apparatus 3800 also includes a sensor controller 3814 that initiates four infrared measurements 3816 of the forehead surface by the infrared sensor 3804 and receives the four infrared measurements 3816. In some implementations, each of the four infrared measurements 3816 of the forehead surface are performed by the infrared sensor 3804 with a period of at least 135 ms (+20 ms) to a maximum of 155 ms between each of the infrared measurements 3816.

If one of the up to 15 infrared measurements 3816 of the forehead surface by the infrared sensor 3804 that is received is invalid, a reading error message 3812 is displayed.

Apparatus 3800 also includes an ambient air temperature controller 3818 that initiates an ambient air temperature (Ta) measurement 3820 and receives the ambient air temperature (Ta) measurement 3820. If the ambient air temperature (Ta) measurement 3820 of the ambient air temperature is invalid, a reading error message 3812 is displayed. The ambient air temperature controller 3818 compares the ambient air temperature (Ta) measurement 3820 to a range of acceptable values, such as the numerical range of 283.15K (10° C.) to 313.15° K (40° C.). If the ambient air temperature (Ta) measurement 3820 is outside of this range, a reading error message 3812 is displayed. The sensor controller 3814 compares all four of the infrared measurements 3816 of the forehead surface by the infrared sensor 3804 to determine whether or not are all four are within 1 Kelvin degree of each other. If all four infrared measurements of the forehead surface by the infrared sensor 3804 are not within 1 Kelvin degree of each other, a reading error message 3812 is displayed.

The sensor controller 3814 averages the four infrared measurements of the forehead surface to provide a received object temperature (Tobj) 3822 when all four infrared measurements of the forehead surface by the infrared sensor 3804 are within 1 degree Kelvin of each other. The sensor controller 3814 also generates a voltage-corrected ambient air temperature (COvTa) 3824 and a voltage-corrected object temperature (COvTobj) 3826 by applying a sensor voltage correction 3828 to the ambient air temperature (Ta) and the object temperature (Tobj) 3822, respectively. For example, the sensor voltage correction 3828 in Kelvin=object temperature (Tobj)–(voltage at sensor–3.00) *0.65. In some implementations, a sensor calibration offset is applied to the voltage-corrected object temperature (COvTobj), resulting in a calibration-corrected voltage-corrected object temperature (COcaCOvTobj) 3830. For example, a sensor calibration offset of 0.60 Kelvin is added to each voltage-corrected object temperature (COvTobj) from the infrared sensor 3804 of a particular manufacturer.

An estimated body core temperature generator 3832 reads an estimated body core temperature 3834 from one or more tables 3836 that are stored in a memory 3838 (such as memory 3838 in FIG. 38) that correlates the calibration-corrected voltage-corrected object temperature (COcaCOvTobj) to the body core temperature in reference to the voltage-corrected ambient air temperature (COvTa) 3824. One implementation of the estimated body core temperature generator 3832 in FIG. 38 is apparatus 3900 in FIG. 39. The tables 3836 are also known as body core temperature correlation tables.

A scale converter 3840 converts the estimated body core temperature 3834 from Kelvin to ° C. or ° F., resulting in a converted body core temperature 3842. There is a specific algorithm for pediatrics (<=8 years old) to account for the different physiological response of children in the febrile >101 deg F. range.

FIG. 39-40 are block diagrams of an apparatus 3900 to derive an estimated body core temperature from one or more tables that are stored in a memory that correlate a calibration-corrected voltage-corrected object temperature to the body core temperature in reference to the corrected ambient air temperature, according to an implementation. Apparatus 3900 is one implementation of the estimated body core temperature generator 3832 in FIG. 38.

Apparatus 3900 includes an ambient air temperature operating-range comparator 3902 that is configured to compare the voltage-corrected ambient air temperature (COvTa) (3824 in FIG. 38) to an operational temperature range of the apparatus to determine whether or not the voltage-corrected ambient air temperature (COvTa) 3824 is outside of the operational temperature range of the apparatus. The operational temperature range is from the lowest operational temperature of the apparatus 3900 to the highest operational temperature of the MVS system 3000. In one example, the operational temperature range is 10.0° C. to 40.0° C. In a further example, if the voltage-corrected ambient air temperature (COvTa) is 282.15° K (9.0° C.), which is less than the exemplary lowest operational temperature (10.0° C.), then the voltage-corrected ambient air temperature (COvTa) is outside of the operational temperature range.

Apparatus 3900 includes an ambient air temperature table-range comparator 3904 that determines whether or not the voltage-corrected ambient air temperature (COvTa) 3824 is outside of the range of the tables. For example, if the voltage-corrected ambient air temperature (COvTa) is 287.15° K (14.0° C.), which is less than the lowest ambient air temperature in the tables, then the voltage-corrected ambient air temperature (COvTa) is outside of the range of the tables. In another example, if the voltage-corrected ambient air temperature (COvTa) is 312.25° K (39.1° C.), which is greater than the highest ambient air temperature (37.9° C.) of all of the tables, then the voltage-corrected ambient air temperature (COvTa) is outside of the range of the tables.

When the ambient air temperature table-range comparator 3904 determines that the voltage-corrected ambient air temperature (COvTa) 3824 is outside of the range of the tables, then control passes to an ambient air temperature range-bottom comparator 3906 that is configured to compare the voltage-corrected ambient air temperature (COvTa) (3924 in FIG. 38) to the bottom of the range of the tables to determine whether or not the voltage-corrected ambient air temperature (COvTa) 3824 is less than the range of the tables. The bottom of the range of the tables is the lowest ambient air temperature of all of the tables, such as 14.6° C. In a further example, if the voltage-corrected ambient air temperature (COvTa) is 287.15° K (14.0° C.), which is less than the lowest ambient air temperature (14.6° C.) of the tables, then the voltage-corrected ambient air temperature (COvTa) is less than the bottom of the range of the tables.

When the ambient air temperature range-bottom comparator 3906 determines that the voltage-corrected ambient air temperature (COvTa) 3824 is less than the range of the tables, control passes to an estimated body core temperature calculator for hypo ambient air temperatures 3908 sets the estimated body core temperature 3834 to the calibration-corrected voltage-corrected object temperature (COcaCOvTobj) 3830+0.19° K for each degree that the voltage-corrected ambient air temperature (COvTa) is below the lowest ambient body core table.

For example, when the voltage-corrected ambient air temperature (COvTa) is 12.6° C., which is less than the range of the tables, 14.6° C., and the calibration-corrected voltage-corrected object temperature (COcaCOvTobj) 3830 is 29° C. (302.15° K) then the estimated body core temperature calculator for hypo ambient air temperatures 3908 sets the estimated body core temperature 3834 to 302.15° K+(0.19° K*(14.6° C.–12.6° C.)), which is 302.53° K.

When the ambient air temperature range-bottom comparator 3906 determines that the voltage-corrected ambient air temperature (COvTa) 3824 is not less than the range of the tables, control passes to an estimated body core temperature calculator 3910 for hyper ambient air temperatures that sets the estimated body core temperature 3834 to the calibration-corrected voltage-corrected object temperature (COcaCOvTobj) 3830-0.13° K for each degree that the voltage-corrected ambient air temperature (COvTa) is above the highest ambient body core table.

For example, when the voltage-corrected ambient air temperature (COvTa) is 45.9° C., which is above the range of all of the tables, (43.9° C.), and the calibration-corrected voltage-corrected object temperature (COcaCOvTobj) 3830 is 29° C. (302.15° K) then the estimated body core temperature calculator 3910 for hyper ambient air temperatures sets the estimated body core temperature 3834 to 302.15° K−(0.13° K*(45.9° C.−43.9° C.)), which is 301.89° K.

When the ambient air temperature table-range comparator 3904 determines that the voltage-corrected ambient air temperature (COvTa) 3824 is not outside of the range of the tables, then control passes to an ambient air temperature table comparator 3912 that determines whether or not the voltage-corrected ambient air temperature (COvTa) is exactly equal to the ambient air temperature of one of the tables, when the estimated body core temperature calculator 3910 for hyper ambient air temperatures determines that the voltage-corrected ambient air temperature (COvTa) is within of the range of the tables. When the ambient air temperature table comparator 3912 determines that the voltage-corrected ambient air temperature (COvTa) is exactly equal to the ambient air temperature of one of the tables, then the estimated body core temperature table value selector for exact ambient air temperatures 3914 sets the estimated body core temperature 3834 to the body core temperature of that one table, indexed by the calibration-corrected voltage-corrected object temperature (COcaCOvTobj) 3830.

For example, when the voltage-corrected ambient air temperature (COvTa) is 34.4° C. (the ambient air temperature of Table D) and the calibration-corrected voltage-corrected object temperature (COcaCOvTobj) 3830 is 29.1° C., then the estimated body core temperature table value selector for exact ambient air temperatures 3914 sets the estimated body core temperature 3834 to 29.85 C, which is the body core temperature of Table D indexed at the calibration-corrected voltage-corrected object temperature (COcaCOvTobj) 3830 of 29.1° C.

Apparatus 3900 includes a table interpolation selector 3916. When the ambient air temperature table comparator 3912 determines that the voltage-corrected ambient air temperature (COvTa) is not exactly equal to the ambient air temperature of one of the tables, then the table interpolation selector 3916 identifies the two tables which the voltage-corrected ambient air temperature (COvTa) falls between.

For example, if the voltage-corrected ambient air temperature (COvTa) is 293.25° K (20.1° C.), this ambient value falls between the tables for ambient air temperatures of 19.6° C. and 24.6° C., in which case, the 19.6° C. table is selected as the Lower Body Core Table and the 24.6° C. table is selected as the Higher Body Core Table.

Thereafter, apparatus 3900 includes a table interpolation weight calculator 3920 that calculates a weighting between the lower table and the higher table, the table interpolation weights 3922.

For example, when Tamb_bc_low (the voltage-corrected ambient air temperature (COvTa) for the Lower Body Core Table)=19.6° C. and T amb_bc_high (the voltage-corrected ambient air temperature (COvTa) for the Higher Body Core Table)=24.6 C, then the amb_diff=(Tamb_bc_high−Tamb_bc_low/100)=(24.6−19.6)/100=0.050° C. Further, the Higher Table Weighting=100/((Tamb−Tamb_bc_low)/amb_diff)=100/((20.1−19.6)/0.050)=10% and the Lower Table Weighting=100−Higher Table Weighting=100−10=90%.

Apparatus 3900 includes a body core temperature reader 3924 that reads the core body core temperature that is associated with the sensed forehead temperature from each of the two tables, the Lower Body Core Table and the Higher Body Core Table. The calibration-corrected voltage-corrected object temperature (COcaCOvTobj) 3830 is used as the index into the two tables.

Apparatus 3900 also includes a correction value calculator 3926 that calculates a correction value 3928 for each of the Lower Body Core Table and the Higher Body Core Table. For example, where each of the tables has an entry of calibration-corrected voltage-corrected object temperature (COcaCOvTobj) 3830 for each 0.1° Kelvin, to calculate to a resolution of 0.01° Kelvin, the linear difference is applied to the two table values that the calibration-corrected voltage-corrected object temperature (COcaCOvTobj) 3830 falls between.

For example, when the calibration-corrected voltage-corrected object temperature (COcaCOvTobj) 3830 is 309.03° K, then the calibration-corrected voltage-corrected object temperature (COcaCOvTobj) 3830 falls between 309.00 and 309.10. The correction value 3928 is equal to a+((b−a)*0.03), where a=body core correction value for 309.0° K and b=body curve correction value for 309.1° K.

Thereafter, apparatus 3900 includes an estimated body core temperature calculator for interpolated tables 3930 that determines the body core temperature of the sensed forehead temperature in reference to the ambient air temperature by summing the weighted body core temperatures from the two tables. The estimated body core temperature is determined to equal (Tcor_low*Lower Table Weighting/100)+(Tcor_high*Higher Table Weighting/100).

For example, when the voltage-corrected ambient air temperature (COvTa) is 293.25° K (20.10° C.), then in this case 90% (⁹⁰⁄₁₀₀) of the Table) and 10% (¹⁰⁄₁₀₀) are summed to set the estimated body core temperature 3834.

The comparator 3902, comparator 3904 and comparator 3906 can be arranged in any order relative to each other.

Figure 41:
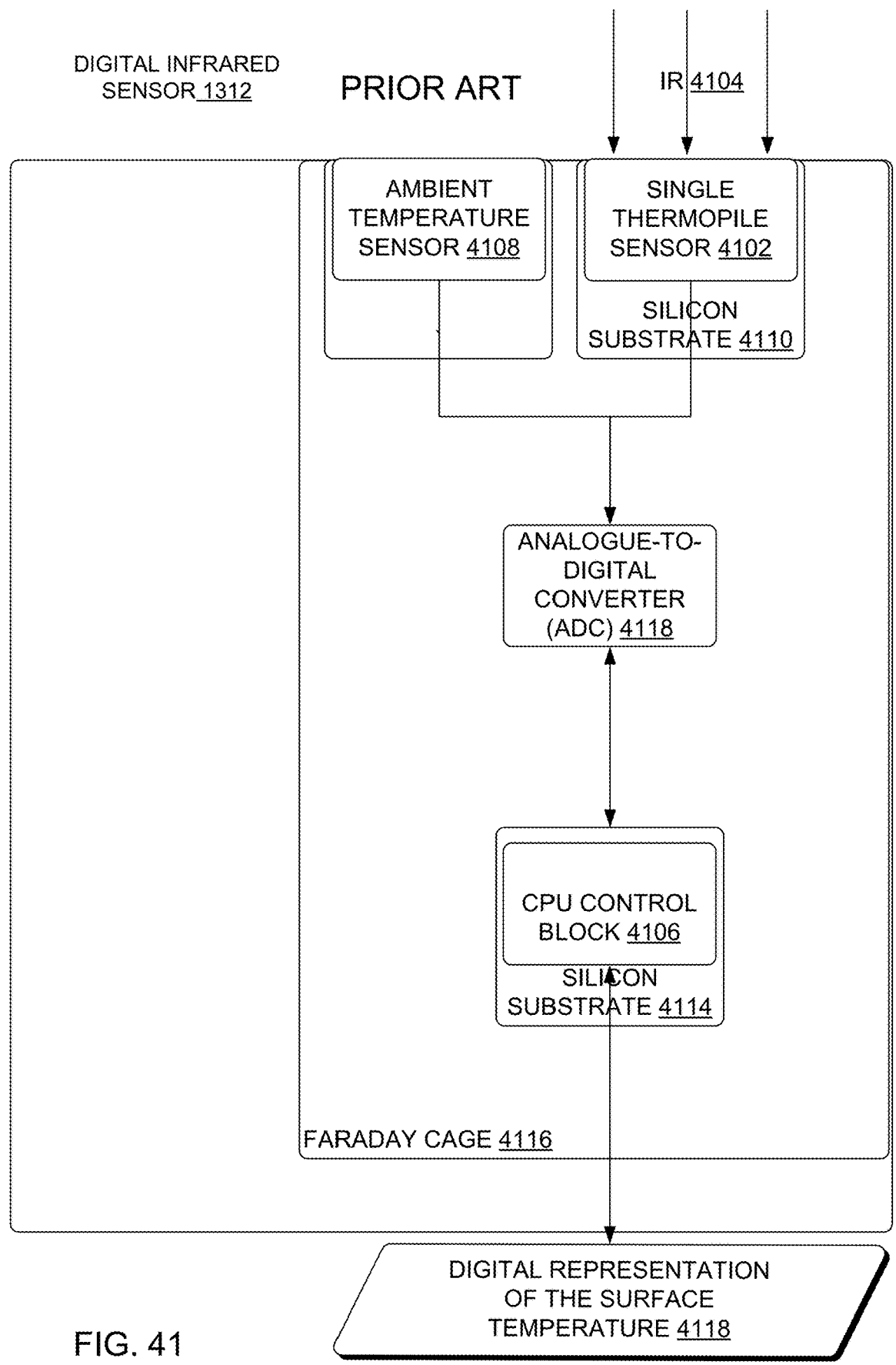
FIG. 41 is a block diagram of a digital infrared sensor, according to an implementation.

FIG. 41 is a block diagram of a digital infrared sensor 1312, according to an implementation. The digital infrared sensor 1312 contains a single thermopile sensor 4102 that senses only infrared electromagnetic energy 4104. The digital infrared sensor 1312 contains a CPU control block 4106 and an ambient air temperature sensor 4108, such as a thermocouple. The single thermopile sensor 4102, the ambient air temperature sensor 4108 and the CPU control block 4106 are on separate silicon substrates 4110, 4112 and 4114 respectively. The CPU control block 4106 digitizes the output of the single thermopile sensor 4102 and the ambient air temperature sensor 4108.

The digital infrared sensor 1312 has a Faraday cage 4116 surrounding the single thermopile sensor 4102, the CPU control block 4106 and the ambient air temperature sensor 4108 to prevent electromagnetic (EMF) interference in the single thermopile sensor 4102, the CPU control block 4106 and the ambient air temperature sensor 4108 that shields the components in the Faraday cage 4116 from outside electromagnetic interference, which improves the accuracy and the repeatability of a device that estimates body core temperature from the ambient and object temperature generated by the digital infrared sensor 1312. The digital IR sensor 1312 also requires less calibration in the field after manufacturing, and possibly no calibration in the field after manufacturing because in the digital infrared sensor 1312, the single thermopile sensor 4102, the CPU control block 4106 and the ambient air temperature sensor 4108 are in close proximity to each other, which lowers temperature differences between the single thermopile sensor 4102, the CPU control block 4106 and the ambient air temperature sensor 4108, which minimizes or eliminates calibration drift over time because they are based on the same substrate material and exposed to the same temperature and voltage variations. In comparison, conventional infrared temperature sensors do not include a Faraday cage 4116 that surrounds the single thermopile sensor 4102, the CPU control block 4106 and the ambient air temperature sensor 4108. The Faraday cage 4116 can be a metal box or a metal mesh box. In the implementation where the Faraday cage 4116 is a metal box, the metal box has an aperture where the single thermopile sensor 4102 is located so that the field of view of the infrared electromagnetic energy 4104 is not affected by the Faraday cage 4116 so that the infrared electromagnetic energy 4104 can pass through the Faraday cage 4116 to the single thermopile sensor 4102. In the implementation where the Faraday cage 4116 is a metal box, the metal box has an aperture where the ambient air temperature sensor 4108 is located so that the atmosphere can pass through the Faraday cage 4116 to the ambient air temperature sensor 4108. In other implementations the ambient air temperature sensor 4108 does not sense the temperature of the atmosphere, but instead senses the temperature of the sensor substrate (silicon) material and surrounding materials because the ambient air temperature sensor 4108 and the target operating environment temperature are required to be as close as possible in order to reduce measurement error, i.e. the ambient air temperature sensor 4108 is to be in thermal equilibrium with the target operating environment.

In some further implementations, the Faraday cage 4116 of the digital infrared sensor 1312 also includes an multichannel analogue-to-digital converter (ADC) 4118 that digitizes an analogue signal from the single thermopile sensor 4102. The ADC 4118 also digitizes an analogue signal from the ambient air temperature sensor 4108. In another implementation where the ADC is not a multichannel ADC, separate ADCs are used to digitize the analogue signal from the single thermopile sensor 4102 and the analogue signal from the ambient air temperature sensor 4108. There is no ADC between the digital infrared sensor 1312 and microprocessor(s), main processor(s) and controller(s) that are outside the digital IR sensor 1312, such as the microprocessor 3502 in FIG. 35.

The single thermopile sensor 4102 of the digital infrared sensor 1312 is tuned to be most sensitive and accurate to the human body core temperature range, such as forehead surface temperature range of 25° C. to 39° C. The benefits of the digital IR sensor 1312 in comparison to conventional analogue infrared temperature sensors include minimization of the temperature difference between the analogue and digital components effects on calibration parameters (when the temperature differences are close there is a smaller ΔT which mimics the calibration environment) and reduction of EMC interference in the datalines. The digital infrared sensor 1312 outputs a digital representation of the surface temperature in absolute Kelvin degrees (° K) that is presented at a digital readout port of the digital infrared sensor 1312. The digital representation of the surface temperature is also known as the body surface temperature in FIG. 41, digital readout signal 3511 in FIG. 35, digital signal that is representative of an infrared signal of a forehead temperature that is detected by the digital infrared sensor in FIG. 59, the body core temperature in FIG. 33, the temperature measurement in FIG. 61, the sensed forehead temperature in FIG. 38 and the numerical representation of the electromagnetic energy of the external source point in FIG. 63.

The digital infrared sensor 1312 is not an analog device or component, such as a thermistor or a resistance temperature detector (RTD). Because the digital infrared sensor 1312 is not a thermistor, there is no need or usefulness in receiving a reference signal of a resister and then determining a relationship between the reference signal and a temperature signal to compute the surface temperature. Furthermore, the digital infrared sensor 1312 is not an array of multiple transistors as in complementary metal oxide (CMOS) devices or charged coupled (CCD) devices. None of the subcomponents in the digital infrared sensor 1312 detect electromagnetic energy in wavelengths of the human visible spectrum (380 nm-750 nm). Neither does the digital infrared sensor 1312 include an infrared lens.

Figure 42:
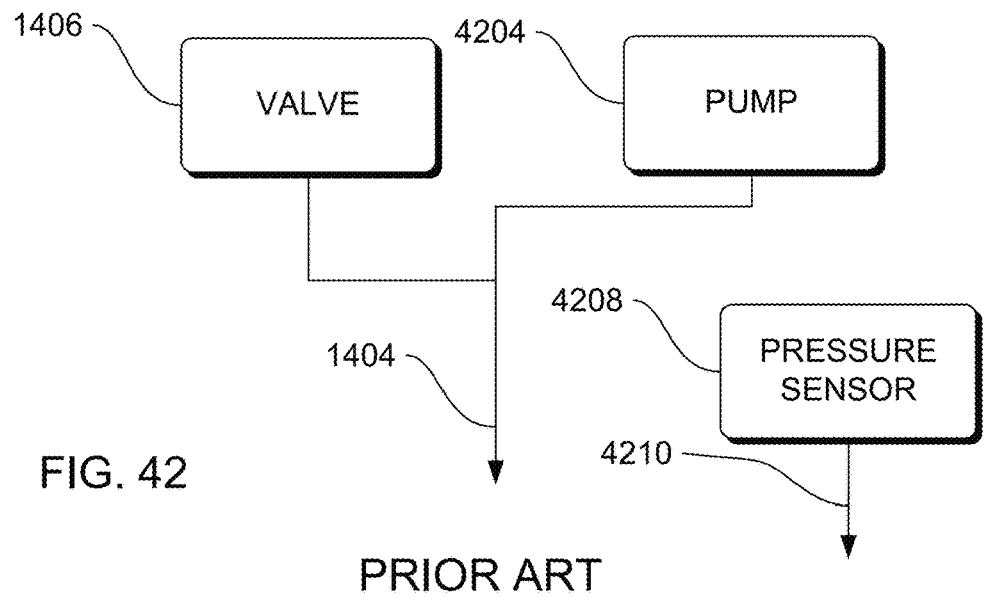
FIG. 42 is a block diagram of pneumatic system components that are internal to the MVS finger cuff smartphone system, according to an implementation.

FIG. 42 is a block diagram of a pneumatic system components 4200, according to an implementation. The pneumatic system components 4200 is one component of the MVS finger cuff 3006 in Fig. The pneumatic system components 4200 are in the MVSFCA 3002, MVSFCA 3102, MVSFCSS 3300, MVSFCA 1900 and the front end of a MVS finger cuff 2000.

The pneumatic system components 4200 includes a pneumatic pump 4204 that is mechanically coupled to an inflatable cuff bladder, such as inflatable cuff bladder 6806 that provides air pressure to inflate the inflatable cuff bladder in the finger occlusion cuff 3016 in FIG. 30. The inflatable cuff bladder 6806 is mechanically coupled to the pneumatic pump 4204 via an air line 421404. The inflatable cuff bladder 6806 is mechanically coupled to a pressure sensor 4208 that measures pneumatic pressure in the inflatable cuff bladder 6806. The air line 4206 is mechanically coupled to a valve 1406 that controls pressure from the pneumatic pump 4204 to the inflatable cuff bladder 6806. The pneumatic system components 4200 is one implementation of the pneumatic engine 3005 and the pneumatic engine 1906.

Figure 43:
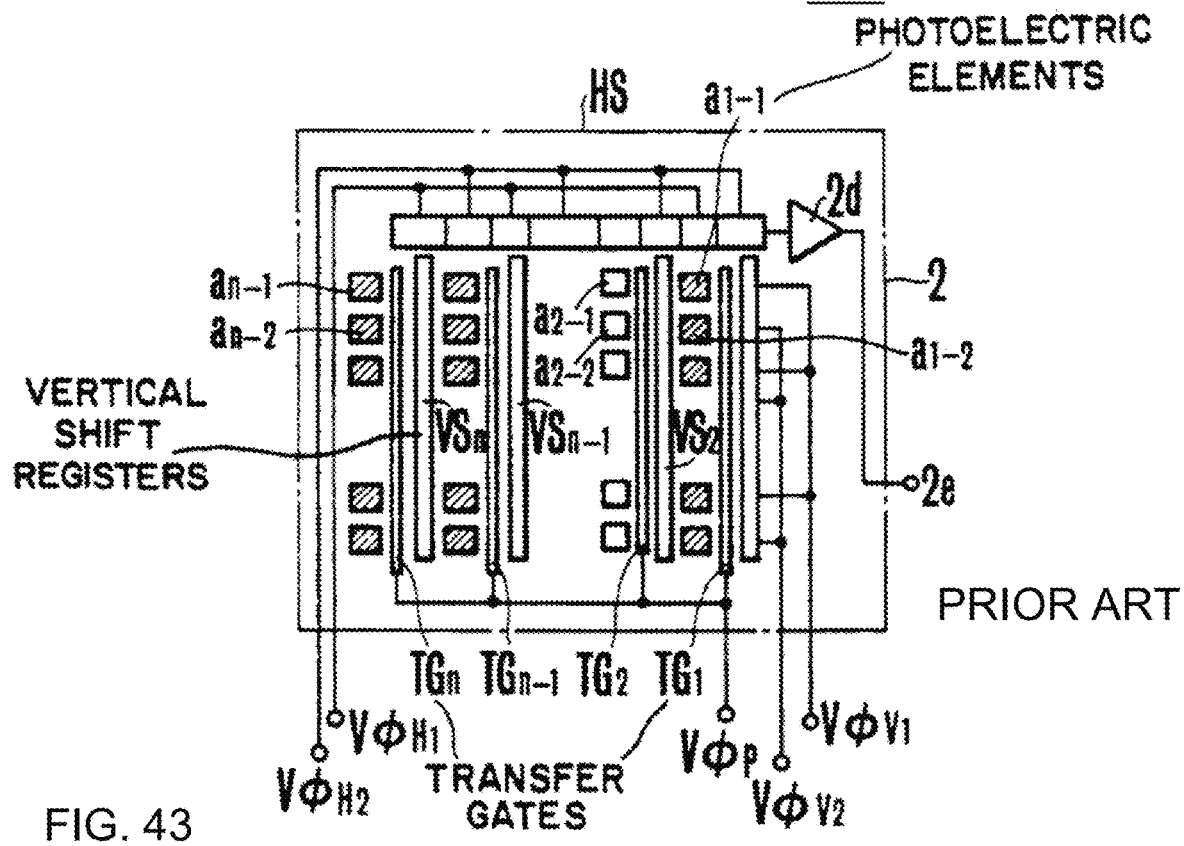
FIG. 43 is a block diagram of a solid-state image transducer, according to an implementation.

FIG. 43 is a block diagram of a solid-state image transducer 2852, according to an implementation. The solid-state image transducer 2852 includes a great number of photoelectric elements, $a_{1..}sub.1$, $a_{2..}sub.1$, . . . , $a_{mn}$, in the minute segment form, transfer gates TG1, TG2, . . . , TGn responsive to a control pulse $V._{\varphi}P$ for transferring the charges stored on the individual photoelectric elements as an image signal to vertical shift registers VS1, VS2, . . . , VSn, and a horizontal shift register HS for transferring the image signal from the vertical shift registers VSs, through a buffer amplifier 2d to an outlet 2e. After the one-frame image signal is stored, the image signal is transferred to vertical shift register by the pulse $V._{\varphi}P$ and the contents of the vertical shift registers VSs are transferred upward line by line in response to a series of control pulses $V._{\varphi}V1$, $V._{\varphi}V2$. During the time interval between the successive two vertical transfer control pulses, the horizontal shift register HS responsive to a series of control pulses $V._{\varphi}H1$, $V._{\varphi}H2$ transfers the contents of the horizontal shift registers HSs in each line row by row to the right as viewed in FIG. 43. As a result, the one-frame image signal is formed by reading out the outputs of the individual photoelectric elements in such order.

Figure 44:
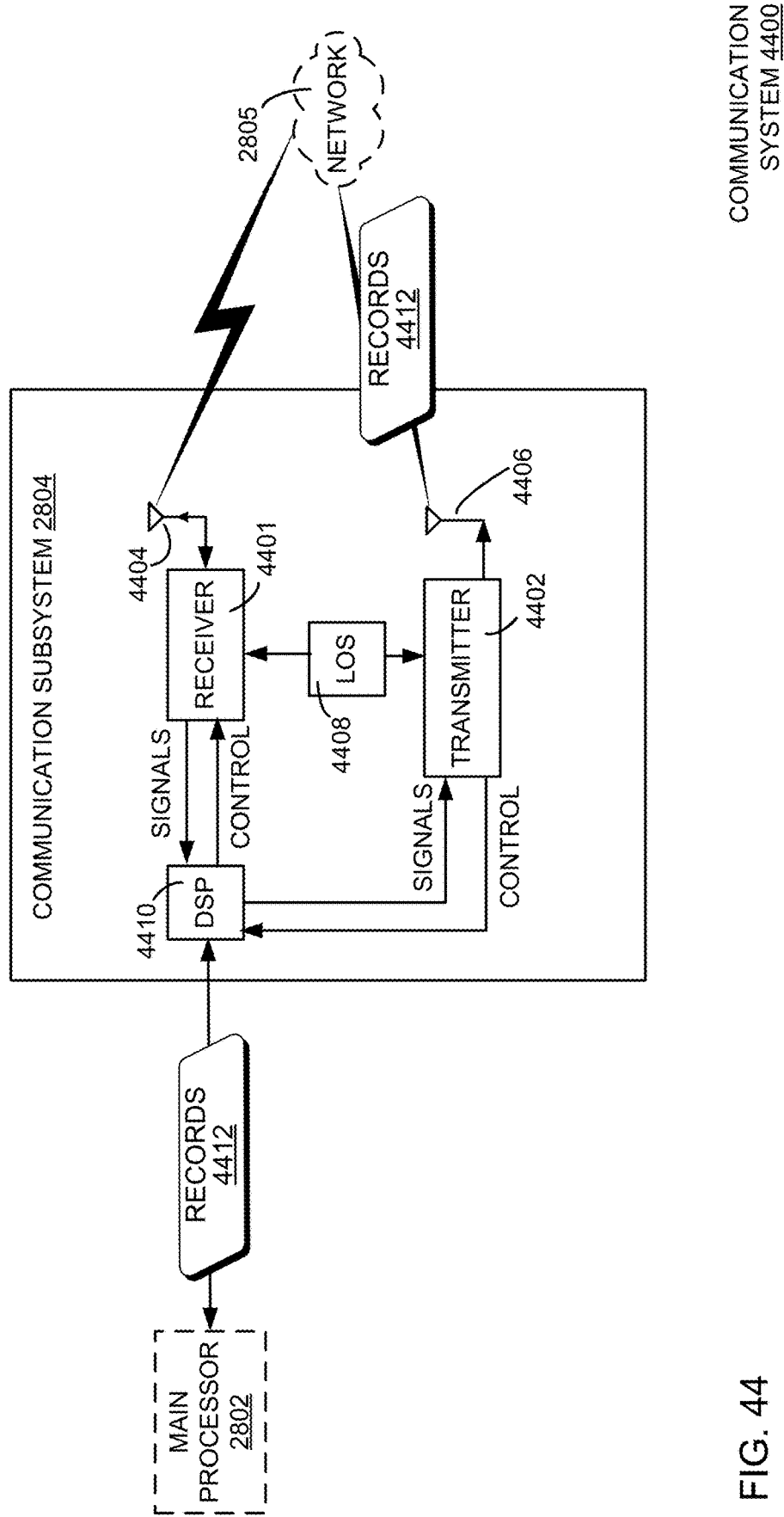
FIG. 44 is a block diagram of a communication system, according to an implementation.

FIG. 44 is a block diagram of a wireless communication system 4400, according to an implementation. The wireless communication system 4400 includes a communication subsystem 2804 that includes a receiver 4401, a transmitter 4402, as well as associated components such as one or more embedded or antennas 4404 and 4406, Local Oscillators (LOs) 4408, and a processing module such as a digital signal processor (DSP) 4410. The particular implementation of the wireless communication subsystem 2804 is dependent upon communication protocols of a wireless network 2805 with which the mobile device is intended to operate. Thus, it should be understood that the implementation illustrated in FIG. 44 serves only as one example. Examples of the mobile device include MVS smartphone 2800, MVS smartphone system in FIG. 3031 and MVS smartphone in FIG. 28-34. Examples of the wireless network 4405 include network 2805 in FIG. 28.

Signals received by the antenna 4404 through the wireless network 4405 are input to the receiver 4401, which may perform such common receiver functions as signal amplification, frequency down conversion, filtering, channel selection, and analog-to-digital (A/D) conversion. A/D conversion of a received signal allows more complex communication functions such as demodulation and decoding to be performed in the DSP 4410. In a similar manner, signals to be transmitted are processed, including modulation and encoding, by the DSP 4410. These DSP-processed signals are input to the transmitter 4402 for digital-to-analog (D/A) conversion, frequency up conversion, filtering, amplification and transmission over the wireless network 4405 via the antenna 4406. The DSP 4410 not only processes communication signals, but also provides for receiver and transmitter control. For example, the gains applied to communication signals in the receiver 4401 and the transmitter 4402 may be adaptively controlled through automatic gain control algorithms implemented in the DSP 4410.

The wireless link between the MVS apparatus 5504 and the wireless network 4405 can contain one or more different channels, typically different RF channels, and associated protocols used between the MVS apparatus 5504 and the wireless network 4405. An RF channel is a limited resource that must be conserved, typically due to limits in overall bandwidth and limited battery power of the MVS apparatus 5504.

When the MVS apparatus 5504 are fully operational, the transmitter 4402 is typically keyed or turned on only when it is transmitting to the wireless network 4405 and is otherwise turned off to conserve resources. Similarly, the receiver 4401 is periodically turned off to conserve power until the receiver 4401 is needed to receive signals or information (if at all) during designated time periods.

Each patient record 4412 is received by the wireless communication subsystem 2804 from the main processor 2802 at the DSP 4410 and then transmitted to the wireless network 4405 through the antenna 4404 of the receiver 4401. In some implementations, each patient record 4412 is a patient file that is managed or controlled by an ambulatory medical facility or a private medical office, such as a Patient Portal Medical Record or a Patient-Generated Health Data (PGHD)) and conforms to the Patient Care Device Technical Framework standard published by the Integrating the Healthcare Enterprise of 820 Jorie Boulevard, Oak Brook, Ill. 60523 or the Fundamentals of Data Exchange standard published by the Personal Connected Health Alliance of 4300 Wilson Boulevard—Suite 250, Arlington, Va. 22203, or data exchange requirement of various EHR and EMR vendors.

Figure 45:
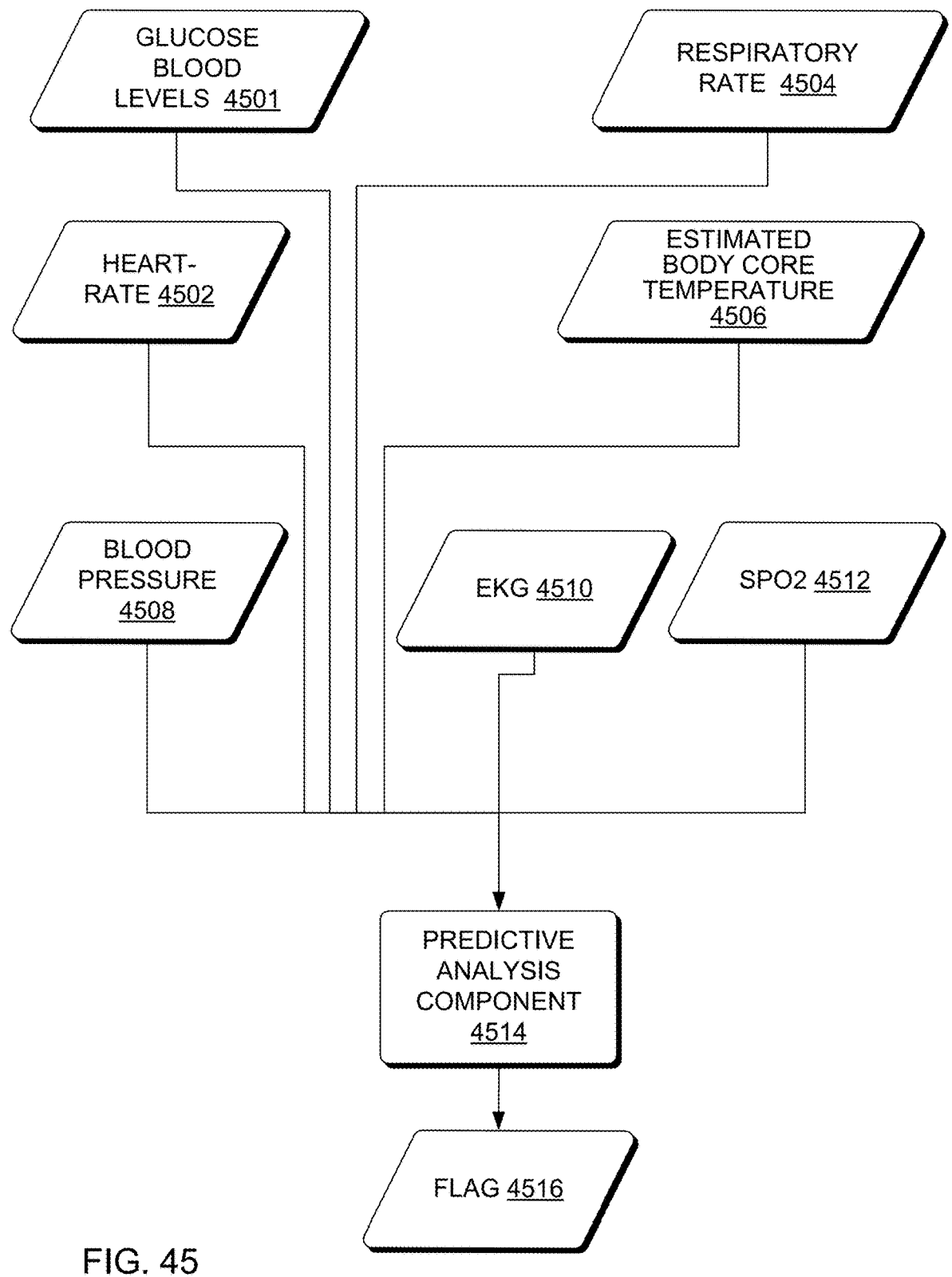
FIG. 45 is a block diagram of an apparatus to generate a predictive analysis of vital signs, according to an implementation.
Figure 55:
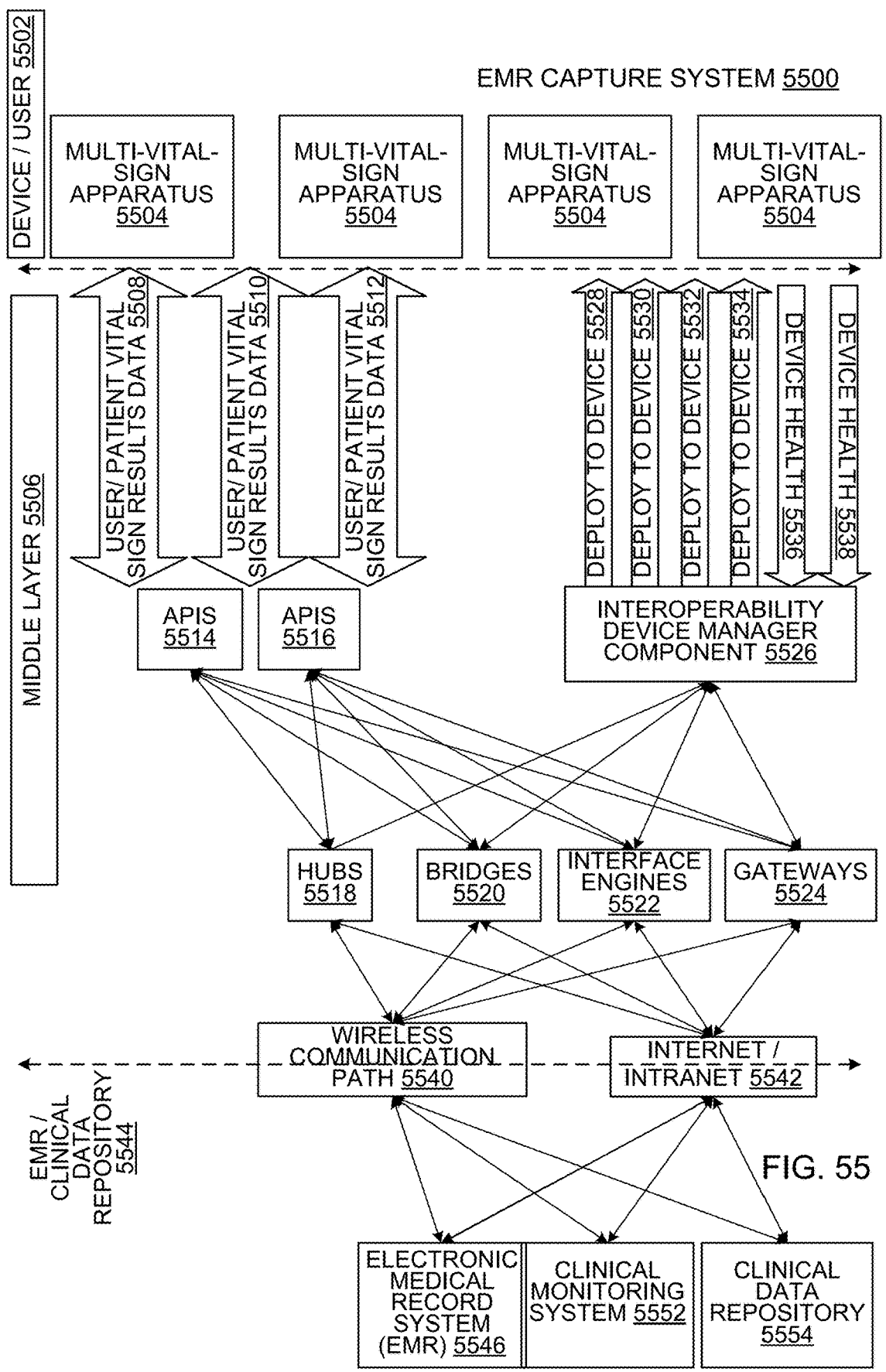
FIG. 55 is a block diagram of an overview of an electronic medical records capture system, according to an implementation.
Figure 56:
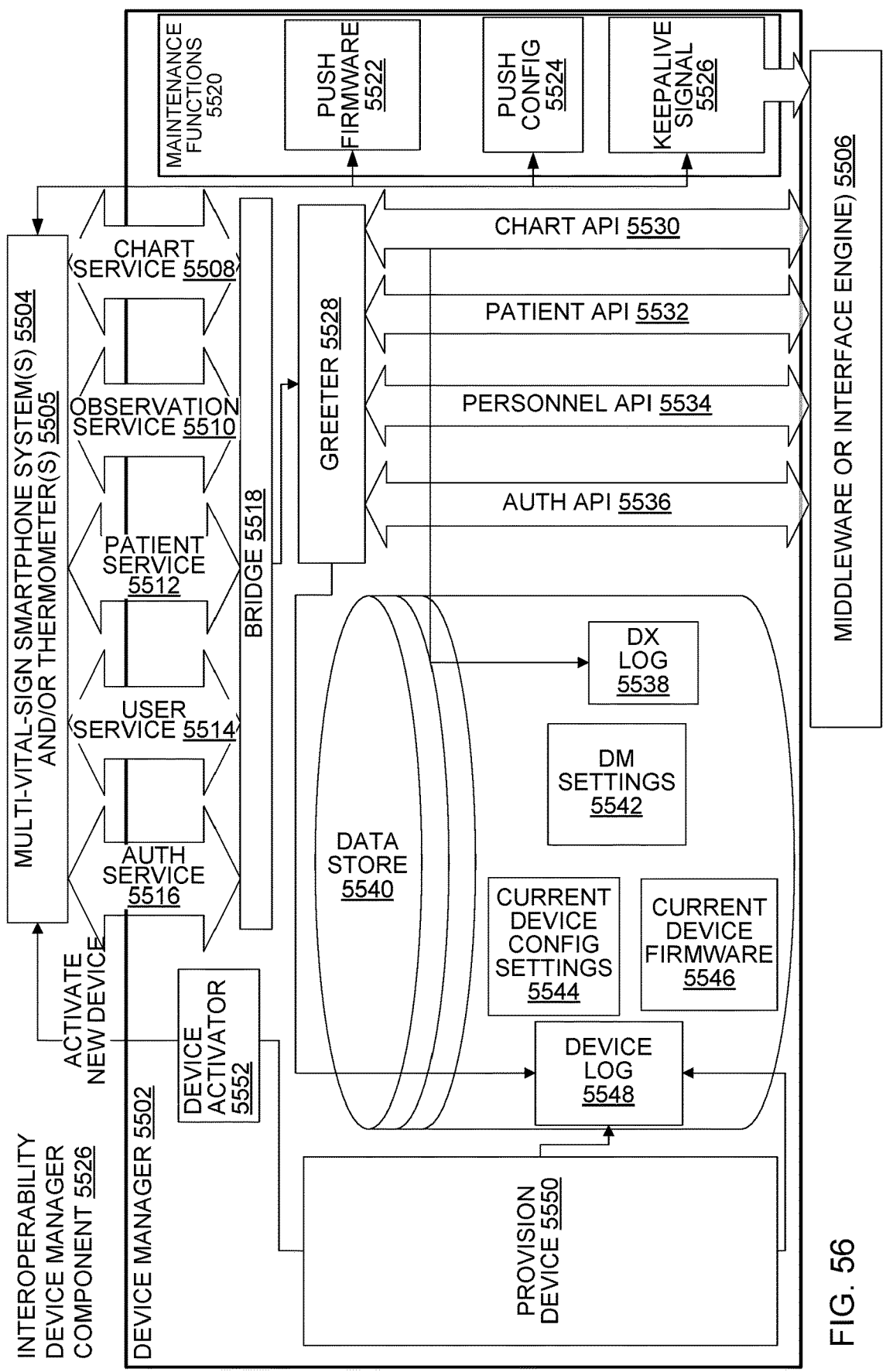
FIG. 56 is a block diagram of a system of interoperation device manager, according to an implementation.
Figure 57:
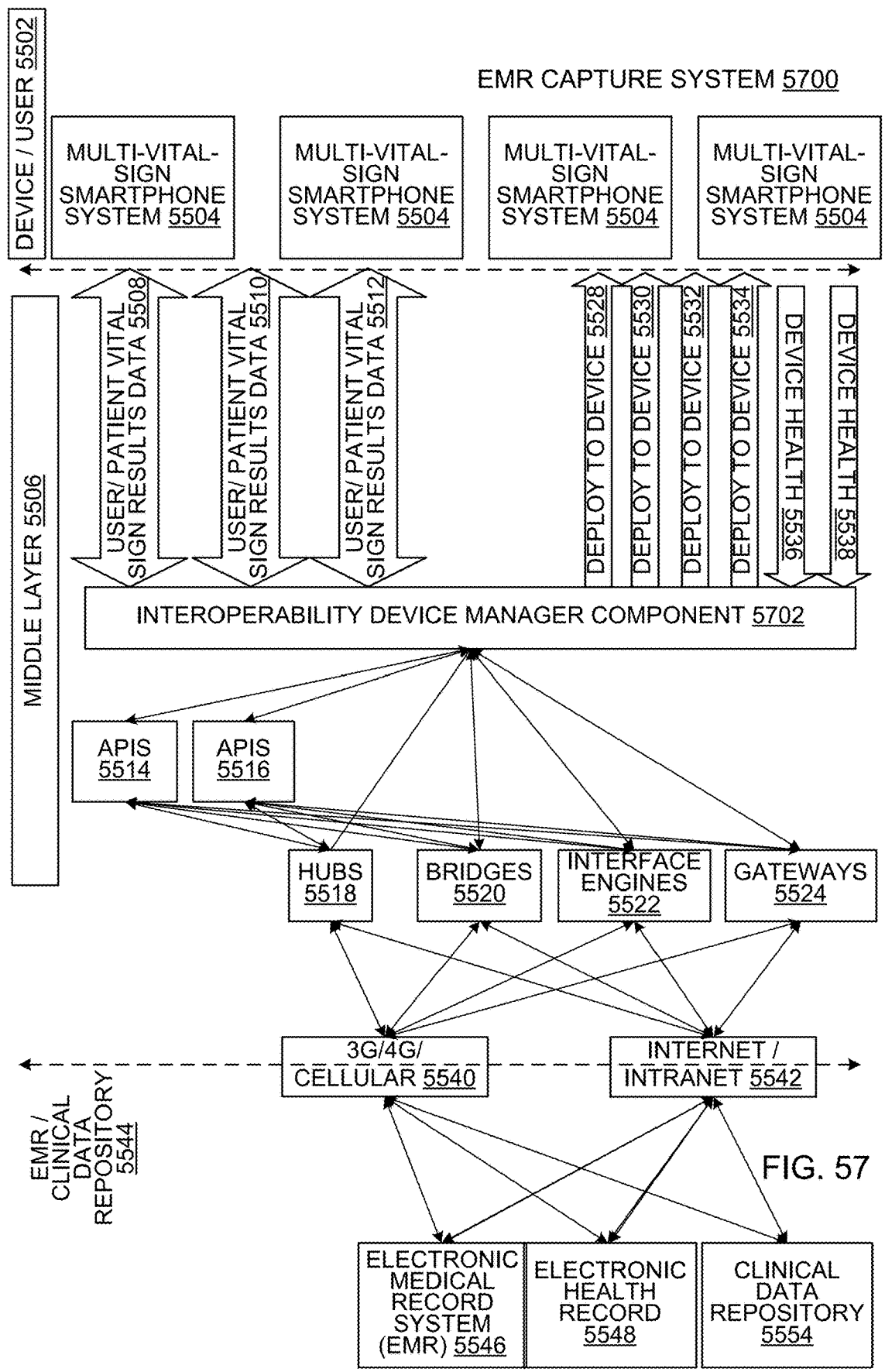
FIG. 57 is a block diagram of apparatus of an EMR capture system, according to an implementation in which an interoperability manager component manages all communications in the middle layer.

FIG. 45 is a block diagram of an apparatus 4500 to generate a predictive analysis of vital signs, according to an implementation. The apparatus 4500 can be implemented on the MVS finger cuff accessory (MVSFCA) 3002 in FIG. 30, the MVS smartphone (MVS Smartphone) 3004 in FIG. 30, the MVS finger cuff accessory (MVSFCA) 3102 in FIG. 31 or the MVS smartphone 3103 in FIG. 31, the sensor management component 3302 in FIG. 33, the microprocessor 3320 in FIG. 33, the MVS finger cuff 1904 in FIG. 19 and FIG. 7, the microprocessor 1902 in FIG. 19, controller 2020 in FIG. 20, the microprocessor 3402 in FIG. 34 and/or main processor 2802 in FIG. 28. In apparatus 4500, blood glucose levels 4501, heartrate data 4502, respiratory rate data 4504, estimated body core temperature data 4506 (such as estimated body core temperature 3520 in FIG. 35 or estimated body core temperature 3612 in FIG. 38-40), blood pressure data 4508 (such as blood pressure 5222 in FIG. 52), EKG data 4510 (such as EKG 5228 in FIG. 52) and/or SpO2 data 4512 is received by a predictive analysis component 4514 that evaluates the data 4501, 4502, 4504, 4506, 4508, 4510 and/or 4512 in terms of percentage change over time. More specifically, the relative change and the rate of change or change in comparison to an established pattern that is described in terms of frequency and amplitude. When the percentage change over time exceeds a predetermined threshold, a flag 4516 is set to indicate an anomaly. The flag 4516 can be transmitted to the EMR/clinical data repository 5544, as shown in FIG. 55-57.

FIG. 46 is a block diagram of an apparatus 4600 of motion amplification, according to an implementation. Apparatus 4600 analyzes the temporal and spatial variations in digital images of an animal subject in order to generate and communicate biological vital signs.

In some implementations, apparatus 4600 includes a forehead skin-pixel-identification module 4602 that identifies pixel-values that are representative of the skin in two or more images 2854. The pixel-values are the values of the pixels in the images 2854. In some implementations the images 2854 are frames of a video. The forehead skin-pixel-identification module 4602 performs block 5404 in FIG. 54. Some implementations of the forehead skin-pixel-identification module 4602 perform an automatic seed point based clustering process on the two or more images 2854. In some implementations, apparatus 4600 includes a frequency filter 4606 that receives the output of the forehead skin-pixel-identification module 4602 and applies a frequency filter to the output of the forehead skin-pixel-identification module 4602. The frequency filter 4606 performs block 5406 in FIG. 54 to process the images 2854 in the frequency domain. In implementations where the apparatus in FIG. 46-54 are implemented on MVS smartphone systems and MVS smartphone systems having an infrared sensor in FIG. 30-34, the images 2854 in FIG. 46-54 are the images 2854 in FIG. 35-40. In some implementations the apparatus in FIG. 46-54 are implemented on the MVS smartphone 2800 in FIG. 28.

In some implementations, apparatus 4600 includes a regional facial clusterial module 4608 that includes a spatial clusterer that is applied to the output of the frequency filter 4606. The regional facial clusterial module 4608 performs block 5408 in FIG. 54. In some implementations the regional facial clusterial module 4608 includes fuzzy clustering, k-means clustering, expectation-maximization process, Ward's apparatus or seed point based clustering.

In some implementations, apparatus 4600 includes a frequency-filter 4610 that applies a frequency filter to the output of the regional facial clusterial module 4608. The frequency-filter 4610 performs block 5410 in FIG. 54. In some implementations, the frequency-filter 4610 is a one-dimensional spatial Fourier Transform, a high pass filter, a low pass filter, a bandpass filter or a weighted bandpass filter. Some implementations of frequency-filter 4610 includes de-noising (e.g. smoothing of the data with a Gaussian filter). The forehead skin-pixel-identification module 4602, the frequency filter 4606, the regional facial clusterial module 4608 and the frequency-filter 4610 amplify temporal motion (as a temporal-motion-amplifier) in the two or more images 2854.

In some implementations, apparatus 4600 includes a temporal-motion identifier 4612 that identifies temporal motion of the output of the frequency-filter 4610. Thus, the temporal motion represents temporal motion of the images 2854. The temporal-motion identifier 4612 performs block 5412 in FIG. 54.

In some implementations, apparatus 4600 includes a biological vital-sign generator 4614 that generates one or more biological vital sign(s) 4616 from the temporal motion. The biological vital sign(s) 4616 are displayed for review by a healthcare worker or stored in a volatile or nonvolatile memory for later analysis, or transmitted to other devices for analysis.

Fuzzy clustering is a class of processes for cluster analysis in which the allocation of data points to clusters is not "hard" (all-or-nothing) but "fuzzy" in the same sense as fuzzy logic. Fuzzy logic being a form of many-valued logic which with reasoning that is approximate rather than fixed and exact. In fuzzy clustering, every point has a degree of belonging to clusters, as in fuzzy logic, rather than belonging completely to just one cluster. Thus, points on the edge of a cluster, may be in the cluster to a lesser degree than points in the center of cluster. Any point x has a set of coefficients giving the degree of being in the kth cluster $w_k(x)$. With fuzzy c-means, the centroid of a cluster is the mean of all points, weighted by a degree of belonging of each point to the cluster:

$$c_k = \frac{\sum_x \omega_k(x)^m x}{\sum_x \omega_k(x)^m}.$$

The degree of belonging, $w_k(x)$, is related inversely to the distance from x to the cluster center as calculated on the previous pass. The degree of belonging, $w_k(x)$ also depends on a vital-sign m that controls how much weight is given to the closest center.

k-means clustering is a process of vector quantization, originally from signal processing, that is popular for cluster analysis in data mining k-means clustering partitions in observations into k clusters in which each observation belongs to the cluster with the nearest mean, serving as a prototype of the cluster. This results in a partitioning of the data space into Voronoi cells. A Voronoi Cell being a region within a Voronoi Diagram that is a set of points which is specified beforehand. A Voronoi Diagram is a technique of dividing space into a number of regions. k-means clustering uses cluster centers to model the data and tends to find clusters of comparable spatial extent, like K-means clustering, but each data point has a fuzzy degree of belonging to each separate cluster.

An expectation-maximization process is an iterative process for finding maximum likelihood or maximum a posteriori (MAP) estimates of vital-signs in statistical models, where the model depends on unobserved latent variables. The expectation-maximization iteration alternates between performing an expectation step, which creates a function for the expectation of the log-likelihood evaluated using the current estimate for the vital-signs, and a maximization step, which computes vital-signs maximizing the expected log-likelihood found on the expectation step. These vital-sign-estimates are then used to determine the distribution of the latent variables in the next expectation step.

The expectation maximization process seeks to find the maximization likelihood expectation of the marginal likelihood by iteratively applying the following two steps:

1. Expectation step (E step): Calculate the expected value of the log likelihood function, with respect to the conditional distribution of Z given X under the current estimate of the vital-signs $\theta^{(t)}$:

$$Q(\theta|\theta^{(t)}) = E_{Z|X,\theta^{(t)}}[\log L(\theta;X,Z)]$$

2. Maximization step (M step): Find the vital-sign that maximizes this quantity:

$$\theta^{(t+1)} = \arg\max_\theta Q(\theta|\theta^{(t)})$$

Note that in typical models to which expectation maximization is applied:

1. The observed data points X may be discrete (taking values in a finite or countably infinite set) or continuous (taking values in an uncountably infinite set). There may in fact be a vector of observations associated with each data point.

2. The missing values (aka latent variables) Z are discrete, drawn from a fixed number of values, and there is one latent variable per observed data point.

3. The vital-signs are continuous, and are of two kinds: Vital-signs that are associated with all data points, and vital-signs associated with a particular value of a latent variable (i.e. associated with all data points whose corresponding latent variable has a particular value).

The Fourier Transform is an important image processing tool which is used to decompose an image into its sine and cosine components. The output of the transformation represents the image in the Fourier or frequency domain, while the input image is the spatial domain equivalent. In the Fourier domain image, each point represents a particular frequency contained in the spatial domain image.

The Discrete Fourier Transform is the sampled Fourier Transform and therefore does not contain all frequencies forming an image, but only a set of samples which is large enough to fully describe the spatial domain image. The number of frequencies corresponds to the number of pixels in the spatial domain image, i.e. the image in the spatial and Fourier domains are of the same size.

For a square image of size N×N, the two-dimensional DFT is given by:

$$F(k,l) = \sum_{i=0}^{N-1}\sum_{j=0}^{N-1} f(i,j) e^{-i2\pi\left(\frac{ki}{N}+\frac{lj}{N}\right)}$$

where f(a,b) is the image in the spatial domain and the exponential term is the basis function corresponding to each point F(k,l) in the Fourier space. The equation can be interpreted as: the value of each point F(k,l) is obtained by multiplying the spatial image with the corresponding base function and summing the result.

The basis functions are sine and cosine waves with increasing frequencies, i.e. F(0,0) represents the DC-component of the image which corresponds to the average brightness and F(N−1,N−1) represents the highest frequency.

A high-pass filter (HPF) is an electronic filter that passes high-frequency signals but attenuates (reduces the amplitude of) signals with frequencies lower than the cutoff frequency. The actual amount of attenuation for each frequency varies from filter to filter. A high-pass filter is usually modeled as a linear time-invariant system. A high-pass filter can also be used in conjunction with a low-pass filter to make a bandpass filter. The simple first-order electronic high-pass filter is implemented by placing an input voltage across the series combination of a capacitor and a resistor and using the voltage across the resistor as an output. The product of the resistance and capacitance (R×C) is the time constant (τ); the product is inversely proportional to the cutoff frequency $f_c$, that is:

$$f_c = \frac{1}{2\pi\tau} = \frac{1}{2\pi RC},$$

where $f_c$ is in hertz, τ is in seconds, R is in ohms, and C is in farads.

A low-pass filter is a filter that passes low-frequency signals and attenuates (reduces the amplitude of) signals with frequencies higher than the cutoff frequency. The actual amount of attenuation for each frequency varies depending on specific filter design. Low-pass filters are also known as high-cut filter, or treble cut filter in audio applications. A low-pass filter is the opposite of a high-pass filter. Low-pass filters provide a smoother form of a signal, removing the short-term fluctuations, and leaving the longer-term trend. One simple low-pass filter circuit consists of a resistor in series with a load, and a capacitor in parallel with the load. The capacitor exhibits reactance, and blocks low-frequency signals, forcing the low-frequency signals through the load instead. At higher frequencies the reactance decreases, and the capacitor effectively functions as a short circuit. The combination of resistance and capacitance gives the time constant of the filter. The break frequency, also called the turnover frequency or cutoff frequency (in hertz), is determined by the time constant.

A band-pass filter is a device that passes frequencies within a certain range and attenuates frequencies outside that range. These filters can also be created by combining a low-pass filter with a high-pass filter. Bandpass is an adjective that describes a type of filter or filtering process; bandpass is distinguished from passband, which refers to the actual portion of affected spectrum. Hence, a dual bandpass filter has two passbands. A bandpass signal is a signal containing a band of frequencies not adjacent to zero frequency, such as a signal that comes out of a bandpass filter.

FIG. 47 is a block diagram of an apparatus 4700 of motion amplification, according to an implementation. Apparatus 4700 analyzes the temporal and spatial motion in digital images of an animal subject in order to generate and communicate biological vital signs.

In some implementations, apparatus 4700 includes a forehead skin-pixel-identification module 4602 that identifies pixel-values that are representative of the skin in two or more images 2854. The forehead skin-pixel-identification module 4602 performs block 5404 in FIG. 54. Some implementations of the forehead skin-pixel-identification module 4602 performs an automatic seed point based clustering process on the images 2854.

In some implementations, apparatus 4700 includes a frequency filter 4606 that receives the output of the forehead skin-pixel-identification module 4602 and applies a frequency filter to the output of the forehead skin-pixel-identification module 4602. The frequency filter 4606 performs block 5406 in FIG. 54 to process the images 2854 in the frequency domain.

In some implementations, apparatus 4700 includes a regional facial clusterial module 4608 that includes a spatial clusterer that is applied to the output of the frequency filter 4606. The regional facial clusterial module 4608 performs block 5408 in FIG. 54. In some implementations the regional facial clusterial module 4608 includes fuzzy clustering, k-means clustering, expectation-maximization process, Ward's apparatus or seed point based clustering.

In some implementations, apparatus 4700 includes a frequency-filter 4610 that applies a frequency filter to the output of the regional facial clusterial module 4608, to generate a temporal motion. The frequency-filter 4610 performs block 54010 in FIG. 54. In some implementations, the frequency-filter 4610 is a one-dimensional spatial Fourier Transform, a high pass filter, a low pass filter, a bandpass filter or a weighted bandpass filter. Some implementations of frequency-filter 4610 includes de-noising (e.g. smoothing of the data with a Gaussian filter). The forehead skin-pixel-identification module 4602, the frequency filter 4606, the regional facial clusterial module 4608 and the frequency-filter 4610 amplify temporal motion in the two or more images 2854.

In some implementations, apparatus 4700 includes a biological vital-sign generator 4614 that generates one or more biological vital sign(s) 4616 from the temporal motion. The biological vital sign(s) 4616 are displayed for review by a healthcare worker or stored in a volatile or nonvolatile memory for later analysis, or transmitted to other devices for analysis.

Figure 48:
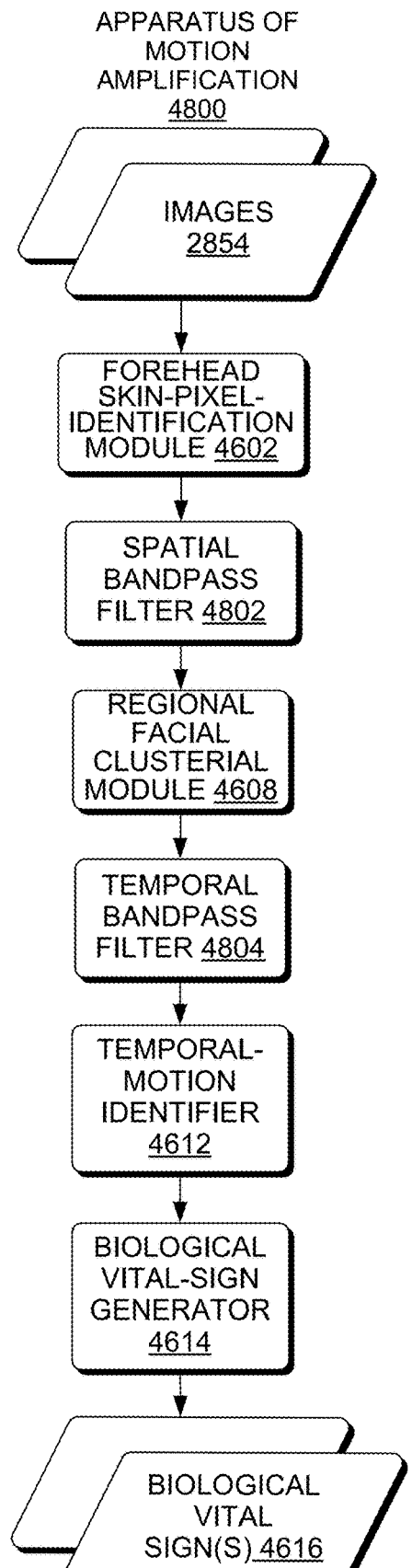
FIG. 48 is a block diagram of an apparatus of motion amplification, according to an implementation.

FIG. 48 is a block diagram of an apparatus 4800 of motion amplification, according to an implementation. Apparatus 4800 analyzes the temporal and spatial motion in digital images of an animal subject in order to generate and communicate biological vital signs.

In some implementations, apparatus 4800 includes a forehead skin-pixel-identification module 4602 that identifies pixel-values that are representative of the skin in two or more images 2854. The forehead skin-pixel-identification module 4602 performs block 5404 in FIG. 54. Some implementations of the forehead skin-pixel-identification module 4602 performs an automatic seed point based clustering process on the images 2854.

In some implementations, apparatus 4800 includes a spatial bandpass filter 4802 that receives the output of the forehead skin-pixel-identification module 4602 and applies a spatial bandpass filter to the output of the forehead skin-pixel-identification module 4602. The spatial bandpass filter 4802 performs blocks 5410 and 5412 in FIG. 54 to process the images 2854 in the spatial domain.

In some implementations, apparatus 4800 includes a regional facial clusterial module 4608 that includes a spatial clusterer that is applied to the output of the frequency filter 4606. In some implementations the regional facial clusterial module 4608 includes fuzzy clustering, k-means clustering, expectation-maximization process, Ward's apparatus or seed point based clustering.

In some implementations, apparatus 4800 includes a temporal bandpass filter 4804 that applies a frequency filter to the output of the regional facial clusterial module 4608. The temporal bandpass filter 4804 performs block 5412 in FIG. 54. In some implementations, the temporal bandpass filter 4804 is a one-dimensional spatial Fourier Transform, a high pass filter, a low pass filter, a bandpass filter or a weighted bandpass filter. Some implementations of temporal bandpass filter 4804 includes de-noising (e.g. smoothing of the data with a Gaussian filter).

The forehead skin-pixel-identification module 4602, the spatial bandpass filter 4802, the regional facial clusterial module 4608 and the temporal bandpass filter 4804 amplify temporal motion in the two or more images 2854.

In some implementations, apparatus 4800 includes a temporal-motion identifier 4612 that identifies temporal motion of the output of the frequency-filter 4610. Thus, the temporal motion represents temporal motion of the images 2854. The temporal-motion identifier 4612 performs block 5306 in FIG. 53 or block 5412 in FIG. 54.

In some implementations, apparatus 4800 includes a biological vital-sign generator 4614 that generates one or more biological vital sign(s) 4616 from the temporal motion. The biological vital sign(s) 4616 are displayed for review by a healthcare worker or stored in a volatile or nonvolatile memory for later analysis, or transmitted to other devices for analysis.

Figure 49:
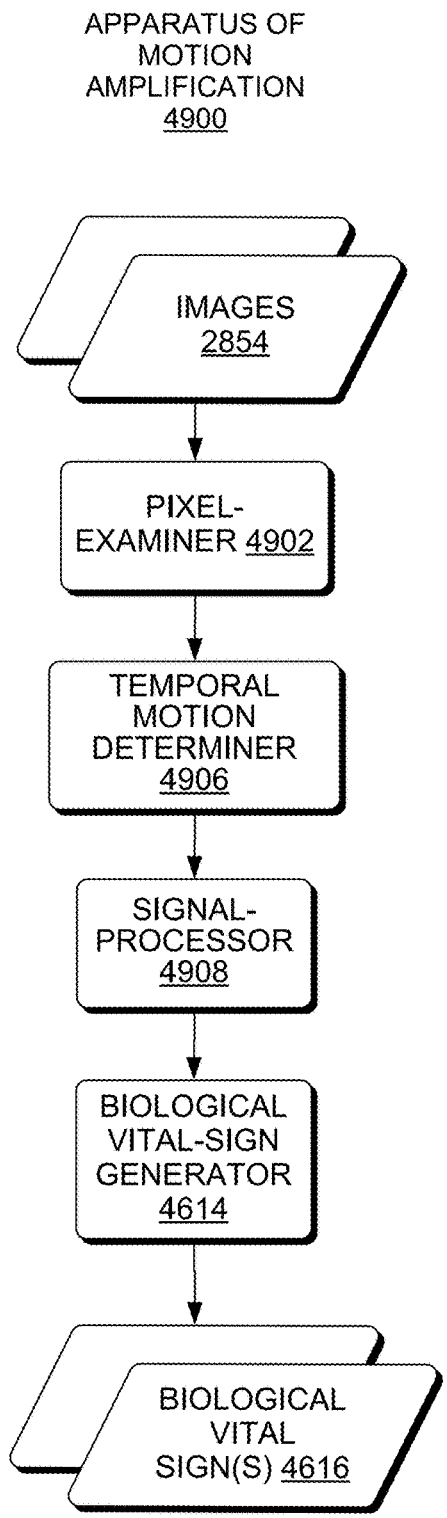
FIG. 49 is a block diagram of an apparatus of motion amplification, according to an implementation.

FIG. 49 is a block diagram of an apparatus 4900 of motion amplification, according to an implementation.

In some implementations, apparatus 4900 includes a pixel-examiner 4902 that examines pixel-values of two or more images 2854. The pixel-examiner 4902 performs block 5404 in FIG. 54.

In some implementations, apparatus 4900 includes a temporal motion determiner 4906 that determines a temporal motion of examined pixel-values. The temporal motion determiner 4906 performs block 5408 in FIG. 54.

In some implementations, apparatus 4900 includes a signal-processor 4908 that applies signal processing to the pixel value temporal motion, generating an amplified-temporal-motion. The signal processing amplifies the temporal motion, even when the temporal motion is small In some implementations, the signal processing performed by signal-processor 4908 is temporal bandpass filtering that analyzes frequencies over time. In some implementations, the signal processing performed by signal-processor 4908 is spatial processing that removes noise. Apparatus 4900 amplifies only small temporal motion in the signal-processing module.

In some implementations, apparatus 4900 includes a biological vital-sign generator 4614 that generates one or more biological vital sign(s) 4616 from the temporal motion. The biological vital sign(s) 4616 are displayed for review by a healthcare worker or stored in a volatile or nonvolatile memory for later analysis, or transmitted to other devices for analysis.

While apparatus 4900 can process large temporal motion, an advantage in apparatus 4900 is provided for small temporal motion. Therefore apparatus 4900 is most effective when the two or more images 2854 have small temporal motion between the two or more images 2854. In some implementations, a biological vital sign is generated from the amplified-temporal-motion of the two or more images 2854 from the signal-processor 4908.

Figure 50:
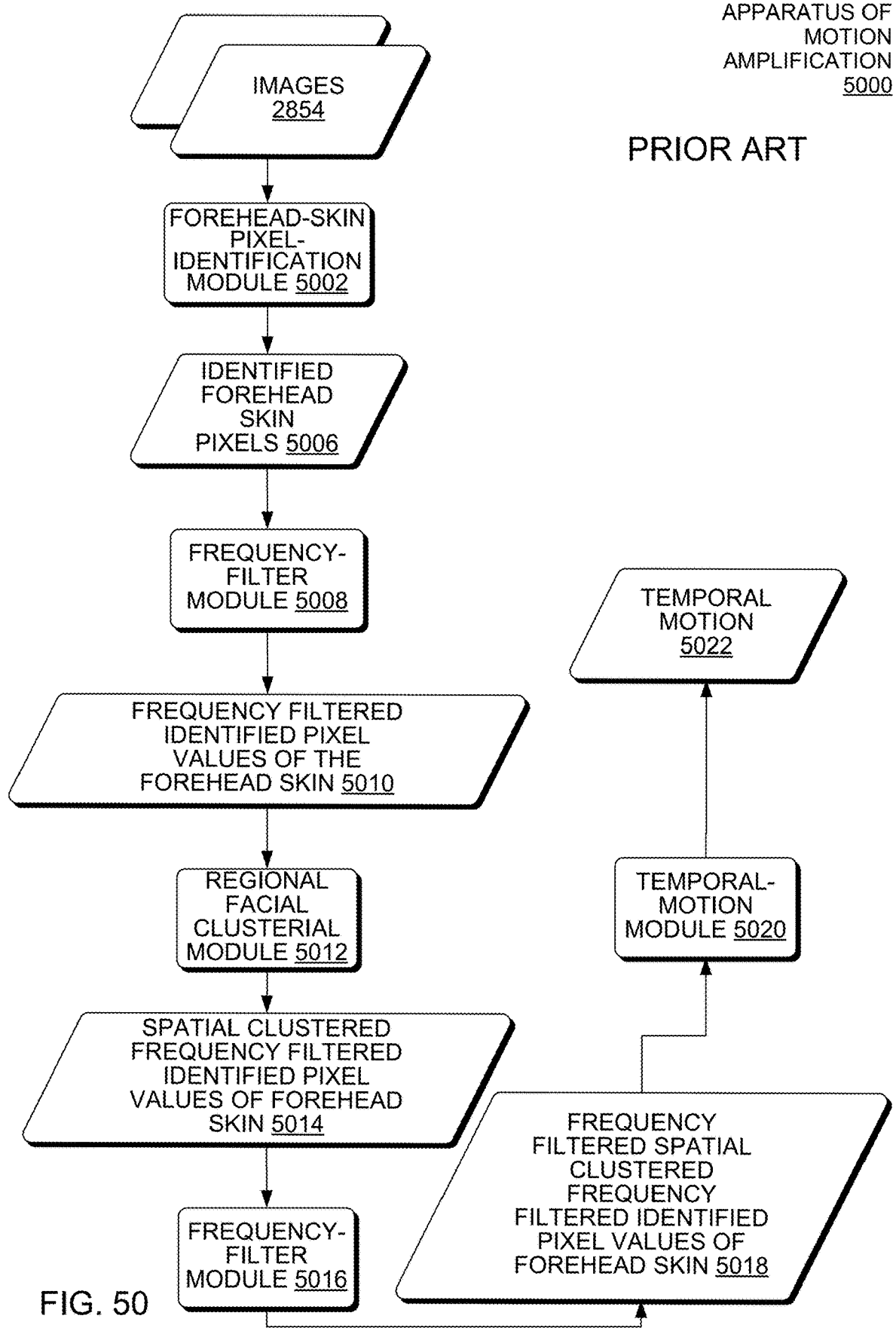
FIG. 50 is a block diagram of an apparatus of motion amplification, according to an implementation.

FIG. 50 is a block diagram of an apparatus 5000 of motion amplification, according to an implementation. Apparatus 5000 analyzes the temporal and spatial motion in digital images of an animal subject in order to generate and communicate biological vital signs.

In some implementations, apparatus 5000 includes a forehead-skin pixel identification module 5002 that identifies pixel-values 5006 that are representative of the skin in two or more images 5004. The forehead-skin pixel identification module 5002 performs block 5404 in FIG. 54. Some implementations of the forehead-skin pixel identification module 5002 perform an automatic seed point based clustering process on the two images 5004.

In some implementations, apparatus 5000 includes a frequency-filter module 5008 that receives the identified pixel-values 5006 that are representative of the skin and applies a frequency filter to the identified pixel-values 5006. The frequency-filter module 5008 performs block 5406 in FIG. 54 to process the images 2854 in the frequency domain. Each of the images 2854 is Fourier transformed, multiplied with a filter function and then re-transformed into the spatial domain. Frequency filtering is based on the Fourier Transform. The operator receives the images 2854 and a filter function in the Fourier domain. The images 2854 are then multiplied with the filter function in a pixel-by-pixel fashion using the formula:

$$G(k,l)=F(k,l)H(k,l)$$

where F(k,l) is the image of identified pixel-values 5006 in the Fourier domain, H(k,l) the filter function and G(k,l) is the frequency filtered identified pixel-values of skin 5010. To obtain the resulting image in the spatial domain, G(k,l) is re-transformed using the inverse Fourier Transform. In some implementations, the frequency-filter module 5008 is a two-dimensional spatial Fourier Transform, a high pass filter, a low pass filter, a bandpass filter or a weighted bandpass filter.

In some implementations, apparatus 5000 includes a spatial-cluster module 5012 that includes a spatial clusterer that is applied to the frequency filtered identified pixel-values of skin 5010, generating spatial clustered frequency filtered identified pixel-values of skin 5014. The spatial-cluster module 5012 performs block 5408 in FIG. 54. In some implementations the spatial-cluster module 5012 includes fuzzy clustering, k-means clustering, expectation-maximization process, Ward's apparatus or seed point based clustering.

In some implementations, apparatus 5000 includes a frequency-filter module 5016 that applies a frequency filter to the spatial clustered frequency filtered identified pixel-values of skin 5014, which generates frequency filtered spatial clustered frequency filtered identified pixel-values of skin 5018. The frequency-filter module 5016 performs block 5410 in FIG. 54. In some implementations, the frequency-filter module 5016 is a one-dimensional spatial Fourier Transform, a high pass filter, a low pass filter, a bandpass filter or a weighted bandpass filter. Some implementations of frequency-filter module 5016 includes de-noising (e.g. smoothing of the data with a Gaussian filter).

The forehead-skin pixel identification module 5002, the frequency-filter module 5008, the spatial-cluster module 5012 and the frequency-filter module 5016 amplify temporal motion in the two or more images 2854.

In some implementations, apparatus 5000 includes a temporal-motion module 5020 that determines temporal motion 5022 of the frequency filtered spatial clustered frequency filtered identified pixel-values of skin 5018. Thus, temporal motion 5022 represents temporal motion of the images 2854. The temporal-motion module 5020 performs block 5412 in FIG. 54.

Figure 51:
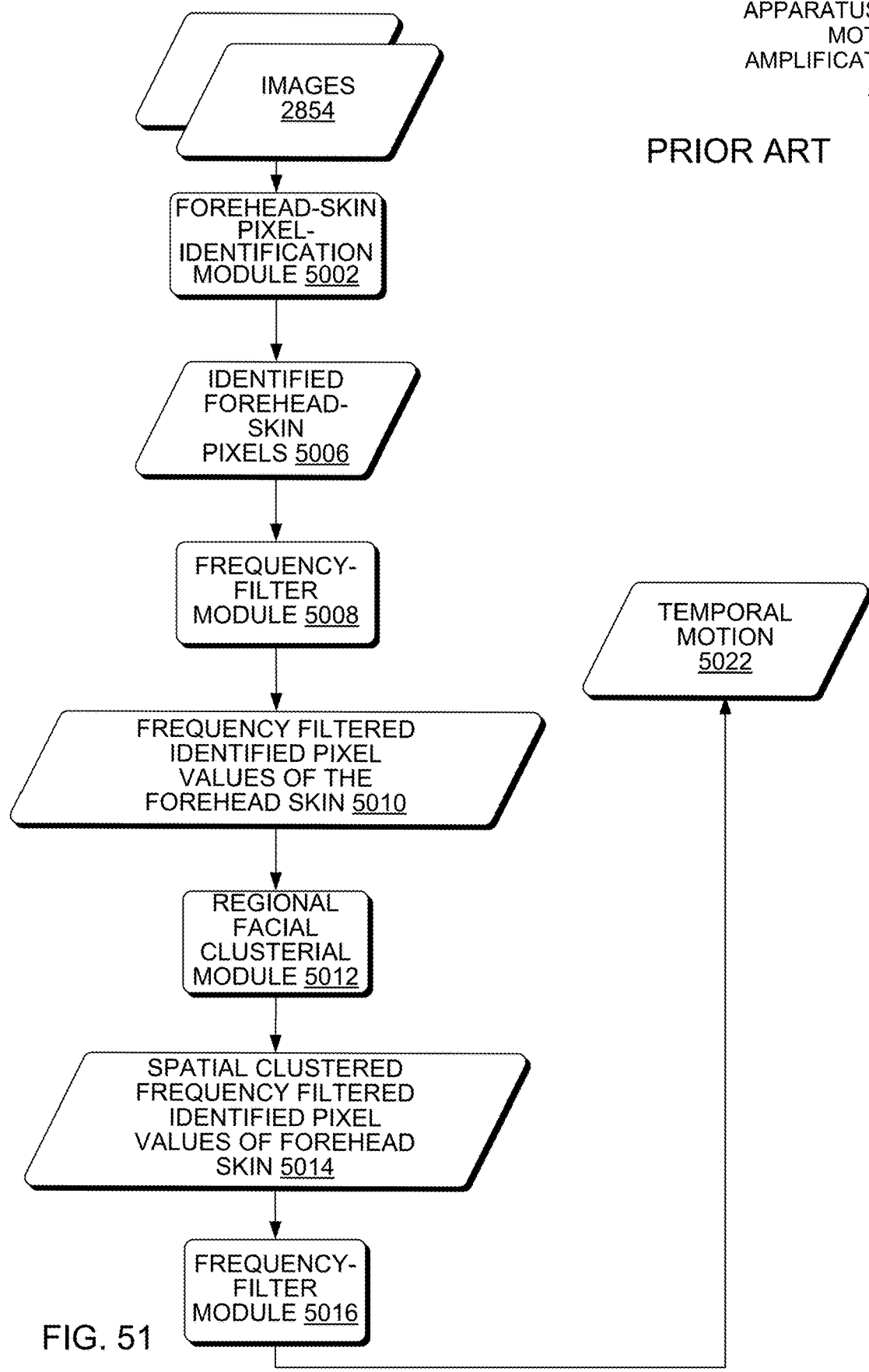
FIG. 51 is a block diagram of an apparatus of motion amplification, according to an implementation.

FIG. 51 is a block diagram of an apparatus 5100 of motion amplification, according to an implementation. Apparatus 5100 analyzes the temporal and spatial motion in digital images of an animal subject in order to generate and communicate biological vital signs.

In some implementations, apparatus 5100 includes a forehead-skin pixel identification module 5002 that identifies pixel-values 5006 that are representative of the skin in two or more images 2854. The forehead-skin pixel identification module 5002 performs block 5404 in FIG. 54. Some implementations of the forehead-skin pixel identification module 5002 perform an automatic seed point based clustering process on the images 2854.

In some implementations, apparatus 5100 includes a frequency-filter module 5008 that receives the identified pixel-values 5006 that are representative of the skin and applies a frequency filter to the identified pixel-values 5006. The frequency-filter module 5008 performs block 5406 in FIG. 54 to process the images 2854 in the frequency domain. Each of the images 2854 is Fourier transformed, multiplied with a filter function and then re-transformed into the spatial domain. Frequency filtering is based on the Fourier Transform. The apparatus 5100 takes the images 2854 and a filter function in the Fourier domain. The images 2854 are then multiplied with the filter function in a pixel-by-pixel fashion using the formula:

$$G(k,l)=F(k,l)H(k,l)$$

where F(k,l) is each of the images 2854 of identified pixel-values 5006 in the Fourier domain, H(k,l) the filter function and G(k,l) is the frequency filtered identified pixel-values of skin 5010. To obtain the resulting image in the spatial domain, G(k,l) is re-transformed using the inverse Fourier Transform. In some implementations, the frequency-filter module 5008 is a two-dimensional spatial Fourier Transform, a high pass filter, a low pass filter, a bandpass filter or a weighted bandpass filter.

In some implementations, apparatus 5100 includes a spatial-cluster module 5012 that includes a spatial clusterer that is applied to the frequency filtered identified pixel-values of skin 5010, generating spatial clustered frequency filtered identified pixel-values of skin 5014. The spatial-cluster module 5012 performs block 5408 in FIG. 54. In some implementations the spatial clustering includes fuzzy clustering, k-means clustering, expectation-maximization process, Ward's apparatus or seed point based clustering.

In some implementations, apparatus 5100 includes a frequency-filter module 5016 that applies a frequency filter to the spatial clustered frequency filtered identified pixel-values of skin 5014, which generates frequency filtered spatial clustered frequency filtered identified pixel-values of skin 5018. The frequency-filter module 5016 performs block 54108 in FIG. 54 to generate a temporal motion 5022. In some implementations, the frequency-filter module 5016 is a one-dimensional spatial Fourier Transform, a high pass filter, a low pass filter, a bandpass filter or a weighted bandpass filter. Some implementations of the frequency-filter module 5016 includes de-noising (e.g. smoothing of the data with a Gaussian filter). The forehead-skin pixel identification module 5002, the frequency-filter module 5008, the spatial-cluster module 5012 and the frequency-filter module 5016 amplify temporal motion in the two or more images 2854.

Figure 52:
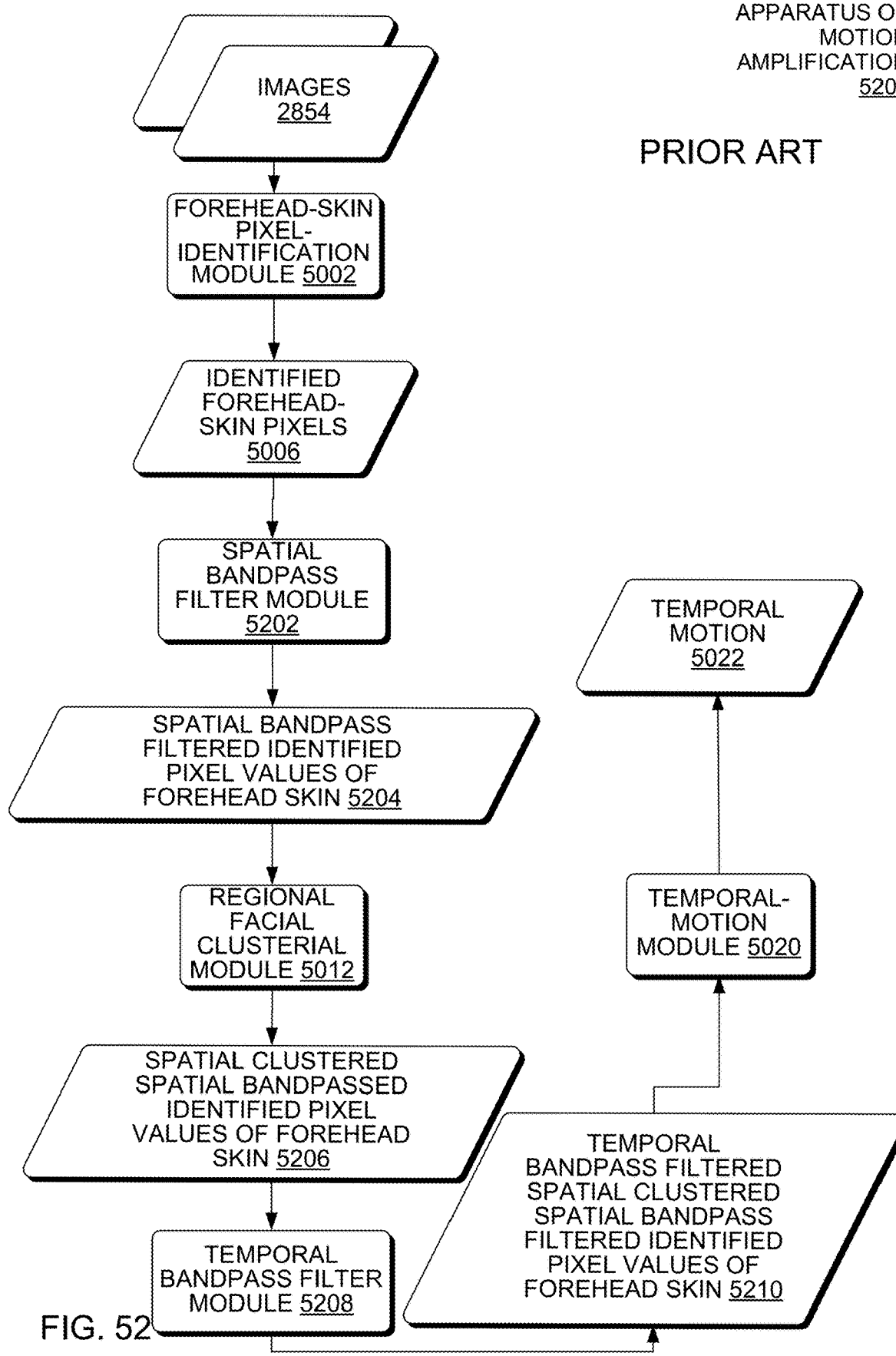
FIG. 52 is a block diagram of an apparatus of motion amplification, according to an implementation.

The frequency-filter module 5016 is operably coupled to one or more modules in FIG. 52 to generate and present any one or a number of biological vital signs from amplified motion in the temporal motion 5022.

FIG. 52 is a block diagram of an apparatus 5200 of motion amplification, according to an implementation. Apparatus 5200 analyzes the temporal and spatial motion in digital images of an animal subject in order to generate and communicate biological vital signs.

In some implementations, apparatus 5200 includes a forehead-skin pixel identification module 5002 that identifies pixel-values 5006 that are representative of the skin in two or more images 2854. The forehead-skin pixel identification module 5002 performs block 5404 in FIG. 28. Some implementations of the forehead-skin pixel identification module 5002 perform an automatic seed point based clustering process on the images 2854. In some implementations, apparatus 5200 includes a spatial bandpass filter module 5202 that applies a spatial bandpass filter to the identified pixel-values 5006, generating spatial bandpassed filtered identified pixel-values of skin 5204. In some implementations, the spatial bandpass filter module 5202 includes a two-dimensional spatial Fourier Transform, a high pass filter, a low pass filter, a bandpass filter or a weighted bandpass filter.

In some implementations, apparatus 5200 includes a spatial-cluster module 5012 that includes a spatial clusterer that is applied to the frequency filtered identified pixel-values of skin 5010, generating spatial clustered spatial bandpassed identified pixel-values of skin 5206. In some implementations the spatial clustering includes fuzzy clustering, k-means clustering, expectation-maximization process, Ward's apparatus or seed point based clustering.

In some implementations, apparatus 5200 includes a temporal bandpass filter module 5208 that applies a temporal bandpass filter to the spatial clustered spatial bandpass filtered identified pixel-values of skin 5206, generating temporal bandpass filtered spatial clustered spatial bandpass filtered identified pixel-values of skin 5210. In some implementations, the temporal bandpass filter is a one-dimensional spatial Fourier Transform, a high pass filter, a low pass filter, a bandpass filter or a weighted bandpass filter.

In some implementations, apparatus 5200 includes a temporal-motion module 5020 that determines temporal motion 5322 of the temporal bandpass filtered spatial clustered spatial bandpass filtered identified pixel-values of skin 5210. Thus, temporal motion 5322 represents temporal motion of the images 2854. The temporal-motion module 5020 is operably coupled to one or more modules in FIG. 52 to generate and present any one of a number of biological vital signs from amplified motion in the temporal motion 5322.

Figure 53:
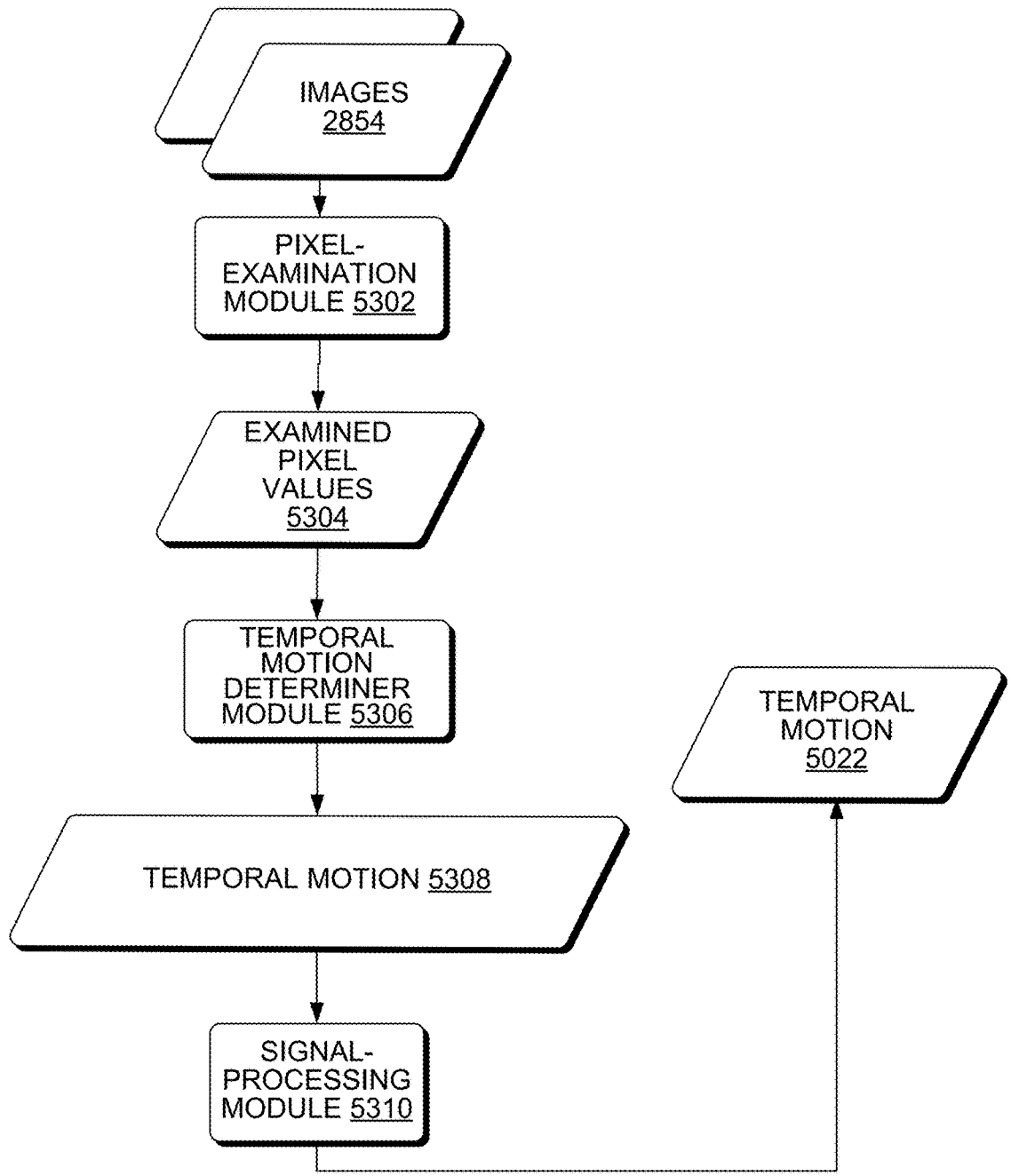
FIG. 53 is an apparatus that performs motion amplification to generate biological vital signs, according to an implementation.

FIG. 53 is a block diagram of an apparatus 5300 of motion amplification, according to an implementation.

In some implementations, apparatus 5300 includes a pixel-examination-module 5302 that examines pixel-values of two or more images 2854, generating examined pixel-values 5304. In some implementations, the pixel-examination-module 5302 performs block 5406 in FIG. 54.

In some implementations, apparatus 5300 includes a temporal motion determiner module 5306 that determines a temporal motion 5308 of the examined pixel-values 5304. In some implementations, the temporal motion determiner module 5306 performs block 5406 in FIG. 54.

In some implementations, apparatus 5300 includes a signal-processing module 5310 that applies signal processing to pixel values of the temporal motion 5308, generating an amplified temporal motion 5322. In some implementations, the signal-processing module 5310 performs block 5408 in FIG. 54. The signal processing amplifies the temporal motion 5308, even when the temporal motion 5308 is small In some implementations, the signal processing performed by signal-processing module 5310 is temporal bandpass filtering that analyzes frequencies over time. In some implementations, the signal processing performed by signal-processing module 5310 is spatial processing that removes noise. Apparatus 5300 amplifies only small temporal motion in the signal-processing module.

While apparatus 5300 can process large temporal motion, an advantage in apparatus 5300 is provided for small temporal motion. Therefore apparatus 5300 is most effective when the two or more images 2854 have small temporal motion between the two or more images 2854. In some implementations, a biological vital sign is generated from the amplified-temporal-motion of the two or more images 2854 from the signal-processing module 5310.

Figure 54:
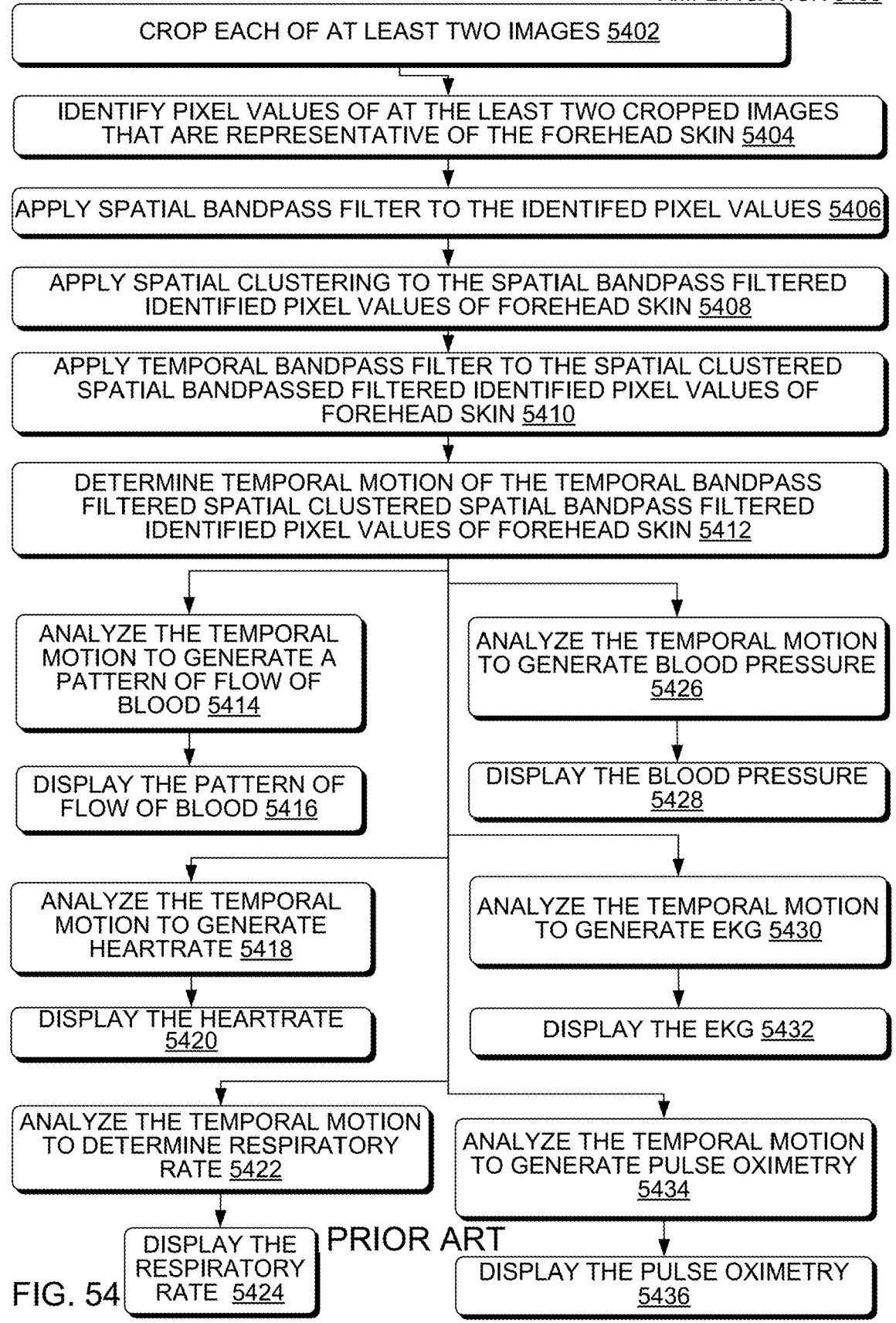
FIG. 54 is a flowchart of a method of motion amplification from which to generate and communicate biological vital signs, according to an implementation.

FIG. 54 is a flowchart of a method 5400 of motion amplification from which to generate and communicate biological vital signs, according to an implementation. FIG. 54 uses spatial and temporal signal processing to generate biological vital signs from a series of digital images.

Method 5400 analyzes the temporal and spatial motion in digital images of an animal subject in order to generate and communicate the biological vital signs.

In some implementations, method 5400 includes cropping plurality of images to exclude areas that do not include a skin region, at block 5402. For example, the excluded area can be a perimeter area around the center of each image, so that an outside border area of the image is excluded. In some implementations of cropping out the border, about 72% of the width and about 72% of the height of each image is cropped out, leaving only 7.8% of the original uncropped image, which eliminates about $^{11}/_{12}$ of each image and reduces the amount of processing time for the remainder of the actions in this process by about 12-fold. This one action alone at block 5402 in method 5400 can reduce the processing time of the plurality of images 2854 by 86%, which is of significant difference to the health workers who used devices that implement method 5400. In some implementations, the remaining area of the image after cropping in a square area and in other implementation the remaining area after cropping is a circular area. Depending upon the topography and shape of the area in the images that has the most pertinent portion of the imaged subject, different geometries and sizes are most beneficial. In other implementations of apparatus 4600, 4700, 4800, 4900, 5000, 5100, 5200 and 5300, a cropper module that performs block 5402 is placed at the beginning of the modules to greatly decrease processing time of the apparatus.

In some implementations, method 5400 includes identifying pixel-values of the plurality of or more cropped images that are representative of the skin, at block 5404. Some implementations of identifying pixel-values that are representative of the skin include performing an automatic seed point based clustering process on the least two images.

In some implementations, method 5400 includes applying a spatial bandpass filter to the identified pixel-values, at block 5406. In some implementations, the spatial filter in block 5402 is a two-dimensional spatial Fourier Transform, a high pass filter, a low pass filter, a bandpass filter or a weighted bandpass filter.

In some implementations, method 5400 includes applying spatial clustering to the spatial bandpass filtered identified pixel-values of skin, at block 5408. In some implementations the spatial clustering includes fuzzy clustering, k-means clustering, expectation-maximization process, Ward's method or seed point based clustering.

In some implementations, method 5400 includes applying a temporal bandpass filter to the spatial clustered spatial bandpass filtered identified pixel-values of skin, at block 5410. In some implementations, the temporal bandpass filter in block 5208 is a one-dimensional spatial Fourier Transform, a high pass filter, a low pass filter, a bandpass filter or a weighted bandpass filter.

In some implementations, method 5400 includes determining temporal motion of the temporal bandpass filtered spatial clustered spatial bandpass filtered identified pixel-values of skin, at block 5412.

In some implementations, method 5400 includes analyzing the temporal motion to generate and visually display a pattern of flow of blood, at block 5414. In some implementations, the pattern flow of blood is generated from motion changes in the pixels and the temporal motion of color changes in the skin. In some implementations, method 5400 includes displaying the pattern of flow of blood for review by a healthcare worker, at block 5416.

In some implementations, method 5400 includes analyzing the temporal motion to generate heartrate, at block 5418. In some implementations, the heartrate is generated from the frequency spectrum of the temporal motion in a frequency range for heart beats, such as (0-10 Hertz). In some implementations, method 5400 includes displaying the heartrate for review by a healthcare worker, at block 5420.

In some implementations, method 5400 includes analyzing the temporal motion to determine respiratory rate, at block 5422. In some implementations, the respiratory rate is generated from the motion of the pixels in a frequency range for respiration (0-5 Hertz). In some implementations, method 5400 includes displaying the respiratory rate for review by a healthcare worker, at block 5424.

In some implementations, method 5400 includes analyzing the temporal motion to generate blood pressure, at block 5426. In some implementations, the blood pressure is generated by analyzing the motion of the pixels and the color changes based on the clustering process and potentially temporal data from the infrared sensor. In some implementations, method 5400 includes displaying the blood pressure for review by a healthcare worker, at block 5428.

In some implementations, method 5400 includes analyzing the temporal motion to generate EKG, at block 5430. In some implementations, method 5400 includes displaying the EKG for review by a healthcare worker, at block 5432.

In some implementations, method 5400 includes analyzing the temporal motion to generate pulse oximetry, at block 5434. In some implementations, the pulse oximetry is generated by analyzing the temporal color changes based in conjunction with the k-means clustering process and potentially temporal data from the infrared sensor. In some implementations, method 5400 includes displaying the pulse oximetry for review by a healthcare worker, at block 5434.

9. Apparatus of Interoperability Device Manager Components of an EMR System

FIG. 55 is a block diagram of apparatus of an electronic medical records (EMR) capture system 5500, according to an implementation. EMR capture system 5500 supports the capture and management of MVS data including blood glucose levels. EMR capture system 5500 includes a device/user layer 5502 that further includes one or more MVS device(s) 5504. Examples of the MVS devices(s) 5504 are shown in FIG. 1-37.

EMR capture system 5500 includes a middle layer 5506 that communicates with the MVS apparatus 5504 in the device/user layer 5502. The middle layer 5506 includes user/patient vital sign results data 5508 that is communicated via cellular communication paths, such as 3G, 4G or a 5G or a Wi-Fi® communication path, user/patient vital sign results data 5510 that is communicated via a Wi-Fi® communication path and user/patient vital sign results data 5512 that is communicated via a Bluetooth® communication path. The middle layer 5506 further includes a first set of application program interfaces 5514 and optionally a second set of application program interfaces 5516 that the user/patient vital sign results data 5508, 5510 and 5512 is communicated to and from the MVS apparatus 5504 in the device/user layer 5502 between one or more hubs 5518, bridges 5520, interface engines 5522 and gateways 5524 in the middle layer 5506. The middle layer 5506 further includes an interoperability device manager component 5526 that deploys data such as primary communication protocol, configuration settings, firmware modifications and representations of an authorized location to the MVS apparatus 5504 in the device/user layer 5502. The interoperability device manager component 5526 sends the data via a 3G, 4G or 5G cellular communication path 5528, a Wi-Fi® communication path 5530, a Bluetooth® communication path 5532 and/or a near-field communication (NFC) path 5534. The interoperability device manager component 5526 receives the device health data via 3G, 4G or 5G cellular communication path 5536 or a Wi-Fi® communication path 5538 from the MVS apparatus 5504 in the device/user layer 5502. Examples of MVS apparatus 5504 include the MVS finger cuffs in FIG. 1-11, MVS finger cuff accessories in FIG. 12-20, MVS finger clips in FIG. 21-27, MVS smartphones in FIG. 28-29, MVS smartphone systems, MVS finger cuff accessories and MVS smartphones in FIG. 30-34 and the MVS devices in FIG. 35-37. The user/patient vital sign results data 5508, 5510 and 5512 can include patient records 4412.

The one or more hubs 5518, bridges 5520, interface engines 5522 and gateways 5524 in the middle layer 5506 communicate via 3G, 4G or 5G cellular communication path 5540 and/or an internet/intranet communication path 5542 to an EMR/clinical data repository 5544. The EMR/clinical data repository 5544 includes an EMR system 5546, a clinical monitoring system 5552 and/or a clinical data repository 5554. The EMR system 5546 is located within or controlled by a hospital facility. One example of Bluetooth® protocol is Bluetooth® Core Specification Version 2.1 published by the Bluetooth® SIG, Inc. Headquarters, 5209 Lake Washington Blvd NE, Suite 350, Kirkland, Wash. 98033. In other implementations, Zigbee® or Z-Wave® can be used instead of Bluetooth®.

FIG. 56 is a block diagram of a system of interoperability device manager component 5526, according to an implementation. The interoperability device manager component 5526 includes a device manager 5602 that connects one or more MVS apparatus 5504 and middleware 5606. The MVS apparatus 5504 are connected to the device manager 5602 through via a plurality of services, such as a chart service 5608, an observation service 5610, a patient service 5612, a user service and/or an authentication service 5616 to a bridge 5618 in the interoperability device manager 5602. The MVS apparatus 5504 are connected to the device manager 5602 to a plurality of maintenance function components 5620, such as push firmware 5622, a push configuration component 5624 and/or a keepalive signal component 5626. The keepalive signal component 5626 is coupled to the middleware 5606. In some implementations, the APIs 5630, 5632, 5634 and 5636 are health date APIs, observation APIs, electronic health record (EHR) or electronic medical record (EMR) APIs.

The bridge 5618 is operably coupled to a greeter component 5628. The greeter component 5628 synchronizes date/time of the interoperability device manager 5602, checks device log, checks device firmware, checks device configuration and performs additional security. The greeter component 5628 is coupled to the keepalive signal component 5626 through a chart application program interface component 5630, a patient application program interface component 5632, a personnel application program interface component 5634 and/or and authentication application program interface component 5636. All charted observations from the chart application program interface component 5630 are stored in a diagnostics log 5638 of a datastore 5640. The datastore 5640 also includes interoperability device manager settings 5642 for the application program interface components 5630, 5632, 5634 and/or 5636, current device configuration settings 5644, current device firmware 5646 and a device log 5648.

The interoperability device manager 5602 also includes a provision device component 5650 that provides network/Wi-Fi® Access, date/time stamps, encryption keys—once for each of the MVS apparatus 5504 for which each MVS apparatus 5504 is registered and marked as 'active' in the device log 5648. The provision device component 5650 activates each new MVS apparatus 5504 on the interoperability device manager component 5526 through a device activator 5652.

FIG. 57 is a block diagram of apparatus of an EMR capture system 5700, according to an implementation in which an interoperability manager component manages all communications in the middle layer. In EMR capture system 5700, an interoperability manager component 5702 manages all communications in the middle layer 5506 between the device/user layer 5502 and the first set of application program interfaces 5514, the optional second set of application program interfaces 5516, one or more hubs 5518, bridges 5520, interface engines 5522 and gateways 5524 in the middle layer 5506. In EMR capture system 5700, the operation of the device/user layer 5502 and the EMR/clinical data repository 5544 is the same as in the EMR capture system 5500.

Some other implementations of an electronic medical records capture system includes a bridge that transfers patient record 4412 from MVS apparatus 5504 to EMR systems in hospital and clinical environments. Each patient record 4412 includes patient measurement data, such as biological vital sign 3536 in FIG. 35-40, blood glucose level 6502 in FIG. 65, biological vital sign 3536 in FIG. 35-40 and biological vital sign 4616 in FIG. 46-61. Examples MVS apparatus 5504 include the MVS smartphone system in FIG. 30, the MVS smartphone systems in FIG. 30-34, the apparatus of motion amplification in FIG. 46-54 and the MVS smartphone 2800. In some implementations, the MVS apparatus 5504 includes a temperature estimation table that is stored in memory. The temperature estimation table is a lookup table that correlates a sensed forehead temperature to a body core temperature. The correlation of sensed forehead temperature to body core temperature is a significant advance in the technology of the MVS smartphone systems in FIG. 30-34, the apparatus of motion amplification in FIG. 46-54 and the MVS smartphone 2800 in FIG. 28, because the correlation has been developed to a highly accurate degree, to an extent of accuracy that surpasses all other MVS smartphone systems, apparatus that estimates a body core temperature, apparatus of motion amplification, hand-held devices, MVS smartphone systems and tablets, that for the first time provides sufficient accuracy to be used in medical clinics. The EMR data capture system includes two important aspects: 1. A server bridge to control the flow of patient measurement data from MVS apparatus 5504 to one or more and to manage local MVS apparatus 5504. 2. The transfer of patient measurement data in a patient record 4412, anonymous, and other patient status information to a cloud based EMR/clinical data repository 5544. The bridge controls and manages the flow of patient measurement data to an EMR/clinical data repository 5544 and another EMR/clinical data repository 5544 and provides management services to MVS apparatus 5504. The bridge provides an interface to: a wide range of proprietary EMR/clinical data repository 5544, location specific services, per hospital, for verification of active operator, and if necessary, patient identifications, and a cloud based EMR/clinical data repository 5544) of one or more MVS apparatus 5504, for the purpose of storing all measurement records in an anonymous manner for analysis. A setup, management and reporting mechanism also provided. The bridge accepts communications from MVS apparatus 5504 to: Data format conversion and transferring patient measurement records to EMR/clinical data repository 5544, manage the firmware and configuration settings of the MVS apparatus 5504, determine current health and status of the MVS apparatus 5504, support device level protocol for communications, TCP/IP. The support device level protocol supports the following core features: authentication of connected device and bridge transfer of patient measurement records to bridge with acknowledgement and acceptance by the bridge or EMR acceptance, support for dynamic update of configuration information and recovery of health and status of the MVS apparatus 5504, support for firmware update mechanism of firmware MVS apparatus 5504. The EMR data capture system provides high availability, 24/7/365, with 99.99% availability. The EMR data capture system provides a scalable server system to meet operational demands in hospital operational environments for one or both of the following deployable cases: 1) A local network at an operational site in which the bridge provides all features and functions in a defined operational network to manage a system of up to 10,000+ MVS apparatus 5504. 2) Remote or cloud based EMR/clinical data repository 5544 in which the bridge provides all services to many individual hospital or clinical sites spread over a wide geographical area, for 1,000,000+ MVS apparatus 5504. The bridge provides a central management system for the MVS apparatus 5504 that provides at least the following functions: 1) configuration management and update of the MVS apparatus 5504 2) device level firmware for all of the MVS apparatus 5504 and 3) management and reporting methods for the MVS apparatus 5504. The management and reporting methods for the MVS apparatus 5504 provides (but not limited to) health and status of the MVS apparatus 5504, battery level, replacement warning of the MVS apparatus 5504, check/calibration nearing warning of the MVS apparatus 5504, rechecking due to rough handling or out of calibration period of the MVS apparatus 5504, history of use, number of measurements, frequency of use etc. of the MVS apparatus 5504, display of current device configuration of the MVS apparatus 5504, Date/time of last device communications with each of the MVS apparatus 5504. The bridge provides extendable features, via software updates, to allow for the addition of enhanced features without the need for additional hardware component installation at the installation site. The bridge provides a device level commission mechanism and interface for the initial setup, configuration and test MVS apparatus 5504 on the network. The bridge supports MVS smartphone systems that are not hand-held. Coverage of the EMR data capture system in a hospital can include various locations, wards, ER rooms, offices, physician's Offices etc. or anywhere where automatic management of patient biological vital sign information is required to be saved to a remote EMR system. The MVS apparatus 5504 can communicate with a third party bridge to provide access to data storage services, EMR systems, MVS smartphone system cloud storage system etc. Networking setup, configuration, performance characteristics etc. are also determined and carried out by the third party bridge or another third party, for the operational environments. The MVS smartphone system can support the network protocols for communication with the third party bridge devices. In some implementations the bridge is a remote cloud based bridge. The remote cloud based bridge and the EMR/clinical data repositories 5544 are operably coupled to the network via the Internet.

In some implementations, a push data model is supported by the EMR data capture system between the MVS apparatus 5504 and the bridge in which connection and data are initially pushed from the MVS apparatus 5504 to the bridge. Once a connection has been established and the MVS apparatus 5504 and the bridge, such as an authenticated communication channel, then the roles may be reversed where the bridge controls the flow of information between the MVS apparatus 5504 and the EMR/clinical data repository 5544. In some implementations, the MVS apparatus 5504 are connected via a wireless communication path, such as a Wi-Fi® connection to Wi-Fi® access point(s). In other implementations, the MVS apparatus 5504 are connected to a docking station via a wireless or physical wired connection, such as local Wi-Fi®, Bluetooth®, Bluetooth® Low Energy (BLE), serial, USB, etc., in which case the docking station then acts as a local pass-through connection and connects to the bridge via a LAN interface and/or cellular or Wi-Fi® link from the docking station to the bridge. In some implementations, the MVS apparatus 5504 are connected via a 3G, 4G or a 5G cellular data communication path to a cellular communication tower which is operably coupled to a cell service provider's cell network which is operably coupled to a bridge/access point/transfer to a LAN or WLAN. In some implementations one or more MVS apparatus 5504 are connected a smartphone via a communication path such as a Bluetooth® communication path, a 3G, 4G or a 5G cellular data communication path, a USB communication path, a Wi-Fi® communication path, or a Wi-Fi® direct communication path to the cell phone; and the smartphone is connected to a cellular communication tower via a 3G, 4G or a 5G cellular data communication path. These portable MVS apparatus 5504 support various power saving modes and as such each device is responsible for the initiation of a connection to the wireless network or a wired network and the subsequent connection to the bridge that meets their own specific operational requirements, which provides the MVS apparatus 5504 additional control over their own power management usage and lifetime. In some implementations in which the MVS apparatus 5504 attempt connection to the bridge, the bridge is allocated a static Internet protocol (IP) address to reduce the IP discovery burden on the MVS apparatus 5504 and thus connect the MVS smartphone system to the bridge more quickly. More specifically, the MVS apparatus 5504 are not required to support specific discovery protocols or domain name service (DNS) in order to determine the IP address of the bridge. It is therefore important in some implementations that the bridge IP address is static and does not change over the operational lifetime of EMR data capture system on the network. In other implementations, a propriety network discovery protocol using UDP or TCP communications methods is implemented. In other implementations, the MVS apparatus 5504 have a HTTP address of a remote sever that acts as a discovery node for the MVS apparatus 5504 to obtain a connection to a remote system or to obtain that remote systems network address. In some implementations installation of a new MVS apparatus 5504 on the network requires configuration of the MVS apparatus 5504 for the bridge of IP address and other essential network configuration and security information. Commissioning of a MVS apparatus 5504 on the network in some implementations is carried out from a management interface on the bridge. In this way a single management tool can be used over all lifecycle phases of a MVS apparatus 5504 on the network, such as deployment, operational and decommissioning. In some implementations the initial network configuration of the MVS apparatus 5504 does not require the MVS apparatus 5504 to support any automated network level configuration protocols, WPS, Zeroconfi etc. Rather the bridge supports a dual network configuration, one for operational use on the operational network of the hospital or clinic, or other location, and an isolated local network, with local DHCP server, for out of the box commissioning of a new MVS apparatus 5504 and for diagnostic test of the MVS apparatus 5504. MVS apparatus 5504 can be factory configured for known network settings and contain a default server IP address on the commissioning network. In addition the MVS apparatus 5504 are required in some implementations to support a protocol based command to reset the MVS apparatus 5504 to network factory defaults for test purposes. In some situations, the firmware revision(s) of the MVS apparatus 5504 are not consistent between all of the MVS apparatus 5504 in the operational environment. Therefore the bridge is backwards compatible with all released firmware revisions from firmware and protocol revision, data content and device settings view point of the MVS apparatus 5504. As a result, different revision levels MVS apparatus 5504 can be supported at the same time on the network by the bridge for all operations.

Implementation Alternatives

Operational Features and Implementation Capability

Some implementations of the EMR data capture systems 5500 and 5700 have limited operational features and implementation capability. A significant function of the EMR data capture systems 5500 and 5700 with the limited operational features and implementation capability in the bridge 5520 is to accept data from a MVS apparatus 5504 and update the EMR/Clinical Data Repository 5544. The EMR/Clinical Data Repository 5544 can be one or more of the following: Electronic Medical Records System (EMR) 5546, Clinical Monitoring System 5552 and/or Clinical Data Repository 5554.

The following limited feature set in some implementations is supported by the EMR data capture systems 5500 and 5700 for the demonstrations:

Implementation to a local IT network on a server of the local IT network, OR located on a remote-hosted network, whichever meets the operational requirements for healthcare system.

Acceptance of patient medical records from a MVS apparatus 5504:
 a. Date and Time
 b. Operator identification
 c. Patient identification
 d. Vital Sign measurement(s)
 e. Device manufacturer, model number and firmware revision Acceptance of limited status information from a MVS apparatus 5504:
 a. Battery Level
 b. Hospital reference
 c. location reference
 d. Manufacturer identification, serial number and firmware revision
 e. Unique identification number Transfer of patient records from a MVS apparatus 5504 to a third party EMR capture system and to the EMR data capture systems 5500 and 5700, respectively in that order.

User interface for status review of known MVS apparatus 5504.

Configuration update control for active devices providing configuration of:
 a. Hospital reference
 b. Unit location reference Limited Operational Features and Implementation Capability The following features are supported limited operational capability:

A Patient Record Information and measurement display interface for use without submission of that data to an EMR/Clinical Data Repository 5544.

Update of device firmware to support and activate determination of blood glucose levels over the wireless network. In some implementations, components for determination of blood glucose levels (or other vital signs) is in the firmware or other nonvolatile memory, but the components are not active or activated as indicated by a flag in flash memory of the device. Subsequently, action is taken to activate the components by changing the flag in the flash memory.

Operational Use

Local Network Based—Single Client

In some implementations, the MVS apparatus 5504 are deployed to a local hospital, or other location, wireless IT network that supports Wi-Fi® enabled devices. The MVS apparatus 5504 supports all local network policy's including any local security policy/protocols, such as WEP, WPA, WPA2, WPA-EPA as part of the connection process for joining the network. In some implementations, the MVS apparatus 5504 operates on both physical and virtual wireless LAN's, WAN's, and the MVS apparatus 5504 are configured for operation on a specific segment of the network. Depending on the IT network structure, when the MVS apparatus 5504 is configured for operation on a specific segment of the network, the MVS apparatus 5504 network connection ability is limited to the areas of the operational environment for which it as be configured. Therefore, the MVS apparatus 5504 in network environments that have different network configurations are configured to ensure that when the MVS apparatus 5504 are used in various locations throughout the environment that the MVS apparatus 5504 has access in all required areas.

In some implementations the bridge 5520 system is located on the same IT network and deployed in accordance with all local IT requirements and policy's and that the MVS apparatus 5504 on this network are able to determine a routable path to the bridge 5520. The MVS apparatus 5504 and the server are not required to implement any network name discovery protocols and therefore the bridge 5520 is required to be allocated static IP address on the network. In the case where a secondary bridge device is deployed to the network as a backup for the primary, or the bridge 5520 supports a dual networking interface capability, then the secondary bridge IP address is also required to be allocated a static IP address. It is important to note that this is a single organization implementation and as such the bridge 5520 is configured to meet the security and access requirements of a single organization.

An implementation of a remote cloud-based bridge 5520 for a single client is similar to the local network case described at the end of the description of FIG. 13, with the exception that the bridge 5520 may not be physically located at the physical site of the MVS apparatus 5504.

The MVS apparatus 5504 include a temperature estimation table (not shown in FIG. 13). The temperature estimation table is stored in memory. The temperature estimation table is a lookup table that correlates a sensed surface temperature to a body core temperature.

The physical locale of the bridge 5520 is transparent to the MVS apparatus 5504.

Remote Based—Multiple Client Support

In some implementations for smaller organizations or for organizations that do not have a supporting IT infrastructure or capability that a remote bridge 5520 system is deployed to support more than one organization. Where the bridge 5520 is deployed to support more than one organization, the bridge 5520 can be hosted as a cloud based system. In this case the MVS apparatus 5504 are located at the operational site for the supported different geographical location organizations and tied to the bridge 5520 via standard networking methods via either private or public infrastructure, or a combination thereof.

Where a remote, i.e. non-local IT network, system is deployed to support more than one hospital or other organization EMR data capture systems 5500 and 5700 includes components that isolate each of the supported organizations security and user access policy's and methods along with isolating all data transfers and supporting each organizations data privacy requirements. In addition system performance is required to be balanced evenly across all organizations. In this case each organization can require their specific EMR data capture systems 5500 and 5700 be used and their EMR data capture systems 5500 and 5700 are concurrently operational with many diverse EMR/Clinical Repository systems such as Electronic Medical Record System EMR 5546, 2, Clinical Monitoring System 5552 and/or Clinical Data Repository 5554.

Single Measurement Update

The primary function of the MVS apparatus 5504 is to take vital sign measurements, for example, blood glucose level, display the result to the operator and to save the patient information and the blood glucose level to an EMR/Clinical Data Repository 5544. Normally the MVS apparatus 5504 are in a low power state waiting for an operator to activate the unit for a patient measurement. Once activated by the operator EMR data capture systems 5500 and 5700 will power up and under normal operating conditions guide the operator through the process of blood glucose level measurement and transmission of the patient record to the bridge 5520 for saving using the EMR data capture systems 5500 and 5700.

Confirmation at each stage of the process by the operator is required, to ensure a valid and identified patient result is obtained and saved to the EMR, the key last confirmation point is: Saving of data to the bridge 5520.

In some implementations, the confirmation at each stage in some implementations is provided by the operator through either the bridge 5520, multi-vital sign capture system(s) 5504, or the EMR/Clinical Data Repository 5544.

When confirmation is provided by the bridge 5520 it is an acknowledgment to the MVS apparatus 5504 that the bridge 5520 has accepted the information for transfer to the EMR/Clinical Data Repository 5544 in a timely manner and is now responsible for the correct management and transfer of that data.

When confirmation is provided by the EMR, the bridge 5520 is one of the mechanisms via which the confirmation is returned to the MVS apparatus 5504. That is the MVS apparatus 5504 sends the data to the bridge 5520 and then waits for the bridge 5520 to send the data to the EMR and for the EMR to respond to the bridge 5520 and then the bridge 5520 to the MVS apparatus 5504, In some implementations depending on the operational network and where the bridge 5520 is physically located, i.e. local or remote, that the type of confirmation is configurable.

In some implementations, the MVS apparatus 5504 maintains an internal non-volatile storage mechanism for unsaved patient records if any or all of these conditions occur: The MVS apparatus 5504 cannot join the network. The MVS apparatus 5504 cannot communicate with the bridge 5520. The MVS apparatus 5504 does not receive level confirmation from either the bridge 5520 or the EMR/Clinical Data Repository 5544. The MVS apparatus 5504 must maintain the internal non-volatile storage mechanism in order to fulfill its primary technical purpose in case of possible operational issues. When the MVS apparatus 5504 has saved records present in internal memory of the MVS apparatus 5504, then the MVS apparatus 5504 attempts to transfer the saved records to the bridge 5520 for processing in a timely automatic manner Periodic Connectivity The MVS apparatus 5504 in order to obtain date/time, configuration setting, provides status information to the bridge 5520, transfers saved patient records and checks for a firmware update to provide a mechanism on a configured interval automatically that powers up and communicates to the configured bridge 5520 without operator intervention.

Accordingly, outside of the normal clinical use activation for the MVS apparatus 5504, the MVS apparatus 5504 can both update its internal settings, and provide status information to the bridge 5520 system.

Automatic Transfer of Saved Patient Measurement Records (PMRs)

If the MVS apparatus 5504 for an unknown reason has been unable to either join the network or connect to the bridge 5520 or receive a bridge 5520 or EMR data level acknowledge that data has been saved the MVS apparatus 5504 allows the primary clinical body core temperature measurement function to be performed and saves the resultant PMR in non-volatile internal memory up to a supported, configured, maximum number of saved patient records on the MVS apparatus 5504.

When the MVS apparatus 5504 are started for a measurement action the MVS apparatus 5504 determines if the MVS apparatus 5504 contains any saved patient records in its internal memory. If one or more saved patient records are detected then the MVS apparatus 5504 attempts to join the network immediately, connect to the bridge 5520 and send the patient records one at a time to the bridge 5520 device while waiting for the required confirmation that the bridge 5520 has accepted the patient record. Note in this case confirmation from the EMR is not required. On receipt of the required validation response from the remote system the MVS apparatus 5504 deletes the patient record from its internal memory. Any saved patient record that is not confirmed as being accepted by the remote device is maintained in the MVS apparatus 5504 internal memory for a transfer attempt on the next power up of the MVS apparatus 5504.

The MVS apparatus 5504 on a configured interval will also carry out this function. In some implementations the MVS apparatus 5504 reduces the interval when saved patient records are present on the MVS apparatus 5504 in order to ensure that the records are transferred to the bridge 5520, and subsequently the EMR/Clinical Data Repository 5544, in a timely manner once the issue has been resolved. When this transfer mechanism is active status information is presented to the operator on the MVS apparatus 5504 screen.

Under this operation it is possible for the bridge 5520 device to receive from a single MVS apparatus 5504 multiple patient record transfer requests in rapid sequence.

Device Configuration

The MVS apparatus 5504 upon 1) connection to the bridge 5520, 2) configured interval or 3) operator initiation, transmits to the bridge 5520 with the model number and all appropriate revisions numbers and unique identification of the MVS apparatus 5504 to allow the bridge 5520 to determine the MVS apparatus 5504 capabilities and specific configurations for that MVS apparatus 5504.

The bridge 5520 acts as the central repository for device configuration, either for a single device, a group of defined devices or an entire model range in which the MVS apparatus 5504 queries the bridge 5520 for the device vital-signs of the MVS apparatus 5504 and if the queried device vital-signs are different from the MVS apparatus 5504, the MVS apparatus 5504 updates the current setting to the new setting values as provided by the bridge 5520.

Device Status Management

In some implementations the bridge 5520 provides a level of device management for the MVS apparatus 5504 being used with EMR data capture systems 5500 and 5700. In some implementations, the bridge 5520 is able to report and determine at least the following:

Group and sort devices by manufacture, device model, revisions information and display devices serial numbers, unique device identification, asset number, revisions, etc. and any other localized identification information configured into the MVS apparatus 5504, e.g. ward location reference or Hospital reference.

The last time a specific unit connected to EMR data capture systems 5500 and 5700.

The current status of the given device, battery level, last error, last date of re-calibration of check, or any other health indicator supported by the MVS apparatus 5504.

Report devices out of their calibration period, or approaching their calibration check.

Report devices that require their internal battery replaced.

Report devices that require re-checking due to a detected device failure or error condition, or that have been treated in a harsh manner or dropped.

Determine if a MVS apparatus 5504 has not connected for a period of time and identify the MVS apparatus 5504 as lost or stolen. If the MVS apparatus 5504 reconnects to the network after this period of time then the MVS apparatus 5504 in some implementations is highlighted as requiring an accuracy check to ensure that it is operational. In some implementations, the MVS apparatus 5504 also supports this capability and after a pre-determined time disconnects from the network to inhibit the measurement function of the MVS apparatus 5504 until a MVS apparatus 5504 level recheck is carried out.

Provide a mechanism to commission and decommission devices onto and off of the network. If a MVS apparatus 5504 has not been specifically commissioned for operation on the network then it in some implementations is not be allowed to access the core services supported by the bridge 5520 even if it has configured for operation on the EMR data capture systems 5500 and 5700.

Firmware Update

In some implementations a firmware update for a given device model is scheduled on the network as opposed to simply occurring. When a MVS apparatus 5504 is activated for a patient measurement firmware, updates are blocked because the update process delays the patient biological vital sign measurement. Instead the bridge 5520 system includes a firmware update roll out mechanism where the date and time of the update can be scheduled and the number of devices being updated concurrently can be controlled.

In some implementations, when a MVS apparatus 5504 connects to the bridge 5520 due to a heartbeat event that the MVS apparatus 5504 queries the bridge 5520 to determine if a firmware update for that model of device is available and verify if the firmware MVS apparatus 5504 (via revision number), is required to be updated. The bridge 5520 responds to the query by the MVS apparatus 5504 based on whether or not a firmware update is available and the defined schedule for the update process. If an update is available at the bridge 5520 but the current time and date is not valid for the schedule then the bridge 5520 transmits a message to the MVS apparatus 5504 that there is an update but that the update process is delayed and update the MVS apparatus 5504 firmware check interval configuration. The firmware check interval setting will then be used by the MVS apparatus 5504 to reconnect to the bridge 5520 on a faster interval than the heartbeat interval in order to facilitate a more rapid update. For e.g. the firmware update schedule on the bridge 5520 in some implementations is set to every night between 2 am and 4 am and the interval timer in some implementations is set to for example, every 15 minutes.

In some implementations the bridge 5520 manages the firmware update process for many different MVS smartphone systems 5504 each with their specific update procedure, activated vital sign determination processes, file formats, and verification methods and from a date and time scheduling mechanism and the number of devices being update concurrently. In addition in some implementations the bridge 5520 will provide a mechanism to manage and validate the firmware update files maintained on the bridge 5520 for use with the MVS apparatus 5504.

This section concludes with short notes below on a number of different aspects of the EMR data capture systems 5500 and 5700 follow on numerous topics:

Remote—single client operation: The bridge 5520 architecture provide remote operation on a hospital network system. Remote operation is seen as external to the network infrastructure that the MVS apparatus 5504 are operational on but considered to be still on the organizations network architecture. This can be the case where a multiple hospital—single organization group has deployed EMR data capture systems 5500 and 5700 but one bridge 5520 device services all hospital locations and the bridge 5520 is located at one of the hospital sites or their IT center.

Remote—multiple client operation: The bridge 5520 architecture in some implementations is limited to remote operation on a cloud based server that supports full functionality for more than one individual separate client concurrently when a cloud based single or multiple server system is deployed to service one or more individual hospital/clinical organizations.

Multiple concurrent EMR support: For a single remote bridge 5520 servicing multiple clients EMR data capture systems 5500 and 5700 supports connectivity to an independent EMR, and a different EMR vendor, concurrently for each supported client. With one bridge 5520 servicing multiple clients in some implementations, each client requires the configuration to send data securely to different EMR/Clinical Data Repositories.

Support Different EMR for same client: The bridge 5520 architecture for operation in a single client organization supports the user by the organization of different EMR/Clinical Data Repository 5544 from different departments of wards in the operational environment. It is not uncommon for a single organization to support multiple different EMR/Clinical Data Repository 5544 for different operational environments, for example, Cardiology and ER. EMR data capture systems 5500 and 5700 in some implementations takes this into account and routes the patient data to the correct EMR/Clinical Data Repository 5544. Therefore the bridge 5520 is informed for a given MVS apparatus 5504 which indicates to the EMR the medical data has to be routed to.

Segregation of operations for multiple client operations on a single bridge 5520:

EMR data capture systems 5500 and 5700 supports per client interfaces and functionality to ensure that each client's configurations, performance, user accounts, security, privacy and data protection are maintained. For single server implementations that service multiple independent hospital groups the bridge 5520 in some implementations maintain all functionality, and performance per client separately and ensure that separate user accounts, bridge 5520 configuration, device operation, patient and non-patient data, interfaces etc. are handled and isolated per client. A multiple cloud based implementation obviates this function as each client includes their own cloud based system.

Multiple organization device support: The bridge 5520 supports at least 1 million+ MVS apparatus 5504 for a remote implementations that services multiple separate hospital systems. The supported MVS apparatus 5504 can be MVS apparatus 5504 from different manufacturers.

EMR capture system support: The MVS apparatus 5504 supports a wide range implementations of the EMR data capture system(s) 5500 and 5700 and is capable of interfacing to any commercially deployed EMR/Clinical Data Repository 5544.

EMR capture system interface and approvals: The bridge 5520 device provides support for all required communication, encryption, security protocols and data formats to support the transfer of PMR information in accordance with all required operational, standards and approval bodies for EMR/Clinical Data Repository 5544 supported by the EMR data capture systems 5500 and 5700.

Remote EMR capture system(s): The bridge 5520 supports interfacing to the required EMR/Clinical Data Repository 5544 independent of the EMR data capture system(s) 5500 and 5700 location, either locally on the same network infrastructure or external to the network that the bridge 5520 is resided on or a combination of both. The EMR data capture systems 5500 and 5700, or systems, that the bridge 5520 is required to interact with and save the patient to can not be located on the same network or bridge 5520 implementation location, therefore the bridge 5520 implementation in some implementations ensure that the route to the EMR exists, and is reliable.

Bridge buffering of device patient records: The bridge 5520 device provides a mechanism to buffer received PMRs from connected MVS apparatus 5504 in the event of a communications failure to the EMR/Clinical Data Repository 5544, and when communications has been reestablished subsequently transfer the buffered measurement records to the EMR. From time to time in normal operation, the network connection from the bridge 5520 is lost. If communications has been lost to the configured EMR data capture system(s) 5500 and 5700 then the bridge 5520 in some implementations accepts measurement records from the MVS apparatus 5504 and buffers the measurement records until communications has be reestablished. Buffering the measurement records allows the medical facility to transfer the current data of the medical facility to the bridge 5520 for secure subsequent processing. In this event the bridge 5520 will respond to the MVS apparatus 5504 that either 1. Dynamic validation of EMR acceptance is not possible, or 2. The bridge 5520 has accepted the data correctly.

Bridge 5520 real time acknowledge of EMR save to device: The bridge 5520 provides a mechanism to pass to the MVS apparatus 5504 confirmation that the EMR has accepted and saved the PMR. The bridge 5520 when configured to provide the MVS apparatus 5504 with real time confirmation that the EMR/Clinical Data Repository 5544 (s) have accepted and validated the PMR. This is a configuration option supported by the bridge 5520.

Bridge 5520 real time acknowledgement of acceptance of device PMR: The bridge 5520 provides a mechanism to pass to the MVS apparatus 5504 confirmation that the bridge 5520 has accepted the PMR for subsequent processing to the EMR. The MVS apparatus 5504 in some implementations verifies that the bridge 5520 has accepted the PMR and informs the operator of the MVS apparatus 5504 that the data is secure. This level of confirmation to the MVS apparatus 5504 is considered the minimum level acceptable for use by the EMR data capture systems 5500 and 5700. Real time acknowledgement by the bridge 5520 of acceptance of the PMR from the device is a configuration option supported by the bridge 5520.

Bridge Date and Time: The bridge 5520 maintains internal date and time against the local network time source or a source recommended by the IT staff for the network. All transitions and logging events in some implementations are time stamped in the logs of the bridge 5520. The MVS apparatus 5504 will query the bridge 5520 for the current date and time to update its internal RTC. The internal time MVS apparatus 5504 can be maintained to a +/−1 second accuracy level, although there is no requirement to maintain time on the MVS apparatus 5504 to sub one-second intervals.

Graphical User Interface: The bridge 5520 device provides a graphical user interface to present system information to the operator, or operators of EMR data capture systems 5500 and 5700. The user interface presented to the user for interaction with EMR data capture systems 5500 and 5700 in some implementations can be graphical in nature and use modern user interface practices, controls and methods that are common use on other systems of this type. Command line or shell interfaces are not acceptable for operator use though can be provided for use by system admin staff.

Logging and log management: The bridge 5520 is required to provide a logging capability that logs all actions carried out on the bridge 5520 and provides a user interface to manage the logging information. Standard logging facilities are acceptable for this function for all server and user actions. Advanced logging of all device communications and data transfers in some implementations is also provided, that can be enabled/disable per MVS smartphone system or for product range of MVS smartphone system.

User Accounts: The bridge 5520 device provides a mechanism to support user accounts on the MVS apparatus 5504 for access control purposes. Standard methods for user access control are acceptable that complies with the operational requirements for the install/implementation site.

User Access Control: The bridge 5520 device supports multiple user access control that defines the access control privileges for each type of user. Multiple accounts of each supported account type are to be support. Access to EMR data capture systems 5500 and 5700 in some implementations be controlled at a functional level, In some implementations, the following levels of access is provided:

System Admin: provides access to all features and functions of EMR data capture systems 5500 and 5700, server and device based.

Device Admin: provides access only to all device related features and functions supported by the EMR data capture systems 5500 and 5700.

Device Operator: provides access only to device usage.

Device Installer: provides access only to device commissioning and test capabilities.

A user account can be configured for permissions for one or more account types.

Multi-User Support: The bridge 5520 device is required to provide concurrent multi-user support for access and management of the bridge 5520 system across all functions. Providing multiple user access is deemed a necessary operational feature to support.

Modify User Accounts: The bridge 5520 provides a method to create, delete, and edit the supported user accounts and supported access privileges per account.

Bridge Data Corruption/Recovery: The bridge 5520 architecture and implementation in some implementations ensure that under an catastrophic failure of EMR data capture systems 5500 and 5700 or a storage component that no data is lost that has not been confirmed as saved to the either the EMR for PMRs or localize storage for operational data pertaining to the non-patient data maintained by the EMR data capture systems 5500 and 5700. The bridge 5520 supports a method to ensure zero data lost under critical and catastrophic system failure of the bridge 5520 or any of the bridge 5520 components, network interfaces, storage systems, memory contents, etc. for any data handled by the EMR data capture systems 5500 and 5700. In the event of a recovery action where a catastrophic failure has occurred EMR data capture systems 5500 and 5700 supports both the recovery action and its normal operational activities to ensure that EMR data capture systems 5500 and 5700 is active for clinical use.

Bridge availability: The bridge 5520 device is a high availably system for fail safe operation 24/7/365, with 99.99% availability, i.e. "four nines" system. The bridge 5520 implementation meets an availability metric of 99.99%, i.e. a "four nines" system because the bridge 5520 hardware in some implementations is implemented with a redundant dual server configuration to handle single fault conditions. The bridge 5520 has an independent power source or when the installation site has a policy for power loss operation the bridge 5520 installation in some implementations complies with the policy requirements.

Bridge Static IP address and port Number: The bridge 5520 provides a mechanism to configure the bridge 5520 for a primary use static IP address and port number. For MVS apparatus 5504 connection to the bridge 5520, the bridge 5520 in some implementations has a static IP address and that IP address in some implementations is known by the MVS apparatus 5504.

Bridge Dual network capability: The bridge 5520 system provides a mechanism to support a dual operational network interface to allow for failure of the primary network interface. This secondary network interface supports a configurable static IP address and port number. A redundant network connection in some implementations is provided to cover the event that the primary network interface has failed. Note if the bridge 5520 implementation for EMR data capture systems 5500 and 5700 employs two separate bridges 5520 or other redundant mechanism to provide a backup system then this requirement can be relaxed from an operational view point, however EMR data capture systems 5500 and 5700 in some implementations support this mechanism.

Local Wi-Fi® commissioning network: The bridge 5520 provides a mechanism on the local operational network to commission new MVS apparatus 5504 for operational use. EMR data capture systems 5500 and 5700 supplies a localized isolated network for the use of commissioning new devices onto the operational network. The bridge 5520 has a known default IP address on this network and provides a DHCP server for the allocation of IP address to devices on EMR data capture systems 5500 and 5700. The commissioning of new devices is to be considered a core aspect of the bridge 5520 functions. However it is acceptable that a separate non server based application in some implementations will manage the configuration process provided the same user interface is presented to the user and the same device level configuration options are provided. In some implementations, the configuration of a new MVS apparatus 5504 on the network is carried out in two stages: Stage 1: network configuration from the commissioning network to the operational network. Stage 2: Once joined on the operational network specific configuration of the MVS apparatus 5504 for clinical/system function operation.

Remote commissioning of devices: EMR data capture systems 5500 and 5700 provides a mechanism where the bridge 5520 device is not present on the local network for a new device is to be commissioned on the operational network. Even when the bridge 5520 is on a cloud server external to the operational site network new devices in some implementations can be commissioned onto the network in the same manner as if the bridge 5520 was a local server. This does not preclude the installation of a commission relay server on to the operational network that supports this mechanism.

Device setup: The bridge 5520 supports the configuration of a device level network operation and security settings for an existing or new MVS apparatus 5504 on either the commissioning network or the operational network. New devices are configured on the commissioning network. Existing devices on the operational network are also configurable for network and security requirements independent of the network that the MVS apparatus 5504 are currently connected to the bridge 5520 provides the required user interface for the configuration of the network operational and security settings by the operator. Once configured, a method of verifying that the MVS apparatus 5504 have been configured correctly but be presented to the operator to prove that the MVS apparatus 5504 are operational. Devices support a network command to reboot and rejoin the network for this verification purpose.

Bridge Configuration: The bridge provides a mechanism to support configuration of all required specific control options of the bridge 5520. A method to configure the bridge 5520 functions in some implementations is provided for all features where a configuration option enable, disable or a range of vital-signs are required.

Bridge MVS smartphone system acknowledgement method: The bridge 5520 provides a configuration method to control the type of acknowledgement required by the EMR data capture systems 5500 and 5700, one of: device configuration dependent, EMR level acknowledgment, bridge 5520 level acknowledgement. In some implementations, a MVS smartphone system 5504 requires from the bridge an acknowledgement that the PMR has been saved by the EMR data capture systems 5500 and 5700 or accepted for processing by the bridge 5520.

EMR Level: Bridge 5520 confirms save by EMR data capture systems 5500 and 5700.

Bridge Level: bridge 5520 controlled, accepted for processing by the bridge 5520.

Enabled/Disable of firmware updated mechanism: The bridge 5520 provides a method to globally enable or disable the supported MVS apparatus 5504 firmware updated feature. A global enable/disable allows the control of the firmware update process.

Server Management: The bridge 5520 is required to provide a user interface that provides configuration and performance monitoring of the bridge 5520 and platform functions.

System Reporting: The bridge 5520 is required to provide a mechanism to provide standard reports to the operator on all capabilities of the bridge 5520 system. Standard reporting in some implementations includes selection of report vital-sign, sorting of report vital-signs, printing of reports, export of reports to known formats, WORD, excel, PDF etc., identification of reports, organization name, location, page numbers, name of report etc., date and time of log, generate by user type and extent of provides full reporting for all system features and logs, examples are: List of devices known to EMR data capture systems 5500 and 5700, with location reference and date and time of last connection Report on the battery status for all known MVS apparatus 5504. Report on any devices that reported an error Report on devices that have expired there calibration dates. Report on devices that are approaching their calibration dates.

Demo Patient Interface: The bridge 5520 provides a mechanism for demo only purposes where an EMR data capture systems 5500 and 5700 is not available for interfacing to EMR data capture systems 5500 and 5700 to allow patient records received from a given device to be viewed and the biological vital sign data presented. For demonstrations of EMR data capture systems 5500 and 5700 where there is no EMR data capture systems 5500 and 5700 to connect the bridge 5520 the system provides a user interface method to present the data sent to the bridge 5520 by the connected MVS apparatus 5504. In some implementations this patient data interface manages and stores multiple patients and multiple record readings per patient and present the information to the operator in an understandable and consistent manner.

Interface to EMR/clinical data repository 5544: The bridge 5520 device provides an interface to the EMR/clinical data repository 5544 for the purpose of storing patient records. Also, anonymous PMRs are stored for the purposes of data analysis as well as provide a mechanism to monitor the operation of the MVS apparatus 5504.

Device PMRs: The bridge 5520 in some implementations accepts propriety formatted measurement records from MVS apparatus 5504 connected and configured to communicate with the bridge 5520 and translate the received measurement record into a suitable format for transfer to a EMR data capture systems 5500 and 5700. The bridge 5520 is the MVS apparatus 5504 that will take the MVS apparatus 5504 based data and translate that data into a format suitable to pass along to a local or remote EMR/Clinical Data Repository 5544 system using the required protocols of that EMR/Clinical Data Repository 5544.

Device non patient measurement data: The bridge 5520 in some implementations accepts data from connected MVS apparatus 5504 and provides data to a connected device. This is data or setting vital-signs associated with the MVS apparatus 5504 that in some implementations is managed by the bridge 5520, e.g. device configuration settings, firmware images, status information etc.

Device to Bridge 5520 interface protocol: The bridge 5520 supports a MVS apparatus 5504 to bridge 5520 interface protocol, BRIP, for all communications between the MVS apparatus 5504 and the bridge 5520 device. Each device supports a single interface protocol, BRIF and individual device or manufacture level protocols can be supported by the bridge 5520.

Network communications method: The bridge 5520 supports a LAN based interface for processing connection requests and data transfers from remote MVS apparatus 5504. Standard communications methods such as UDP/TCP/IP etc. are supported but the interface is not restricted to this transfer mechanism, the architecture of EMR data capture systems 5500 and 5700 in some implementations support other transfer methods such as UDP. Where more than one MVS apparatus 5504 type is supported in EMR data capture systems 5500 and 5700 the bridge 5520 supports different transfer mechanism concurrently MVS apparatus 5504: The bridge 5520 in some implementations accept connections and measurement data records from MVS apparatus 5504.

Non-conforming MVS apparatus: The bridge 5520 in some implementations accepts connections and measurement data records from non-MVS apparatus 5504 using device interface protocols specific to a given device or manufacture of a range of device. The EMR data capture systems 5500 and 5700 support third party MVS apparatus 5504 to provide the same core features and functions as those outlined in this document. In some implementations, a core system supports all MVS apparatus 5504 connected to EMR data capture systems 5500 and 5700, for the purposes of measurement data, body core temperature, ECG, blood pressure, plus other biological vital signs, both single and continuous measurement based, for transfer to the selected EMR/Clinical Data Repository 5544, along with per device configuration and status monitoring.

Single Vital-sign Measurement Data: The bridge 5520 in some implementations accept and processes for transfer to the configured EMR/Clinical Data Repository 5544, single event measurement data. Single event measurement data is defined as a patient biological vital sign single point measurement such as a patient body core temperature, blood pressure, heart rate or other data that is considered a one-time measurement event for a single measurement vital-sign. This type of data is generated from a MVS apparatus 5504 that supports a single biological vital sign reading.

Multiple Vital-sign Measurement Data: The bridge 5520 in some implementations accept and process for transfer to the EMR multiple event measurement data. Multiple event measurement data is defined as a patient biological vital sign single point measurement such as a patient blood glucose levels or other vital sign that is considered a one-time measurement event for more than one vital sign.

Continuous Vital-sign Measurement Data: The bridge 5520 in some implementations accept and process for transfer to the EMR single vital-sign continuous measurement data. Continuous measurement data is defined as a stream of measurement samples representing a time domain signal for a single or multiple biological vital sign vital-sign.

Unique MVS smartphone system identification: The bridge 5520 supports a unique identifier per MVS apparatus 5504, across all vendors and device types, for the purposes of device identification, reporting and operations. Each MVS apparatus 5504 that is supported by the EMR data capture systems 5500 and 5700 provides a unique identification based on the manufacture, product type, and serial number or other factors such as the FDA UID. The bridge 5520 is required to track, take account of, and report this number in all interactions with the MVS apparatus 5504 and for logging. This device identification can also be used in the authentication process when a MVS apparatus 5504 connects to the bridge 5520.

Device connection authentication: The bridge 5520 provides a mechanism to authenticate a given MVS apparatus 5504 on connection to ensure that the MVS apparatus 5504 are known and allowed to transfer information to the bridge 5520. Access to the bridge 5520 functions in some implementations is controlled in order to restrict access to currently allowed devices only. Acceptance of a MVS apparatus 5504 making connection the bridge 5520 for 2 main rationales. 55. The MVS apparatus 5504 are known to the bridge 5520, and that 2. A management function to control access for a given device, i.e. allow or bar access.

Last connection of device: The bridge 5520 is required maintain a history of the connection dates and times for a given MVS apparatus 5504. This is required from a reporting and logging viewpoint. In some implementations will also be used to determine if a MVS apparatus 5504 are lost/stolen or failed.

Calibration/Checker Monitoring: The bridge 5520 is required to track the valid calibration dates for a given device and present to the operator those devices that are out of calibration or approaching calibration. All MVS apparatus 5504 in some implementations be checked for operation and accuracy on a regular bases. EMR data capture systems 5500 and 5700 can provide the facility to generate a report and highlight devices that are either out of calibration and those approaching calibration. The check carried out by the bridge 5520 is on the expiry date exposed by the MVS apparatus 5504. The bridge 5520 is not required to check the MVS apparatus 5504 for calibration, only report if the MVS apparatus 5504 are out of calibration based on the MVS apparatus 5504 expiry date. In some implementations the expiry date is updated at the time of the MVS apparatus 5504 recalibration check.

Error/Issue monitoring: The bridge 5520 is required to track the issues/errors reported by a given device and present that information to the operator in terms of a system report. Reporting of device level errors dynamically for a given device is diagnostics tool for system management. Providing the issue/error history for a given device provides core system diagnostic information for the MVS apparatus 5504.

Battery Life monitoring: The bridge 5520 is required to track the battery level of a given device and report the battery level information to the operator. EMR data capture systems 5500 and 5700 is to highlight to the operator that a given device has an expired or nearly expired or failed internal battery based on the information exposed by the MVS apparatus 5504. It is the MVS apparatus 5504 responsibility to determine its own internal power source charge level or battery condition. The bridge 5520 can provide a mechanism to report the known battery condition for all devices, e.g. say all devices that have 10% battery level remaining.

Lost/Stolen/Failed monitoring: The bridge 5520 is required to determine for a given MVS apparatus 5504 if it has been lost/stolen/or failed and disable the MVS apparatus 5504 for system operation. Being able to determine if a system has not connected to the bridge 5520 for a period of time is a feature for failed, lost or stolen reporting to the operator. If a MVS apparatus 5504 has not connected to EMR data capture systems 5500 and 5700 for a period of time, EMR data capture systems 5500 and 5700 determines that the MVS apparatus 5504 has been stolen or lost, in this event the operator is informed in terms of a system report and the MVS apparatus 5504 removed from the supported devices list. If and when the MVS apparatus 5504 reconnects to EMR data capture systems 5500 and 5700 the MVS apparatus 5504 are to be lighted as "detected" and forced to be rechecked and re-commissioned again for use on the network.

Reset device to network default: A method to reset a target device or group of selected devices to factory settings for all network parameters in some implementations.

Reset device to factory default: A method to reset a target device or group of selected devices to their factory default settings in some implementations is supported.

Dynamic Device Parameter Configuration: The bridge 5520 provides a mechanism to provide configuration information to a MVS apparatus 5504 when requested by the MVS apparatus 5504 on connection to the bridge 5520 or via the keep device alive mechanism. Upon connecting to a bridge 5520 a MVS apparatus 5504 as part of the communications protocol determines if its current configuration is out of date, if any aspect of the MVS apparatus 5504 configuration is out of date and is required to be updated then the bridge 5520 provides the current configuration information for the MVS apparatus 5504 model and revision. This is intended to be as simple as the MVS apparatus 5504 getting the configuration setting for each of its supported parameters. The bridge 5520 is responsible to ensure that the supplied information is correct for the MVS apparatus 5504 model and revision level.

Device Configuration Grouping: Single device: The bridge 5520 provides a mechanism to configure a single device, based on unique device ID, to known configuration parameters. The bridge 5520 in some implementations allows a single MVS apparatus 5504 to be updated when it connects to the bridge 5520 either via the heart beat method or via operator use. This effectively means that the bridge 5520 provides a method to manage and maintain individual device configuration settings and have those settings available dynamically for when the MVS apparatus 5504 connects. Further the bridge 5520 supports per device configurations for different revisions of device firmware, for example revision 1 of the MVS apparatus 5504 has configuration parameters x, y and z, but revision 2 of the MVS apparatus 5504 has configuration parameters has x, y, z and k and the valid allowed range for the y parameter has been reduced.

Device Configuration Grouping—MVS apparatus 5504 model group: The bridge 5520 provides a mechanism to configure all devices within a model range to known configuration parameters. The facility to reconfigure a selected sub-group of devices that are model x and at revision level all with the same configuration information.

Device Configuration Grouping—selected group within model range: The bridge 5520 provides a mechanism to configure a selected number of devices within the same model range to known configuration parameters. The facility to reconfigure a selected sub-group of devices that are model x and at revision level y Device Configuration Grouping—defined sub group: The bridge 5520 provides a mechanism to configure a selected number of devices with the same model based on device characteristics e.g. revision level, operational location etc. The facility to reconfigure all devices that are model x and at revision level y, OR all model x devices that are in operation in Ward 6 is a feature.

Device Configuration files: The bridge 5520 provides a method to save, load, update and edit a configuration file for a MVS apparatus 5504 model number and/or group settings. The ability to save and load configuration files and change the configuration content in the file is a required feature for EMR data capture systems 5500 and 5700. A file management mechanism in some implementations is also provided for the saved configuration files.

Dynamic configuration content: The bridge 5520 in some implementations dynamically per MVS apparatus 5504 connection determine upon request by the MVS apparatus 5504 the new configuration settings for that device, given that the medical devices connect in a random manner to the bridge 5520, the bridge 5520 is required for the connected device, model, revision, unique identification etc. to maintain the configuration settings for that device.

The bridge 5520 provides a mechanism to control the patient record received from a MVS apparatus 5504 to transfer the record to one or more of the supported EMR/Clinical Data Repository 5544. Where more than one EMR/Clinical Data Repository 5544 is maintained by a single organization, e.g. one for ER, cardiology use and possibility one for outpatients etc. EMR data capture systems 5500 and 5700 in some implementations manage either by specific device configuration or bridge 5520 configuration which EMR the patient record is to be transmitted to by the bridge 5520.

Device Configuration and Status Display: In some implementations, when a MVS apparatus 5504 connects to the bridge 5520 that the MVS apparatus 5504 queries its current configuration settings against the bridge 5520 settings for that specific device type and device as outlined below: 1. A given device based on a unique ID for that device. Note each device is required to be uniquely identified in EMR data capture systems 5500 and 5700. 2. A group of devices allocated to a physical location in the hospital, i.e. Based on a ward number of other unique location reference. Accordingly, in some implementations a group of devices in a given location in some implementations is updated separately from other devices of the same type located in a different location in the same hospital environment, i.e. a recovery ward 1 as opposed to an emergency room. A group of devices based on product type, i.e. all MVS apparatus 5504, updated with the same settings. Bridge 5520 device configuration options adjusted based on MVS apparatus 5504. The bridge 5520 in some implementations adjusts the configuration options presented to the operator based on the capabilities of the MVS apparatus 5504 being configured. Where multiple different MVS apparatus 5504 are supported by the EMR data capture systems 5500 and 5700 it cannot be assumed that each device from a different manufacture or from the same manufacture but a different model of the same device level configuration parameters. Therefore the bridge 5520 in some implementations determine the configuration capabilities for the MVS apparatus 5504 to be configured and present only valid configuration options for that device with valid parameter ranges for these options.

Device parameter Validation: The bridge 5520 provides a mechanism for a given model MVS apparatus 5504 to validate that a given configuration parameter is set within valid parameter ranges for that device model and revision. The bridge 5520 is required based on the MVS apparatus 5504 model and revision level to present valid parameter ranges for the operator to configure a MVS apparatus 5504 level parameter with. Device patient record acceptance check response source. The bridge 5520 provides a mechanism to configure the MVS apparatus 5504 to require either: 1) a confirmation from the bridge 5520 device only that a patient record has been received for processing or 2) a confirmation from the bridge 5520 device that the EMR data capture systems 5500 and 5700 has received and saved the patient information. In some implementations of the configuration of the MVS apparatus 5504 the MVS apparatus 5504 reports to the operator a status indicator.

Device Hospital/Clinic Reference: A device setting to allow an organization identifier to be configured on the MVS apparatus 5504. The MVS apparatus 5504 can be configured with an alphanumeric identification string, max 30 characters that allows the organization to indicate to the hospital/clinic that the MVS apparatus 5504 are in use with, e.g. "Boston General".

Device Ward Location reference: A device setting to allow an operational location identifier to be configured on the MVS apparatus 5504. The MVS apparatus 5504 are to be configured with an alphanumeric identification string, max 30 characters that allows the organization to indicate an operational area within the organization, e.g. "General Ward #5".

Device Asset Number: A device setting to allow an organization asset number to be configured on the MVS apparatus 5504. The MVS apparatus 5504 are to be configured with an alphanumeric identification string, max 30 characters to allow the organization to provide an asset tag for the MVS apparatus 5504.

Display device Manufacture Name, Device Model and Serial Number: A method to display the manufacture name, device model number and device serial number for the unit is provided. EMR data capture systems 5500 and 5700 can provide a method to determine the manufacturer name, model number and device level serial number of for the MVS smartphone system 5504. Alphanumeric identification string, max 60 characters in length for each of the three parameters.

Display MVS apparatus 5504 unique identification reference tag: A method to display the device level unique identifier for the unit. For regulatory traceability reasons each device is to support a unique identification number this number in some implementations be displayed by the EMR data capture systems 5500 and 5700.

Device last Check/Calibration Date: A method to display and set the date of the last check or re-calibration action for the MVS apparatus 5504. This allows the bridge 5520 to determine which devices are required to be re-checked and present that information to the operator of EMR data capture systems 5500 and 5700. All MVS apparatus 5504 with a measurement function are required to be checked for accuracy on a regular basis. EMR data capture systems 5500 and 5700 provides a mechanism to update the MVS apparatus 5504 date of last check/calibration when a device level check has been carried out.

10. Methods of Multi-Vital-Sign_Detection and Communication

In this section, the particular methods performed by FIGS. 13, 30, 35, 36, 37 and 41 are described by reference to a series of flowcharts.

Figure 58:
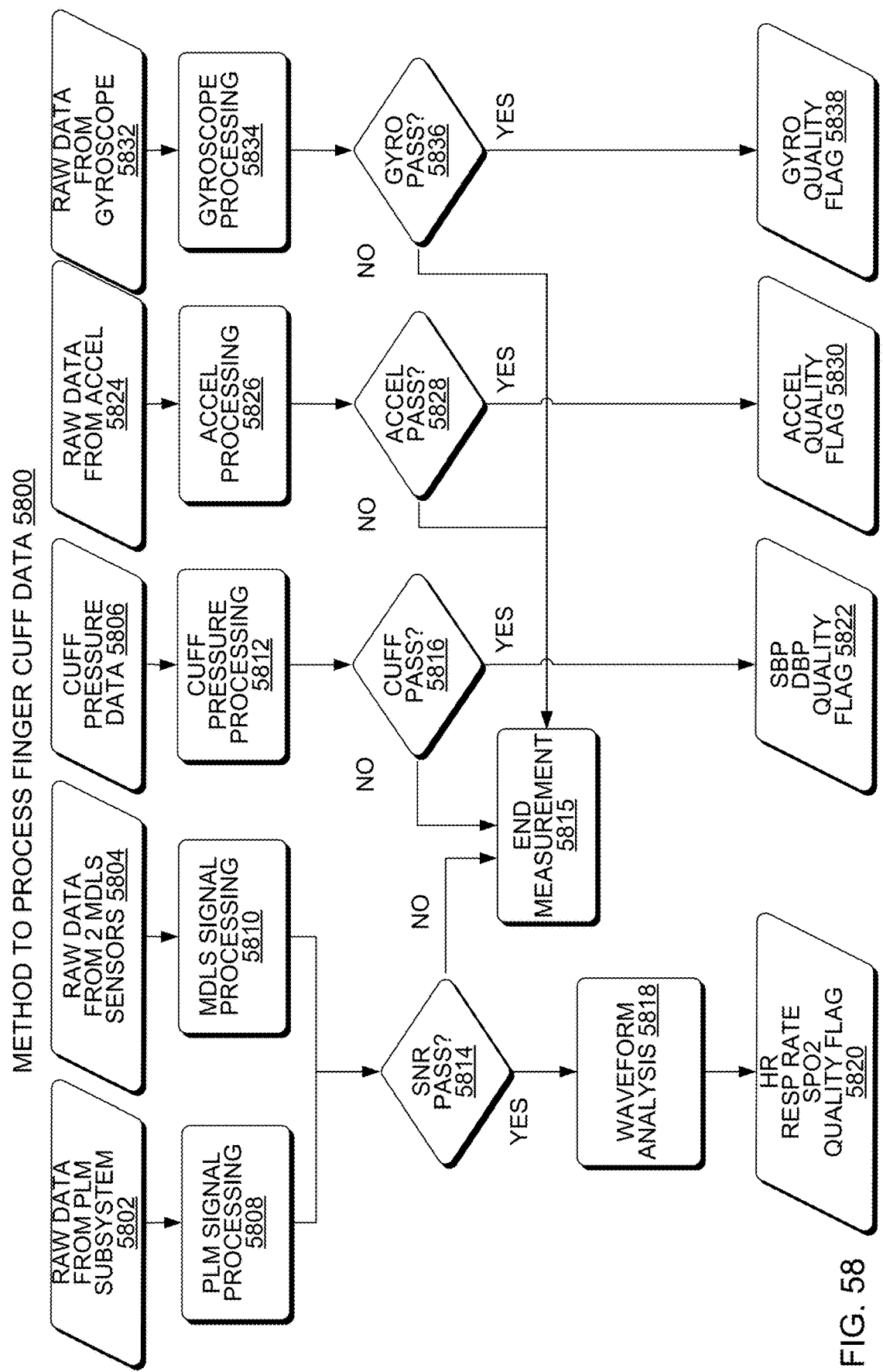
FIG. 58 is a flowchart of a method to perform real time quality check on finger cuff data, according to an implementation.

FIG. 58 is a flowchart of a method 5800 to perform real time quality check on finger cuff data, according to an implementation. The method 5800 uses signals from physiological light monitoring (PLM) subsystems to perform quality check. The method 5800 can be performed by any of the printed circuit boards or any of the microprocessors in FIG. 1-37, such as the printed circuit board 106 in FIGS. 1-7 and 12, the MVS finger cuff accessory (MVSFCA) 3002 in FIG. 30, the MVSFCA 3102 in FIG. 31, the sensor management component 3302 in FIG. 33, the microprocessor 3320 in FIG. 33, the MVS finger cuff 1904 in FIG. 19 and FIG. 11, the microprocessor 1902 in FIG. 19, controller 2020 in FIG. 20, the microprocessor 3502 in FIGS. 35-40 and 41 and/or main processor 2802 in FIG. 28.

In method 5800, raw data 5802 is received from a PLM subsystem, such as PLM subsystem in the MVS finger cuff in FIG. 1-18, 1904 in FIGS. 19, 31 and 33, FIG. 21-27, 30-34 and/or 3544 in FIG. 35-40, raw data 5804 is received from two mDLS sensors, such as mDLS sensor in the MVS finger cuff in FIG. 1-18, 1904 in FIGS. 19, 31 and 33 and/or 3542 in FIG. 35-40, raw data 5806 is received from pressure cuff, such as MVS finger cuff in FIG. 1-18, 1904 in FIGS. 19, 31 and 33 and/or 3542 in FIG. 35-40 and/or the pressure sensor 4208 in FIG. 42, raw data 5824 is received from an accelerometer and raw data 5832 is received from a three-axis gyroscope. The raw data 5806 received from the pressure cuff can be received from the pneumatic pressure sensor 4208 in FIG. 42.

The raw data 5802 that is received from the PLM subsystem is analyzed in PLM signal processing 5808, the raw data 5804 that is received from the mDLS sensors is analyzed in mDLS signal processing 5810, the raw data 5806 that is received from the pressure cuff is analyzed in cuff pressure processing 5812, the raw data 5824 that is received from the accelerometer is analyzed in accelerometer processing 5826 and the raw data 5832 that is received from the three axis gyroscope is analyzed in gyroscope processing 5834. If the analysis in the PLM signal processing 5808 and the mDLS signal processing 5810 indicates a poor signal-to-noise ratio 5814 in the raw data 5802 that is received from the PLM subsystem or the raw data 5804 that is received from the mDLS sensors, the measurement is ended 5815. If the analysis in the PLM signal processing 5808 and the mDLS signal processing 5810 indicates a good signal-to-noise ratio 5814 in both the raw data 5802 that is received from the PLM subsystem and the raw data 5804 that is received from the mDLS sensors, then a waveform analysis 5818 is performed on both the raw data 5802 that is received from the PLM subsystem and the raw data 5804 that is received from the mDLS sensors. If the analysis in the cuff pressure processing 5812 indicates the bladder of the finger occlusion cuff can not be inflated to a required pressure or that the required amount of pressure can not be maintained in the bladder of the MVS finger cuff 5816 then the measurement is ended 5815. If the analysis in the accelerometer processing 5826 indicates unreliable data from the accelerometer, then the measurement is ended 5815. If the analysis in the three axis gyroscope processing 5834 indicates unreliable data from the three axis gyroscope, then the measurement is ended 5815.

From the waveform analysis 5818 that is performed on both the raw data 5802 that is received from the PLM subsystem and the raw data 5804 that is received from the mDLS sensors, flags indicating that status of heartrate, respiratory rate and/or are generated 5820. From the cuff pressure processing 5812, flags indicating the blood pressure (diastolic and systolic) are generated 5822. From the accelerometer processing 5826, flags indicating the quality of the accelerometer data 5824 are generated 5830. From the three axis gyroscope processing 5834, flags indicating the quality of the three axis gyroscope data 5832 are generated 5838.

Figure 59:
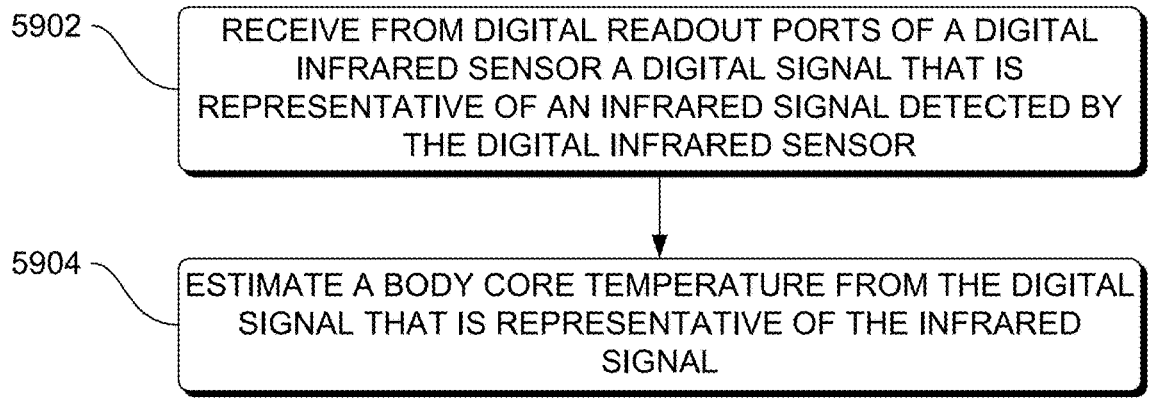
FIG. 59 is a flowchart of a method to estimate a body core temperature from a digital infrared sensor, according to an implementation.

FIG. 59 is a flowchart of a method 5900 to estimate a body core temperature from a digital infrared sensor, according to an implementation. Method 5900 includes receiving from the digital readout ports of a digital infrared sensor a digital signal that is representative of an infrared signal of a forehead temperature that is detected by the digital infrared sensor, at block 5902. No signal that is representative of the infrared signal is received from an analog infrared sensor.

Method 5900 also includes estimating a body core temperature from the digital signal that is representative of the infrared signal, at block 5904.

Figure 60:
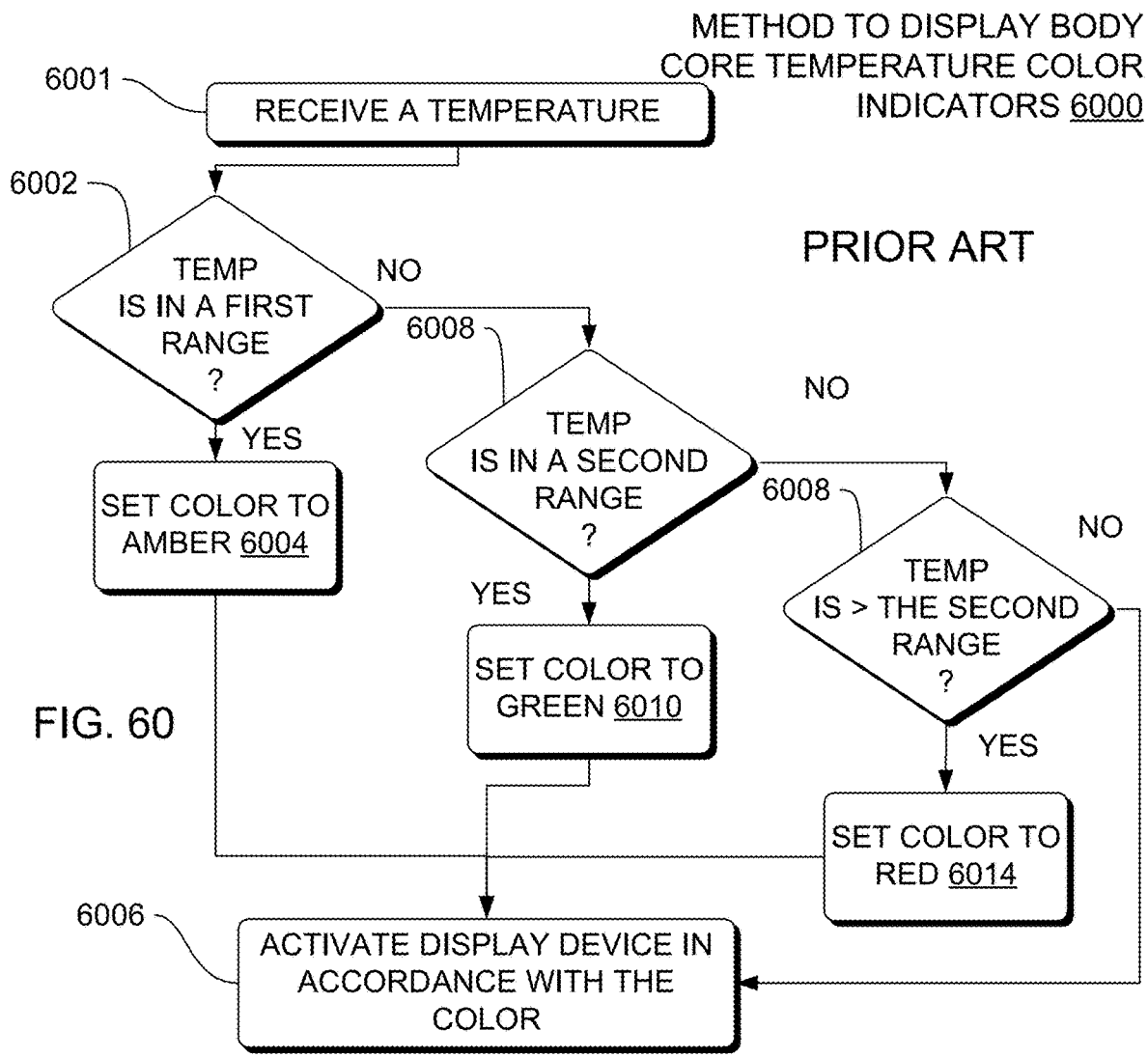
FIG. 60 is a flowchart of a method to display body core temperature color indicators, according to an implementation of three colors.

FIG. 60 is a flowchart of a method 6000 to display body core temperature color indicators, according to an implementation of three colors. Method 6000 provides color rendering to indicate a general range of a body core temperature.

Method 6000 includes receiving the body core temperature (such as digital readout signal 3511 that is representative of the infrared signal 3516 of the forehead in FIG. 35), at block 6001.

Method 6000 also includes determining whether or not the body core temperature is in a first range, such as a range of 32.0° C. and 37.3° C., at block 6002. If the body core temperature is in the first range, then the color is set to 'amber' to indicate a body core temperature that is low, at block 6004 and a lighting emitting diode (LED) (such as LED 316) or the background of the display of the smartphone is activated in accordance with the color, at block 6006.

If the body core temperature is not the first range, then method 6000 also includes determining whether or not the body core temperature is in a second range that is immediately adjacent and higher than the first range, such as a range of 37.4° C. and 35.0° C., at block 6008. If the body core temperature is in the second range, then the color is set to green to indicate no medical concern, at block 6010 and the LED (such as LED 316) or the background of the display is activated in accordance with the color, at block 6006.

If the body core temperature is not the second range, then method 6000 also includes determining whether or not the body core temperature is over the second range, at block 6012. If the body core temperature is over the second range, then the color is set to 'red' to indicate alert, at block 6012 and the LED (such as LED 316) or the background is activated in accordance with the color, at block 6006.

Method 6000 assumes that body core temperature is in gradients of 10ths of a degree. Other body core temperature range boundaries are used in accordance with other gradients of body core temperature sensing.

In some implementations, some pixels in the LED or the display are activated as an amber color when the body core temperature is between a first range of 36.3° C. and 37.3° C. (97.3° F. to 99.1° F.)., some pixels in the display are activated as a green when the body core temperature is between a second range of 37.4° C. and 37.9° C. (99.3° F. to 100.2° F.), the LED or some pixels in the display are activated as a red color when the body core temperature is greater than the second range (a least 35° C. (100.4° F.)).

Figure 61:
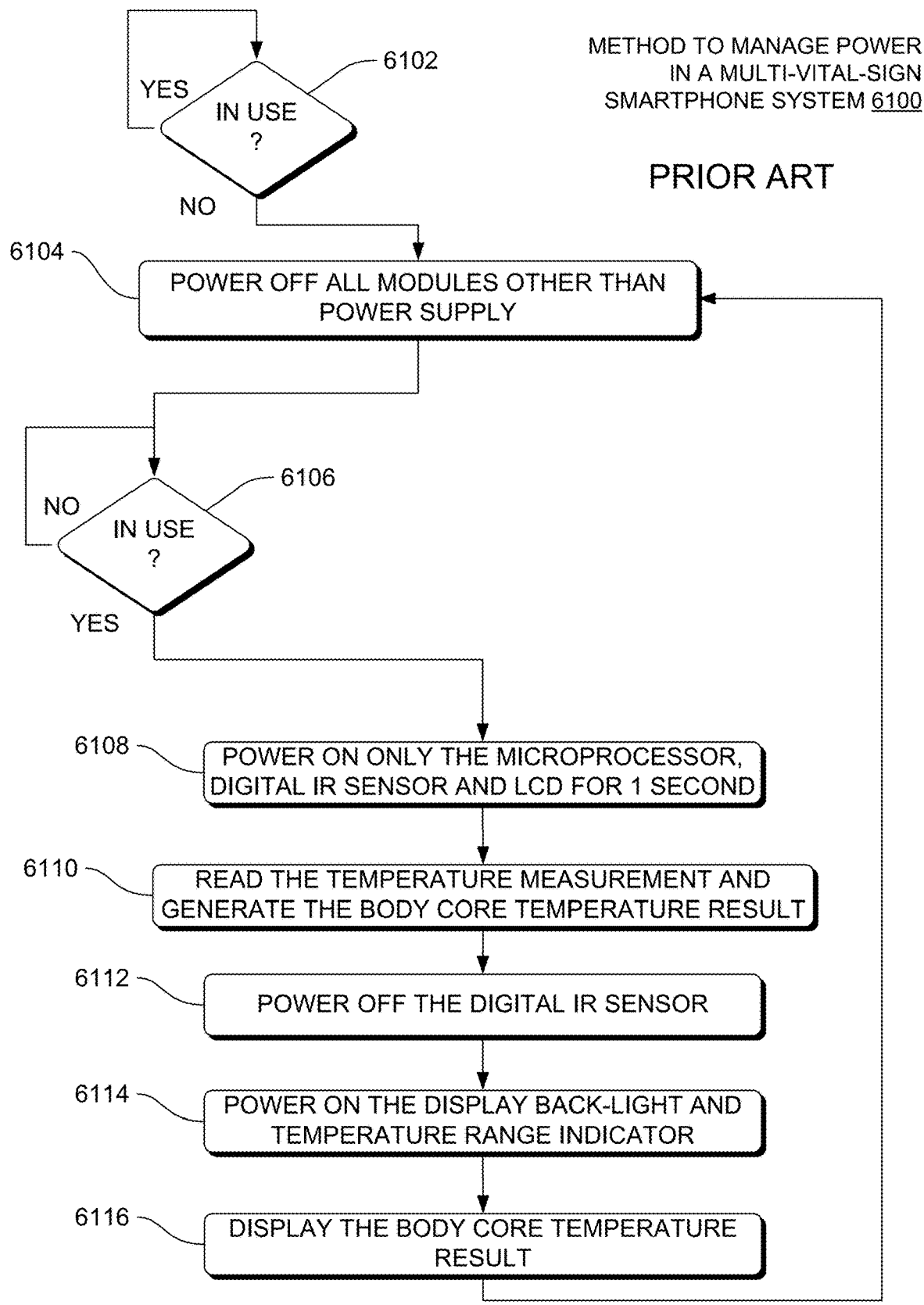
FIG. 61 is a flowchart of a method to manage power in a MVS smartphone system having a digital infrared sensor, according to an implementation.

FIG. 61 is a flowchart of a method 6100 to manage power in a non-touch device having a digital infrared sensor, according to an implementation. The method 6100 manages power in the devices 1-37, in order to reduce heat pollution in the digital infrared sensor.

To prevent or at least reduce heat transfer between digital infrared sensor 3508 and a microprocessor (such as the digital infrared sensor 3508 and the microprocessor 3502, main processor 2802 in FIG. 28, the components of the MVS smartphone systems in FIG. 30-34, the apparatus that estimates a body core temperature in FIG. 38-41), the apparatus of motion amplification in FIG. 46-54 and the MVS smartphone 2800 are power controlled, i.e. sub-systems are turned on and off, and the sub-systems are only activated when needed in the measurement and display process, which reduces power consumption and thus heat generation by the microprocessor 3502, or main processor 2802 in FIG. 28, of the MVS smartphone systems in FIG. 30-34, the apparatus that estimates a body core temperature in FIG. 38-40, the apparatus of motion amplification in FIG. 46-54, the MVS smartphone 2800, respectively. When not in use, at block 6102, the MVS smartphone systems in FIG. 30-34, the apparatus that estimates a body core temperature in FIG. 38-41, the apparatus of motion amplification in FIG. 46-54 and the MVS smartphone 2800 are completely powered-off, at block 6104 (including the main PCB having the microprocessor 3502, main processor 2802 in FIG. 28 and the sensor PCB having the digital infrared sensor 3508) and not drawing any power, other than a power supply, i.e. a boost regulator, which has the effect that the MVS smartphone systems in FIG. 1-37, the apparatus that estimates a body core temperature in FIG. 38-40, the apparatus of motion amplification in FIG. 46-54 and the MVS smartphone 2800 draw only micro-amps from the battery 3504 while in the off state, which is required for the life time requirement of 3 years of operation, but which also means that in the non-use state there is very little powered circuitry in the MVS smartphone systems in FIG. 30-34, the apparatus of motion amplification in FIG. 46-54 and the MVS smartphone 2800 and therefore very little heat generated in the MVS smartphone systems in FIG. 30-34, the apparatus of motion amplification in FIG. 46-54 and the MVS smartphone 2800.

When the MVS smartphone systems in FIG. 30-34, the apparatus that estimates a body core temperature in FIG. 38-40, the apparatus of motion amplification in FIG. 46-54 and the MVS smartphone 2800 are started by the operator, at block 6106, only the microprocessor 3502, microprocessor 3502, main processor 2802. In FIG. 28, main processor 2802 in FIG. 28, digital infrared sensor 3508, and in some implementations low power LCD (e.g. display device 3514) are turned on for the first 1 second, at block 6108, to take the temperature measurement via the digital infrared sensor 3508 and generate the body core temperature result via a microprocessor in FIG. 1-37 at block 6110. In this way, the main heat generating components (the display device 3514, the main PCB having the microprocessor 3502 and the sensor PCB having the digital infrared sensor 3508), the display back-light and the body core temperature traffic light) are not on and therefore not generating heat during the critical start-up and measurement process, no more than 1 second. After the measurement process of block 6110 has been completed, the digital infrared sensor 3508 is turned off, at block 6112, to reduce current usage from the batteries and heat generation, and also the display back-light and temperature range indicators are turned on, at block 6114.

The measurement result is displayed for 4 seconds, at block 6116, and then the MVS smartphone systems in FIG. 30-34, the apparatus that estimates a body core temperature in FIG. 1-37, the apparatus of motion amplification in FIG. 46-54 and the MVS smartphone 2800 are put in low power-off state, at block 6118.

In some implementations of methods and apparatus of FIG. 1-37 an operator can take the temperature of a subject and from the temperatures to estimate the temperature at a number of other locations of the subject.

The correlation of action can include a calculation based on Formula 1:

$$T_{body} = |f_{stb}(T_{surface\ temp}) + f_{ntc}(T_{ntc}) + F4_{body}|$$ Formula 1 where $T_{body}$ is the temperature of a body or subject
where $f_{stb}$ is a mathematical formula of a surface of a body
where $f_{ntc}$ is mathematical formula for ambient air temperature reading
where $T_{surface\ temp}$ is a surface temperature estimated from the sensing.
where $T_{ntc}$ is an ambient air temperature reading
where $F4_{body}$ is a calibration difference in axillary mode, which is stored or set in a memory of the apparatus either during manufacturing or in the field. The apparatus also sets, stores and retrieves $F4_{oral}$, $F4_{core}$, and $F4_{rectal}$ in the memory.
$f_{ntc}(T_{ntc})$ is a bias in consideration of the temperature sensing mode. For example $f_{axillary}(T_{axillary})=0.2°$ C., $f_{oral}(T_{oral})=0.4°$ C., $f_{rectal}(T_{rectal})=0.5°$ C. and $f_{core}(T_{core})=0.3°$ C.

Apparatus in FIG. 46-54 use spatial and temporal signal processing to generate a biological vital sign from a series of digital images.

Figure 62:
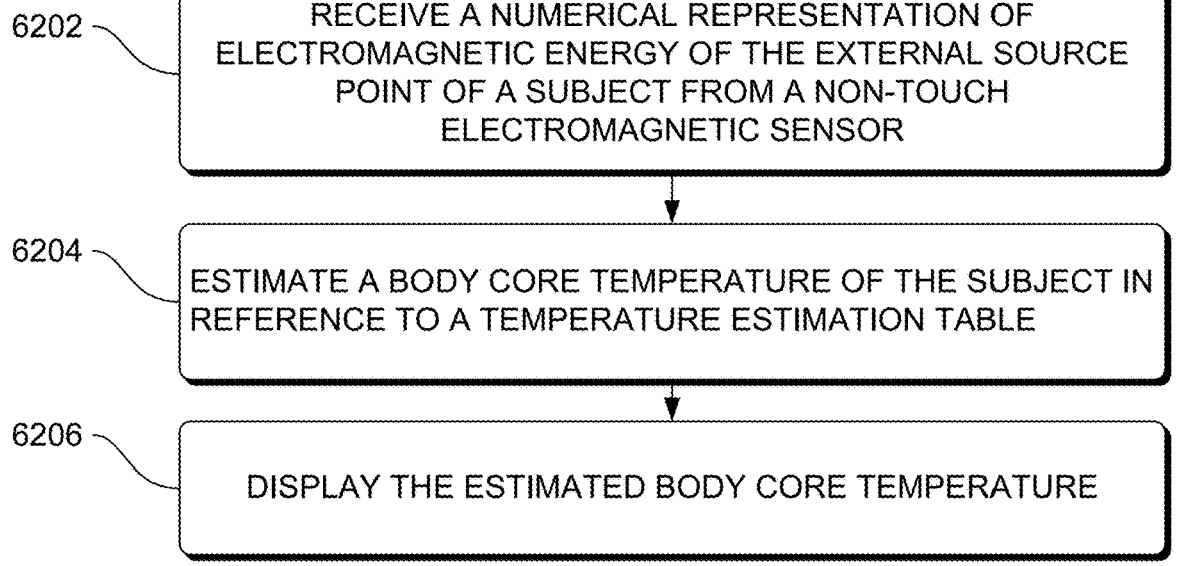
FIG. 62 is a flowchart of a method to estimate a body core temperature from an external source point in reference to a body core temperature correlation table, according to an implementation.

FIG. 62 is a flowchart of a method 6200 to estimate a body core temperature from an external source point in reference to a body core temperature correlation table, according to an implementation.

Method 6200 includes receiving from a non-touch electromagnetic sensor a numerical representation of electromagnetic energy of the external source point of a subject, at block 6202.

Method 6200 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 6204. The estimating at block 6204 is based on a body core temperature correlation table representing the body core temperature and the numerical representation of the electromagnetic energy of the external source point.

A body core temperature correlation table provides best results because a linear or a quadratic relationship provides inaccurate estimates of body core temperature, yet a quartic relationship, a quintic relationship, sextic relationship, a septic relationship or an octic relationship provide estimates along a highly irregular curve that is far too wavy or twisting with relatively sharp deviations.

Method 6200 also includes displaying the body core temperature, at block 6206.

Figure 63:
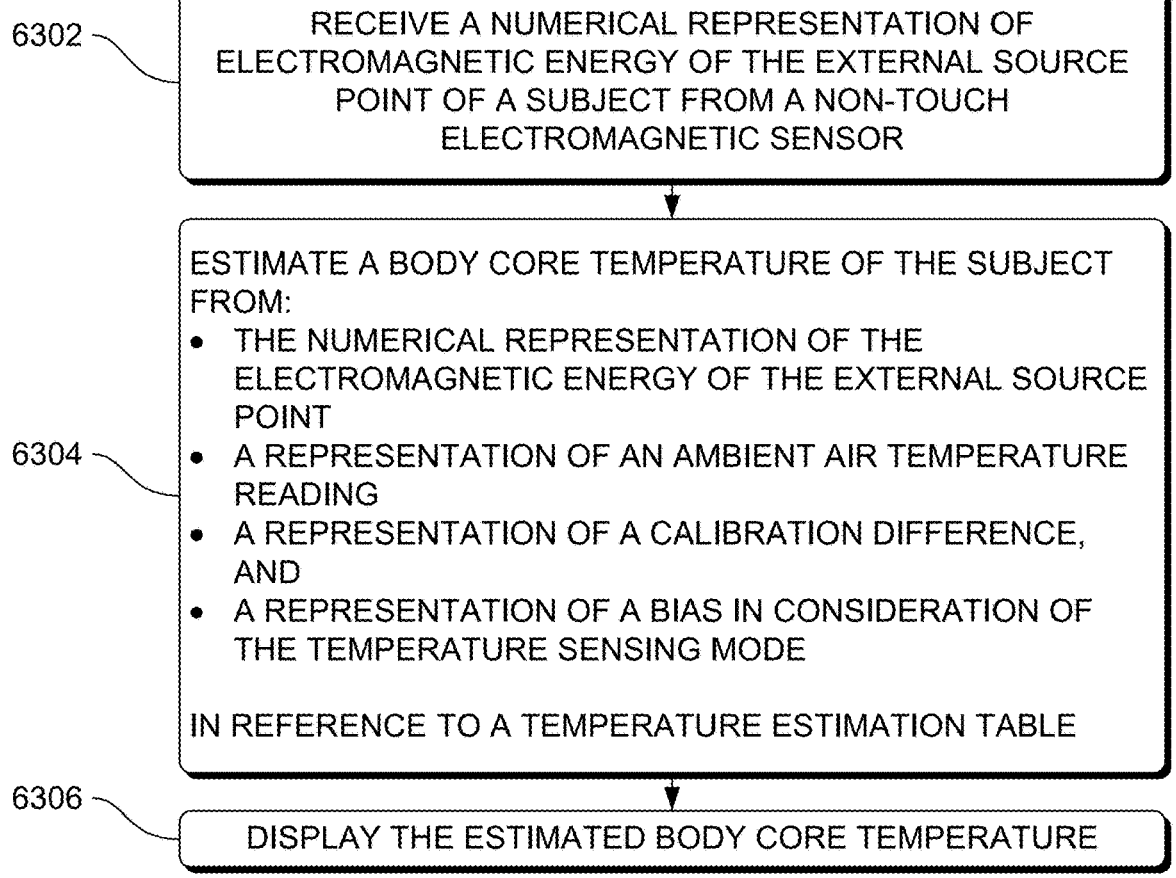
FIG. 63 is a flowchart of a method to estimate a body core temperature from an external source point and other measurements in reference to a body core temperature correlation table, according to an implementation.

FIG. 63 is a flowchart of a method 6300 to estimate a body core temperature from an external source point and other measurements in reference to a body core temperature correlation table, according to an implementation;

Method 6300 includes receiving from a non-touch electromagnetic sensor a numerical representation of electromagnetic energy of the external source point of a subject, at block 6302.

Method 6300 also includes estimating the body core temperature of the subject from the numerical representation of the electromagnetic energy of the external source point, a representation of an ambient air temperature reading, a representation of a calibration difference, and a representation of a bias in consideration of the temperature sensing mode, at block 6304. The estimating at block 6304 is based on a body core temperature correlation table representing three thermal ranges between the body core temperature and the numerical representation of the electromagnetic energy of the external source point.

Method 6300 also includes displaying the body core temperature, at block 6206.

In some implementations, methods 5400 and 5800-6400 are implemented as a sequence of instructions which, when executed by a microprocessor in FIG. 1-37, cause the processor to perform the respective method. In other implementations, methods 5400 and 5800-6400 are implemented as a computer-accessible medium having computer executable instructions capable of directing a microprocessor, such as microprocessor in FIG. 1-37, to perform the respective method. In different implementations, the medium is a magnetic medium, an electronic medium, or an optical medium.

FIG. 64 is a block diagram of a method of MVS (MVS) detection and communication method 6400, according to an implementation. The MVS detection and communication method 6400 in FIG. 64 can include any combination and permutation of three general processes including glucose and other monitoring at block 6402, temperature monitoring at block 6404 and motion amplification monitoring 6406.

The glucose and other monitoring 6402 in FIG. 64 includes receiving data from a SpO2/glucose subsystem having photodiode receivers of ER at block 6408. One example of the SpO2/glucose subsystem is Physiological Light Monitoring (PLM) subsystem in FIG. 1 and Physiological Light Monitoring (PLM) subsystem 304 in FIG. 3. In some implementations, the glucose and other monitoring 6402 also includes estimating a blood glucose level from the data of the photodiode receivers at block 6410. In some implementations, the glucose and other monitoring at block 6402 includes estimating an SpO2 level from the data of the photodiode receivers 6412. The glucose and other monitoring 6402 thereafter includes estimating a heart rate, a respiration rate, a heart rate variability and a blood pressure diastolic from the data of the photodiode receivers at block 6414.

One implementation of the temperature monitoring 6404 in FIG. 64 includes detecting through an infrared sensor an infrared signal that is representative of a body surface temperature at block 6416, receiving the body surface temperature from the digital infrared sensor at block 6418 and providing a vital sign (such as a body core temperature) correlated to the body surface temperature at block 6420.

Other implementations of the temperature monitoring 6404 in FIG. 64 include methods in FIG. 59-63. The temperature monitoring 6404 in FIG. 64 can be performed by apparatus in FIGS. 12-27, 30-36, 38-41 and 45.

The motion amplification monitoring at block 6406 in FIG. 64 includes examining pixel values of a plurality of images at block 6424, determining a temporal motion of the pixel values between the plurality of images being below a particular threshold at block 6426, amplifying the temporal motion resulting in an amplified temporal motion at block 6428 and visualizing a pattern of flow of blood in the amplified temporal-motion in the plurality of images and block 6430.

After completion of the glucose and other monitoring 6402, the temperature monitoring 6404 and/or the motion amplification monitoring 6406, the vital signs are transmitted from a wireless communication subsystem via a short distance wireless communication path at block 6432. In some implementations, the vital signs are transmitted by the communication subsystem through an Internet Protocol tunnel at block 6434. One implementation of the communication subsystem is communication subsystem 2804 In FIG. 44.

11. Displays of Multi-Vital-Sign Smartphones

FIG. 65 is a display screen 6500 of the MVS smartphone 3103 showing results of successful multi-vital sign measurements, according to an implementation. The display screen 6500 includes display of the blood glucose levels 6502, heartrate variability 6504, battery charge level 6506, measured blood pressure 6510 (systolic and diastolic in terms of millimeters of mercury) of the patient, measured core temperature 6512, measured heartrate in beats per minute 6514, measured SpO2 levels 6516 in the patient bloodstream and/or measured respiratory rate 6518 in terms of breaths per minute of the patient. Other data that can be displayed by display screen 6500 is level of Wi-Fi® connectivity or the level of Bluetooth® connectivity or the level of cellular connectivity, the current time and the patient name of the patient whose vital signs are measured. In other implementations, Zigbee® or Z-Wave® can be used instead of Bluetooth®.

CONCLUSION

A MVS device senses blood glucose levels, body core temperature, heart rate, heart rate variability, respiration, SpO2, blood flow and/or blood pressure and transmits the vital signs to an electronic medical record system. In some implementations, the transmission is performed through a smartphone. A technical effect of the apparatus and methods disclosed herein is wireless electronic transmission of a plurality of vital signs, including blood glucose levels from an electromagnetic sensor, to an electronic medical record system. Another technical effect of the apparatus and methods disclosed herein is generating a temporal motion of images from which a biological vital sign can be transmitted to an electronic medical record system. Although specific implementations are illustrated and described herein, it will be appreciated by those of ordinary skill in the art that any arrangement which is generated to achieve the same purpose may be substituted for the specific implementations shown. This application is intended to cover any adaptations or variations. Further implementations of power supply to all devices includes A/C power both as a supplemental power supply to battery power and as a substitute power supply.

In particular, one of skill in the art will readily appreciate that the names of the methods and apparatus are not intended to limit implementations. Furthermore, additional methods and apparatus can be added to the modules, functions can be rearranged among the modules, and new modules to correspond to future enhancements and physical devices used in implementations can be introduced without departing from the scope of implementations. One of skill in the art will readily recognize that implementations are applicable to future vital sign and non-touch temperature sensing devices, different temperature measuring sites on humans or animals, new communication protocols for transmission (of user service, patient service, observation service, and chart service) and all current and future application programming interfaces and new display devices.

The terminology used in this application meant to include all temperature sensors, processors and operator environments and alternate technologies which provide the same functionality as described herein.

The invention claimed is:

1. An apparatus to determine a plurality of vital signs, the apparatus comprising:
   a microprocessor;
   a wireless communication subsystem that is operably coupled to the microprocessor and that is configured to transmit a representation of the plurality of vital signs, the plurality of vital signs including a temperature, an amount of glucose and an amount of oxygen;

a digital infrared sensor that is operably coupled to the microprocessor with no analog-to-digital converter being operably coupled between the digital infrared sensor and the microprocessor, the digital infrared sensor having only digital readout ports, the digital infrared sensor having no analog sensor readout ports, the digital infrared sensor including a Faraday cage surrounding a single thermopile sensor and a central processing unit control block that digitizes output of the single thermopile sensor; and a first housing that contains the microprocessor, the wireless communication subsystem and the digital infrared sensor;

a glucose subsystem that includes a second housing, the housing including a source-detector assembly having a first side and a second side;

the first side having two transmitters of electromagnetic radiation in a 375-415 nm frequency range and a 920-960 nm frequency range and a first photodiode receiver of electromagnetic radiation in a 350-1100 nm range to measure an amount of electromagnetic radiation that is reflected by a subject that is positioned between the first side and the second side, wherein the microprocessor is configured to receive from the digital readout ports a digital signal that is representative of an infrared signal of the temperature that is detected by the digital infrared sensor and the microprocessor is configured to determine the plurality of vital signs from data from the first photodiode receiver and from the digital signal that is representative of the infrared signal in reference to a plurality of tables that are stored in a memory that correlate the temperature to the plurality of vital signs, a finger occlusion cuff having a third housing;

a central longitudinal axis of the third housing of the finger occlusion cuff is not coaxial with a central longitudinal axis of the second housing of the glucose subsystem, wherein the second housing and the third housing are aligned so that a finger can be inserted through the finger occlusion cuff and into the glucose subsystem, wherein the second housing of the glucose subsystem is mounted to the first housing, wherein the third housing of the finger occlusion cuff is mounted to the first housing, wherein the microprocessor is configured to determine an indication of the amount of glucose in the subject calculated from a ratio of electromagnetic radiation received in the 375-415 nm frequency range in comparison to electromagnetic radiation received in the 920-960 nm frequency range, wherein the microprocessor is configured to determine an indication of the amount of oxygen in the subject calculated from a ratio of electromagnetic radiation received in a 640-680 nm frequency range in comparison to electromagnetic radiation received in a 920-960 nm frequency range, wherein a connection is established by the wireless communication subsystem to an external device and the plurality of vital signs are pushed from the apparatus through the wireless communication subsystem, wherein the connection further comprises an authenticated communication channel.

2. The apparatus of claim 1, wherein the first photodiode receiver of electromagnetic radiation in the first side receives the electromagnetic radiation in the 375-415 nm frequency range.

3. The apparatus of claim 1 further comprising a camera that is operably coupled to the microprocessor and configured to provide a plurality of images to the microprocessor, the microprocessor further comprising:
a cropper module that is configured to receive the plurality of images and that is configured to crop each of the plurality of images to exclude a border area of the images, generating a plurality of cropped images,
a pixel-examination-module configured to examine pixel-values of the plurality of cropped images,
a temporal-variation module to determine a temporal variation of the pixel-values between the plurality of cropped images being below a particular threshold,
a signal processing module configured to amplify the temporal variation resulting in an amplified-temporal-variation, and
a visualizer to visualize a pattern of flow of blood in the amplified-temporal-variation in the plurality of images.

4. The apparatus of claim 1 wherein electromagnetic radiation in the 375-415 nm frequency range is received by the first photodiode receiver of electromagnetic radiation.

5. The apparatus of claim 1 further comprising:
a first circuit board including the microprocessor and a first digital interface operably coupled to the microprocessor; and
the first housing that contains the first circuit board and that does not contain the camera.

6. The apparatus of claim 1 wherein the wireless communication subsystem transmits via a short distance wireless communication path.

7. The apparatus of claim 5 further comprising:
a second circuit board in a smartphone, the smartphone having a fourth housing and the camera; and
a second digital interface, the second digital interface being operably coupled to the first digital interface and the second digital interface being operably coupled to the digital infrared sensor.

* * * * *